(12) United States Patent
Moon et al.

(10) Patent No.: US 11,993,616 B2
(45) Date of Patent: May 28, 2024

(54) COMPOUND AND OPTICAL FILM COMPRISING SAME

(71) Applicant: LG CHEM, LTD., Seoul (KR)

(72) Inventors: Sang Pil Moon, Daejeon (KR); Duy Hieu Le, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 318 days.

(21) Appl. No.: 17/626,978

(22) PCT Filed: Feb. 24, 2021

(86) PCT No.: PCT/KR2021/002329
§ 371 (c)(1),
(2) Date: Jan. 13, 2022

(87) PCT Pub. No.: WO2021/177650
PCT Pub. Date: Sep. 10, 2021

(65) Prior Publication Data
US 2022/0402942 A1    Dec. 22, 2022

(30) Foreign Application Priority Data

Mar. 4, 2020   (KR) .................. 10-2020-0027193
Mar. 4, 2020   (KR) .................. 10-2020-0027203

(51) Int. Cl.
*C07F 3/04*    (2006.01)
*C07F 15/00*   (2006.01)
(Continued)

(52) U.S. Cl.
CPC ............ *C07F 3/04* (2013.01); *C07F 15/0066* (2013.01); *C07F 15/045* (2013.01);
(Continued)

(58) Field of Classification Search
CPC ...... C07F 3/04; C07F 15/0066; C07F 15/045; C07F 15/065; H10K 85/654; H10K 85/652; H10K 85/656; H10K 85/6574; H10K 85/6572; H10K 85/331; H10K 85/30; H10K 85/381; H10K 59/38
See application file for complete search history.

(56) References Cited

U.S. PATENT DOCUMENTS

2017/0349822 A1    12/2017   Lee et al.
2020/0035932 A1*   1/2020    Yoshioka .......... H01L 27/14643

FOREIGN PATENT DOCUMENTS

CN    110698487 A    1/2020
JP    H10-162430 A   6/1998
(Continued)

OTHER PUBLICATIONS

International Search Report and Written Opinion issued for International Application No. PCT/KR2021/002329 dated Jun. 21, 2021, 8 pages.

*Primary Examiner* — Evan P Dzierzynski
*Assistant Examiner* — Nathaniel J Lee
(74) *Attorney, Agent, or Firm* — ROTHWELL, FIGG, ERNST & MANBECK, P.C.

(57) ABSTRACT

The present specification relates to a compound represented by Chemical Formula 1, a composition for forming an optical film and an optical film comprising the same, and a display device comprising the optical film.

18 Claims, 3 Drawing Sheets

(51) Int. Cl.
*C07F 15/04* (2006.01)
*C07F 15/06* (2006.01)
*H10K 59/38* (2023.01)
*H10K 85/30* (2023.01)
*H10K 85/60* (2023.01)

(52) U.S. Cl.
CPC ........... *C07F 15/065* (2013.01); *H10K 59/38* (2023.02); *H10K 85/30* (2023.02); *H10K 85/331* (2023.02); *H10K 85/381* (2023.02); *H10K 85/652* (2023.02); *H10K 85/654* (2023.02); *H10K 85/656* (2023.02); *H10K 85/6572* (2023.02); *H10K 85/6574* (2023.02)

(56) References Cited

FOREIGN PATENT DOCUMENTS

| | | | | |
|---|---|---|---|---|
| JP | 2003-057436 A | | 2/2003 | |
| JP | 2003057436 A | * | 2/2003 | ............. C09B 23/04 |
| KR | 2000-0011622 A | | 2/2000 | |
| KR | 10-2011-0084120 A | | 7/2011 | |
| KR | 10-2011-0101756 A | | 9/2011 | |
| KR | 10-1590299 B1 | | 2/2016 | |
| KR | 10-2016-0071343 A | | 6/2016 | |
| WO | 2018-186389 A | | 10/2018 | |

* cited by examiner

[FIG. 1]
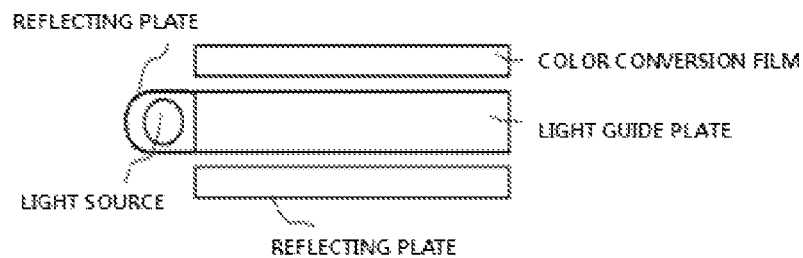
[FIG. 2]
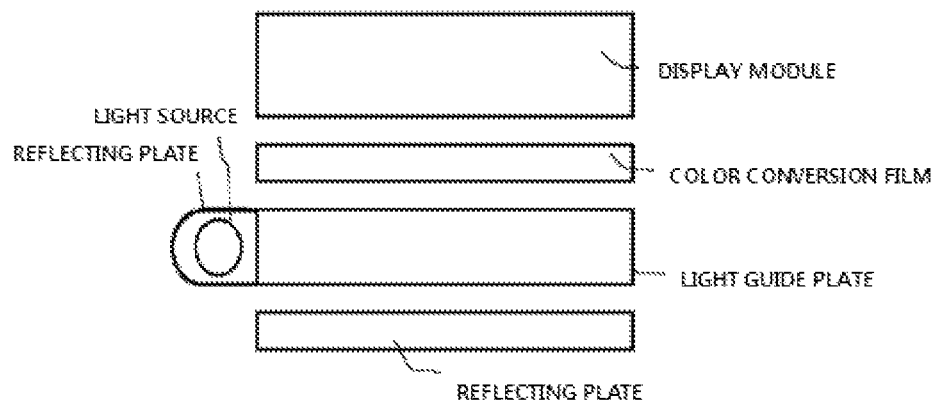
[FIG. 3]
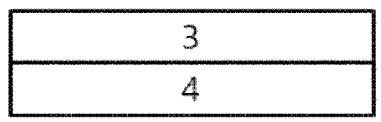
[FIG. 4]
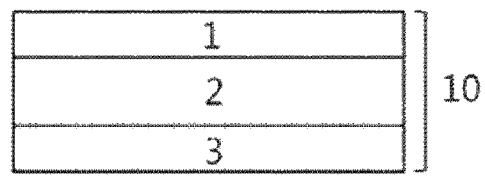

[FIG. 5]
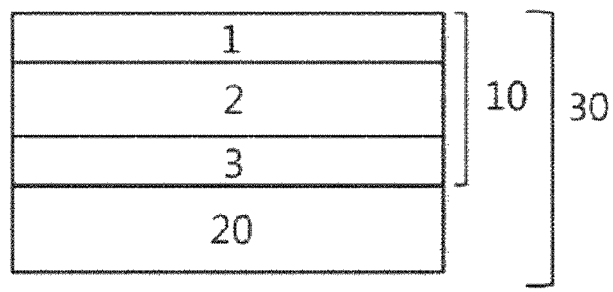
[FIG. 6]
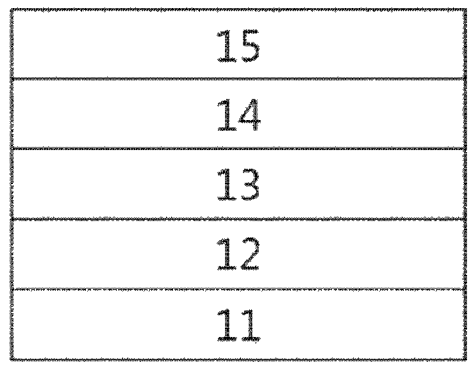
[FIG. 7]
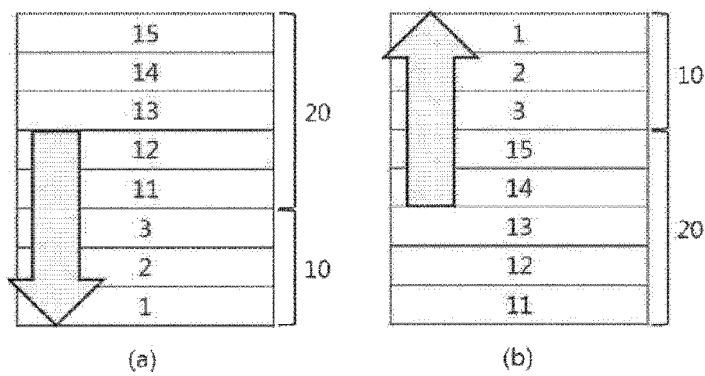

【FIG. 8】

| 15 |
|---|
| 14 |
| 13 |
| 12 |
| R　G　B ]16 |

(a)

| R　G　B ]16 |
|---|
| 14 |
| 13 |
| 12 |
| 11 |

(b)

COMPOUND AND OPTICAL FILM COMPRISING SAME

This application is a 35 U.S.C. 371 National Phase Entry application from PCT/KR2021/002329, filed on Feb. 24, 2021, which claims priority to and the benefits of Korean Patent Application No. 10-2020-0027193, filed with the Korean Intellectual Property Office on Mar. 4, 2020, the entire contents of which are incorporated herein by reference.

This application claims priority to and the benefits of Korean Patent Application No. 10-2020-0027203, filed with the Korean Intellectual Property Office on Mar. 4, 2020, the entire contents of which are incorporated herein by reference.

TECHNICAL FIELD

The present specification relates to a compound, a composition for forming an optical film and an optical film including the same, and a display device including the optical film.

BACKGROUND OF THE INVENTION

Existing light emitting diodes (LED) are obtained by mixing a green phosphorescent substance and a red phosphorescent substance to a blue light emitting diode, or mixing a yellow phosphorescent substance and a blue-green phosphorescent substance to a UV light emitting diode. However, with such a method, it is difficult to control colors, and therefore, color rendering is not favorable. Accordingly, color gamut declines.

In order to overcome such color gamut decline and to reduce production costs, methods of obtaining green and red in a manner of filming quantum dots and binding the dots to a blue LED have been recently tried. However, cadmium series quantum dots have safety problems, and other quantum dots have significantly reduced efficiency compared to cadmium series quantum dots. In addition, quantum dots have reduced stability for oxygen and water, and have a disadvantage in that the performance is significantly degraded when aggregated. Furthermore, unit costs of production are high since, when producing quantum dots, maintaining the sizes to be constant is difficult.

Existing compounds having a $BF_2$ or $B(CN)_2$-based BODIPY structure provide, as a fluorescent dye having high light efficiency and a narrow full width at half maximum, excellent optical properties when used in an optical film, but have insufficient light resistance and heat resistance to be commercialized, and development of compounds having high durability has been required.

BRIEF SUMMARY OF THE INVENTION

The present specification is directed to providing a compound, a composition for forming an optical film including the compound, an optical film formed using the composition, and a display device including the optical film.

One embodiment of the present specification provides a compound represented by the following Chemical Formula 1.

[Chemical Formula 1]

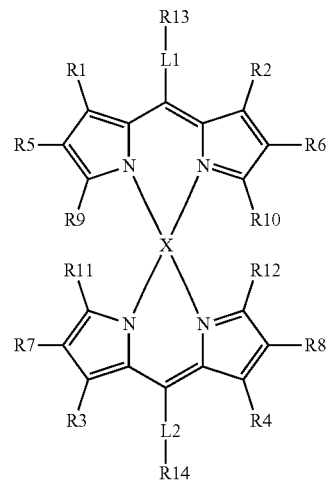

In Chemical Formula 1,

R1 to R8 are the same as or different from each other, and each independently hydrogen; a halogen group; an aldehyde group; a nitrile group; a nitro group; a substituted or unsubstituted ester group; a substituted or unsubstituted amide group; a substituted or unsubstituted alkyl group; a substituted or unsubstituted cycloalkyl group; a substituted or unsubstituted aryl group; a substituted or unsubstituted aryloxy group; a substituted or unsubstituted arylthio group; or a substituted or unsubstituted heteroaryl group, R9 to R12 are the same as or different from each other, and each independently hydrogen; a substituted or unsubstituted alkyl group; a substituted or unsubstituted cycloalkyl group; or -L-R, L1, L2 and L are the same as or different from each other, and each independently O or S, R is a substituted or unsubstituted alkyl group; a substituted or unsubstituted aryl group; or a substituted or unsubstituted heteroaryl group, R13 and R14 are the same as or different from each other, and each independently a substituted or unsubstituted aryl group; or a substituted or unsubstituted heteroaryl group, and X is Zn, Co, Ni or Pd.

In addition, one embodiment of the present specification provides a composition for forming an optical film, the composition comprising a binder resin; and the compound.

In addition, one embodiment of the present specification provides an optical film comprising a resin matrix into which the compound is dispersed.

In addition, one embodiment of the present specification provides a display device comprising the optical film.

Advantageous Effects

A compound according to one embodiment of the present specification is effective in increasing light resistance and heat resistance when used in an optical film such as a color conversion film and an adhesive film. Accordingly, by using the compound as a light absorbing material of a color conversion film, an optical film having excellent luminance (brightness) and color gamut, and having excellent durability can be manufactured.

BRIEF DESCRIPTION OF DRAWINGS

FIG. 1 is a mimetic diagram of using a color conversion film according to one embodiment of the present specification in a backlight unit.

FIG. 2 is a mimetic diagram illustrating a structure of a display device including a color conversion film according to one embodiment of the present specification.

FIG. 3 illustrates a structure when a release layer is provided on one surface of an adhesive film according to one embodiment of the present specification.

FIG. 4 illustrates a structure of an adhesive optical filter according to one embodiment of the present specification.

FIG. 5 illustrates a structure of an OLED device, one example of a display device according to one embodiment of the present specification.

FIG. 6 illustrates a structure of an OLED panel according to one embodiment of the present specification.

FIG. 7 illustrates an OLED device having a bottom emission structure and an OLED device having a top emission structure according to the present specification.

FIG. 8 illustrates a structure of an OLED panel provided with a color filter-formed substrate according to the present specification.

REFERENCE NUMERAL

1: Anti-Reflection Film
2: Base
3: Adhesive Film
4: Release Layer
10: Adhesive Optical Filter
11: Substrate
12: Lower Electrode
13: Organic Material Layer
14: Upper Electrode
15: Encapsulation Substrate
16: Color Filter-Formed Substrate
20: OLED Panel
30: OLED Device

DETAILED DESCRIPTION OF THE INVENTION

Hereinafter, the present specification will be described in more detail.

One embodiment of the present specification provides a compound represented by the following Chemical Formula 1.

[Chemical Formula 1]

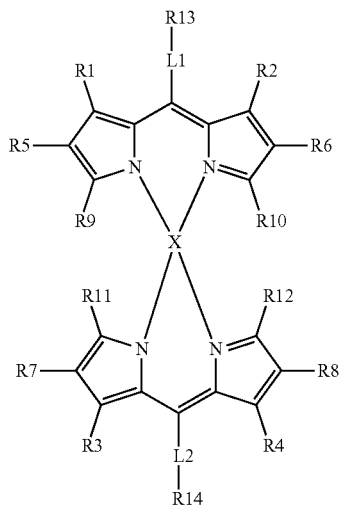

In Chemical Formula 1,
R1 to R8 are the same as or different from each other, and each independently hydrogen; a halogen group; an aldehyde group; a nitrile group; a nitro group; a substituted or unsubstituted ester group; a substituted or unsubstituted amide group; a substituted or unsubstituted alkyl group; a substituted or unsubstituted cycloalkyl group; a substituted or unsubstituted aryl group; a substituted or unsubstituted aryloxy group; a substituted or unsubstituted arylthio group; or a substituted or unsubstituted heteroaryl group, R9 to R12 are the same as or different from each other, and each independently hydrogen; a substituted or unsubstituted alkyl group; a substituted or unsubstituted cycloalkyl group; or -L-R, L1, L2 and L are the same as or different from each other, and each independently O or S, R is a substituted or unsubstituted alkyl group; a substituted or unsubstituted aryl group; or a substituted or unsubstituted heteroaryl group, R13 and R14 are the same as or different from each other, and each independently a substituted or unsubstituted aryl group; or a substituted or unsubstituted heteroaryl group, and X is Zn, Co, Ni or Pd.

Compounds for an optical film having a BODIPY structure provide excellent optical properties, however, existing compounds have limits in commercialization due to insufficient light resistance and heat resistance. In view of the above, the inventors of the present disclosure introduce the compound represented by Chemical Formula 1 to an optical film to enhance light resistance and heat resistance. Specifically, the compound represented by Chemical Formula 1 includes an electron withdrawing group as a substituent, which is advantageous in terms of light resistance and heat resistance, and, by including O or S at positions of L1 and L2, has advantages of readily synthesizing compounds with a short wavelength while maintaining high reliability of BODIPY metal complex compounds. Accordingly, an optical film having excellent optical properties and excellent reliability may be provided when using the compound represented by Chemical Formula 1.

In addition, when R9 to R12 are -L-R, O or S is included, and therefore, an effect of protecting a BODIPY metal complex core by a steric effect and an effect of more stabilizing the BODIPY metal complex core itself electronically are obtained, which is more advantageous in terms of heat resistance and light resistance compared to when R9 to R12 do not include O or S.

In the present specification, one member being placed "on" another member includes not only a case of the one member being in contact with the another member but a case of still another member being present between the two members.

In the present specification, a certain part "including" certain constituents means capable of further including other constituents, and does not exclude other constituents unless particularly stated on the contrary.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of deuterium; a halogen group; a hydroxyl group; oxygen (=O); an amine group; a nitro group; a nitrile group; a silyl group; an alkyl group; a cycloalkyl group; a haloalkyl group; an alkoxy group; an aryloxy group; an alkenyl group; an aryl group; an alkoxyaryl group; and a heteroaryl group, or being substituted with a substituent linking two or more substituents among the substituents illustrated above, or having no substituents.

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylhexyl, 4-methylhexyl, 5-methylhexyl and the like, but are not limited thereto.

In the present specification, the amine group may be selected from the group consisting of —NH$_2$; a monoalkylamine group; a dialkylamine group; an N-alkylamine group; a monoarylamine group; a diarylamine group; an N-arylheteroarylamine group; an N-alkylheteroarylamine group, a monoheteroarylamine group and a diheteroarylamine group, and, although not particularly limited thereto, the number of carbon atoms is preferably from 1 to 30.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the halogen group is fluorine, chlorine, bromine or iodine.

In the present specification, the haloalkyl group represents an alkyl group in which hydrogen atoms of the alkyl group are replaced by the same or a different halogen group. The haloalkyl group may be linear or branched, and although not particularly limited thereto, the number of carbon atoms is preferably from 1 to 10. Specific examples thereof may include —CH$_2$Cl, —CF$_3$, —CH$_2$CF$_3$, —CF$_2$CF$_3$ and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

In the present specification, the alkenyl group may be linear or branched, and although not particularly limited thereto, the number of carbon atoms is preferably from 2 to 30. In the present specification, the alkynyl group may be linear or branched, and although not particularly limited thereto, the number of carbon atoms is preferably from 2 to 30. Specific examples thereof may include alkynyl groups such as ethynyl, propynyl, 2-methyl-2-propynyl, 2-butynyl or 2-pentynyl, and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a triphenylene group, a pyrenyl group, a perylenyl group, a chrysenyl group, a fluorenyl group and the like, but are not limited thereto.

In the present specification, the alkoxyaryl group means an aryl group substituted with an alkoxy group, and the descriptions provided above are applied to the alkoxy group and the aryl group.

In the present specification, the aryl group in the aryloxy group and the arylthio group is the same as the examples of the aryl group described above. Specific examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and examples of the arylthio group may include a phenylthio group, a 2-methylphenylthio group, a 4-tert-butylphenylthio group and the like, however, the aryloxy group and the arylthiol group are not limited thereto.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or polycyclic. Examples of the heteroaryl group may include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a phenothiazinyl group, a dibenzofuranyl group and the like, but are not limited thereto.

In one embodiment of the present specification, the aldehyde group may be represented by —CHO, the nitro group may be represented by —NO$_2$, the ester group may be represented by —COOR, and the amide group may be represented by —(C=O)NR'R". R, R' and R" are the same as or different from each other and each independently a substituted or unsubstituted alkyl group; a substituted or unsubstituted aryl group; or a substituted or unsubstituted heteroaryl group, and R' and R" may bond to each other to form a ring.

In one embodiment of the present specification, the coumarin group and the chromone group are respectively represented by

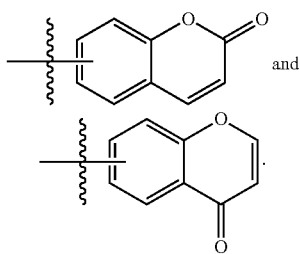

and

In the present specification, the "full width at half maximum" means, in a maximum absorption peak of light absorbing from an external light source, a width of the absorption peak at half the maximum height, and is measured in a film state. In other words, the full width at half maximum is measured by irradiating light in a state of preparing a target compound in a film form either alone or after mixing with other components that do not affect the measuring of the full width at half maximum instead of in a solution state.

In one embodiment of the present specification, R1 to R8 are the same as or different from each other, and each independently hydrogen; a halogen group; a nitrile group; a nitro group; —CHO; —COOR; —(C=O)NR'R"; a linear or branched alkyl group; a fluoroalkyl group; a cycloalkyl group unsubstituted or substituted with an alkyl group; an aryl group unsubstituted or substituted with one or more substituents selected from among a nitrile group, a halogen group, an alkyl group and a fluoroalkyl group; a polycyclic heteroaryl group; an aryloxy group unsubstituted or substituted with one or more substituents selected from among a halogen group and an alkyl group; or an arylthio group unsubstituted or substituted with one or more substituents selected from among a halogen group and an alkyl group, and R, R' and R" are the same as or different from each other and each independently a substituted or unsubstituted alkyl group; a substituted or unsubstituted aryl group; or a substituted or unsubstituted heteroaryl group, and R' and R" may bond to each other to form a ring.

In one embodiment of the present specification, R1 to R8 are each hydrogen; a halogen group; a nitrile group; a nitro group; —CHO; —COOR; —(C=O)NR'R"; a $C_1$-$C_{10}$ alkyl group; a $C_1$-$C_{10}$ fluoroalkyl group; a $C_3$-$C_{12}$ cycloalkyl group; a $C_5$-$C_{15}$ alkylcycloalkyl group; an aryl group unsubstituted or substituted with one or more substituents selected from among a nitrile group, a halogen group, a $C_1$-$C_{10}$ alkyl group and a fluoroalkyl group; a $C_6$-$C_{10}$ aryloxy group unsubstituted or substituted with one or more substituents selected from among an alkyl group and a halogen group; a $C_6$-$C_{10}$ arylthio group unsubstituted or substituted with one or more substituents selected from among an alkyl group and a halogen group; or an O-including heteroaryl group, R, R' and R" are each a $C_1$-$C_{10}$ alkyl group; a $C_2$-$C_{10}$ alkoxyalkyl group; a $C_5$-$C_{15}$ alkylaryl group; a $C_5$-$C_{15}$ nitroaryl group; a $C_5$-$C_{15}$ arylalkyl group unsubstituted or substituted with NO$_2$; or an O-including heteroaryl group unsubstituted or substituted with =O, and R' and R" may bond to each other to form an O-including hydrocarbon ring.

In one embodiment of the present specification, R1 to R8 are each hydrogen; fluorine; chlorine; bromine; —CN; —NO$_2$; —CHO; —COOR; —(C=O)NR'R"; a $C_1$-$C_5$ alkyl group; a $C_1$-$C_5$ fluoroalkyl group; a $C_3$-$C_8$ cycloalkyl group; a $C_5$-$C_{10}$ alkylcycloalkyl group; a phenyl group unsubstituted or substituted with one or more substituents selected from among —CN, fluorine, a $C_1$-$C_5$ alkyl group and a trifluoroalkyl group; a phenoxy group unsubstituted or substituted with one or more substituents selected from among a $C_1$-$C_5$ alkyl group, fluorine, chlorine and bromine; a phenylthio group unsubstituted or substituted with one or more substituents selected from among a $C_1$-$C_5$ alkyl group, fluorine, chlorine and bromine; or an O-including polycyclic heteroaryl group, R, R' and R" are each a $C_1$-$C_5$ alkyl group; a $C_2$-$C_5$ alkoxyalkyl group; a $C_8$-$C_{12}$ alkylaryl group; a $C_8$-$C_{12}$ nitroaryl group; a benzyl group unsubstituted or substituted with NO$_2$; or a benzopyranyl group unsubstituted or substituted with =O, and when R' and R" are each a $C_1$-$C_5$ alkyl group and a $C_2$-$C_5$ alkoxyalkyl group, R' and R" may bond to each other to form an O-including hydrocarbon ring.

In one embodiment of the present specification, R1 to R8 are each hydrogen; fluorine; chlorine; bromine; —CN; —NO$_2$; —CHO; —COOR; —(C=O)NR'R"; a methyl group; an ethyl group; a propyl group; a t-butyl group; —CF$_3$; a cyclopropyl group; a cyclobutyl group; a cyclopentyl group; a cyclohexyl group; a methylcyclohexyl group; a propylcyclohexyl group; a phenyl group unsubstituted or substituted with —CN, fluorine, a methyl group, an ethyl group, a propyl group, a t-butyl group or —CF$_3$; a phenoxy group substituted with a t-butyl group or fluorine; a phenylthio group substituted with chlorine; or a dibenzofuranyl group, R, R' and R" are each a methyl group; an ethyl group; a methoxyethyl group; a t-butylphenyl group; a nitrophenyl group; a nitrobenzyl group; or a coumarin group, and by R' and R" bonding to each other to form an O-including hydrocarbon ring, NR'R" may become a morpholinyl group.
In one embodiment of the present specification, Chemical Formula 1 is any one of the following Chemical Formulae 1-1 to 1-16.
[Chemical Formula 1-1]
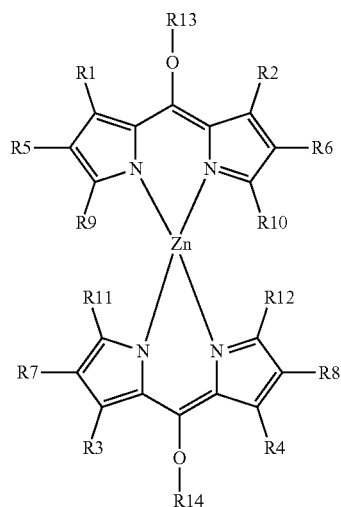
[Chemical Formula 1-2]
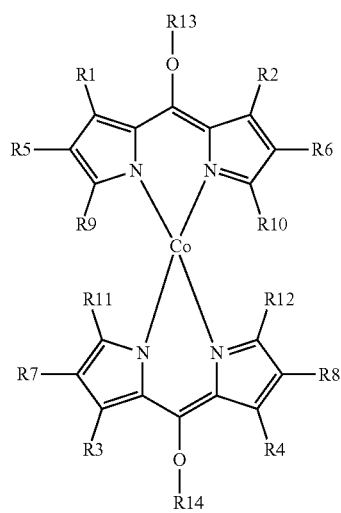
[Chemical Formula 1-3]
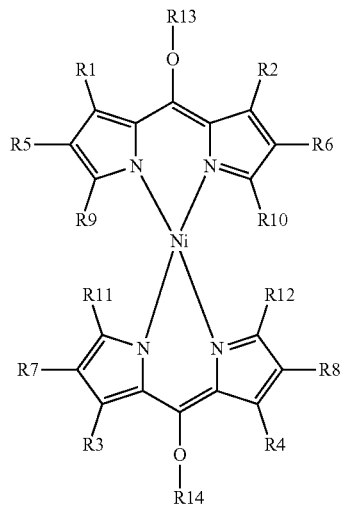
[Chemical Formula 1-4]
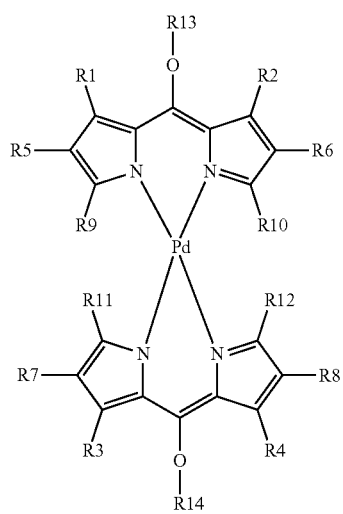
[Chemical Formula 1-5]
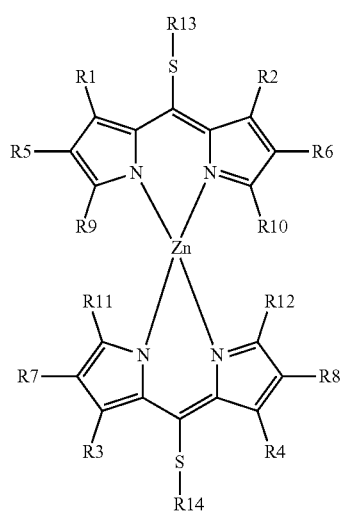

[Chemical Formula 1-6]
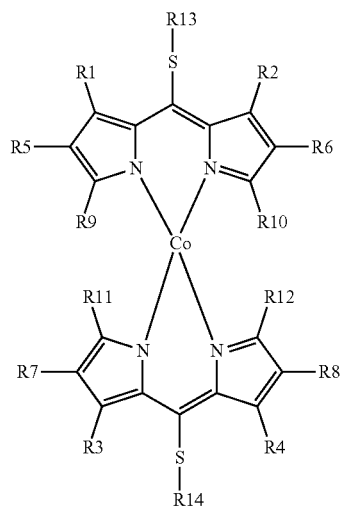
[Chemical Formula 1-7]
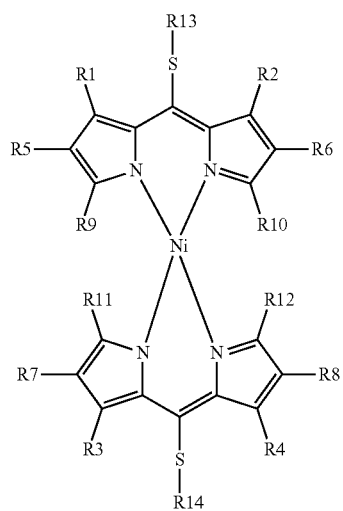
[Chemical Formula 1-8]
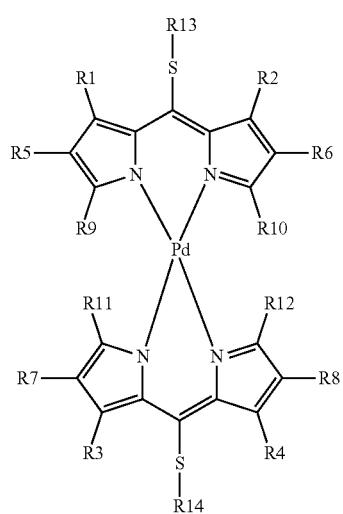
[Chemical Formula 1-9]
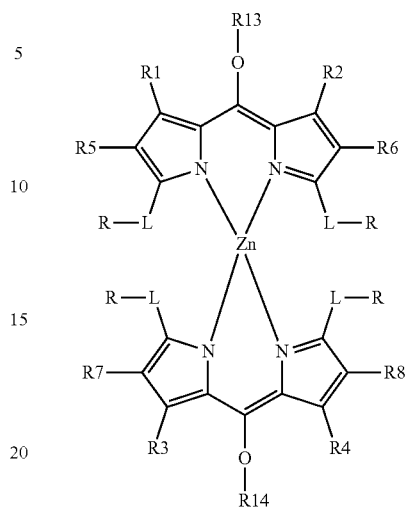
[Chemical Formula 1-10]
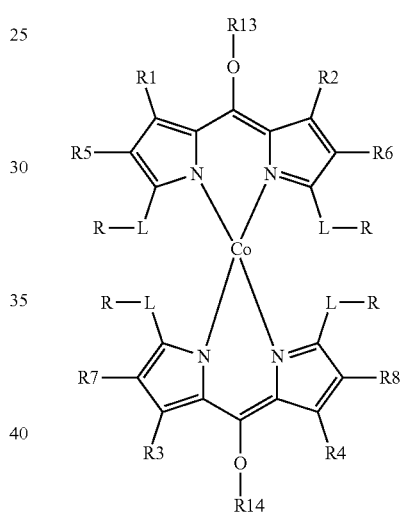
[Chemical Formula 1-11]
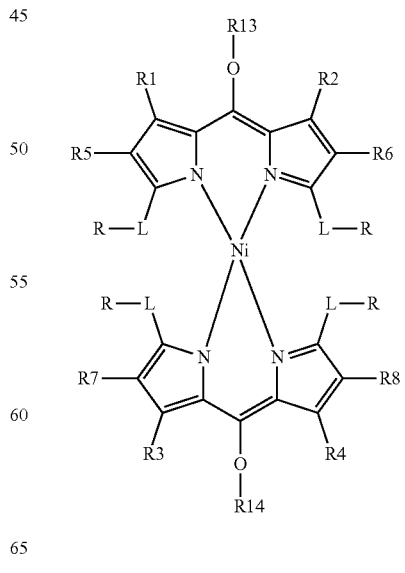

[Chemical Formula 1-12]

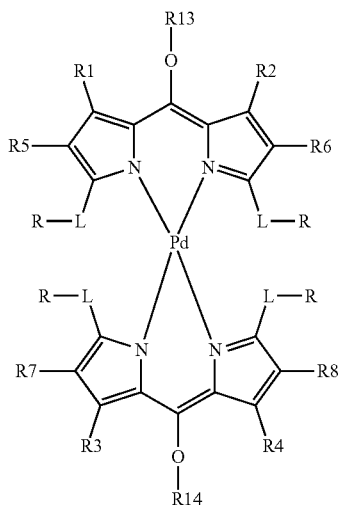

[Chemical Formula 1-13]

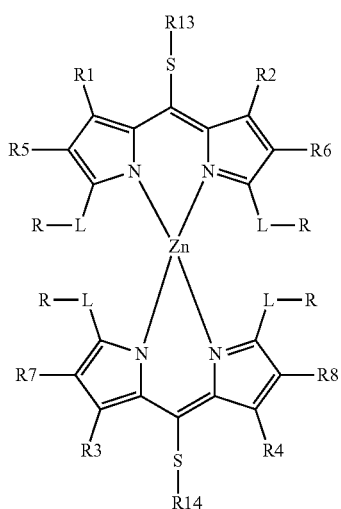

[Chemical Formula 1-14]

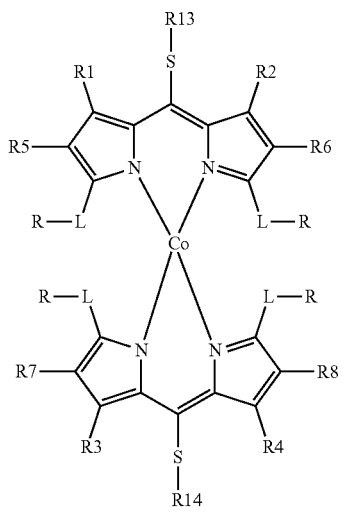

[Chemical Formula 1-15]

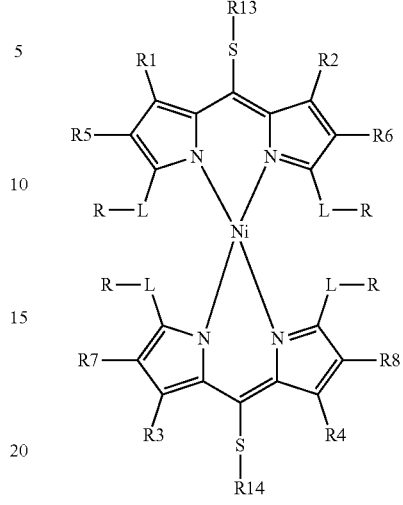

[Chemical Formula 1-16]

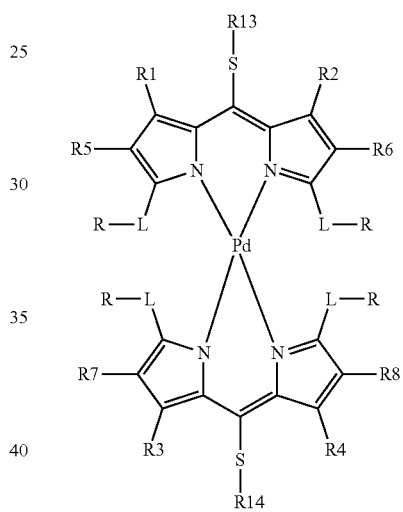

In Chemical Formulae 1-1 to 1-16,
R1 to R14, L and R have the same definitions as in Chemical Formula 1.

In one embodiment of the present specification, R9 to R12 are the same as or different from each other, and each independently hydrogen; a linear or branched alkyl group; or a cycloalkyl group unsubstituted or substituted with an alkyl group.

In one embodiment of the present specification, R9 to R12 are each hydrogen.

In one embodiment of the present specification, R9 to R12 are each a $C_1$-$C_{10}$ alkyl group.

In one embodiment of the present specification, R9 to R12 are each a $C_1$-$C_{10}$ linear alkyl group.

In one embodiment of the present specification, R9 to R12 are each a $C_1$-$C_5$ alkyl group.

In one embodiment of the present specification, R9 to R12 are each a $C_1$-$C_5$ linear alkyl group.

In one embodiment of the present specification, R9 to R12 are each a $C_1$-$C_3$ alkyl group.

In one embodiment of the present specification, R9 to R12 are each a $C_1$-$C_3$ linear alkyl group.

In one embodiment of the present specification, R9 to R12 are each a methyl group or a propyl group.

In one embodiment of the present specification, R9 to R12 are each a cycloalkyl group unsubstituted or substituted with a $C_1$-$C_{10}$ alkyl group.

In one embodiment of the present specification, R9 to R12 are each a $C_3$-$C_2$ cycloalkyl group.

In one embodiment of the present specification, R9 to R12 are each a $C_3$-$C_8$ cycloalkyl group.

In one embodiment of the present specification, R9 to R12 are each a cyclopropyl group, a cyclobutyl group, a cyclopentyl group or a cyclohexyl group.

In one embodiment of the present specification, R9 to R12 are each a $C_5$-$C_{15}$ alkylcycloalkyl group.

In one embodiment of the present specification, R9 to R12 are each a $C_5$-$C_{10}$ alkylcycloalkyl group.

In one embodiment of the present specification, R9 to R12 are each a methylcyclohexyl group or a propylcyclohexyl group.

In one embodiment of the present specification, R9 to R12 are -L-R.

In one embodiment of the present specification, when L is O, a short wavelength light absorber is readily synthesized.

In one embodiment of the present specification, when L is S, a long wavelength light absorber is readily synthesized, and a compound having a relatively wider full width at half maximum of the corresponding absorption peak may be synthesized.

In one embodiment of the present specification, R is a substituted or unsubstituted alkyl group; an aryl group unsubstituted or substituted with one or more substituents selected from among a nitrile group, a nitro group, a halogen group, an alkyl group and an alkoxy group; or a substituted or unsubstituted heteroaryl group including one or more of N and O.

In one embodiment of the present specification, R is alkyl group unsubstituted or substituted with halogen group.

In one embodiment of the present specification, R is an alkyl group unsubstituted or substituted with fluorine.

In one embodiment of the present specification, R is a hexafluoropropanyl group.

In one embodiment of the present specification, R is a perfluoroalkyl group.

In one embodiment of the present specification, R is a perfluoroethyl group.

In one embodiment of the present specification, R is a phenyl group unsubstituted or substituted with one or more substituents selected from among a nitrile group, a nitro group, a halogen group, a $C_1$-$C_{10}$ alkyl group, a $C_1$-$C_{10}$ fluoroalkyl group and a $C_1$-$C_{10}$ alkoxy group.

In one embodiment of the present specification, R is a phenyl group unsubstituted or substituted with one or more substituents selected from among —CN, —$NO_2$, fluorine, chlorine, a methyl group, a t-butyl group, —$CF_3$ and a methoxy group.

In one embodiment of the present specification, R is an N- or O-including heteroaryl group unsubstituted or substituted with =O.

In one embodiment of the present specification, R is an N-including monocyclic or polycyclic heteroaryl group; an O-including monocyclic or polycyclic heteroaryl group unsubstituted or substituted with =O.

In one embodiment of the present specification, R is an N-including monocyclic heteroaryl group; an O-including polycyclic heteroaryl group; or a benzopyranyl group unsubstituted or substituted with =O.

In one embodiment of the present specification, R is a pyridinyl group, a dibenzofuranyl group, a coumarin group or a chromone group.

In one embodiment of the present specification, R13 and R14 are the same as or different from each other, and each independently an aryl group unsubstituted or substituted with one or more substituents selected from among an alkyl group, a fluoroalkyl group, a halogen group, a nitrile group, an alkoxy group, an alkoxyaryl group and an aryl group; a heteroaryl group unsubstituted or substituted with an alkyl group or =O; or a substituted or unsubstituted heteroaryl group including one or more of N and O.

In one embodiment of the present specification, R13 and R14 are each an aryl group unsubstituted or substituted with one or more substituents selected from among a methyl group, an ethyl group, a propyl group, a t-butyl group, fluorine, a trifluoromethyl group, a nitrile group, a methoxy group and a phenyl group; or a heteroaryl group unsubstituted or substituted with a methyl group or =O.

In one embodiment of the present specification, R13 and R14 are each a phenyl group unsubstituted or substituted with one or more substituents selected from among a methyl group, an ethyl group, a propyl group, a t-butyl group, fluorine, a trifluoromethyl group, a nitrile group, a methoxy group and a phenyl group; a dibenzofuranyl group; a pyridine group unsubstituted or substituted with a methyl group; or a benzopyranyl group unsubstituted or substituted with =O.

In one embodiment of the present specification, examples of the benzopyranyl group substituted with =O may include a coumarin group, a chromone group and the like.

In one embodiment of the present specification, R13 and R14 are each a phenyl group unsubstituted or substituted with one or more substituents selected from among a nitrile group, a halogen group, a $C_1$-$C_{10}$ alkyl group, a $C_1$-$C_{10}$ alkoxy group, a $C_5$-$C_{10}$ aryl group and a $C_7$-$C_{15}$ alkoxyaryl group.

In one embodiment of the present specification, R13 and R14 are each a phenyl group unsubstituted or substituted with one or more substituents selected from among —CN, chlorine, fluorine, a methyl group, an ethyl group, a propyl group, a t-butyl group, a methoxy group, a phenyl group and a methoxyphenyl group.

In one embodiment of the present specification, R13 and R14 are each a naphthyl group.

In one embodiment of the present specification, R13 and R14 are each an N- or O-including heteroaryl group unsubstituted or substituted with =O.

In one embodiment of the present specification, R13 and R14 are each an N-including polycyclic heteroaryl group; or a benzopyranyl group unsubstituted or substituted with =O.

In one embodiment of the present specification, R13 and R14 are each a carbazole group, a coumarin group or a chromone group.

In one embodiment of the present specification, the compound represented by Chemical Formula 1 is represented by any one of the following structures.

17
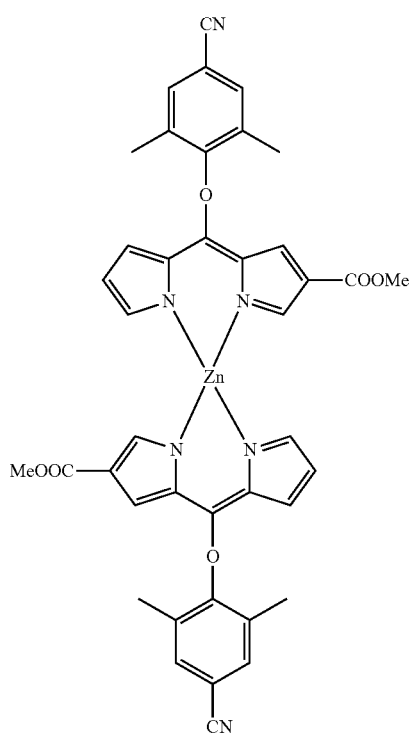
18
-continued
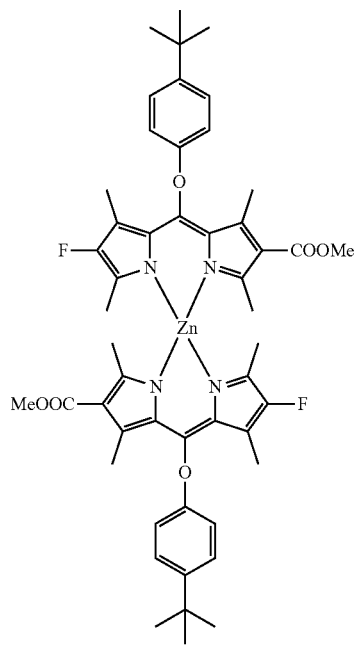
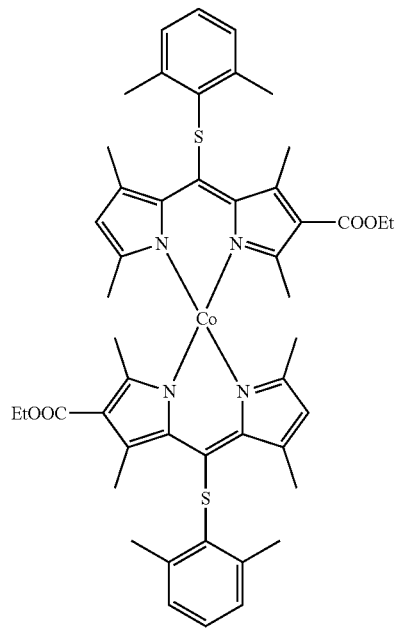
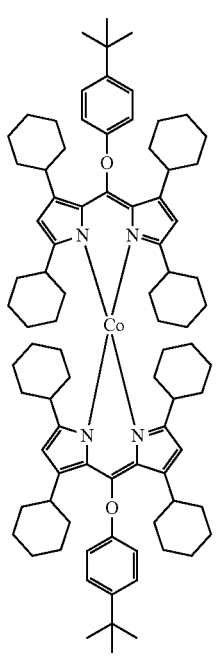

-continued
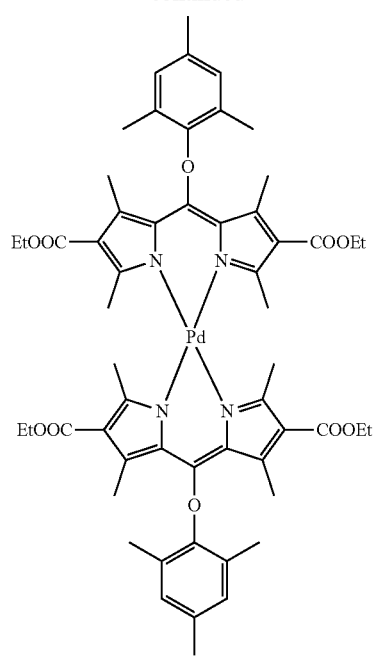
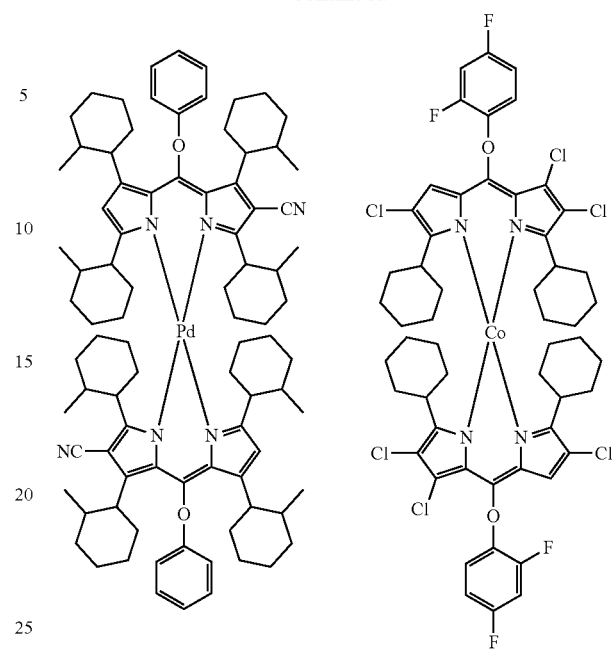
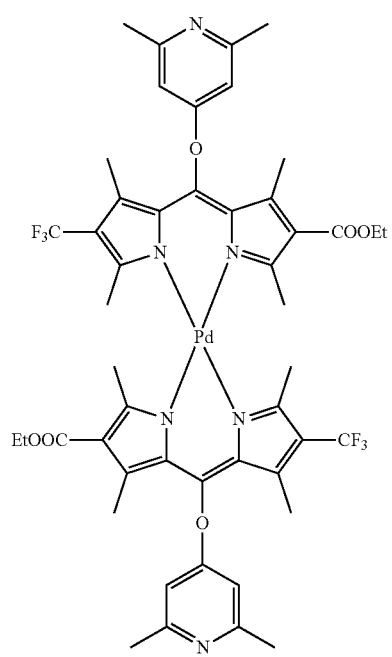
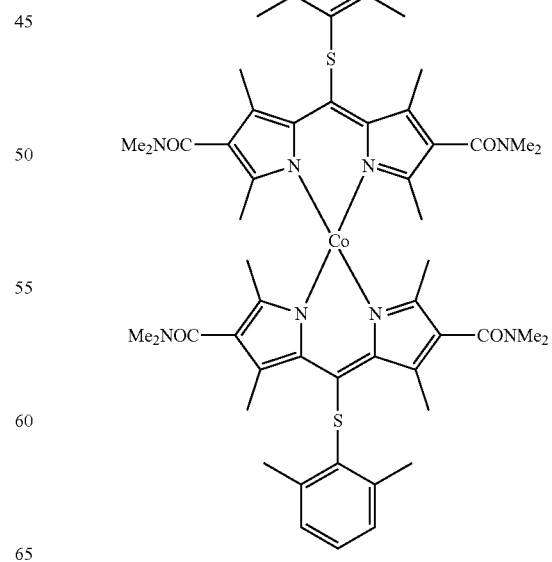

-continued
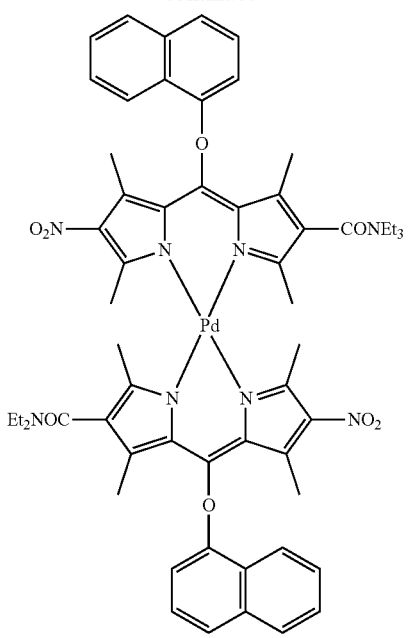
-continued
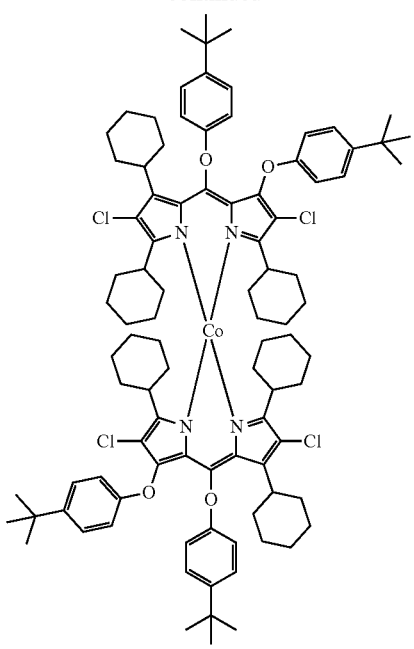
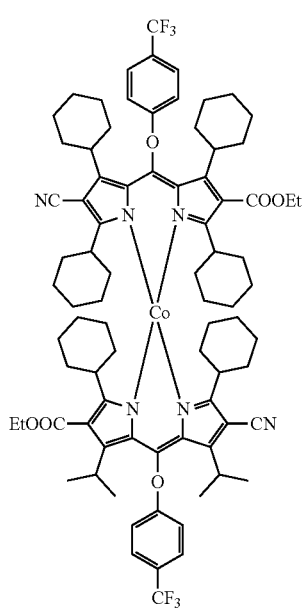
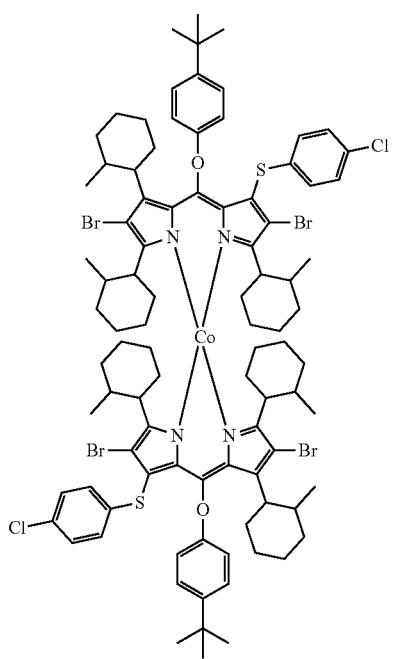

-continued
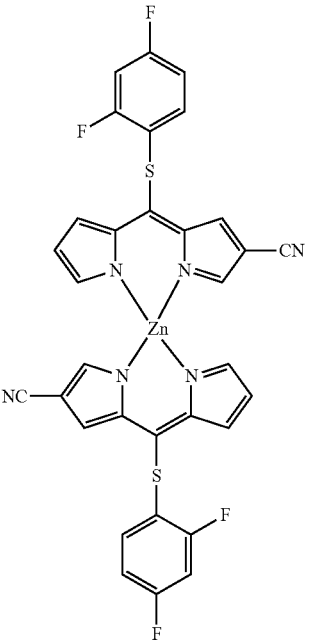
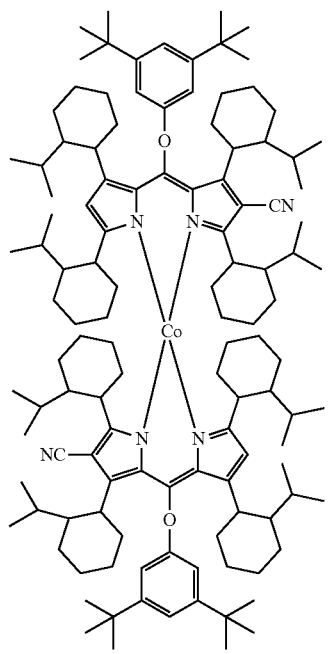
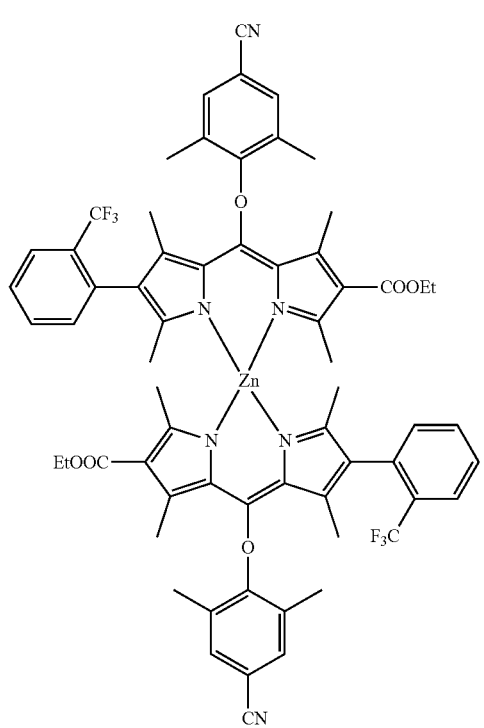
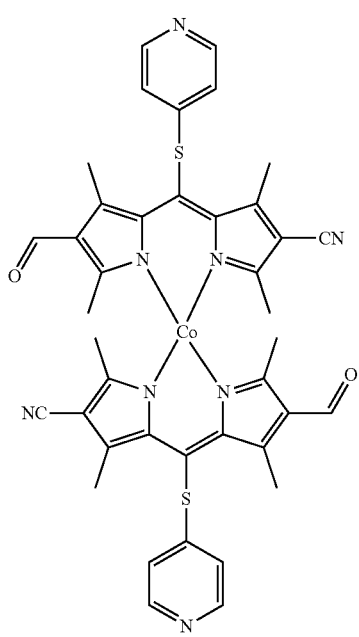

25
-continued
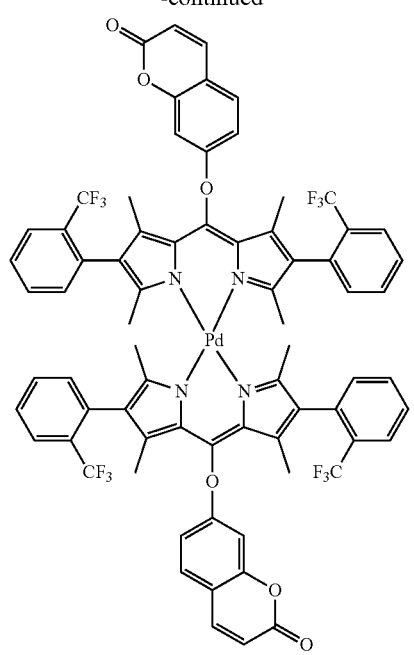
26
-continued
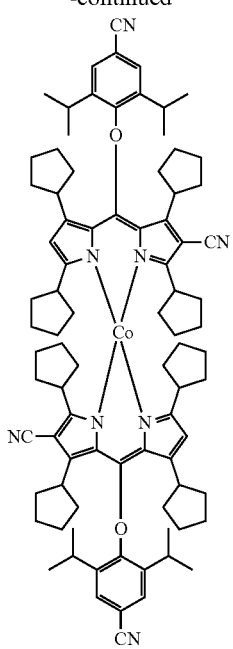
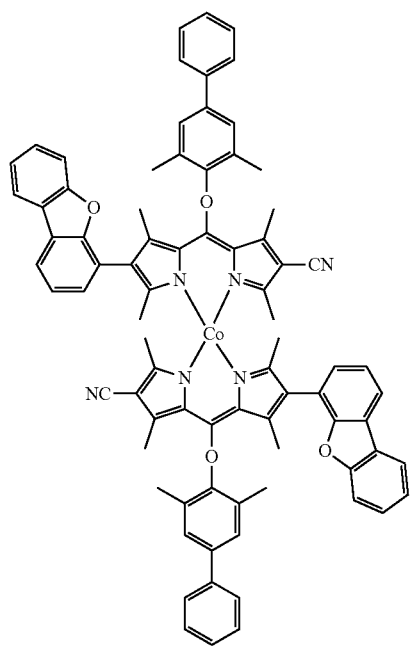
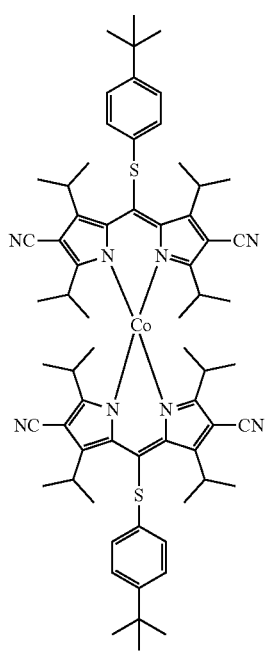

-continued
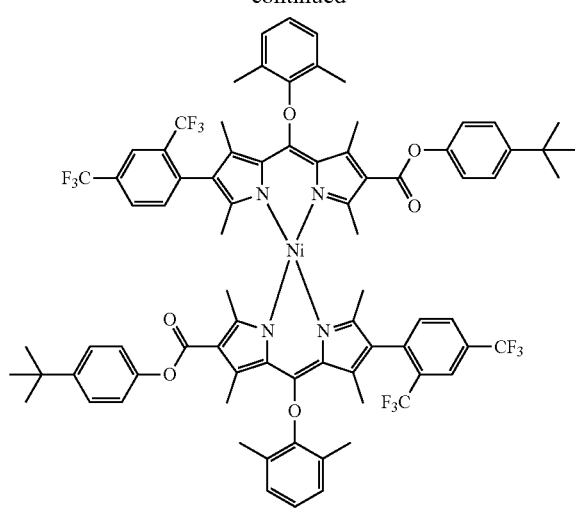
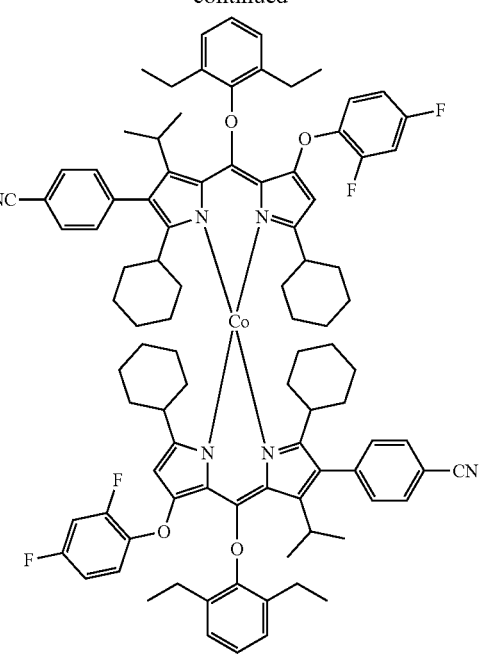
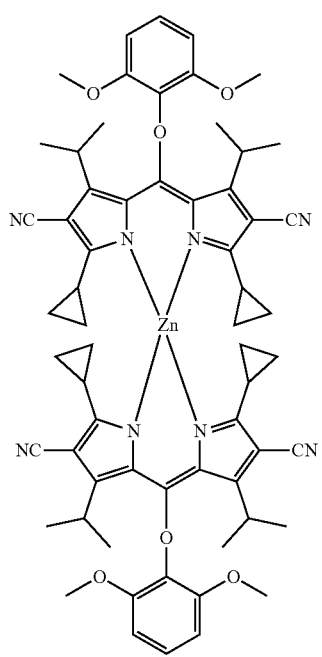
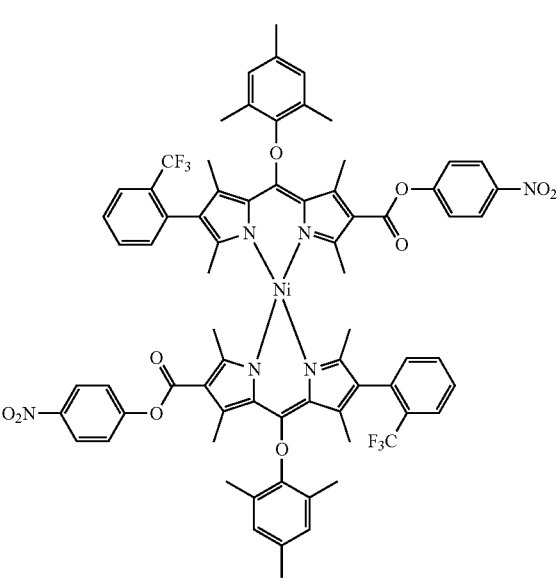

29
-continued
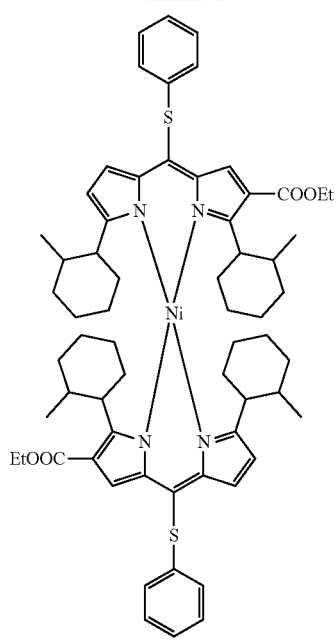
30
-continued
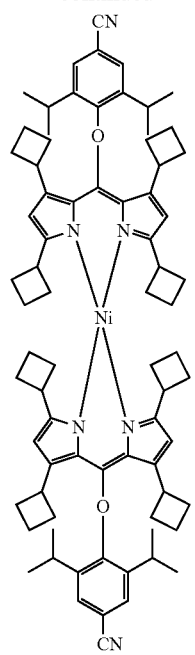
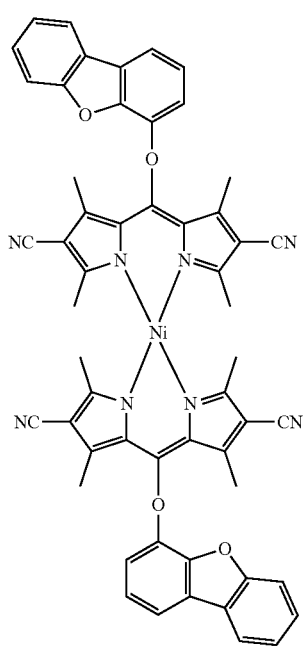
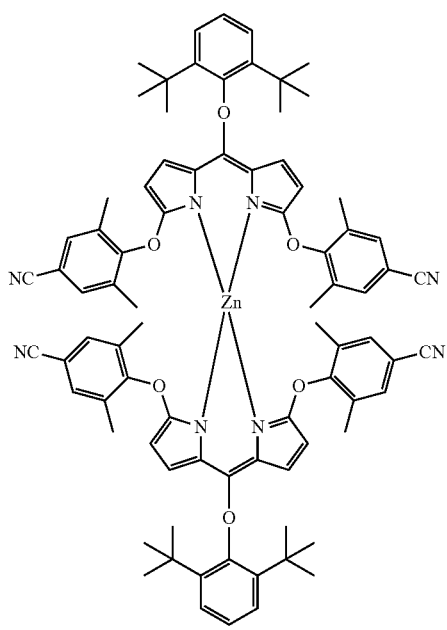

31
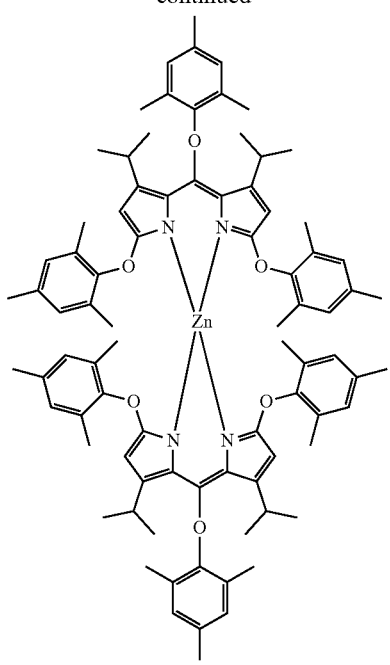
32
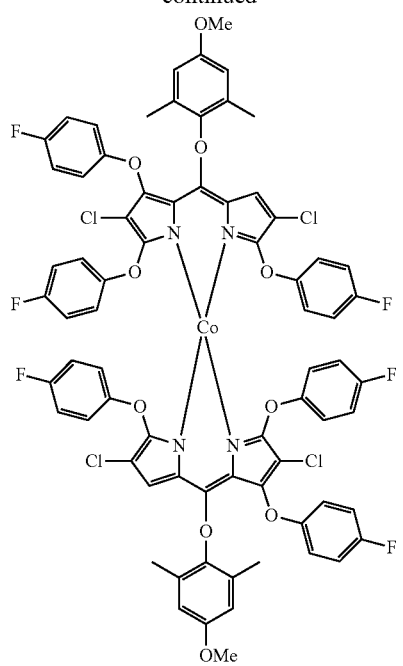
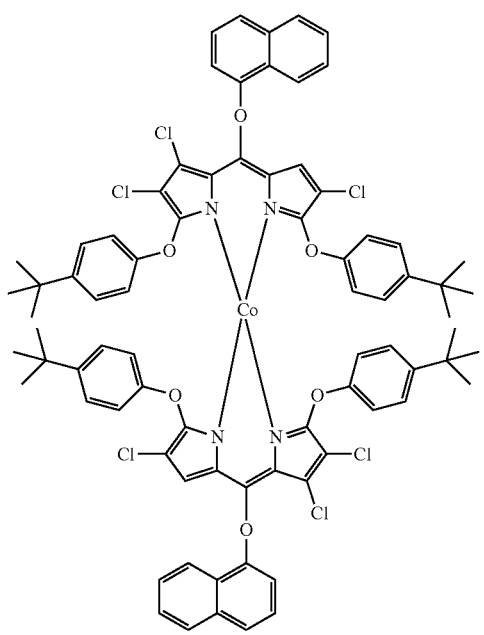
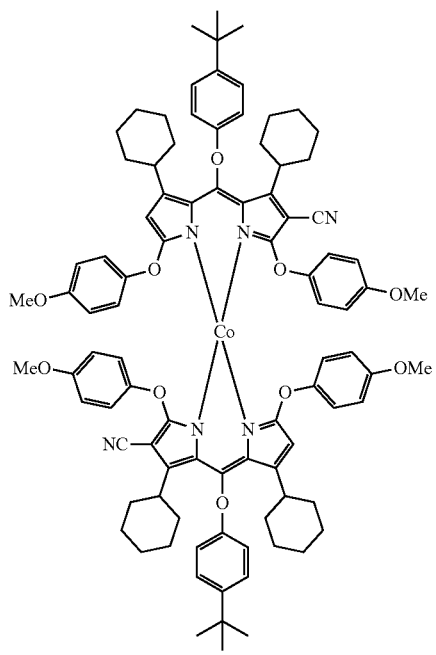

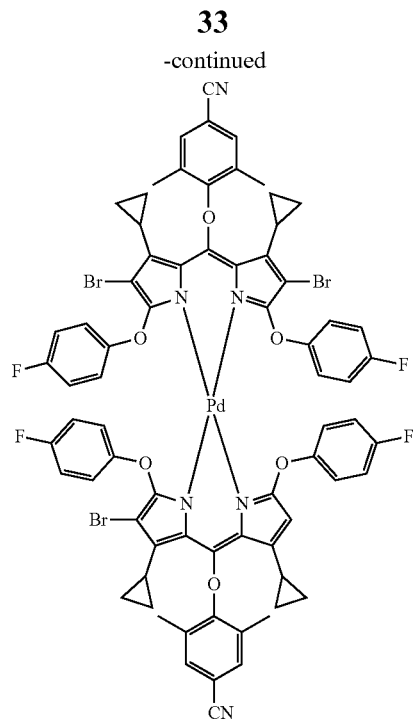
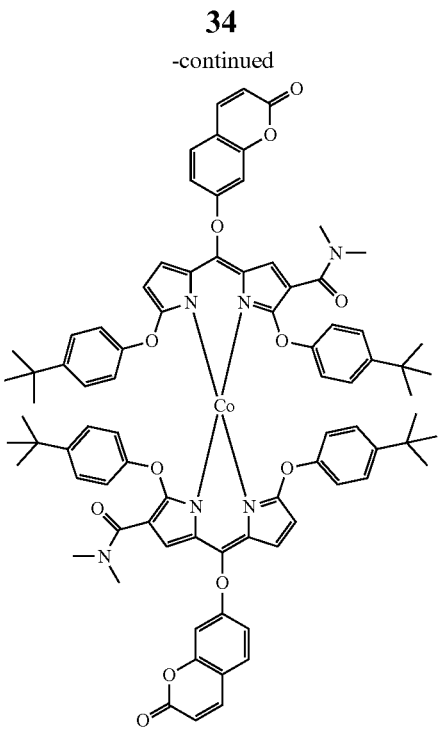
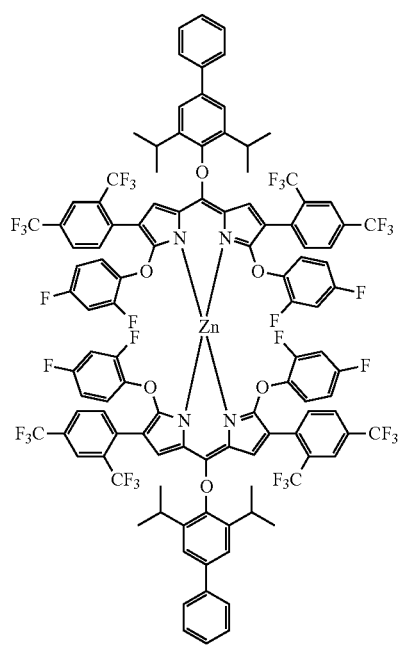
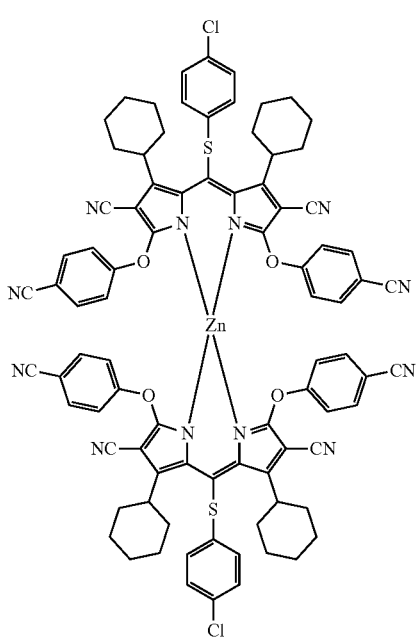

35
-continued
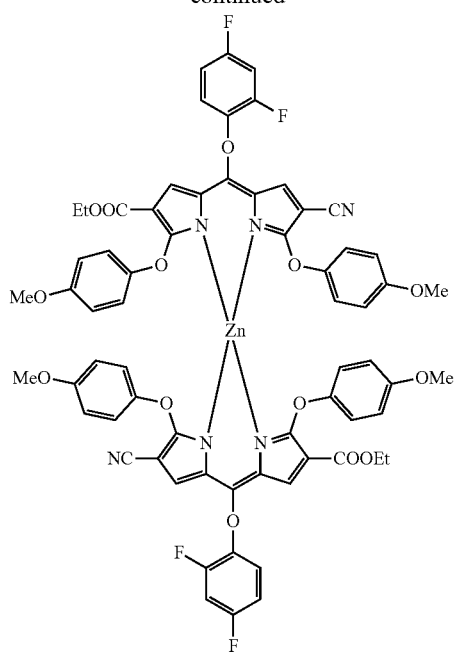
36
-continued
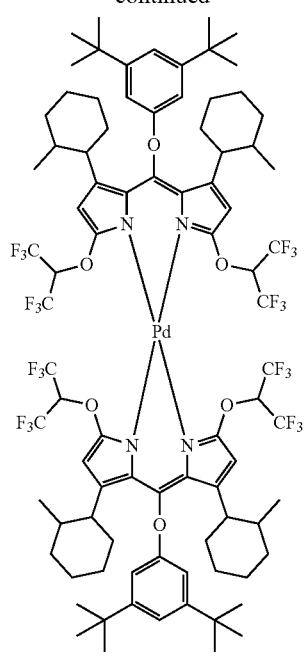
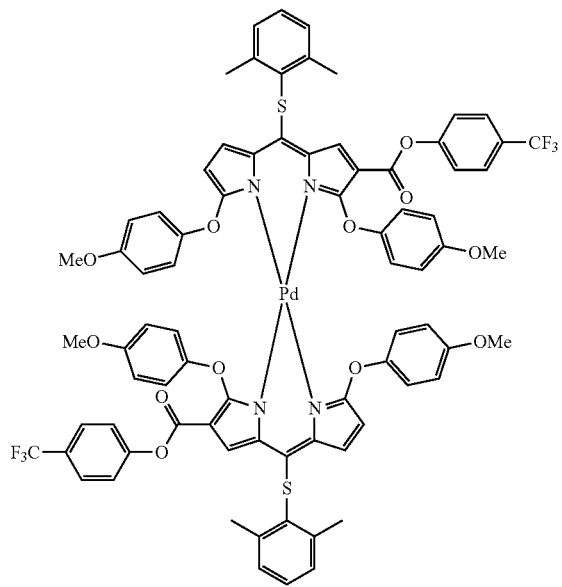
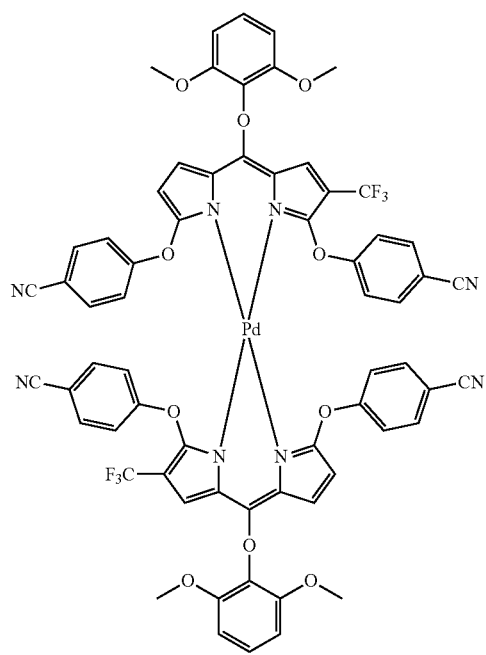

-continued
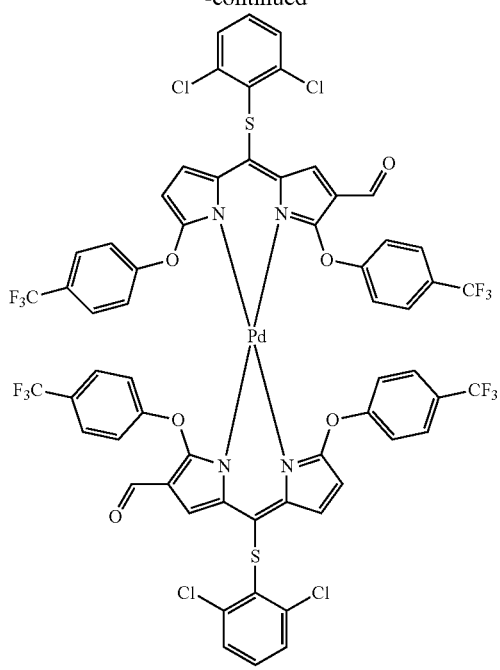
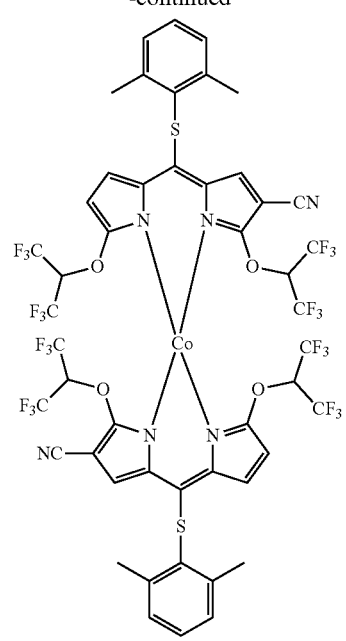
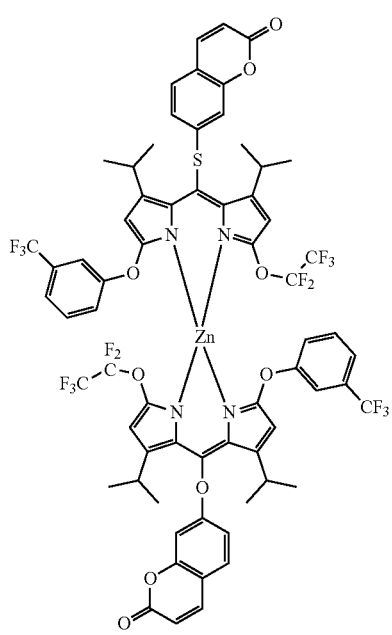
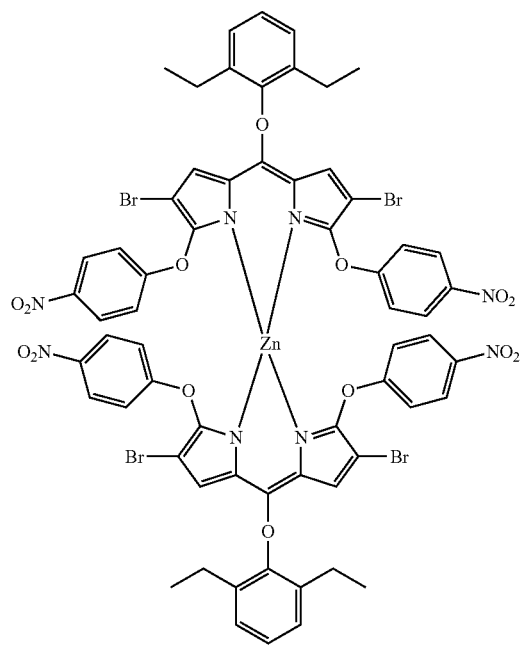

39
-continued
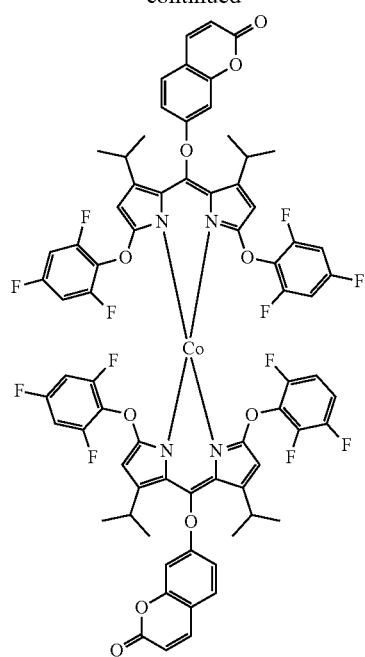
40
-continued
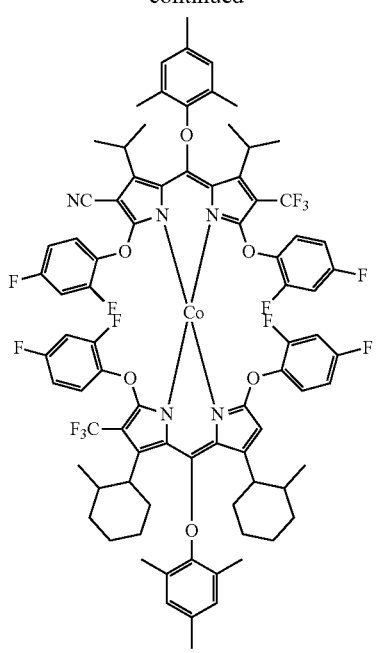
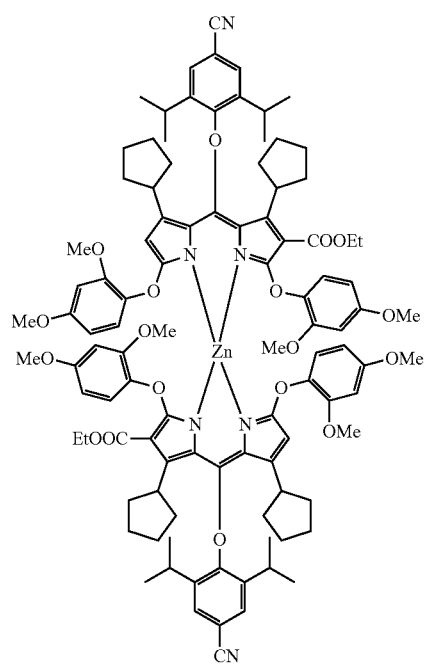
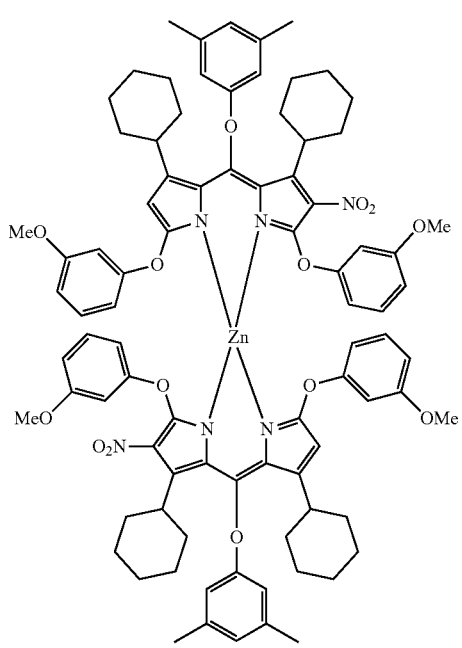

-continued
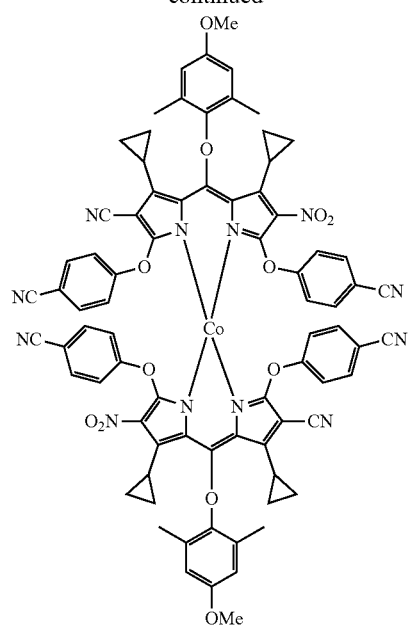
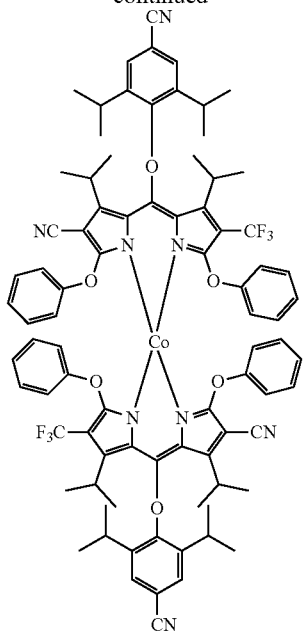
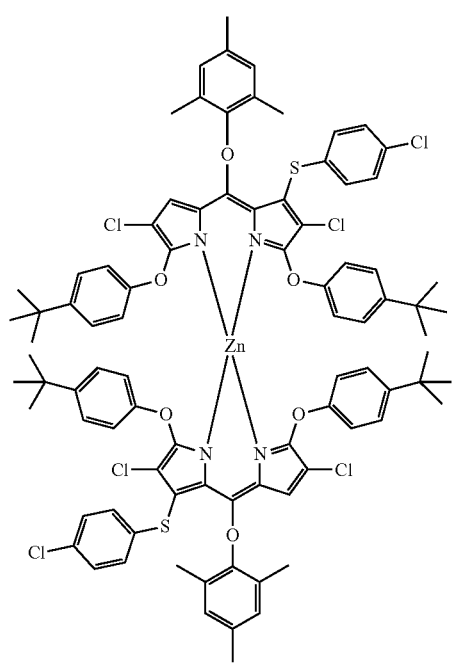
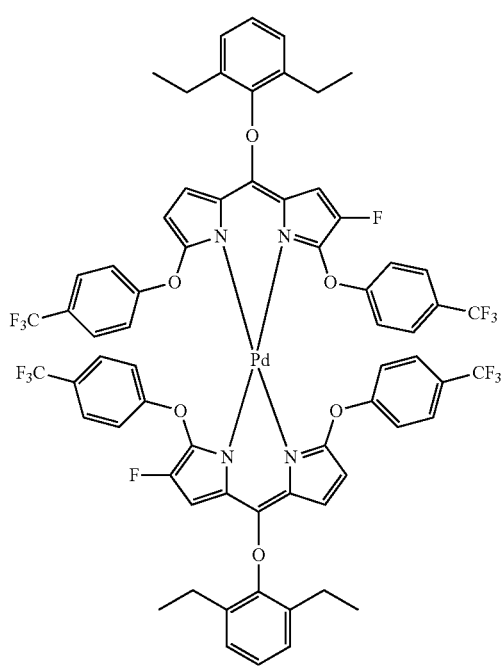

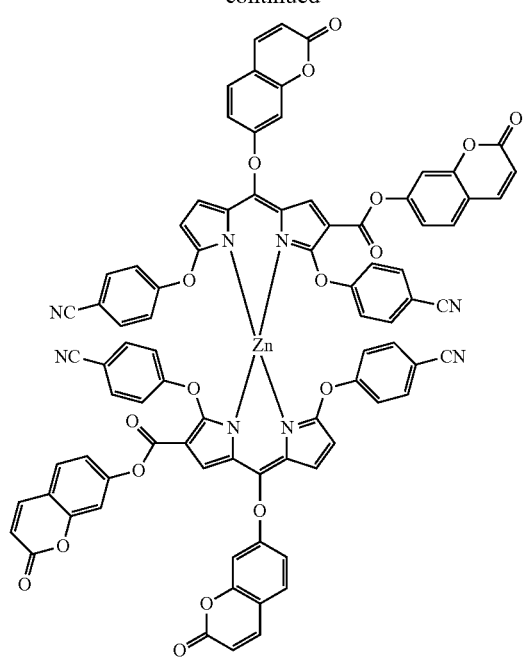
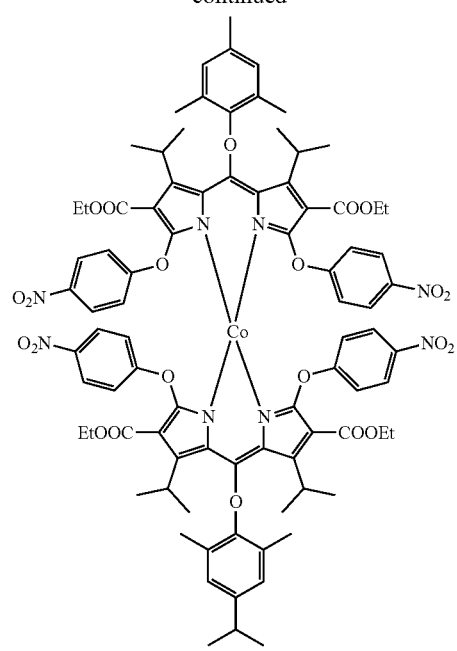
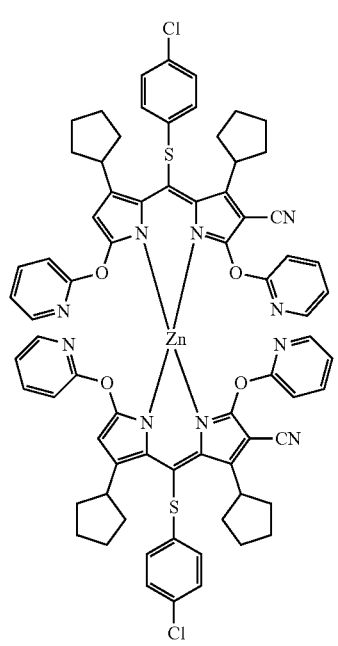
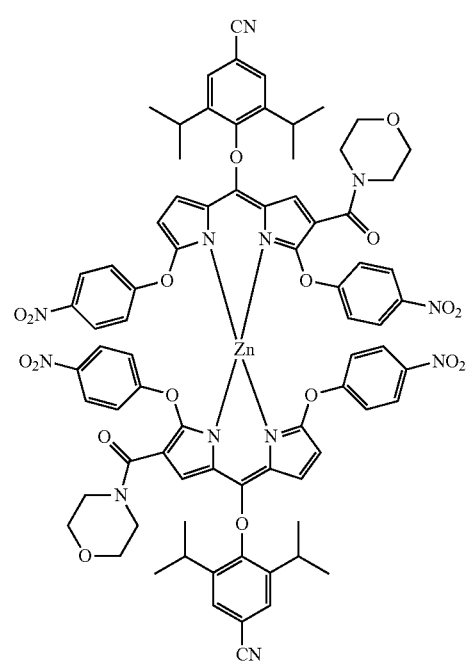

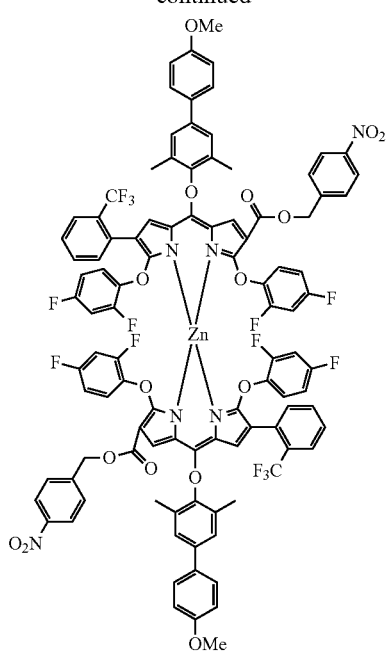
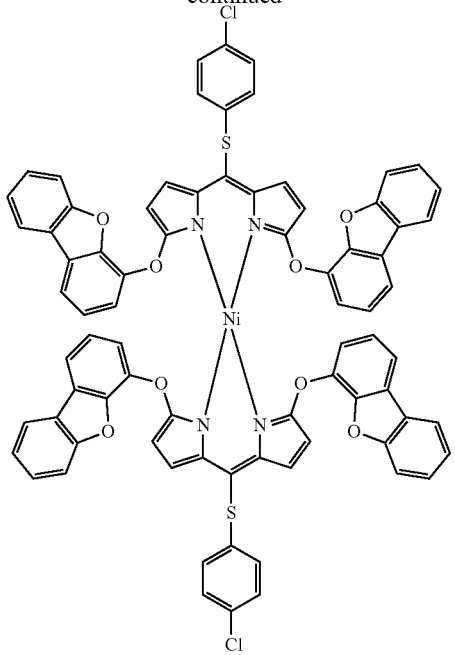
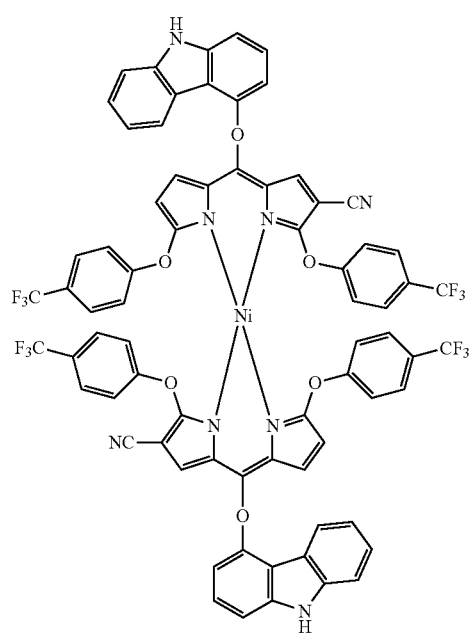
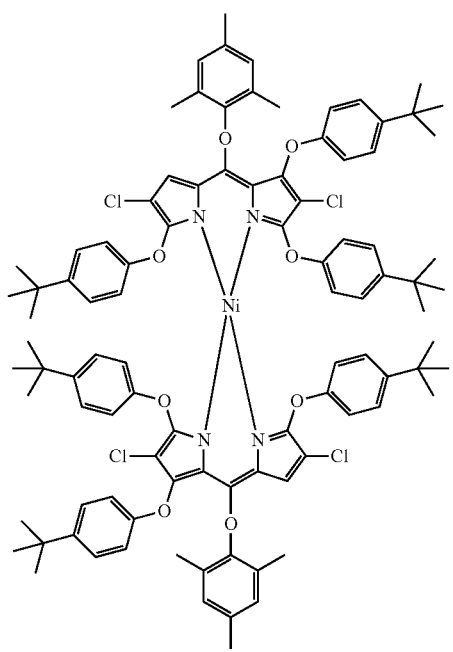

47
-continued
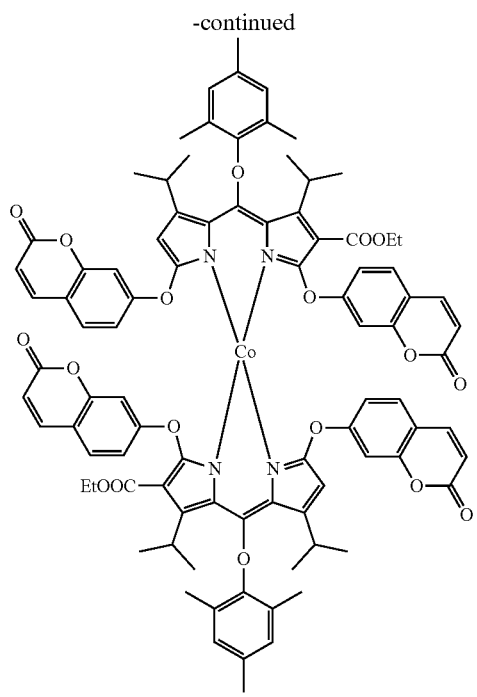
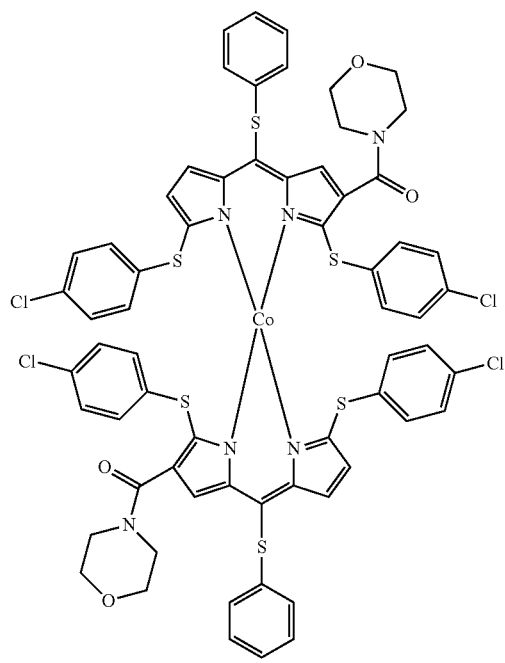
48
-continued
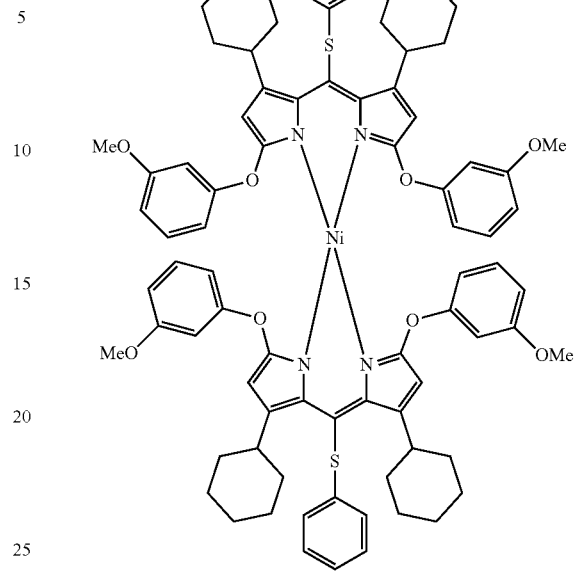
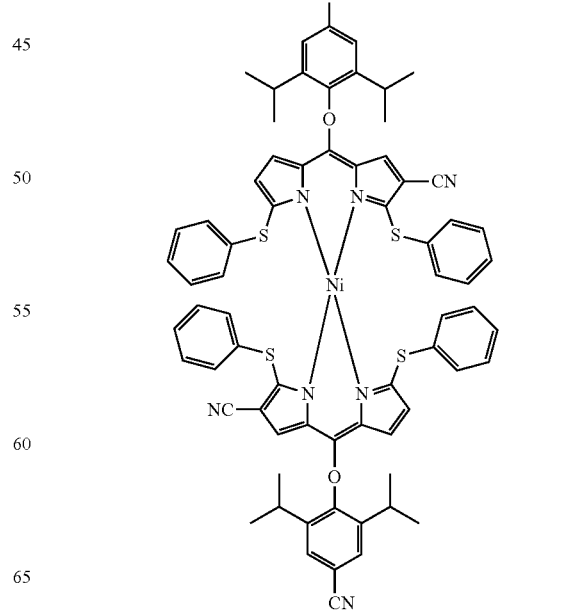

-continued

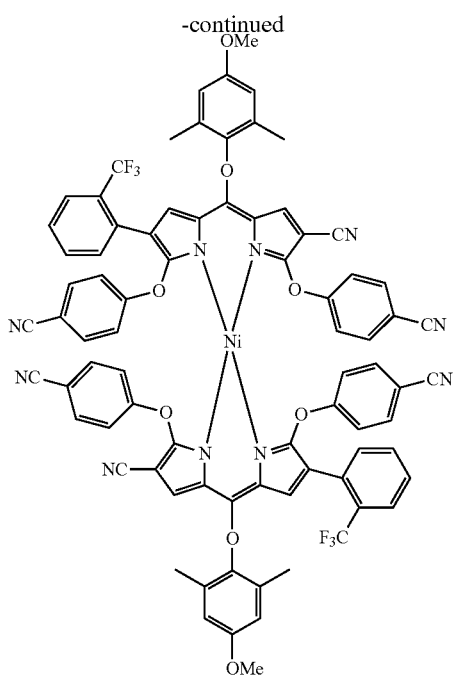

In the structures, Me means a methyl group, and Et means an ethyl group.

One embodiment of the present specification provides a composition for forming an optical film, the composition including a binder resin; and the compound described above. Specifically, the composition for forming an optical film is a composition for forming a color conversion film or a composition for forming an adhesive film.

In one embodiment of the present specification, a content of the compound represented by Chemical Formula 1 is from 0.001 wt % to 10 wt % with respect to 100 wt % of the binder resin. When the compound represented by Chemical Formula 1 is included in the above-mentioned range, an advantage of preparing a uniform composition is obtained.

In one embodiment of the present specification, the binder resin is a copolymer resin of a monomer providing mechanical strength; and a monomer providing alkali solubility.

The monomer providing mechanical strength of the film may be any one or more of unsaturated carboxylic acid esters; aromatic vinyls; unsaturated ethers; unsaturated imides; and acid anhydrides.

Specific examples of the unsaturated carboxylic acid ester may include benzyl (meth)acrylate, methyl (meth)acrylate, ethyl (meth)acrylate, butyl (meth)acrylate, dimethylaminoethyl (meth)acrylate, isobutyl (meth)acrylate, t-butyl (meth)acrylate, cyclohexyl (meth)acrylate, isobornyl (meth)acrylate, ethylhexyl (meth)acrylate, 2-phenoxyethyl (meth)acrylate, tetrahydrofurfuryl (meth)acrylate, hydroxyethyl (meth)acrylate, 2-hydroxypropyl (meth)acrylate, 2-hydroxy-3-chloropropyl (meth)acrylate, 4-hydroxybutyl (meth)acrylate, acyloctyloxy-2-hydroxypropyl (meth)acrylate, glycerol (meth)acrylate, 2-methoxyethyl (meth)acrylate, 3-methoxybutyl (meth)acrylate, ethoxy diethylene glycol (meth)acrylate, methoxy triethylene glycol (meth)acrylate, methoxy tripropylene glycol (meth)acrylate, poly(ethylene glycol)methyl ether (meth)acrylate, phenoxy diethylene glycol (meth)acrylate, p-nonylphenoxy polyethylene glycol (meth)acrylate, p-nonylphenoxy polypropylene glycol (meth)acrylate, glycidyl (meth)acrylate, tetrafluoropropyl (meth)acrylate, 1,1,1,3,3,3-hexafluoroisopropyl (meth)acrylate, octafluoropentyl (meth)acrylate, heptadecafluorodecyl (meth)acrylate, tribromophenyl (meth)acrylate, methyl α-hydroxymethyl acrylate, ethyl α-hydroxymethyl acrylate, propyl α-hydroxymethyl acrylate, butyl α-hydroxymethyl acrylate and the like, but are not limited thereto.

Specific examples of the aromatic vinyl may include styrene, α-methylstyrene, (o,m,p)-vinyl toluene, (o,m,p)-methoxystyrene, (o,m,p)-chlorostyrene and the like, but are not limited thereto.

Specific examples of the unsaturated ether may include vinyl methyl ether, vinyl ethyl ether, allyl glycidyl ether and the like, but are not limited thereto.

Specific examples of the unsaturated imide may include N-phenylmaleimide, N-(4-chlorophenyl)maleimide, N-(4-hydroxyphenyl)maleimide, N-cyclohexylmaleimide and the like, but are not limited thereto.

Specific examples of the acid anhydride may include maleic anhydride, methyl maleic anhydride, tetrahydrophthalic anhydride and the like, but are not limited thereto.

The monomer providing alkali solubility may be a monomer containing an acid group. Specific examples of the monomer containing an acid group may include (meth)acrylic acid, crotonic acid, itaconic acid, maleic acid, fumaric acid, monomethyl maleic acid, isoprenesulfonic acid, styrenesulfonic acid, 5-norbornene-2-carboxylic acid and the like, but are not limited thereto.

In one embodiment of the present specification, the binder resin is SAN (styrene-acrylonitrile-based).

In one embodiment of the present specification, the binder resin has a weight average molecular weight of 1,000 g/mol to 200,000 g/mol.

In one embodiment of the present specification, a content of the binder resin may be from 1 wt % to 50 wt % in 100 wt % of the composition for forming an optical film.

In one embodiment of the present specification, the composition for forming an optical film may further include a functional monomer, a photoinitiator and a solvent.

In one embodiment of the present specification, the functional monomer may be a monofunctional monomer or a multifunctional monomer. The monofunctional monomer may be one or more types selected from among polyethylene glycol mono(meth)acrylate, polypropylene glycol mono(meth)acrylate and phenoxyethyl (meth)acrylate, and the multifunctional monomer may be one or more types selected from among polyethylene glycol (meth)acrylate, polypropylene glycol (meth)acrylate, trimethylolethane triacrylate, trimethylolpropane triacrylate, neopentyl glycol (meth)acrylate, pentaerythritol tetraacrylate, pentaerythritol triacrylate, dipentaerythritol pentaacrylate and dipentaerythritol hexaacrylate, however, the monofunctional monomer or the multifunctional monomer are not limited thereto.

In one embodiment of the present specification, a content of the functional monomer may be from 1 wt % to 30 wt % in 100 wt % of the composition for forming an optical film.

In one embodiment of the present specification, the photoinitiator is not particularly limited as long as it is an initiator generating radicals by light to trigger crosslinkage, and examples thereof may include one or more types selected from the group consisting of acetophenone-based compounds, biimidazole-based compounds, triazine-based compounds and oxime-based compounds.

Examples of the acetophenone-based compound may include 2-hydroxy-2-methyl-1-phenylpropan-1-one, 1-(4-isopropylphenyl)-2-hydroxy-2-methylpropan-1-one, 4-(2-hydroxyethoxy)-phenyl-(2-hydroxy-2-propyl)ketone, 1-hydroxycyclohexyl phenyl ketone, benzoin methyl ether, benzoin ethyl ether, benzoin isobutyl ether, benzoin butyl ether, 2,2-dimethoxy-2-phenylacetophenone, 2-methyl-(4-methylthio)phenyl-2-morpholino-1-propan-1-one, 2-benzyl-2-dimethylamino-1-(4-morpholinophenyl)-butan-1-one, 2-(4-bromo-benzyl-2-dimethylamino-1-(4-morpholinophenyl)-butan-1-one, 2-methyl-1-[4-(methylthio)phenyl]-2-morpholinopropan-1-one or the like, but are not limited thereto.

Examples of the biimidazole-based compound may include 2,2-bis(2-chlorophenyl)-4,4',5,5'-tetraphenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetraphenyl biimidazole, 2,2'-bis(o-chlorophenyl)-4,4',5,5'-tetraphenyl-1,2'-biimidazole or the like, but are not limited thereto.

Examples of the triazine-based compound may include 3-{4-[2,4-bis(trichloromethyl)-s-triazin-6-yl]phenylthio}propionic acid, 1,1,1,3,3,3-hexafluoroisopropyl-3-{4-[2,4-bis(trichloromethyl)-s-triazin-6-yl]phenylthio}propionate, ethyl-2-{4-[2,4-bis(trichloromethyl)-s-triazin-6-yl]phenylthio}acetate, 2-epoxyethyl-2-{4-[2,4-bis(trichloromethyl)-s-triazin-6-yl]phenylthio}acetate, cyclohexyl-2-{4-[2,4-bis(trichloromethyl)-s-triazin-6-yl]phenylthio}acetate, benzyl-2-{4-[2,4-bis(trichloromethyl)-s-triazin-6-yl]phenylthio}acetate, 3-{chloro-4-[2,4-bis(trichloromethyl)-s-triazin-6-yl]phenylthio}propionic acid, 3-{4-[2,4-bis(trichloromethyl)-s-triazin-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3-butadienyl-s-triazine, 2-trichloromethyl-4-amino-6-p-methoxystyryl-s-triazine or the like, but are not limited thereto.

Examples of the oxime-based compound may include 1,2-octadiene-1-(4-phenylthio)phenyl-2-(o-benzoyloxime) (Ciba Specialty Chemicals, CGI124), ethanone-1-(9-ethyl)-6-(2-methylbenzoyl-3-yl)-1-(O-acetyloxime) (CGI242), N-1919 (Adeka Corporation) or the like, but are not limited thereto.

A content of the photoinitiator may be from 0.1 wt % to 10 wt % in 100 wt % of the composition for forming an optical film.

In one embodiment of the present specification, as the solvent, one or more types selected from among xylene, methyl ethyl ketone, methyl cellosolve, ethyl cellosolve, propyl cellosolve, ethylene glycol dimethyl ether, ethylene glycol diethyl ether, ethylene glycol methylethyl ether, propylene glycol dimethyl ether, propyl glycol diethyl ether, propylene glycol methylethyl ether, 2-ethoxypropanol, 2-methoxypropanol, 3-methoxybutanol, cyclopentanone, cyclohexanone, propylene glycol methyl ether acetate, propylene glycol ethyl ether acetate, 3-methoxybutyl acetate, ethyl 3-ethoxy propionate, ethyl cellosolve acetate, methyl cellosolve acetate, butyl acetate and dipropylene glycol monomethyl ether may be used, however, the solvent is not limited thereto.

In one embodiment of the present specification, the composition for forming an optical film may further include additives such as a curing agent, a surfactant, an adhesion promoter, an adhesion aid, an ultraviolet absorber, an antioxidant and an anti-aggregation agent, and a content of the additive may be from 0.1 wt % to 10 wt % in 100 wt % of the composition for forming an optical film.

In one embodiment of the present specification, the remainder other than the compound represented by Chemical Formula 1, the binder resin, the functional monomer, the photoinitiator and the additive may all be a solvent.

In one embodiment of the present specification, the optical film includes a resin matrix into which the compound is dispersed. The optical film is a color conversion film or an adhesive film.

The resin matrix means a result obtained by removing the solvent from the composition for forming an optical film described above, and thermal curing or UV curing the solvent-removed composition. Specifically, the resin matrix means a state in which the binder resin and the functional monomer are polymerized into a chain structure and solidified, and the compound represented by Chemical Formula 1, the additive and the like are uniformly distributed between the polymerized chains.

In another embodiment of the present specification, the optical film includes a cured material of the composition for forming an optical film. The cured material is obtained by drying the solvent included in the composition and then curing the solvent-dried composition, and means that each of the constituents included in the composition are cross-linked through chemical and/or physical bonding.

In one embodiment of the present specification, a content of the compound represented by Chemical Formula 1 is from 0.001 wt % to 10 wt % in 100 wt % of the optical film. The content of the compound represented by Chemical Formula 1 in the optical film may be identified through an indirect method of measuring absorption efficiency through optical properties in the film.

The optical film may include one type of the compound, or two or more types thereof.

Hereinafter, the optical film is described dividing into cases where the optical film is a color conversion film and where the optical film is an adhesive film.

In one embodiment of the present specification, when the optical film is a color conversion film, a full width at half maximum of the absorption peak is from 30 nm to 70 nm, and the maximum absorption peak is present in a range of 480 nm to 550 nm when irradiating light including a wavelength of 450 nm.

The color conversion film may further include an additional fluorescent material in addition to the compound represented by Chemical Formula 1. When using a light source emitting blue light, the color conversion film preferably includes both a green light emitting fluorescent material and a red light emitting fluorescent material. In addition, when using a light source emitting blue light and green light, the color conversion film may only include a red light emitting fluorescent material. However, the color conversion film is not limited thereto, and even when using a light source emitting blue light, the color conversion film may only include a red light emitting compound when a separate film including a green light emitting fluorescent material is laminated. On the other hand, even when using a light source emitting blue light, the color conversion film may only include a green light emitting compound when a separate film including a red light emitting fluorescent material is laminated.

The color conversion film may further include an additional layer including another resin matrix into which a compound absorbing light in a wavelength different from the wavelength of the compound represented by Chemical Formula 1 is dispersed. The compound absorbing light in a wavelength different from the wavelength of the compound represented by Chemical Formula 1 may also be the compound represented by Chemical Formula 1, or may be other known light absorbing materials.

In one embodiment of the present specification, the color conversion film further includes light diffusing particles. By dispersing light diffusing particles into the color conversion film instead of a light diffusing film used in the art for enhancing luminance, higher luminance may be obtained compared to using a separate light diffusing film, and an adhering process may be skipped as well.

As the light diffusing particles, particles having a higher refractive index than the resin matrix may be used, and examples thereof may include $TiO_2$, silica, borosilicate, alumina, sapphire, air or other air-filled hollow beads or particles (for example, air/gas-filled glass or polymer); polystyrene, polycarbonate, polymethyl methacrylate, acryl, methyl methacrylate, styrene, a melamine resin, a formaldehyde resin, or polymer particles including melamine and formaldehyde resins, or any suitable combination thereof.

In one embodiment of the present specification, the light diffusing particles may have a particle diameter in a range of 0.1 μm to 5 μm, for example, in a range of 0.3 μm to 1 μm. A content of the light diffusing particles may be determined as necessary, and for example, may be in a range of 1 parts by weight to 30 parts by weight based on 100 parts by weight of the resin matrix.

In one embodiment of the present specification, the color conversion film may have a thickness of 2 μm to 200 μm. Particularly, the color conversion film may exhibit high luminance even with a small thickness of 2 μm to 20 μm. This is due to the fact that the content of the fluorescent material molecules included in the unit volume is higher compared to quantum dots.

In one embodiment of the present specification, a base may be provided on one surface of the color conversion film. This base may function as a support when preparing the color conversion film. Types of the base are not particularly limited, and the material or thickness is not limited as long as it is transparent and is capable of functioning as the support. Herein, being transparent means having visible light transmittance of 70% or higher. For example, a polyethylene terephthalate (PET) film may be used as the base.

In one embodiment of the present specification, the color conversion film may be prepared using a method of coating and drying the composition for forming a color conversion film described above on a base; or a method of extruding and filming the compound represented by Chemical Formula 1 described above with a resin.

In one embodiment of the present specification, the process of coating the composition for forming a color conversion film on a base may use a roll-to-roll process. For example, a process of unwinding a base from a base-wound roll, coating the composition for forming a color conversion film on one surface of the base, drying the result, and then winding the result again on the roll may be used. When a roll-to-roll process is used, viscosity of the composition is preferably determined in a range capable of conducting the process, and for example, may be determined in a range of 200 cps to 2,000 cps.

As the coating method, various known methods may be used, and for example, various coating methods such as spin coating, die coating, comma coating and reverse comma coating may be used.

After the coating, a drying process is conducted. The drying process may be conducted under a condition required to remove a solvent. For example, a color conversion film including a fluorescent material including the compound represented by Chemical Formula 1 having target thickness and concentration may be obtained on a base by carrying out the drying in an oven located close to a coater under a condition to sufficiently evaporate a solvent, in a direction of the base progressing during the coating process.

In one embodiment of the present specification, when the compound represented by Chemical Formula 1 is extruded and filmed with a resin, extrusion methods known in the art may be used, and for example, the color conversion film may be prepared by extruding the compound represented by Chemical Formula 1 with a polycarbonate (PC)-based, a poly(meth)acryl-based and/or a styrene-acrylonitrile (SAN)-based resin.

In one embodiment of the present specification, the color conversion film may have a protective film or a barrier film provided on at least one surface. As the protective film or the barrier film, those known in the art may be used.

In one embodiment of the present specification, a backlight unit includes the color conversion film described above. The backlight unit may have backlight unit constitutions known in the art except for including the color conversion film.

FIG. 1 illustrates a mimetic diagram of a backlight unit structure according to one embodiment. According to FIG. 1, the color conversion film including the compound represented by Chemical Formula 1 is provided on a surface opposite to a surface facing a reflecting plate of a light guide plate. FIG. 1 illustrates a constitution including a light source and a reflecting plate surrounding the light source, however, the constitution is not limited to such a structure, and may vary depending on the backlight unit structure known in the art. In addition, as the light source, a direct type as well as a side chain type may be used, and the reflecting plate or the reflective layer may not be included or may be replaced with other constituents as necessary, and as necessary, an additional film such as a light diffusing film, a light concentrating film or a brightness enhancement film may be further provided. Preferably, a prism sheet, a multilayer reflective polarizer film, a light concentrating film or a brightness enhancement film is further provided on the color conversion film.

In the constitution of the backlight unit as in FIG. 1, a scattering pattern may be provided as necessary on an upper surface or a lower surface of the light guide plate. Light introduced into the light guide plate has non-uniform light distribution due to repetition of optical processes such as reflection, total reflection, refraction and transmission, and the scattering pattern may be used to induce the non-uniform light distribution to uniform brightness.

One embodiment of the present specification provides a display device including the backlight unit. The display device is not particularly limited as long as it includes the backlight unit. For example, the display device includes a display module and the backlight unit. FIG. 2 illustrates a structure of the display device. However, the structure is not limited thereto, and between the display module and the backlight unit, an additional film such as a light diffusing film, a light concentrating film or a luminance enhancing film may be further provided as necessary.

In the present specification, when the optical film is an adhesive film, the adhesive film may function as an optical adhesive layer. The function as an optical adhesive layer means forming a black color adhesive film incorporating an organic dye capable of absorbing visible light, and an OLED panel including the same suppresses high panel reflectance. In other words, visible light transmittance of the adhesive film may be controlled in a range of approximately 30% to 90%, and transmittance in a visible region may be properly adjusted depending on the panel reflectance and the reflected color.

In one embodiment of the present application, the adhesive film may have a thickness of greater than or equal to 3 μm and less than or equal to 100 μm.

In another embodiment, the adhesive film may have a thickness of greater than or equal to 3 μm and less than or equal to 100 μm, preferably greater than or equal to 5 μm and less than or equal to 80 μm, and more preferably greater than or equal to 10 μm and less than or equal to 50 μm.

In one embodiment of the present specification, a release layer may be provided on one surface of the adhesive film. FIG. 3 illustrates a structure when a release layer (4) is provided on one surface of the adhesive film (3) according to one embodiment of the present specification.

In the present specification, the release layer means a transparent layer formed on one surface of the adhesive film through a release treatment, and, as long as it does not adversely affect in the manufacturing process of the adhesive film, may be employed without limit in terms of materials, thicknesses, properties and the like. The release layer provided on one surface of the adhesive film may be removed after manufacturing the adhesive film.

The release layer may include one or more selected from the group consisting of acetate-based, polyester-based, polyethersulphone-based, polycarbonate-based, polyamide-based, polyimide-based, polyolefin-based, cycloolefin-based, polyurethane-based, acryl-based, fluorine-based and silicone-based resins, but is not limited thereto.

The release layer may have a thickness of greater than or equal to 10 nm and less than or equal to 1,000 nm, preferably greater than or equal to 20 nm and less than or equal to 800 nm, and more preferably greater than or equal to 40 nm and less than or equal to 100 nm, however, the thickness is not limited thereto. In the present specification, the adhesive film may be manufactured by coating the adhesive composition described above on the release layer or a base using a bar coater. The adhesive film may be manufactured by coating the adhesive composition described above on a base using a bar coater, and then drying the result. Descriptions on the base will be provided later. The methods of coating and drying are not particularly limited, and methods used in the art may be properly employed.

One embodiment of the present specification provides an adhesive optical filter including an adhesive film; and an anti-reflection film provided on one surface of the adhesive film.

In addition, one embodiment of the present specification provides an adhesive optical filter further including a base between the adhesive film and the anti-reflection film.

FIG. 4 illustrates a structure of the adhesive optical filter according to the present specification. The adhesive optical filter (10) includes a base (2); the adhesive film (3) provided on one surface of the base (2); and an anti-reflection film (1) provided on a surface opposite to the surface where the base (2) and the adhesive film (3) are in contact with each other.

In one embodiment of the present specification, the base of the adhesive optical filter may be selected from the group consisting of PET (polyethylene terephthalate), TAC (cellulose triacetate), polyester, PC (polycarbonate), PI (polyimide), PEN (polyethylene naphthalate), PEEK (polyether ether ketone), PAR (polyarylate), PCO (polycyclic olefin), polynorbornene, PES (polyethersulphone) and COP (cycloolefin polymer).

In one embodiment of the present application, the base of the adhesive optical filter may have a thickness of greater than or equal to 10 μm and less than or equal to 200 μm, preferably greater than or equal to 15 μm and less than or equal to 100 μm, and more preferably greater than or equal to 20 μm and less than or equal to 75 μm.

In addition, the base is preferably transparent. The base being transparent referred herein means that light transmittance of visible light (400 nm to 700 nm) is 80% or greater. When the base has transparency in the above-mentioned range, the laminated adhesive film may be thin-filmed.

In the present specification, the anti-reflection film functions to suppress external light reflection, and those used in the art may be employed without limit. The thickness of the anti-reflection film is not particularly limited, and may be set considering the total thickness of the display device of the present specification or aiming effects. In order to suppress high panel reflectance of an OLED panel, a black color adhesive film incorporating an organic dye that absorbs visible light is formed.

Specifically, the anti-reflection film may be formed by laminating or mixing low refractive and high refractive layers in order to minimize external light reflection. This may be manufactured using a method of dry method or wet method, and the dry method is to form by laminating a plurality of thin-film layers using deposition, sputtering or the like. The wet method is normally to form a double layer using a resin with a refractive index of 1.5 or greater and a resin with a refractive index of less 1.5, and the high refractive layer with a refractive index of 1.5 or greater may be formed using a (meth)acrylate resin and the like, and as the low refractive layer with a refractive index of less 1.5, a (meth)acrylate-based resin and a fluorine-based (meth)acrylate-based resin may be used either alone or as a mixture. Herein, in order to form a layer with a lower refractive index of 1.45 or less, silica fine particles or hollow silica particles may be further included in the fluorine-based resin.

The adhesive optical filter may be manufactured by consecutively laminating an anti-reflection film provided on one surface of a base, and then laminating the adhesive film on a surface opposite to the surface in contact with the anti-reflection film of the base.

In addition, the adhesive optical filter may be manufactured by laminating an anti-reflection film provided on one surface of a base, preparing the adhesive film separately, and then attaching the adhesive film on a surface opposite to the surface in contact with the anti-reflection film laminated on the base.

The method of laminating the anti-reflection film on one surface of the base and the method of laminating the adhesive film on a surface opposite to the surface in contact with the anti-reflection film of the base are not particularly limited, and, for example, methods such as coating may be employed, and other methods used in the art may be properly employed.

One embodiment of the present specification provides a display device including the adhesive optical filter.

When the display device includes the adhesive optical filter, haze is not caused, and very superior light resistance reliability is obtained.

In one embodiment of the present specification, the display device is an OLED device including an OLED panel; and the adhesive optical filter provided on one surface of the OLED panel.

In other words, the display device may be illustrated as an OLED (organic light emitting diode) device.

FIG. 5 illustrates a structure of an OLED device (30), one example of the display device according to one embodiment of the present specification. The OLED device (30) of the present specification may include an OLED panel (20) and an adhesive optical filter (10) provided on one surface of the OLED panel (20) and having the adhesive film (3), the base (2) and the anti-reflection film (1) consecutively formed therein. Specifically, in the OLED device (30), one surface where the OLED panel (20) and the adhesive optical filter (10) are in contact with each other is a surface opposite to the surface where the adhesive film (3) and the base (2) are in contact with each other.

In the OLED device, the descriptions provided above are applied to the adhesive optical filter.

In the present specification, the OLED panel may consecutively include a substrate, a lower electrode, an organic material layer and an upper electrode. The organic material layer may include an organic material capable of emitting light when a voltage is applied to the lower electrode and the upper electrode. Any one of the lower electrode and the upper electrode may be an anode, and the other one may be a cathode. The anode is an electrode where holes are injected, and may be made with conductive materials having high work function. The cathode is an electrode where electrons are injected, and may be made with conductive materials having low work function. As the anode, a transparent metal oxide layer such as ITO (indium tin oxide) or IZO (indium zinc oxide) having high work function may be commonly used, and as the cathode, a metal electrode having low work function may be used. An organic material layer is generally transparent, and a transparent display may be obtained when the upper electrode and the lower electrode are made to be transparent. In one example, a transparent display may be obtained when the thickness of the upper electrode or the lower electrode is employed to be very thin.

FIG. 6 illustrates of a structure of the OLED panel according to one embodiment of the present specification, and it may be identified that the OLED panel consecutively includes a substrate (11); a lower electrode (12); an organic material layer (13); and an upper electrode (14). The OLED panel may further include an encapsulation substrate (15), which functions to prevent inflow of moisture and/or oxygen from the outside, on the upper electrode.

The organic material layer may include a light emitting layer, and may further include a common layer for charge injection and transport. Specifically, the common layer for charge injection and transport may include a hole transporting layer, a hole injecting layer, an electron injecting layer and an electron transporting layer for balancing electrons and holes, but is not limited thereto.

The adhesive optical filter may be disposed on a side of the OLED panel where light emits. For example, the adhesive optical filter may be disposed on an outer side of the substrate in a bottom emission structure where light emits toward the substrate side, and the adhesive optical filter may be disposed on an outer side of the encapsulation substrate in a top emission structure where light emits toward the encapsulation substrate side.

Specifically, (a) of FIG. 7 illustrates the OLED device when the OLED panel (20) has a bottom emission structure, and in the bottom emission structure side where light emits from the organic material layer (13) toward the substrate (11) side, the adhesive optical filter (10) may be provided on a surface opposite to the surface where the substrate (11) and the lower electrode (12) are in contact with other, and a surface opposite to the surface in contact with the base (2) of the adhesive film (3) included in the adhesive optical filter (10) is provided in contact with the substrate (11) of the OLED panel (20).

(b) of FIG. 7 illustrates the OLED device when the OLED panel (20) has a top emission structure, and in the top emission structure where light emits from the organic material layer (13) toward the encapsulation substrate (15) side, the adhesive optical filter (10) may be provided on a surface opposite to the surface where the encapsulation substrate (15) and the upper electrode (14) are in contact with each other, and a surface opposite to the surface in contact with the base (2) of the adhesive film (3) included in the adhesive optical filter (10) is provided in contact with the encapsulation substrate (15) of the OLED panel (20).

Although not illustrated in the drawings, the OLED panel may have a dual emission structure, and when the OLED panel has a dual emission structure, the adhesive optical filter may be provided on both outermost side surfaces of the OLED panel, and may also be provided on one outermost side surface of the OLED panel.

The adhesive optical filter may improve visibility and display performance by minimizing external light from being reflected by a reflective layer made of a metal such as an electrode and a wire of the OLED panel and coming out of the outer side of the OLED panel. The outer side of the OLED panel means an outer side of the encapsulation substrate in the top emission, and means an outer side of the substrate in the bottom emission.

In one example, the OLED panel may further include a color filter-formed substrate as necessary. The color filter means a layer formed by coating color resists of red, green and blue in a specific pattern, and, when light passes through, displaying colors through each color filter.

(a) of FIG. 8 illustrates a structure of the OLED panel in a bottom emission structure provided with the color filter-formed substrate (16), and the color filter-formed substrate (16) may be disposed on a surface opposite to the surface where a lower electrode (12) and an organic material layer (13) are in contact with each other. Herein, the OLED panel may have a structure consecutively including an encapsulation substrate (15), an upper electrode (14), the organic material layer (13), a metal electrode (cathode) that is the lower electrode (12) and the color filter-formed substrate (16).

(b) of FIG. 8 illustrates a structure of the OLED panel in a top emission structure provided with the color filter-formed substrate (16), and the color filter-formed substrate (16) may be disposed on a surface opposite to the surface where a transparent upper electrode (14) and an organic material layer (13) are in contact with each other. Herein, the OLED panel may have a structure consecutively including the color filter-formed substrate (16), the upper electrode (14), the organic material layer (13), a lower electrode (12) and a substrate (11). As illustrated, the color filter (16) may include red (R), green (G) and blue (B) regions, and although not separately indicated in the drawing, a black matrix for separating the regions may be further included. When a color filter is present in the OLED panel, lower panel reflectance may be obtained compared when a color filter is not present. Specifically, when a red, green and blue color filter is present in front of a light emitting layer of an OLED, high reflectance in a metal electrode located at the back surface of the light emitting layer is reduced. The panel reflectance means electrode reflection, and specifically means that external light penetrating into the OLED panel is reflected by an electrode included in the OLED panel.

The OLED panel may be employed without particular limit as long as it is used in the art, but may have average reflectance of approximately 30% to 50% in a wavelength range of 400 nm to 600 nm, and may also be an OLED panel with 25% or less. The average reflectance may be expressed as a sum of regular reflected light obtained by light from a light source entering the reflective surface and reflected at the same angle and diffused reflected light that is light scattered and reflected in various directions instead of being regular reflected due to irregularities or curves on the surface, and is expressed by averaging 400 nm to 600 nm reflectance values among the measured reflectance values for each wavelength.

Hereinafter, the present specification will be described in detail with reference to examples. However, the examples according to the present specification may be modified to various other forms, and the scope of the present specification is not to be construed as being limited to the examples described below. The examples of the present specification are provided in order to more fully describe the present specification to those having average knowledge in the art.

EXAMPLE

Preparation Example 1

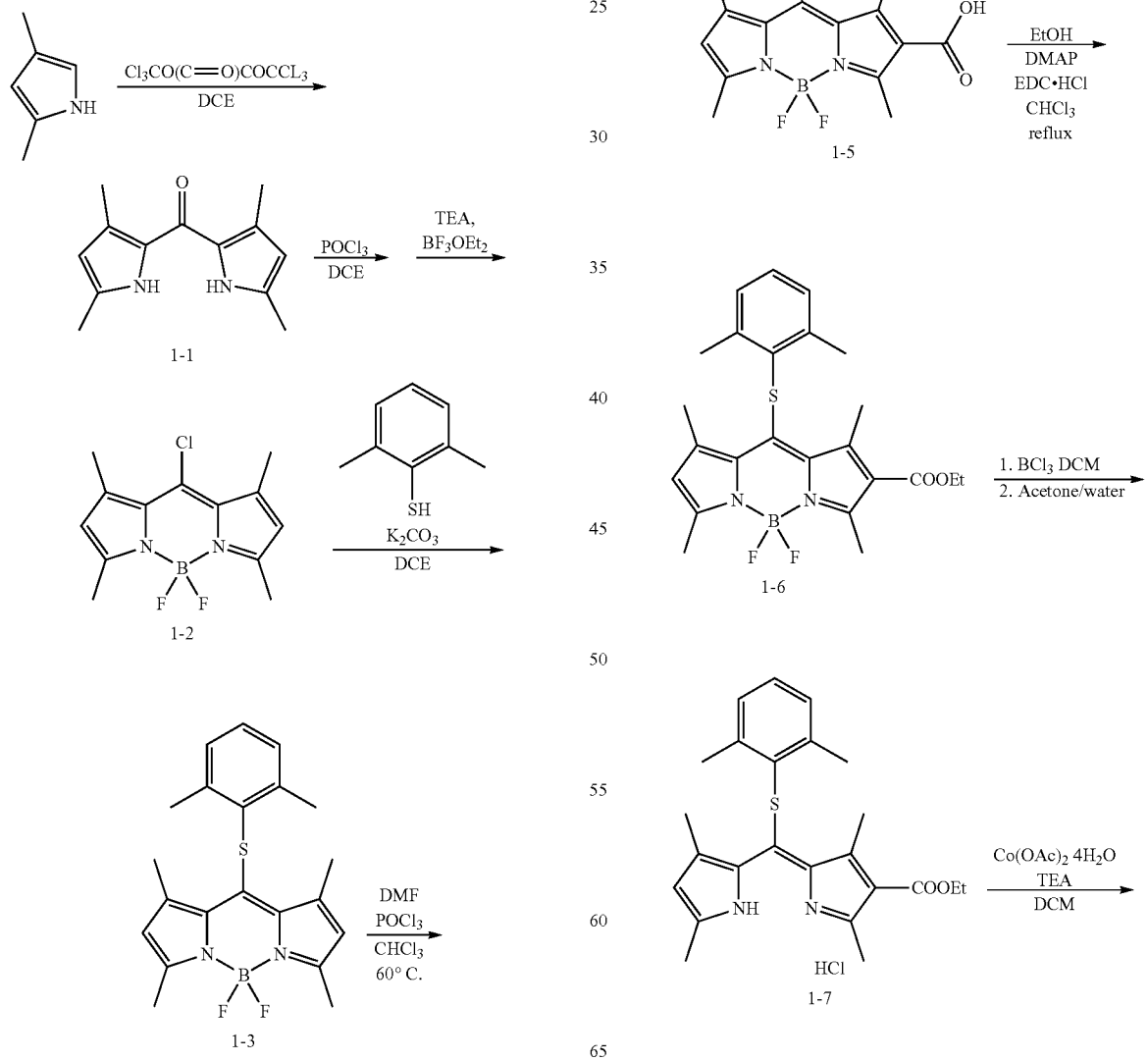

-continued

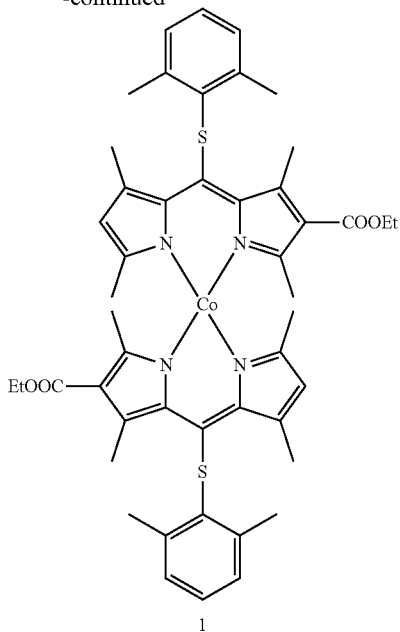

1

Synthesis of Compound 1-1

To 2,4-dimethylpyrrole (50.0 g, 1.0 equivalent), a solution dissolving triphosgene (0.3 equivalent) in dichloroethane (DCE) was slowly introduced while stirring well. A solution dissolving trimethylamine (TEA) (0.1 equivalent) in dichloroethane was further introduced to the reaction solution under the nitrogen atmosphere at 0° C., and the result was kept for 2 hours. After that, 2,4-dimethylpyrrole (1.0 equivalent) was further introduced to the reaction solution, and the result was heated for 30 minutes at approximately 80° C. After identifying the completion of the reaction, the result was extracted using dichloromethane and an aqueous sodium bicarbonate solution. The extracted organic layer was dried with sodium sulfate, and then a silica gel column was used to secure purified and separated Compound 1-1 (59.0 g, yield 51.9%).

Synthesis of Compound 1-2

Compound 1-1 (59.0 g) was stirred well and dissolved in a dichloroethane solvent. After cooling the reaction solution to 0° C. using ice water, phosphorous oxychloride (POCl$_3$) (2.0 equivalent) was introduced thereto, and the result was heated for 3 hours. After the reaction was finished, the result was cooled to room temperature, and after introducing triethylamine (10.0 equivalent) thereto, the temperature was maintained at 0° C. using ice water. A boron trifluoride ethyl ether complex (BF$_3$·OEt$_2$) (11.0 equivalent) was further introduced slowly thereto, and the result was further stirred for approximately 2 hours at room temperature. After identifying the completion of the reaction, the result was extracted using dichloromethane and water. The extracted organic layer was dried with sodium sulfate, and filtered using a silica pad to secure purified and separated Compound 1-2 (61.0 g, yield 79.1%).

Synthesis of Compound 1-3

Compound 1-2 (4.0 g) was stirred well and dissolved in a dichloroethane solvent. 2,6-Dimethylbenzenethiol (1.0 equivalent) and potassium carbonate (3.0 equivalent) were introduced thereto. The result was stirred at room temperature under the nitrogen atmosphere. After identifying the completion of the reaction, the result was extracted using diethyl ether and an aqueous sodium carbonate solution. The extracted organic layer was dried with sodium sulfate, and then a silica gel column was used to secure purified and separated Compound 1-3 (4.9 g, yield 90.1%).

Synthesis of Compound 1-4

Under the nitrogen atmosphere at 0° C., phosphorous oxychloride (POCl$_3$) (2.0 equivalent) and N,N-dimethylformamide (DMF) (3.0 equivalent) were introduced to a chloroform solvent, and the mixture was stirred well for 1 hour. After 1 hour, Compound 1-3 (4.9 g) was introduced to the mixture solution, and the result was stirred under reflux at 60° C. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 1-4 (4.4 g, yield 83.7%) was secured.

Synthesis of Compound 1-5

Compound 1-4 (4.4 g) was stirred well and dissolved in a tetrahydrofuran (THF) solvent. Amidosulfonic acid (1.5 equivalent) dissolved in water was introduced thereto, and the result was stirred at room temperature. The reaction solution was cooled to 0° C., and the result was stirred well while slowly introducing sodium chlorite (1.0 equivalent) dissolved in water thereto. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 1-5 (3.9 g, yield 85.3%).

Synthesis of Compound 1-6

Compound 1-5 (3.9 g) was stirred well and dissolved in a chloroform solvent. Ethanol (30 equivalent), 4-dimethylaminopyridine (DMAP) (2.2 equivalent) and N-(3-dimethylaminopropyl)-N'-ethylcarbodiimide hydrochloride (EDC-HCl) (2.2 equivalent) were introduced thereto, and the result was stirred under reflux. After the reaction was completed, the reaction solution was cooled to room temperature, and extracted using chloroform and water. The extracted organic layer was dried with sodium sulfate and, after removing the solvent by vacuum distillation, recrystallized using ethanol. Through the recrystallization, purified and separated Compound 1-6 (3.4 g, yield 81.8%) was secured.

Synthesis of Compound 1-7

Compound 1-6 (3.4 g) was stirred well and dissolved in a dichloromethane (DCM) solvent. A boron trichloride 1.0 M heptane solution (1.0 equivalent) was slowly added dropwise thereto. When the reaction was completed, the solvent was vacuum distilled at a low temperature of 30° C. or lower, then acetone and water in a ratio of 10/1 (volume ratio) were introduced to the reaction solution remaining in the container, and the result was stirred well again. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 1-7 (2.7 g, yield 81.4%) was secured.

Synthesis of Compound 1

Compound 1-7 (2.7 g) was stirred well and dissolved in a dichloromethane solvent. Cobalt acetate tetrahydrate (0.50 equivalent) was introduced to the reaction solution in a solid state, and triethylamine (2.5 equivalent) was further introduced thereto. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 1 (2.2 g, yield 83.0%) was secured.

HR LC/MS/MS m/z calculated for $C_{48}H_{54}CoN_4O_4S_2$ (M+): 873.2918; found: 873.2924.

Preparation Example 2

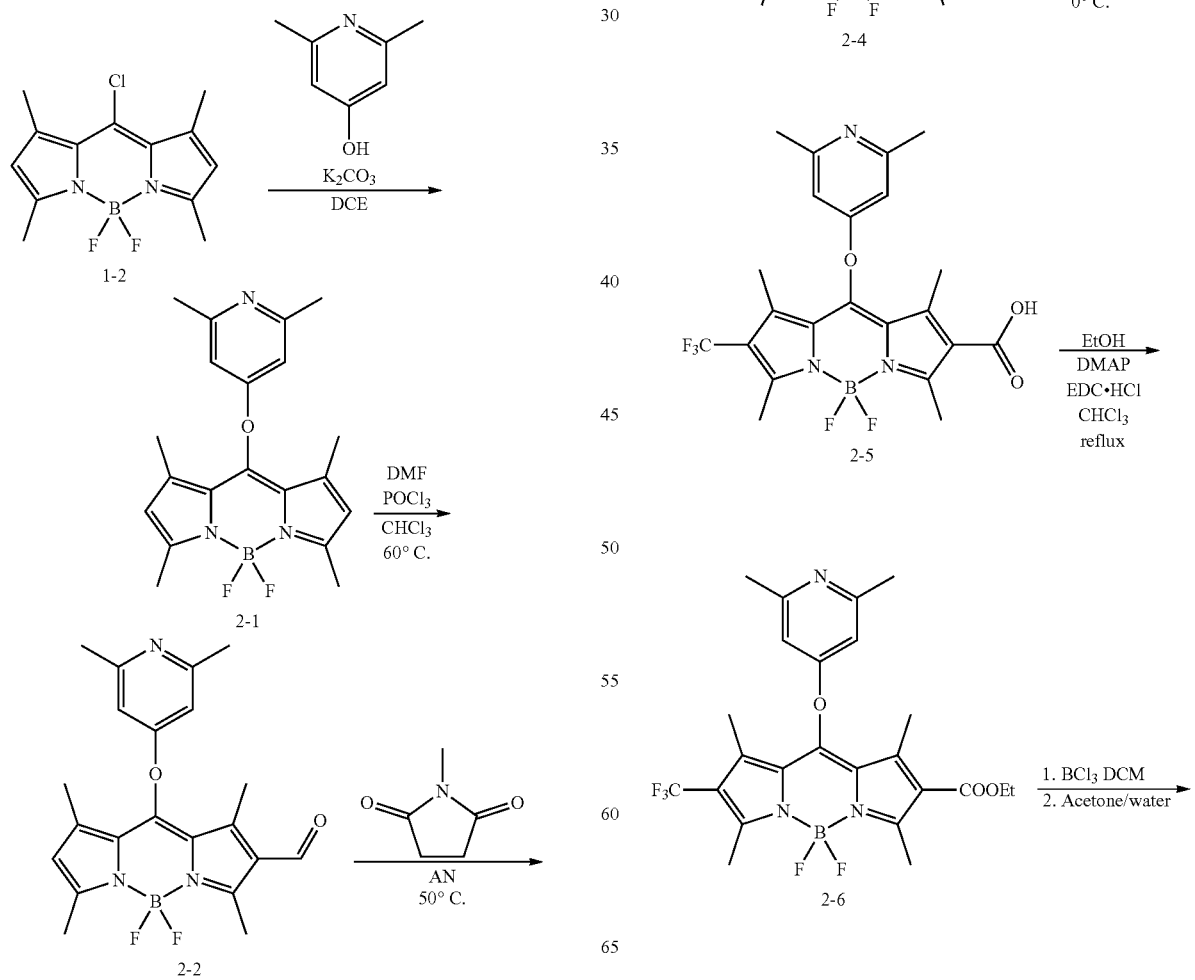

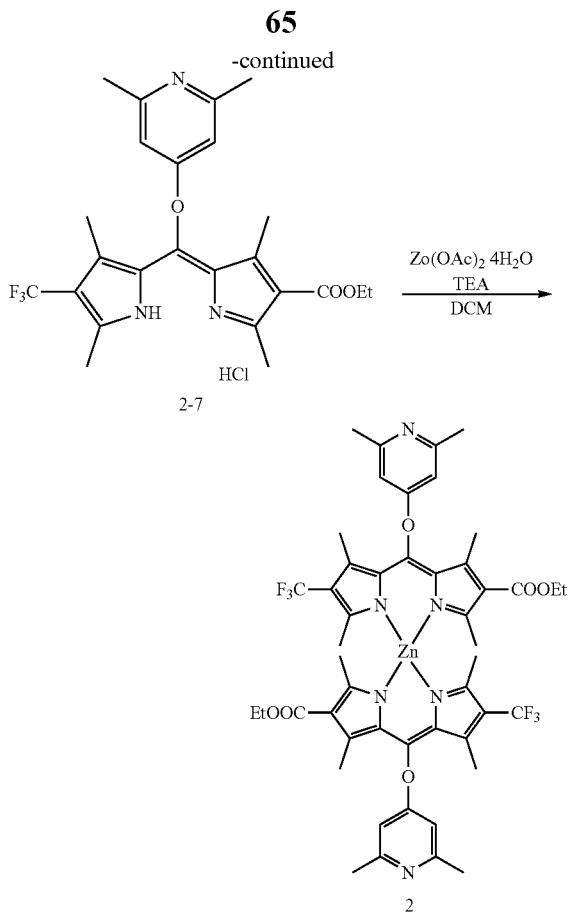

Synthesis of Compound 2-1

Synthesis was progressed in the same manner as in Synthesis of Compound 1-3 except that 2,6-dimethyl-4-hydroxypyridine (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 2-1 (4.8 g, yield 91.8%).

Synthesis of Compound 2-2

Synthesis was progressed in the same manner as in Synthesis of Compound 1-4 except that Compound 2-1 (4.8 g) was used instead of Compound 1-3. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 2-2 (4.6 g, yield 89.1%) was secured.

Synthesis of Compound 2-3

Compound 2-2 (4.6 g) was stirred well and dissolved in an acetonitrile (AN) solvent. N-iodosuccinimide (NIS) (3.0 equivalent) was slowly introduced thereto at room temperature. The result was heated to 60° C. and stirred to proceed a reaction, and after the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 2-3 (5.5 g, yield 90.8%) was secured.

Synthesis of Compound 2-4

Under the nitrogen atmosphere at 0° C., silver fluoride (AgF) (2.0 equivalent) was introduced to an N,N-dimethylformamide solvent, and stirred well. Trimethyltrifluoromethylsilane (TMSCF$_3$) (2.0 equivalent) was slowly added dropwise to the reaction solution while maintaining the temperature. The result was stirred well for 30 minutes while slowly raising the temperature to room temperature. When the reaction solution became uniform, Cu powder (2.0 equivalent) was introduced thereto, and the result was stirred well for 2 hours. After 2 hours, Compound 2-3 (5.5 g) was introduced to the mixture solution, and the result was heated to 60° C. and stirred. After the reaction was completed, water was introduced to the reaction solution, and the result was stirred well and filtered to obtain a material in a solid state. This was extracted again using ethyl acetate and hexane. The extracted organic layer was dried with sodium sulfate, and after removing the solvent by vacuum distillation, Compound 2-4 (3.9 g, yield 79.7%) was secured without further purification.

Synthesis of Compound 2-5

Synthesis was progressed in the same manner as in Synthesis of Compound 1-5 except that Compound 2-4 (3.9 g) was used instead of Compound 1-4. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 2-5 (3.4 g, yield 84.3%).

Synthesis of Compound 2-6

Synthesis was progressed in the same manner as in Synthesis of Compound 1-6 except that Compound 2-5 (3.4 g) was used instead of Compound 1-5. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 2-6 (3.1 g, yield 86.2%) was secured.

Synthesis of Compound 2-7

Synthesis was progressed in the same manner as in Synthesis of Compound 1-7 except that Compound 2-6 (3.1 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol.

Through the recrystallization, purified and separated Compound 2-7 (2.6 g, yield 85.8%) was secured.

Synthesis of Compound 2

Synthesis was progressed in the same manner as in Synthesis of Compound 1 except that Compound 2-7 (2.6 g) was used instead of Compound 1-7, and zinc acetate dihydrate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 2 (2.1 g, yield 81.6%) was secured.

HR LC/MS/MS m/z calculated for $C_{48}H_{50}F_6N_6O_6Zn$ (M+): 984.2987; found: 984.2981.

Preparation Example 3

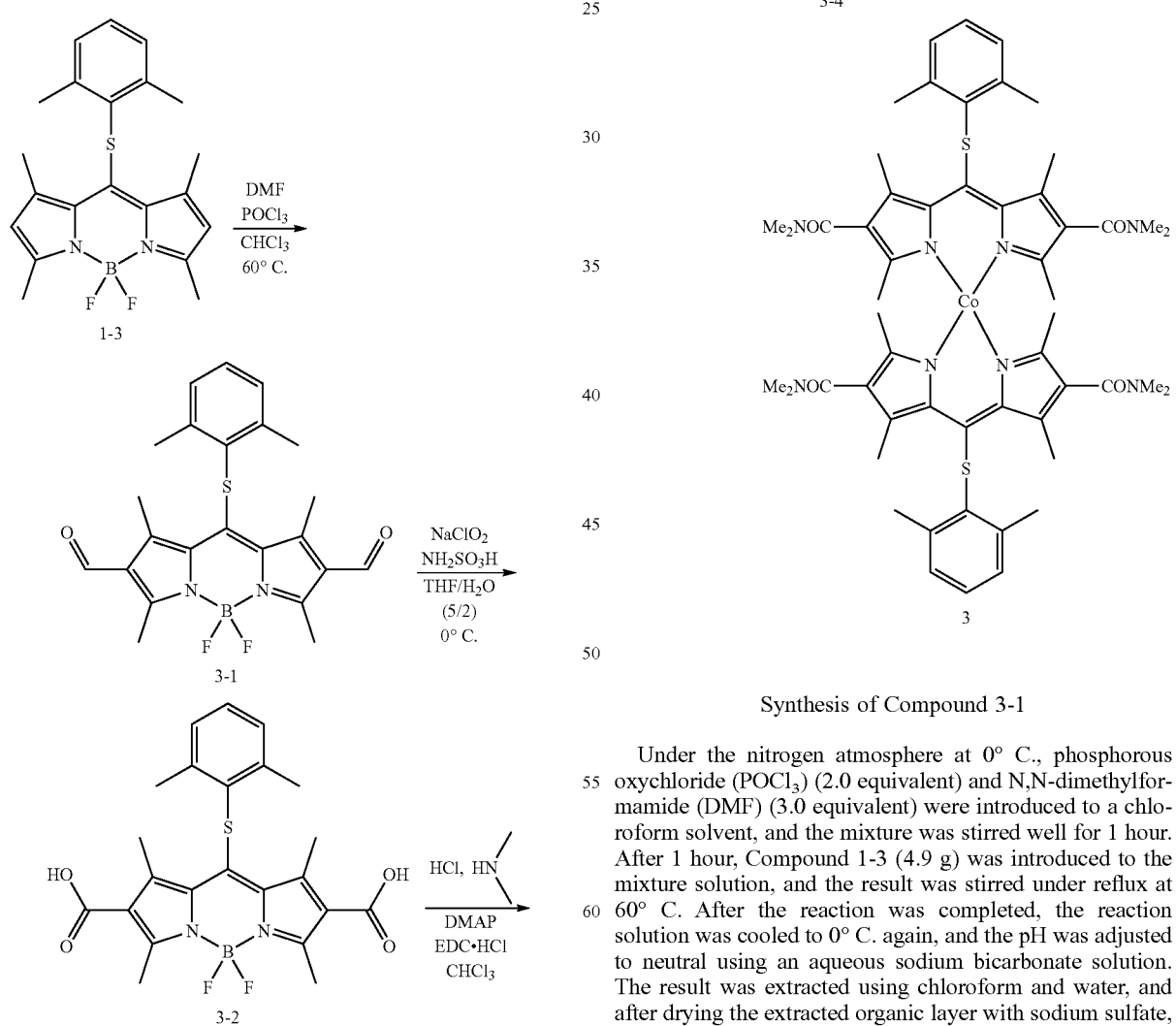

Synthesis of Compound 3-1

Under the nitrogen atmosphere at 0° C., phosphorous oxychloride ($POCl_3$) (2.0 equivalent) and N,N-dimethylformamide (DMF) (3.0 equivalent) were introduced to a chloroform solvent, and the mixture was stirred well for 1 hour. After 1 hour, Compound 1-3 (4.9 g) was introduced to the mixture solution, and the result was stirred under reflux at 60° C. After the reaction was completed, the reaction solution was cooled to 0° C. again, and the pH was adjusted to neutral using an aqueous sodium bicarbonate solution. The result was extracted using chloroform and water, and after drying the extracted organic layer with sodium sulfate, the solvent was removed by vacuum distillation. After that, the same reaction was proceeded once again with the reaction solution. After the reaction proceeded twice was all completed, the result was recrystallized using methanol. Through the recrystallization, purified and separated Compound 3-1 (3.3 g, yield 82.3%) was secured.

Synthesis of Compound 3-2

Compound 3-1 (3.3 g) was stirred well and dissolved in a tetrahydrofuran solvent. Amidosulfonic acid (3.0 equivalent) dissolved in water was introduced thereto, and the result was stirred at room temperature. The reaction solution was cooled to 0° C., and the result was stirred well while slowly introducing sodium chlorite (2.0 equivalent) dissolved in water thereto. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 3-2 (2.9 g, yield 81.9%).

Synthesis of Compound 3-3

Compound 3-2 (2.9 g) was stirred well and dissolved in a chloroform solvent. Dimethylamine hydrochloride salt (4.2 equivalent), 4-dimethylaminopyridine (DMAP) (4.4 equivalent) and N-(3-dimethylaminopropyl)-N'-ethylcarbodiimide hydrochloride (EDC-HCl) (4.4 equivalent) were introduced thereto, and the result was stirred at room temperature. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 3-3 (2.8 g, yield 86.6%) was secured.

Synthesis of Compound 3-4

Synthesis was progressed in the same manner as in Synthesis of Compound 1-7 except that Compound 3-3 (2.8 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 3-4 (2.3 g, yield 83.9%) was secured.

Synthesis of Compound 3

Synthesis was progressed in the same manner as in Synthesis of Compound 1 except that Compound 3-4 (2.3 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 3 (1.9 g, yield 83.9%) was secured.

HR LC/MS/MS m/z calculated for $C_{54}H_{66}CoN_8O_4S_2$ (M+): 1013.3980; found: 1013.3984.

Preparation Example 4

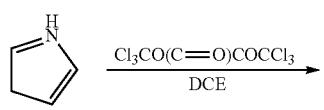

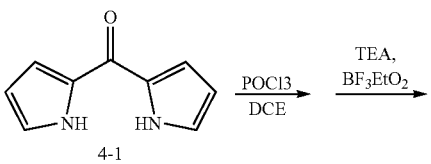

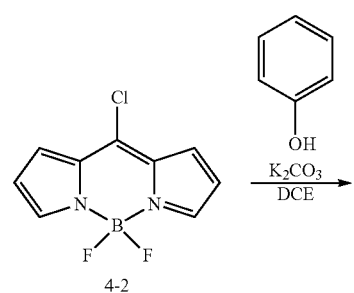

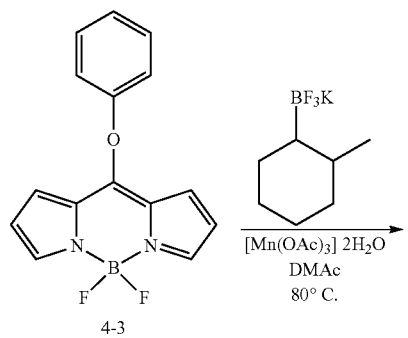

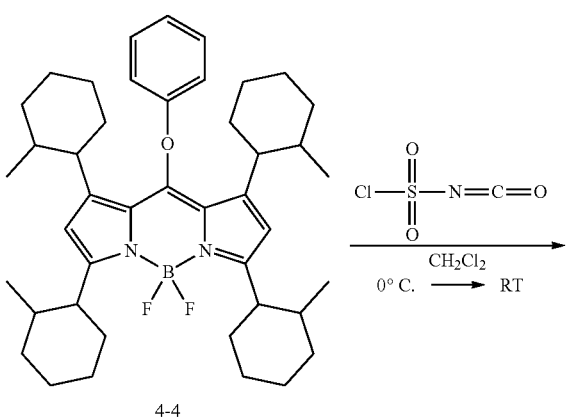

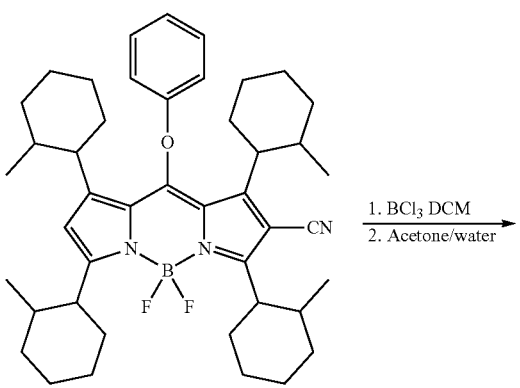

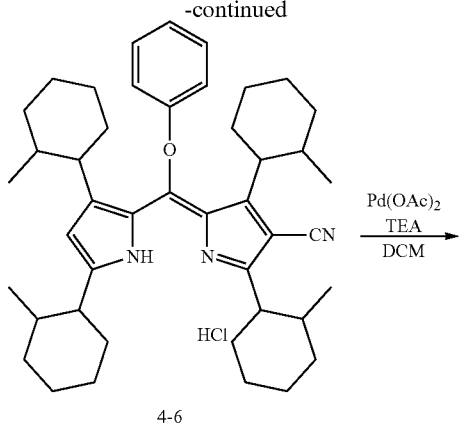

4-6

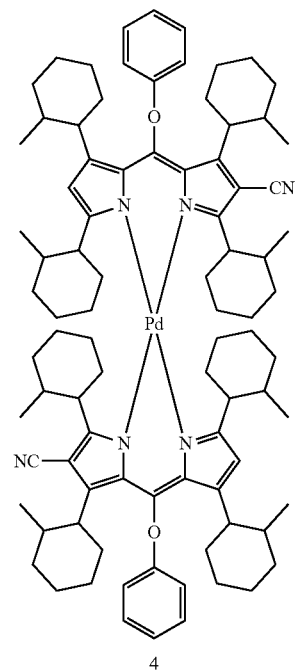

4

Synthesis of Compound 4-2

Synthesis was progressed in the same manner as in Synthesis of Compound 1-2 except that Compound 4-1 (40.0 g) was used instead of Compound 1-1. After identifying the completion of the reaction, the result was extracted using dichloromethane and water. The extracted organic layer was dried with sodium sulfate, and filtered using a silica pad to secure purified and separated Compound 4-2 (33.0 g, yield 58.4%).

Synthesis of Compound 4-3

Synthesis was progressed in the same manner as in Synthesis of Compound 1-3 except that Compound 4-2 (4.0 g) was used instead of Compound 1-2, and phenol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 4-3 (4.5 g, yield 89.7%).

Synthesis of Compound 4-4

Compound 4-3 (4.5 g) was stirred well and dissolved in an N,N-dimethylacetamide solvent. 2-Methylcyclohexyltrifluoroborate potassium salt (6.0 equivalent) and manganese acetate hydrate (10.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 4-4 (4.3 g, yield 40.6%).

Synthesis of Compound 4-5

Compound 4-4 (4.3 g) was stirred well and dissolved in a dichloromethane solvent. After cooling the reaction solution to 0° C. using ice water, chlorosulfonyl isocyanate (2.0 equivalent) was introduced thereto, and the result was stirred at room temperature. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 4-5 (4.1 g, yield 91.9%) was secured.

Synthesis of Compound 4-6

Synthesis was progressed in the same manner as in Synthesis of Compound 1-7 except that Compound 4-5 (4.1 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 4-6 (3.1 g, yield 76.9%) was secured.

Synthesis of Compound 4

Synthesis was progressed in the same manner as in Synthesis of Compound 1 except that Compound 4-6 (3.1 g) was used instead of Compound 1-6, and palladium acetate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 4 (2.8 g, yield 88.3%) was secured.

HR LC/MS/MS m/z calculated for $C_{88}H_{116}N_6O_2Pd$ (M+): 1394.8195; found: 1394.8199.

Preparation Example 5
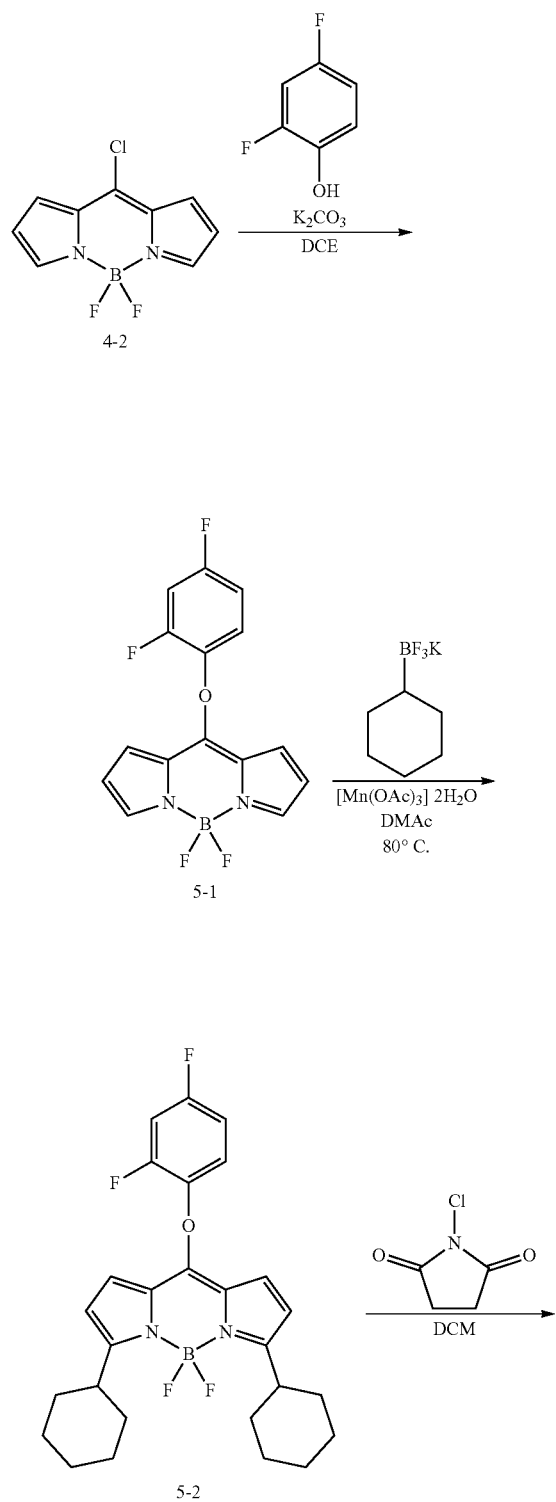
4-2
5-1
5-2
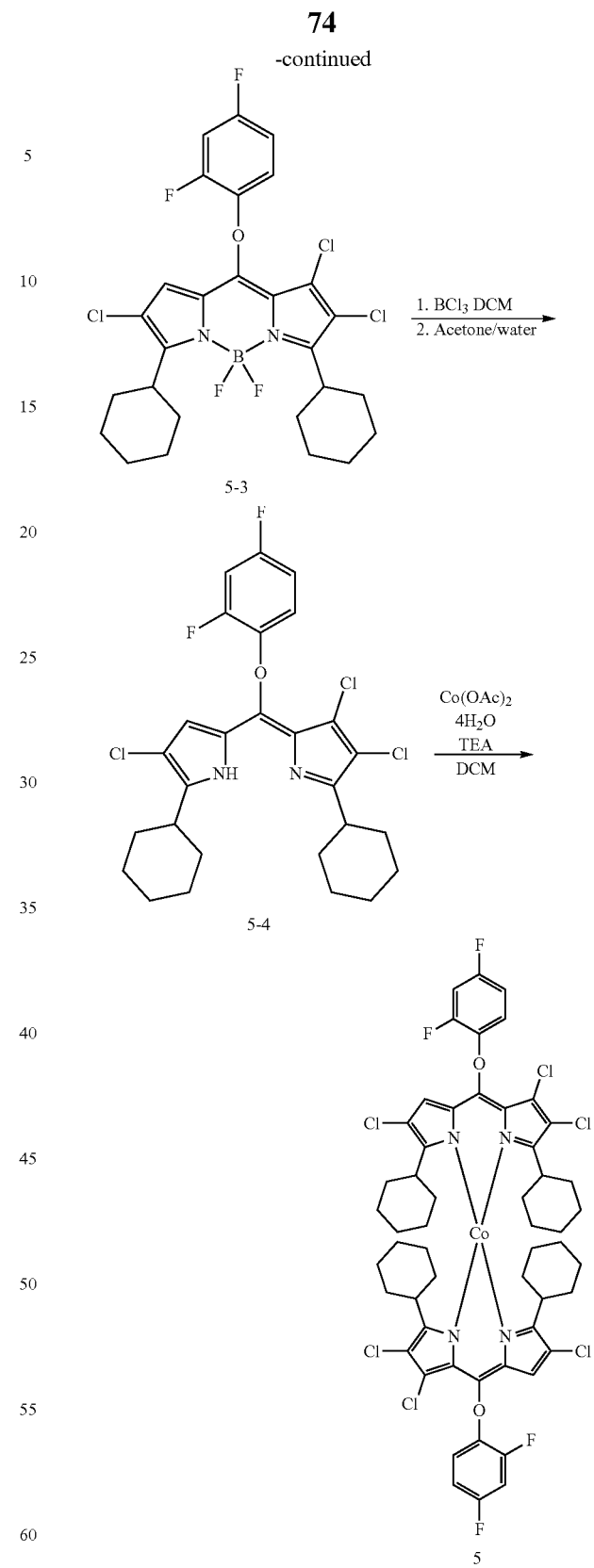
5-3
5-4
5
Synthesis of Compound 5-1
Synthesis was progressed in the same manner as in Synthesis of Compound 1-3 except that Compound 4-2 (4.0 g) was used instead of Compound 1-2, and 2,4-difluorophenol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 5-1 (4.0 g, yield 70.7%).

Synthesis of Compound 5-2

Compound 5-1 (4.0 g) was stirred well and dissolved in an N,N-dimethylacetamide (DMAc) solvent. Cyclohexyltrifluoroborate potassium salt (3.0 equivalent) and manganese acetate hydrate (5.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 5-2 (4.3 g, yield 71.0%).

Synthesis of Compound 5-3

Compound 5-2 (4.3 g) was stirred well and dissolved in a dichloromethane solvent. N-chlorosuccinimide (NCS) (3.5 equivalent) was slowly introduced thereto at room temperature. The result was stirred at room temperature to proceed a reaction, and after the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 5-3 (4.1 g, yield 78.6%) was secured.

Synthesis of Compound 5-4

Synthesis was progressed in the same manner as in Synthesis of Compound 1-7 except that Compound 5-3 (4.1 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 5-4 (3.4 g, yield 84.6%) was secured.

Synthesis of Compound 5

Synthesis was progressed in the same manner as in Synthesis of Compound 1 except that Compound 5-4 (3.4 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 5 (2.9 g, yield 86.5%) was secured.

HR LC/MS/MS m/z calculated for $C_{54}H_{52}Cl_6CoF_4N_4O_2$ (M+): 1133.1490; found: 1133.1496.

Preparation Example 6

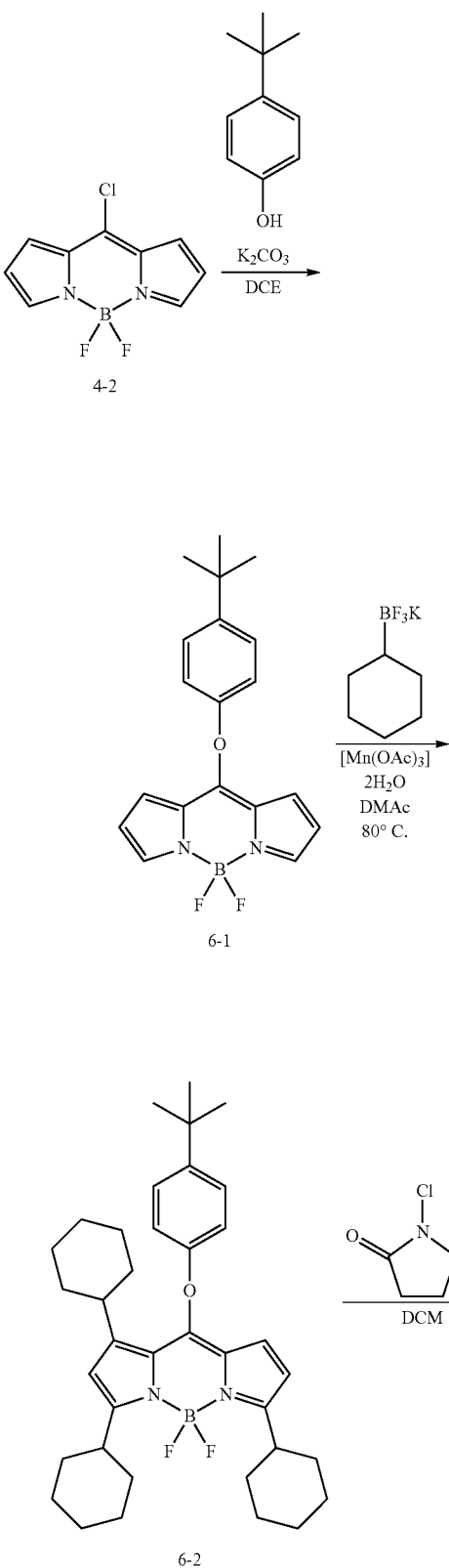

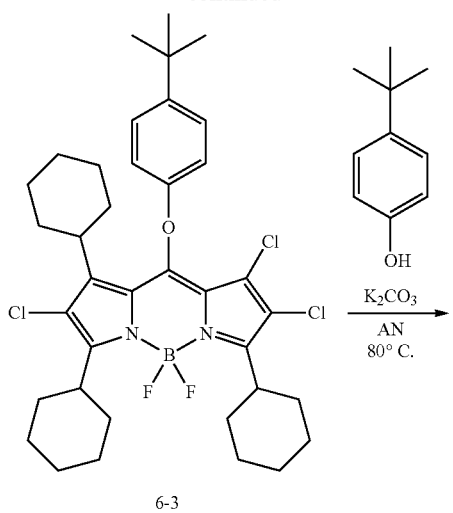

6-3

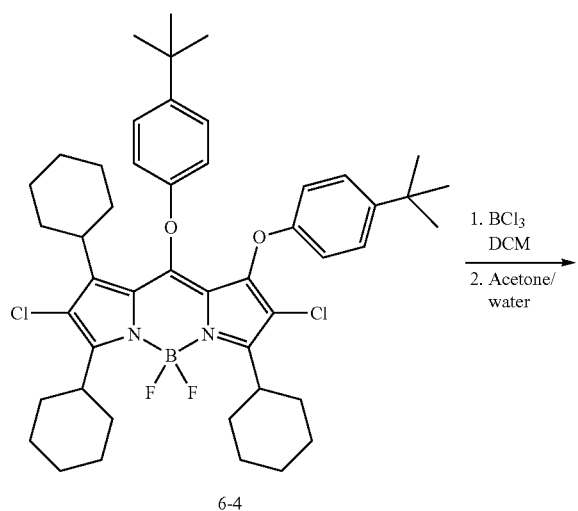

6-4

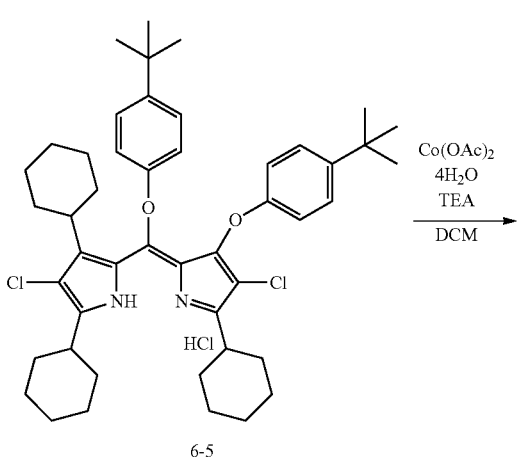

6-5

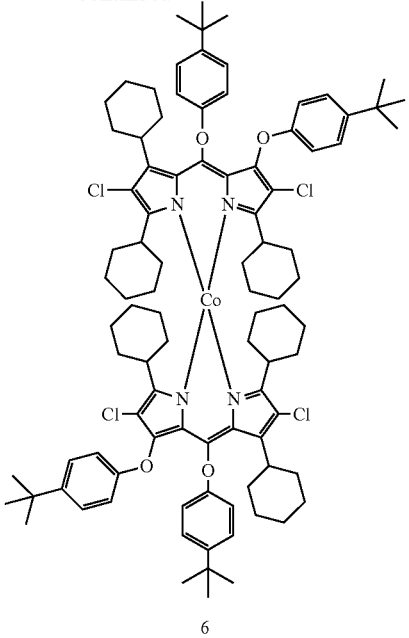

6

Synthesis of Compound 6-1

Synthesis was progressed in the same manner as in Synthesis of Compound 1-3 except that Compound 4-2 (4.0 g) was used instead of Compound 1-2, and 4-t-butylphenol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 6-1 (5.4 g, yield 89.9%).

Synthesis of Compound 6-2

Compound 6-1 (5.4 g) was stirred well and dissolved in an N,N-dimethylacetamide solvent. 2-Methylcyclohexyltrifluoroborate potassium salt (4.0 equivalent) and manganese acetate hydrate (8.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 6-2 (3.8 g, yield 40.8%).

Synthesis of Compound 6-3

Synthesis was progressed in the same manner as in Synthesis of Compound 5-3 except that Compound 6-2 (3.8 g) was used instead of Compound 5-2. After the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 6-3 (3.5 g, yield 78.3%) was secured.

Synthesis of Compound 6-4

Compound 6-3 (3.5 g) was stirred well and dissolved in an acetonitrile solvent. Potassium carbonate (4.0 equivalent) and 4-t-butylphenol (2.0 equivalent) were introduced thereto, and the reaction solution was heated to 80° C. and stirred under reflux. After the reaction was completed, the result was extracted using chloroform and water. The extracted organic layer was dried with sodium sulfate and, after removing the solvent by vacuum distillation, recrystallized using methanol. Through the recrystallization, purified and separated Compound 6-4 (3.6 g, yield 88.3%) was secured.

Synthesis of Compound 6-5

Synthesis was progressed in the same manner as in Synthesis of Compound 1-7 except that Compound 6-4 (3.6 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 6-5 (3.1 g, yield 87.3%) was secured.

Synthesis of Compound 6

Synthesis was progressed in the same manner as in Synthesis of Compound 1 except that Compound 6-5 (3.1 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 6 (2.7 g, yield 88.0%) was secured.

HR LC/MS/MS m/z calculated for $C_{94}H_{118}Cl_4CoN_4O_4$ (M+): 1565.7239; found: 1565.7245.

Preparation Example 7

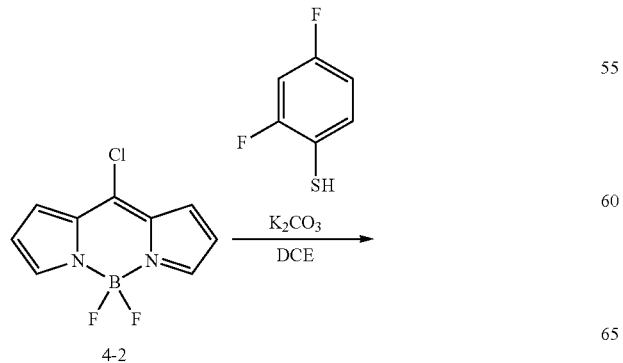

4-2

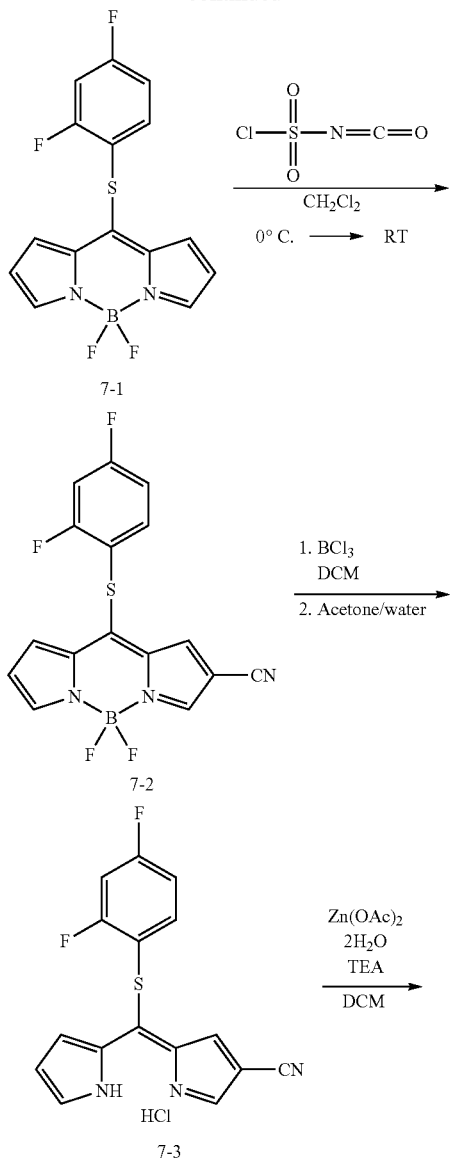

7-1

7-2

7-3

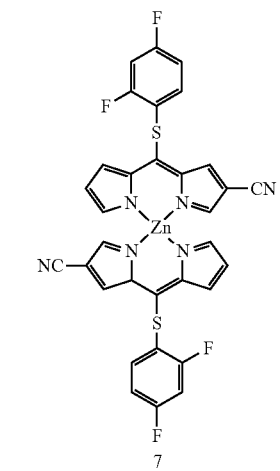

7

Synthesis of Compound 7-1

Synthesis was progressed in the same manner as in Synthesis of Compound 1-3 except that Compound 4-2 (4.0 g) was used instead of Compound 1-2, and 2,6-difluorobenzenethiol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 7-1 (5.3 g, yield 89.3%).

Synthesis of Compound 7-2

Synthesis was progressed in the same manner as in Synthesis of Compound 4-5 except that Compound 7-1 (5.3 g) was used instead of Compound 4-4. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 7-2 (4.4 g, yield 77.3%) was secured.

Synthesis of Compound 7-3

Synthesis was progressed in the same manner as in Synthesis of Compound 1-7 except that Compound 7-2 (4.4 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 7-3 (3.3 g, yield 77.4%) was secured.

Synthesis of Compound 7

Synthesis was progressed in the same manner as in Synthesis of Compound 1 except that Compound 7-3 (3.3 g) was used instead of Compound 1-7, and zinc acetate dihydrate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 7 (2.8 g, yield 86.0%) was secured.

HR LC/MS/MS m/z calculated for $C_{32}H_{16}F_4N_6S_2Zn$ (M+): 688.0105; found: 688.0111.

Preparation Example 8

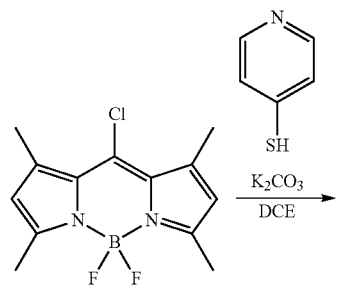

1-2

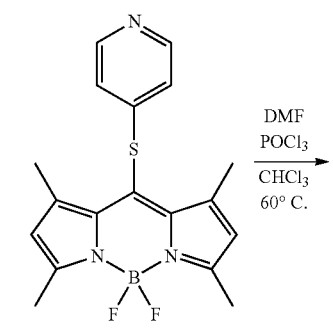

8-1

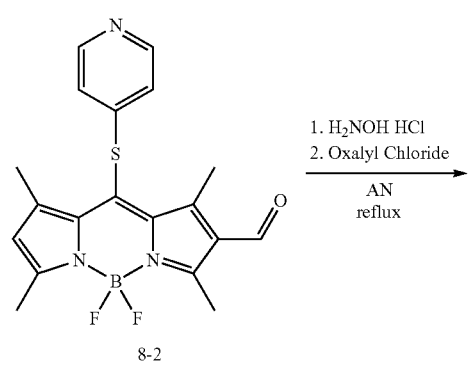

8-2

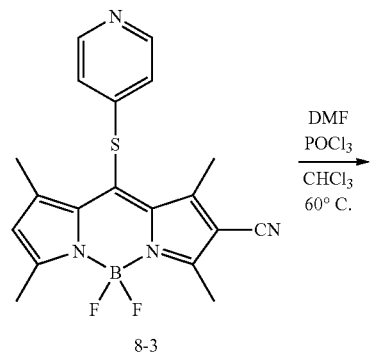

8-3

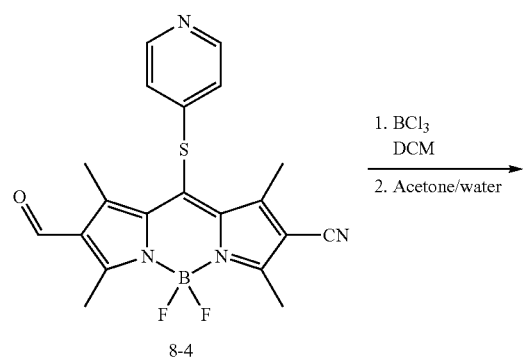

8-4

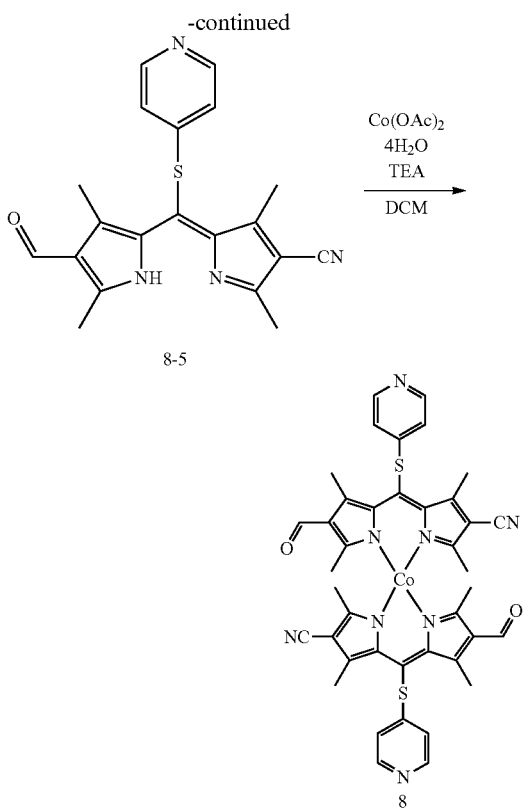

Synthesis of Compound 8-1

Synthesis was progressed in the same manner as in Synthesis of Compound 1-3 except that 4-mercaptopyridine (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 8-1 (4.4 g, yield 87.0%).

Synthesis of Compound 8-2

Synthesis was progressed in the same manner as in Synthesis of Compound 1-4 except that Compound 8-1 (4.4 g) was used instead of Compound 1-3. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 8-2 (4.1 g, yield 86.4%) was secured.

Synthesis of Compound 8-3

Compound 8-2 (4.1 g) was stirred well and dissolved in an acetonitrile solvent. Hydroxylamine hydrochloride salt (1.5 equivalent) was introduced thereto, and the reaction solution was stirred under reflux. When the reaction was completed, the reaction solution was cooled to 0° C. using ice water, and oxalyl chloride (1.5 equivalent) was further introduced thereto. The reaction solution was stirred under reflux again. When the reaction was completed, the result was extracted using chloroform and water, and the organic layer was dried using sodium sulfate. The solvent was removed by vacuum distillation, and the result was recrystallized using methanol. Through the recrystallization, purified and separated Compound 8-3 (3.8 g, yield 93.4%) was secured.

Synthesis of Compound 8-4

Synthesis was progressed in the same manner as in Synthesis of Compound 1-4 except that Compound 8-3 (3.8 g) was used instead of Compound 1-3. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 8-4 (3.5 g, yield 85.8%) was secured.

Synthesis of Compound 8-5

Synthesis was progressed in the same manner as in Synthesis of Compound 1-7 except that Compound 8-4 (3.5 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 8-5 (3.1 g, yield 91.1%) was secured.

Synthesis of Compound 8

Synthesis was progressed in the same manner as in Synthesis of Compound 1 except that Compound 8-5 (3.1 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 8 (2.6 g, yield 85.6%) was secured.

HR LC/MS/MS m/z calculated for $C_{40}H_{34}CoN_8O_2S_2$ (M+): 781.1578; found: 781.1584.

Preparation Example 9

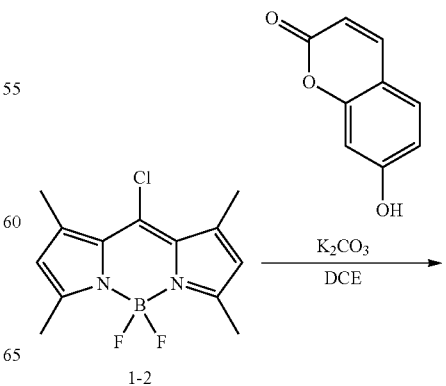

-continued

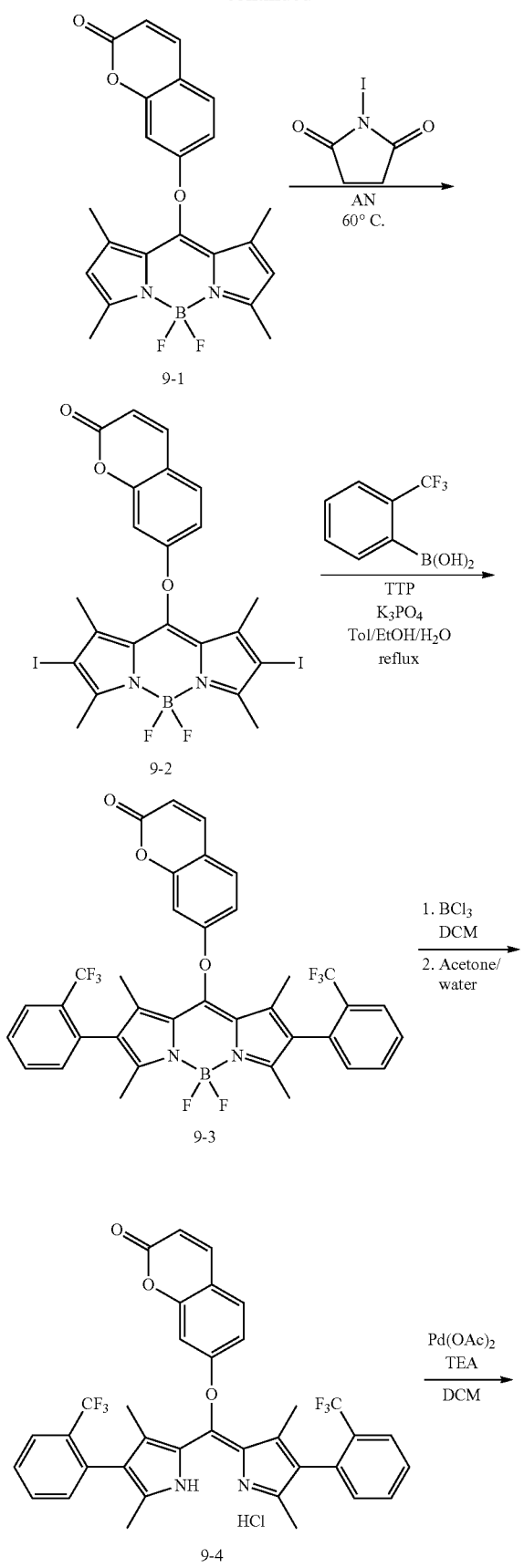

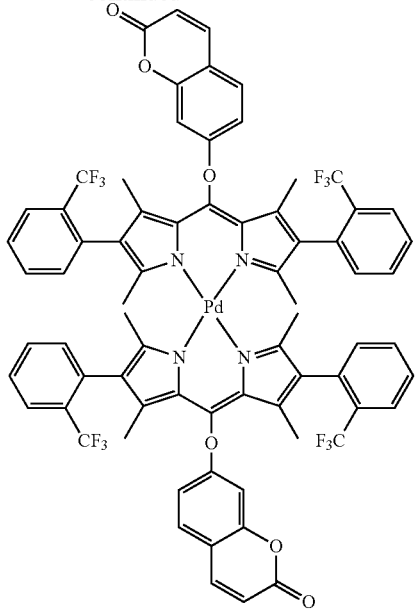

Synthesis of Compound 9-1

Synthesis was progressed in the same manner as in Synthesis of Compound 1-3 except that 7-hydroxycoumarin (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 9-1 (5.0 g, yield 86.5%).

Synthesis of Compound 9-2

Compound 9-1 (5.0 g) was stirred well and dissolved in an acetonitrile solvent. N-iodosuccinimide (NIS) (6.0 equivalent) was slowly introduced thereto at room temperature. The result was heated to 60° C. and stirred to proceed a reaction, and after the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 9-2 (6.5 g, yield 80.4%) was secured.

Synthesis of Compound 9-3

Compound 9-2 (6.5 g) was introduced to a solvent with a toluene/ethanol/water ratio of 2/2/1 (volume ratio), stirred well and dissolved therein. 2-Trifluoromethylphenylboronic acid (4.2 equivalent) and tripotassium phosphate (10.0 equivalent) were introduced thereto, and the result was heated to 80° C. and stirred for 30 minutes. After 30 minutes, tetrakistriphenylphosphine palladium (0.20 equivalent) was introduced to the heated reaction solution, and the result was stirred under reflux. When the reaction was completed, the result was extracted using chloroform and water. The extracted organic layer was dried with sodium sulfate and, after removing the solvent by vacuum distillation, recrystallized using methanol. Through the recrystallization, purified and separated Compound 9-3 (5.3 g, yield 77.3%) was secured.

Synthesis of Compound 9-4

Synthesis was progressed in the same manner as in Synthesis of Compound 1-7 except that Compound 9-3 (5.3 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 9-4 (4.4 g, yield 84.4%) was secured.

Synthesis of Compound 9

Synthesis was progressed in the same manner as in Synthesis of Compound 1 except that Compound 9-4 (4.4 g) was used instead of Compound 1-6, and palladium acetate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 9 (3.7 g, yield 82.2%) was secured.

HR LC/MS/MS m/z calculated for $C_{72}H_{50}F_{12}N_4O_6Pd$ (M+): 1400.2574; found: 1400.2578.

Preparation Example 10

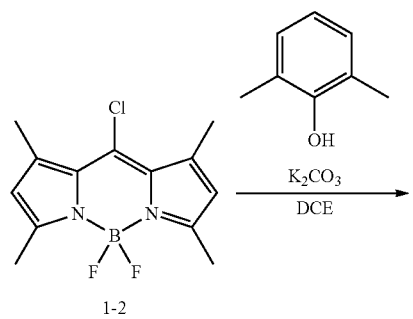

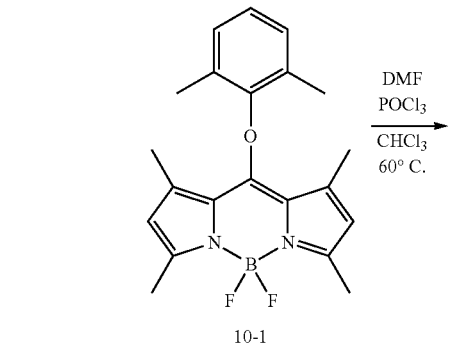

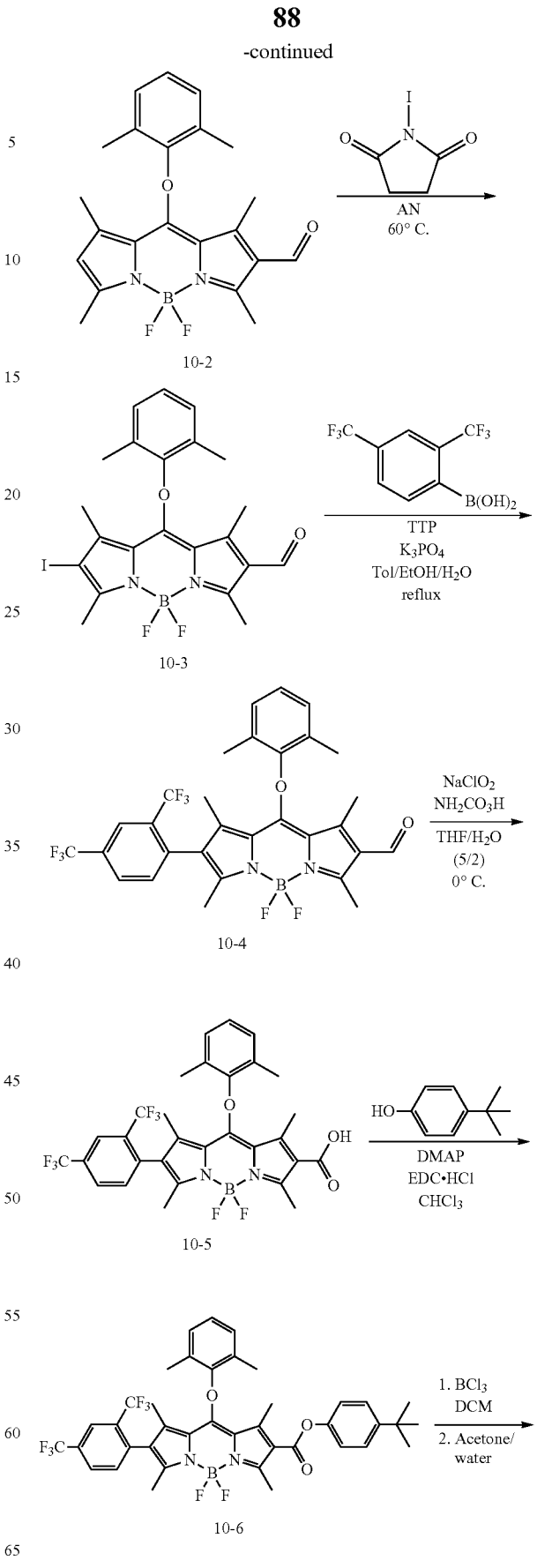

-continued

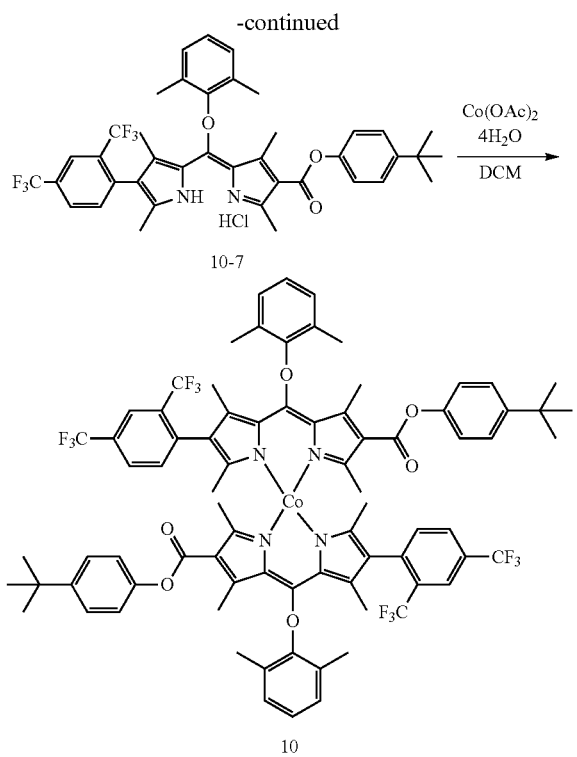

10

Synthesis of Compound 10-1

Synthesis was progressed in the same manner as in Synthesis of Compound 1-3 except that 2,6-dimethylphenol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 10-1 (4.5 g, yield 86.3%).

Synthesis of Compound 10-2

Synthesis was progressed in the same manner as in Synthesis of Compound 1-4 except that Compound 10-1 (4.5 g) was used instead of Compound 1-3. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 10-2 (4.4 g, yield 90.9%) was secured.

Synthesis of Compound 10-3

Synthesis was progressed in the same manner as in Synthesis of Compound 2-3 except that Compound 10-2 (4.4 g) was used instead of Compound 2-2. After the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 10-3 (5.2 g, yield 89.7%) was secured.

Synthesis of Compound 10-4

Compound 10-3 (5.2 g) was introduced to a solvent with a toluene/ethanol/water ratio of 2/2/1 (volume ratio), stirred well and dissolved therein. 2,4-Bistrifluoromethylphenylboronic acid (2.1 equivalent) and tripotassium phosphate (5.0 equivalent) were introduced thereto, and the result was heated to 80° C. and stirred for 30 minutes. After 30 minutes, tetrakistriphenylphosphine palladium (0.20 equivalent) was introduced to the heated reaction solution, and the result was stirred under reflux. When the reaction was completed, the result was extracted using chloroform and water. The extracted organic layer was dried with sodium sulfate and, after removing the solvent by vacuum distillation, recrystallized using methanol. Through the recrystallization, purified and separated Compound 10-4 (4.7 g, yield 77.6%) was secured.

Synthesis of Compound 10-5

Synthesis was progressed in the same manner as in Synthesis of Compound 1-5 except that Compound 10-4 (4.7 g) was used instead of Compound 1-4. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 10-5 (4.1 g, yield 85.0%).

Synthesis of Compound 10-6

Compound 10-5 (4.1 g) was stirred well and dissolved in a chloroform solvent. 4-t-Butylphenol (2.0 equivalent), 4-dimethylaminopyridine (DMAP) (2.2 equivalent) and N-(3-dimethylaminopropyl)-N'-ethylcarbodiimide hydrochloride (EDC-HCl) (2.2 equivalent) were introduced thereto, and the result was stirred well. After the reaction was completed, the result was extracted using chloroform and water. The extracted organic layer was dried with sodium sulfate and, after removing the solvent by vacuum distillation, recrystallized using ethanol. Through the recrystallization, purified and separated Compound 10-6 (3.6 g, yield 72.5%) was secured.

Synthesis of Compound 10-7

Synthesis was progressed in the same manner as in Synthesis of Compound 1-7 except that Compound 10-6 (3.6 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 10-7 (3.0 g, yield 84.6%) was secured.

Synthesis of Compound 10

Synthesis was progressed in the same manner as in Synthesis of Compound 1 except that Compound 10-7 (3.0 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 10 (2.4 g, yield 80.9%) was secured.
HR LC/MS/MS m/z calculated for $C_{80}H_{74}CoF_{12}N_4O_6$ (M+): 1473.4749; found: 1473.4755.
Preparation Example 11
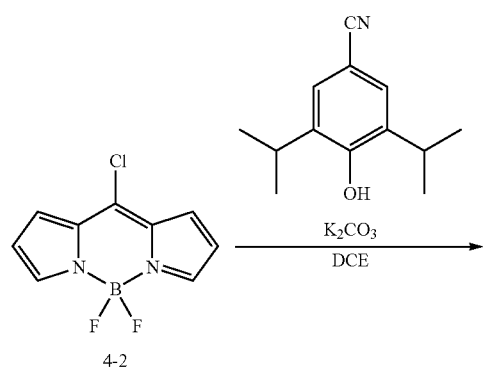
4-2
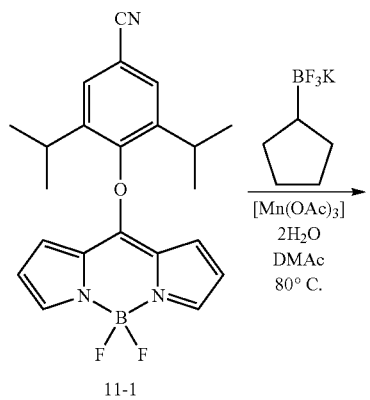
11-1
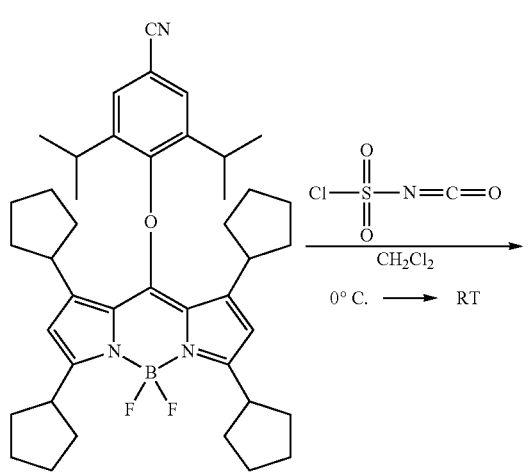
11-2
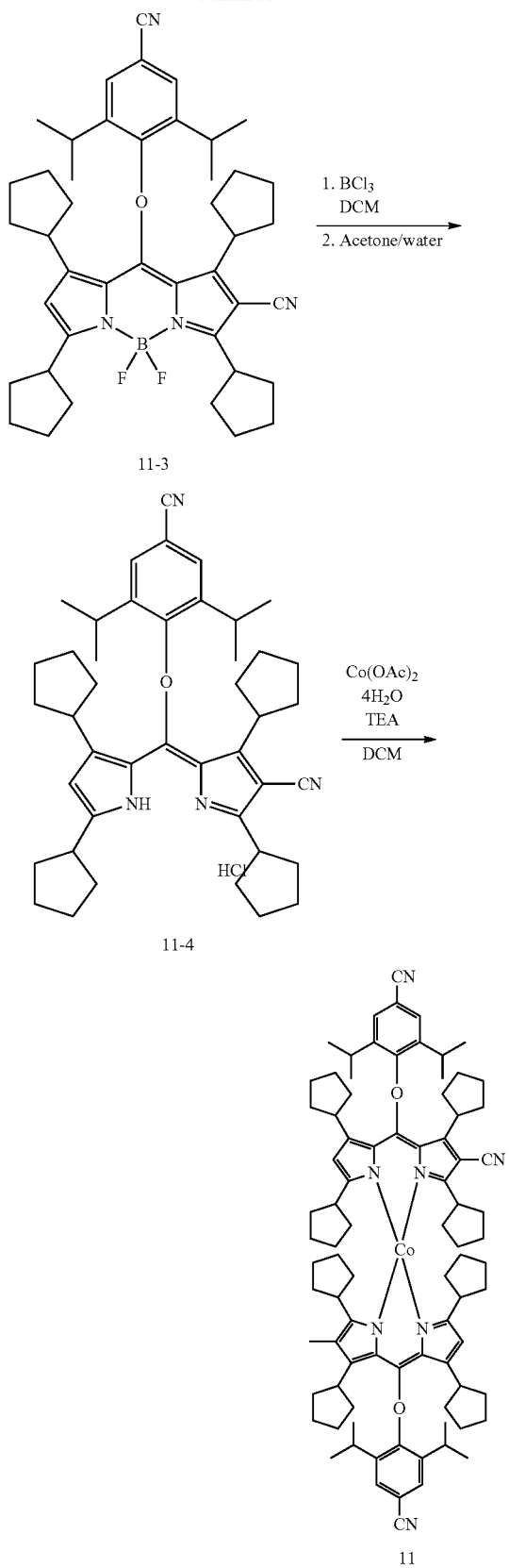
11-3
11-4
11

Synthesis of Compound 11-1

Synthesis was progressed in the same manner as in Synthesis of Compound 1-3 except that Compound 4-2 (4.0 g) was used instead of Compound 1-2, and 4-hydroxy-3,5-diisopropylbenzonitrile (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 11-1 (4.5 g, yield 64.8%).

Synthesis of Compound 11-2

Synthesis was progressed in the same manner as in Synthesis of Compound 4-4 except that Compound 11-1 (4.5 g) was used instead of Compound 4-3, and cyclopentyltrifluoroborate potassium salt was used instead of 2-methylcyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 11-2 (4.8 g, yield 63.0%).

Synthesis of Compound 11-3

Synthesis was progressed in the same manner as in Synthesis of Compound 4-5 except that Compound 11-2 (4.8 g) was used instead of Compound 4-4. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 11-3 (4.3 g, yield 86.3%) was secured.

Synthesis of Compound 11-4

Synthesis was progressed in the same manner as in Synthesis of Compound 1-7 except that Compound 11-3 (4.3 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 11-4 (3.8 g, yield 89.9%) was secured.

Synthesis of Compound 11

Synthesis was progressed in the same manner as in Synthesis of Compound 1 except that Compound 11-4 (3.8 g) was used instead of Compound 1-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 11 (3.3 g, yield 87.9%) was secured.

HR LC/MS/MS m/z calculated for $C_{86}H_{106}CoN_8O_2$ (M+): 1341.7771; found: 1341.7777.

Preparation Example 12

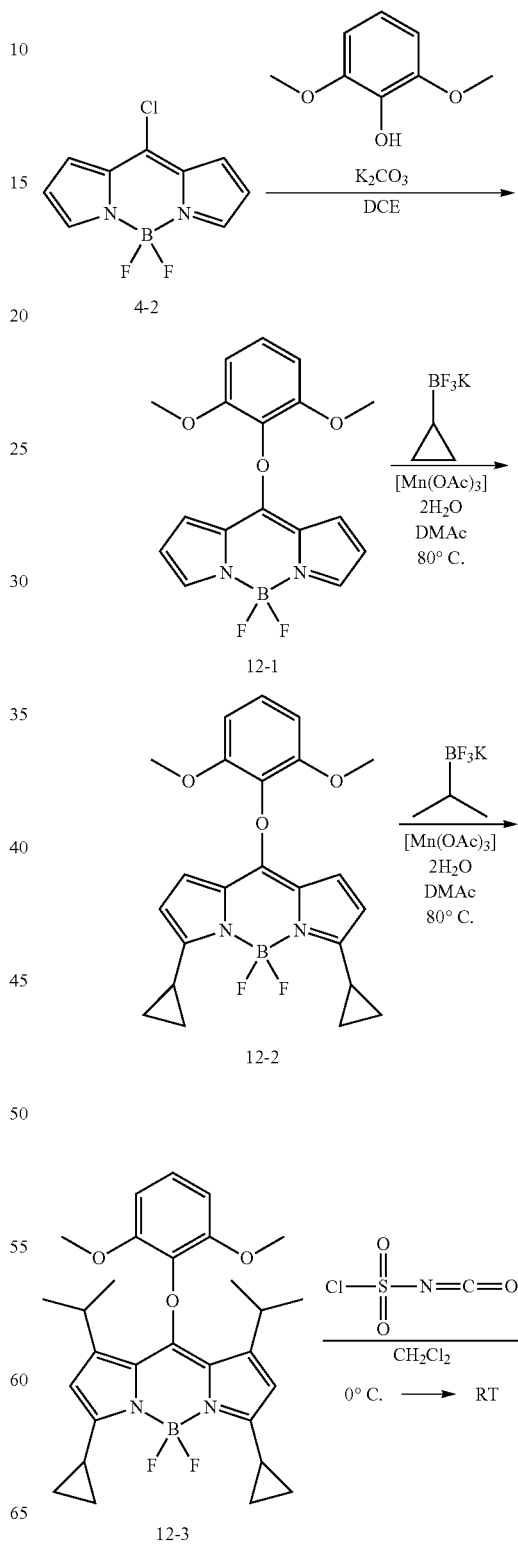

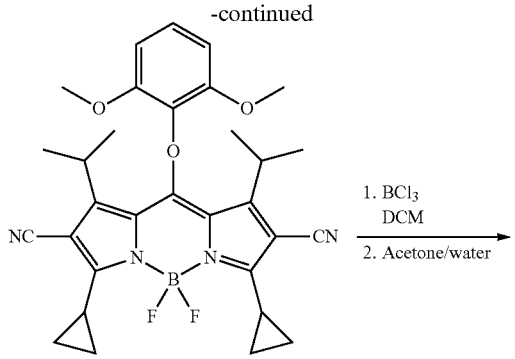

12-4

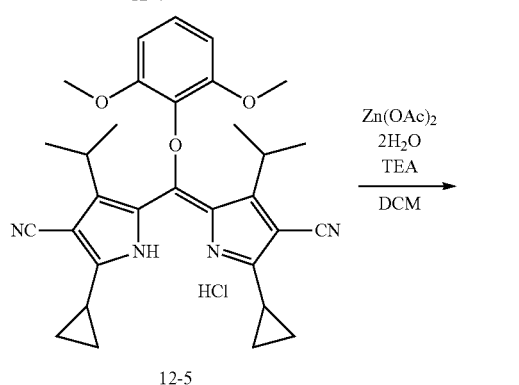

12-5

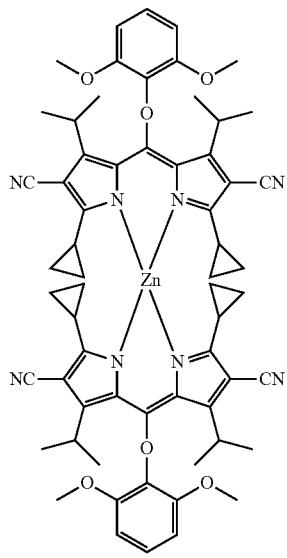

12

Synthesis of Compound 12-1

Synthesis was progressed in the same manner as in Synthesis of Compound 1-3 except that Compound 4-2 (4.0 g) was used instead of Compound 1-2, and 2,6-dimethoxyphenol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 12-1 (5.2 g, yield 85.5%).

Synthesis of Compound 12-2

Compound 12-1 (5.2 g) was stirred well and dissolved in an N,N-dimethylacetamide solvent. Cyclopropyltrifluoroborate potassium salt (3.0 equivalent) and manganese acetate hydrate (5.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 12-2 (4.4 g, yield 68.6%).

Synthesis of Compound 12-3

Synthesis was progressed in the same manner as in Synthesis of Compound 12-2 except that Compound 12-2 (4.4 g) was used instead of Compound 12-1, and isopropyltrifluoroborate potassium salt was used instead of cyclopropyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 12-3 (4.3 g, yield 81.5%).

Synthesis of Compound 12-4

Compound 12-3 (4.3 g) was stirred well and dissolved in a dichloromethane solvent. After cooling the reaction solution to 0° C. using ice water, chlorosulfonyl isocyanate (5.0 equivalent) was introduced thereto, and the result was stirred at room temperature. When the reaction was completed, N,N-dimethylformamide (10.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 12-4 (3.9 g, yield 82.6%) was secured.

Synthesis of Compound 12-5

Synthesis was progressed in the same manner as in Synthesis of Compound 1-7 except that Compound 12-4 (3.9 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 12-5 (3.3 g, yield 86.4%) was secured.

Synthesis of Compound 12

Synthesis was progressed in the same manner as in Synthesis of Compound 1 except that Compound 12-5 (3.3 g) was used instead of Compound 1-7, and zinc acetate dihydrate was used instead of cobalt acetate tetrahydrate.

After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 12 (2.7 g, yield 82.5%) was secured.

HR LC/MS/MS m/z calculated for $C_{62}H_{66}N_8O_6Zn$ (M+): 1082.4397; found: 1082.4391.

Preparation Example 13

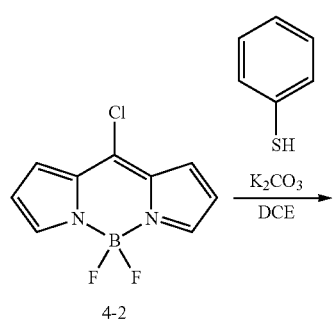

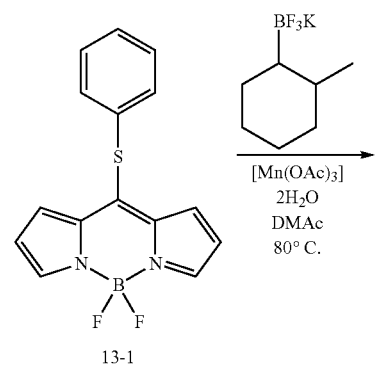

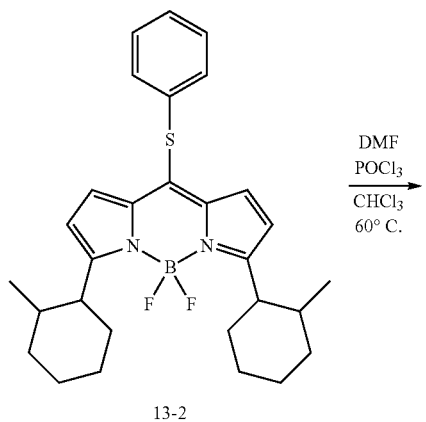

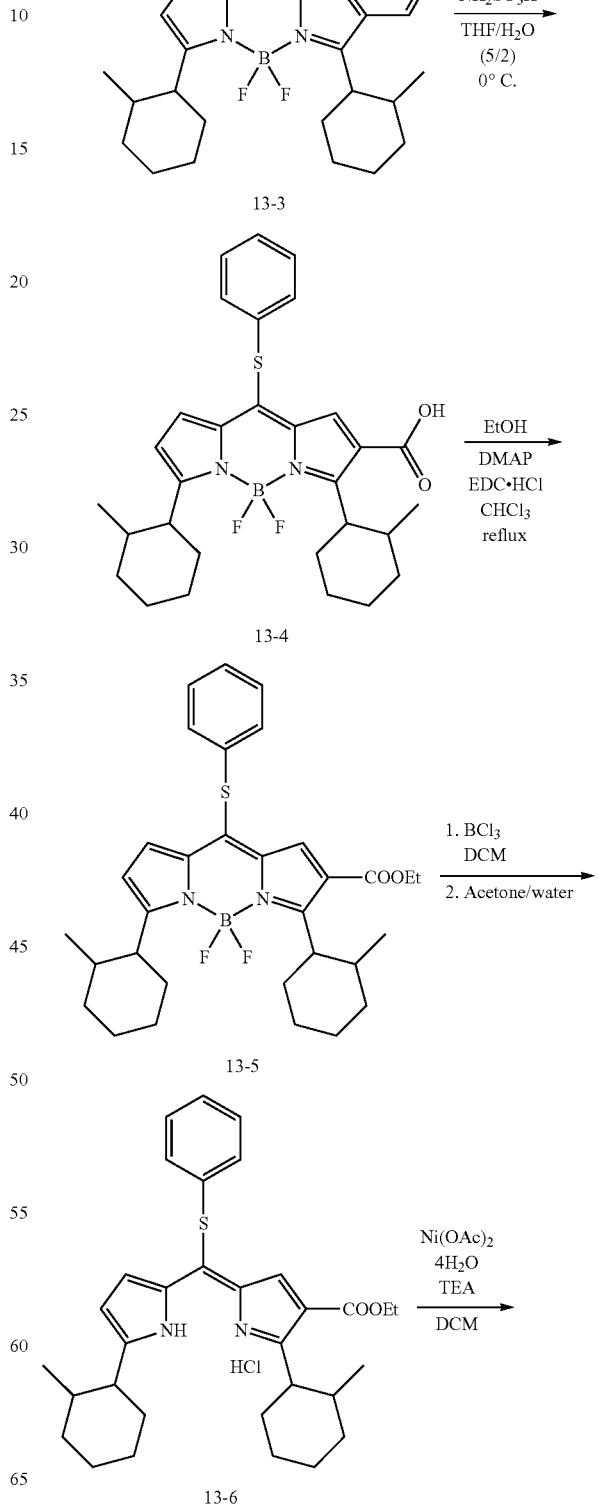

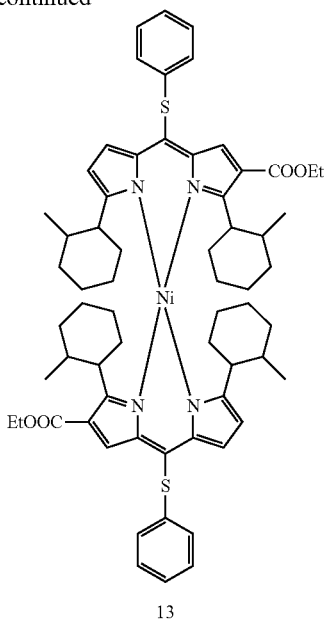

13

Synthesis of Compound 13-1

Synthesis was progressed in the same manner as in Synthesis of Compound 1-3 except that Compound 4-2 (4.0 g) was used instead of Compound 1-2, and benzenethiol (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 13-1 (4.5 g, yield 84.9%).

Synthesis of Compound 13-2

Synthesis was progressed in the same manner as in Synthesis of Compound 12-2 except that Compound 13-1 (4.5 g) was used instead of Compound 12-1, and 2-methylcyclohexyltrifluoroborate potassium salt was used instead of cyclopropyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 13-2 (4.8 g, yield 65.0%).

Synthesis of Compound 13-3

Synthesis was progressed in the same manner as in Synthesis of Compound 1-4 except that Compound 13-2 (4.8 g) was used instead of Compound 1-3. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 13-3 (4.3 g, yield 84.8%) was secured.

Synthesis of Compound 13-4

Synthesis was progressed in the same manner as in Synthesis of Compound 1-5 except that Compound 13-3 (4.3 g) was used instead of Compound 1-4. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 13-4 (3.7 g, yield 83.5%).

Synthesis of Compound 13-5

Synthesis was progressed in the same manner as in Synthesis of Compound 1-6 except that Compound 13-4 (3.7 g) was used instead of Compound 1-5. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 13-5 (3.2 g, yield 82.2%) was secured.

Synthesis of Compound 13-6

Synthesis was progressed in the same manner as in Synthesis of Compound 1-7 except that Compound 13-5 (3.2 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 13-6 (2.7 g, yield 86.1%) was secured.

Synthesis of Compound 13

Synthesis was progressed in the same manner as in Synthesis of Compound 1 except that Compound 13-6 (2.7 g) was used instead of Compound 1-7, and nickel acetate tetrahydrate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 13 (2.2 g, yield 82.7%) was secured.

HR LC/MS/MS m/z calculated for $C_{64}H_{78}N_4NiO_4S_2$ (M+): 1088.4818; found: 1088.4822.

Preparation Example 14

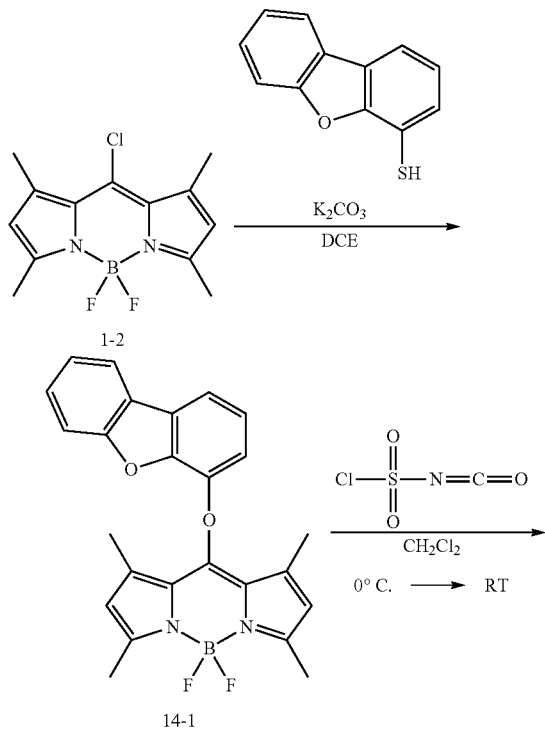

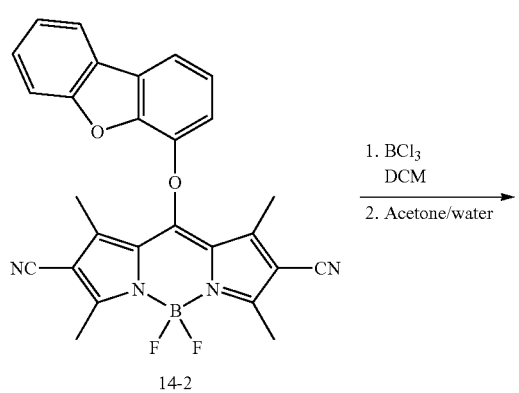

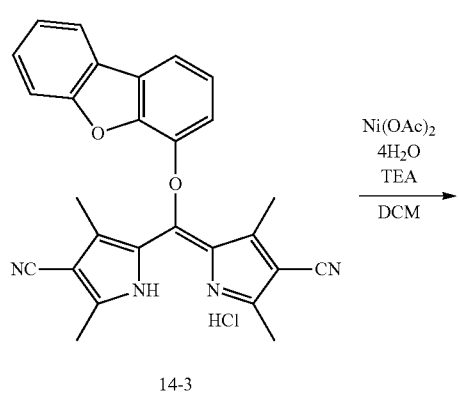

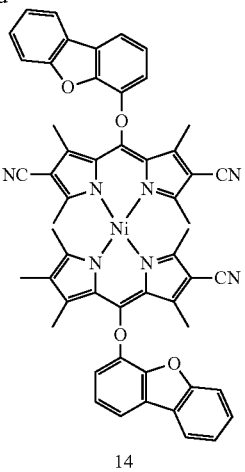

Synthesis of Compound 14-1

Synthesis was progressed in the same manner as in Synthesis of Compound 1-3 except that 4-hydroxydibenzofuran (1.0 equivalent) was used instead of 2,6-dimethylbenzenethiol. After identifying the completion of the reaction, the result was extracted using dichloromethane and an aqueous sodium bicarbonate solution. The extracted organic layer was dried with sodium sulfate, and then a silica gel column was used to secure purified and separated Compound 14-1 (5.1 g, yield 83.7%).

Synthesis of Compound 14-2

Synthesis was progressed in the same manner as in Synthesis of Compound 12-4 except that Compound 14-1 (5.1 g) was used instead of Compound 12-3. When the reaction was completed, N,N-dimethylformamide (10.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 14-2 (4.1 g, yield 72.0%) was secured.

Synthesis of Compound 14-3

Synthesis was progressed in the same manner as in Synthesis of Compound 1-7 except that Compound 14-2 (4.1 g) was used instead of Compound 1-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 14-3 (3.5 g, yield 87.4%) was secured.

Synthesis of Compound 14

Synthesis was progressed in the same manner as in Synthesis of Compound 1 except that Compound 14-3 (3.5 g) was used instead of Compound 1-7, and nickel acetate tetrahydrate was used instead of cobalt acetate tetrahydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 14 (2.7 g, yield 78.5%) was secured.
HR LC/MS/MS m/z calculated for $C_{54}H_{38}N_8NiO_4$ (M+): 920.2369; found: 920.2377.
Preparation Example 15
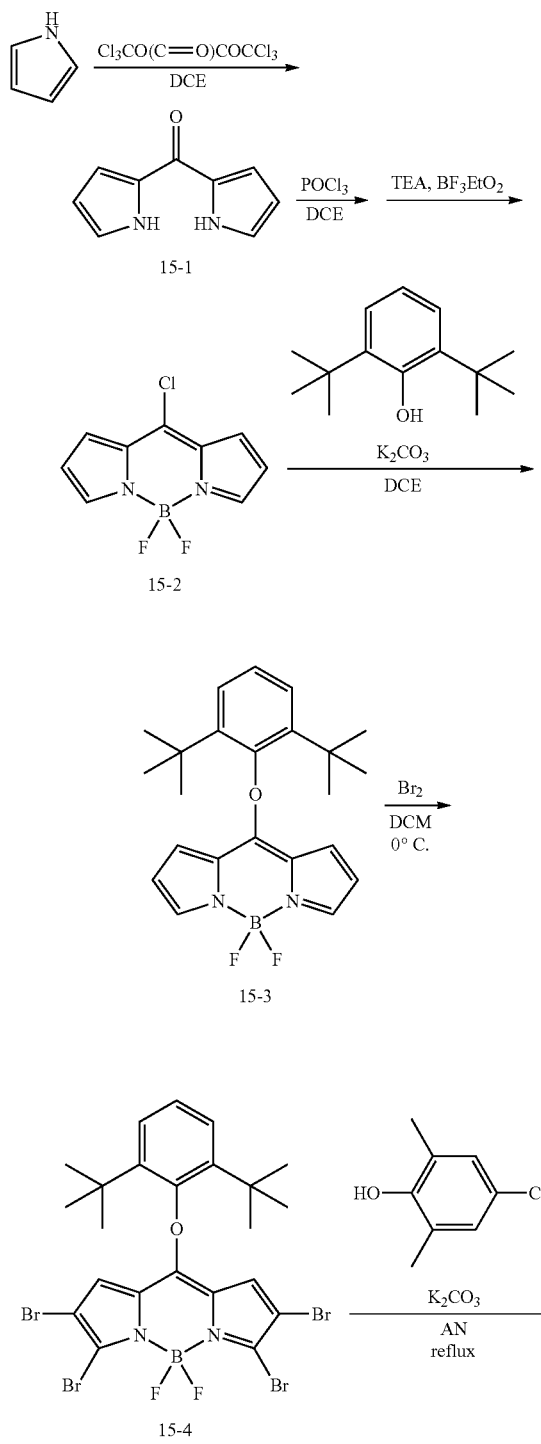
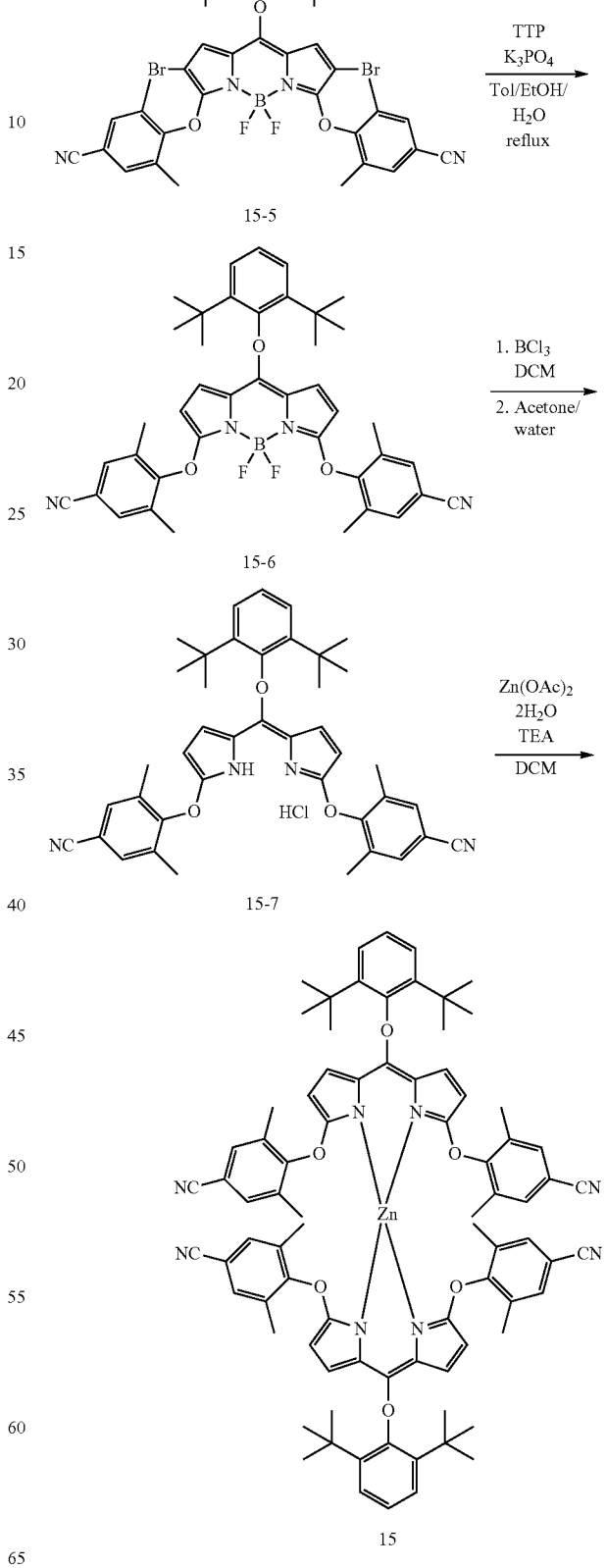

Synthesis of Compound 15-1

To pyrrole (50.0 g, 1.0 equivalent), a solution dissolving triphosgene (0.3 equivalent) in dichloroethane (DCE) was slowly introduced while stirring well. A solution dissolving trimethylamine (TEA) (0.1 equivalent) in dichloroethane was further introduced to the reaction solution under the nitrogen atmosphere at 0° C., and the result was kept for 2 hours. After that, pyrrole (1.0 equivalent) was further introduced to the reaction solution, and the result was heated for 30 minutes at approximately 80° C. After identifying the completion of the reaction, the result was extracted using dichloromethane and an aqueous sodium bicarbonate solution. The extracted organic layer was dried with sodium sulfate, and then a silica gel column was used to secure purified and separated Compound 15-1 (40.0 g, yield 33.5%).

Synthesis of Compound 15-2

Compound 15-1 (40.0 g) was stirred well and dissolved in a dichloroethane solvent. After cooling the reaction solution to 0° C. using ice water, phosphorous oxychloride ($POCl_3$) (2.0 equivalent) was introduced thereto, and the result was heated for 3 hours. After the reaction was finished, the result was cooled to room temperature, and after introducing triethylamine (10.0 equivalent) thereto, the temperature was maintained at 0° C. using ice water. A boron trifluoride ethyl ether complex ($BF_3 \cdot OEt_2$) (11.0 equivalent) was further introduced slowly thereto, and the result was further stirred for approximately 2 hours at room temperature. After identifying the completion of the reaction, the result was extracted using dichloromethane and water. The extracted organic layer was dried with sodium sulfate, and filtered using a silica pad to secure purified and separated Compound 15-2 (33.0 g, yield 58.4%).

Synthesis of Compound 15-3

Compound 15-2 (4.0 g) was stirred well and dissolved in a dichloroethane solvent. 2,6-Di-t-butylphenol (1.0 equivalent) and potassium carbonate (3.0 equivalent) were introduced thereto. The result was stirred at room temperature under the nitrogen atmosphere. After identifying the completion of the reaction, the result was extracted using diethyl ether and an aqueous sodium carbonate solution. The extracted organic layer was dried with sodium sulfate, and then a silica gel column was used to secure purified and separated Compound 15-3 (6.5 g, yield 92.8%).

Synthesis of Compound 15-4

Compound 15-3 (4.0 g) was stirred well and dissolved in a dichloromethane solvent. The temperature was maintained at 0° C. using ice water. Liquid bromine (4.0 equivalent) mixed with dichloromethane was slowly introduced thereto while maintaining 0° C., and the reaction solution was stirred. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 15-4 (6.4 g, yield 89.1%).

Synthesis of Compound 15-5

Compound 15-4 (4.0 g) was stirred well and dissolved in an acetonitrile (AN) solvent. Sodium carbonate (8.0 equivalent) and 4-hydroxy-3,5-dimethylbenzonitrile (4.0 equivalent) were introduced thereto, and the reaction solution was heated to 80° C. and stirred under reflux. After the reaction was completed, the result was extracted using chloroform and water. The extracted organic layer was dried with sodium sulfate and, after removing the solvent by vacuum distillation, recrystallized using methanol. Through the recrystallization, purified and separated Compound 15-5 (4.2 g, yield 88.5%) was secured.

Synthesis of Compound 15-6

Compound 15-5 (4.2 g) was introduced to a solvent with a toluene/ethanol/water ratio of 2/2/1 (volume ratio), stirred well and dissolved therein. Tripotassium phosphate (5.0 equivalent) was introduced thereto, and the result was heated to 80° C. and stirred for 30 minutes. After 30 minutes, tetrakistriphenylphosphine palladium (0.20 equivalent) was introduced to the heated reaction solution, and the result was stirred under reflux. When the reaction was completed, the result was extracted using chloroform and water. The extracted organic layer was dried with sodium sulfate and, after removing the solvent by vacuum distillation, recrystallized using methanol. Through the recrystallization, purified and separated Compound 15-6 (2.6 g, yield 76.1%) was secured.

Synthesis of Compound 15-7

Compound 15-6 (2.6 g) was stirred well and dissolved in a dichloromethane solvent. A boron trichloride 1.0 M heptane solution (1.0 equivalent) was slowly added dropwise thereto. When the reaction was completed, the solvent was vacuum distilled at a low temperature of 30° C. or lower, then acetone and water in a ratio of 10/1 (volume ratio) were introduced to the reaction solution remaining in the container, and the result was stirred well again. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 15-7 (2.1 g, yield 82.1%) was secured.

Synthesis of Compound 15

Compound 15-7 (2.1 g) was stirred well and dissolved in a dichloromethane solvent. Zinc acetate dihydrate (0.50 equivalent) was introduced to the reaction solution in a solid state, and triethylamine (2.5 equivalent) was further introduced thereto. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 15 (1.8 g, yield 86.3%) was secured.

HR LC/MS/MS m/z calculated for $C_{82}H_{82}N_8O_6Zn$ (M+): 1338.5649; found: 1338.5657.

Preparation Example 16
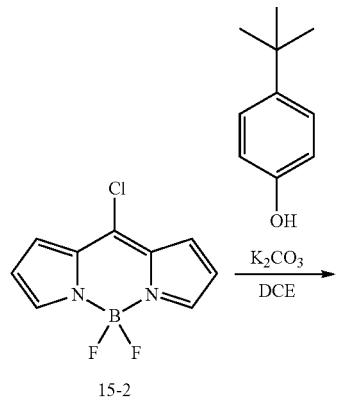
15-2
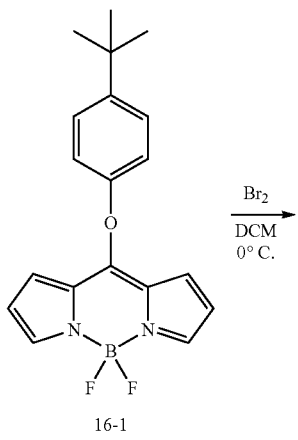
16-1
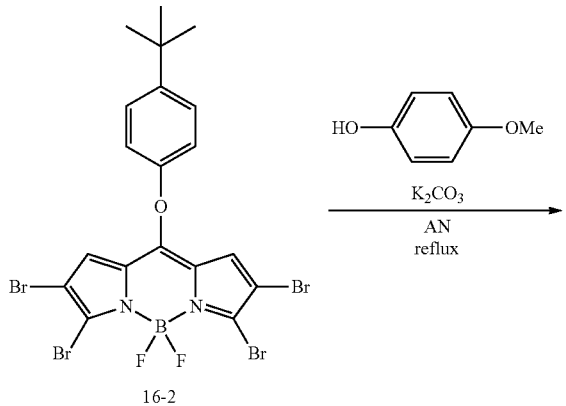
16-2
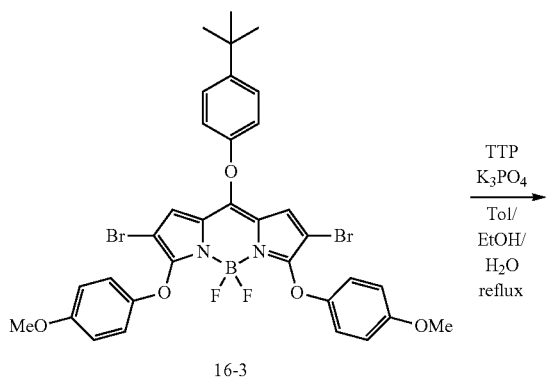
16-3
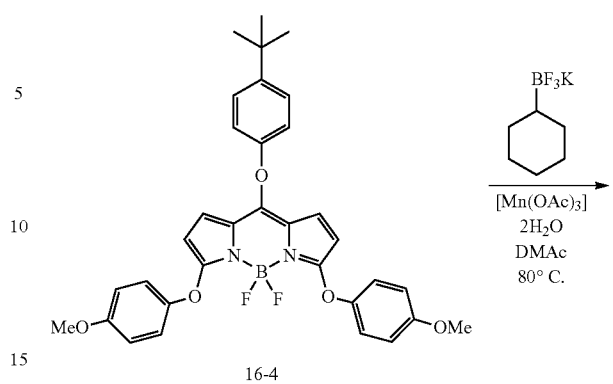
16-4
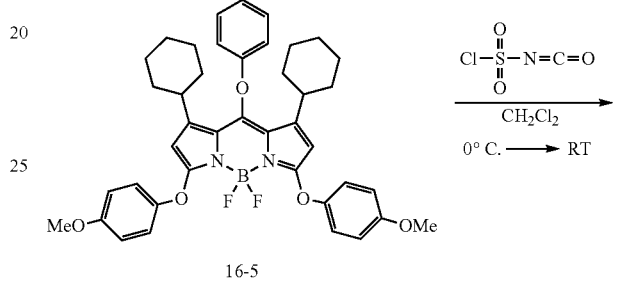
16-5
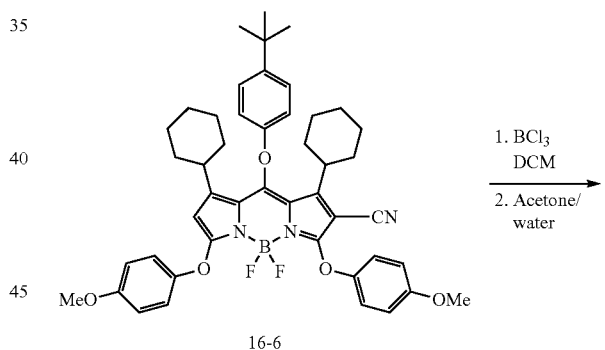
16-6
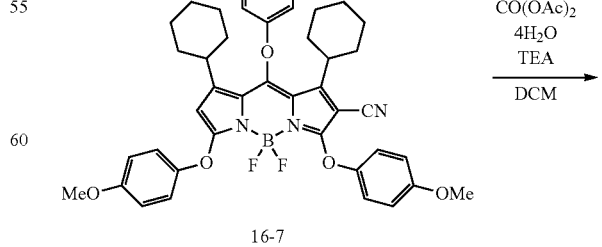
16-7

-continued

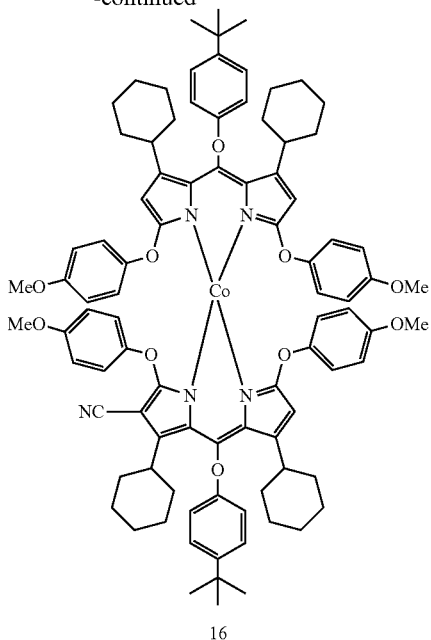

16

Synthesis of Compound 16-1

Synthesis was progressed in the same manner as in Synthesis of Compound 15-3 except that 4-t-butylphenol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 16-1 (5.4 g, yield 89.9%).

Synthesis of Compound 16-2

Synthesis was progressed in the same manner as in Synthesis of Compound 15-4 except that Compound 16-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 16-2 (6.9 g, yield 89.5%).

Synthesis of Compound 16-3

Synthesis was progressed in the same manner as in Synthesis of Compound 15-5 except that Compound 16-2 (4.0 g) was used instead of Compound 15-4, and 4-methoxyphenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 16-3 (3.8 g, yield 83.9%) was secured.

Synthesis of Compound 16-4

Synthesis was progressed in the same manner as in Synthesis of Compound 15-6 except that Compound 16-3 (3.8 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 16-4 (2.2 g, yield 73.5%) was secured.

Synthesis of Compound 16-5

Compound 16-4 (2.2 g) was stirred well and dissolved in an N,N-dimethylacetamide (DMAc) solvent. Cyclohexyltrifluoroborate potassium salt (3.0 equivalent) and manganese acetate hydrate (5.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran (THF), dried by introducing sodium sulfate thereto, and filtered. The solvent was removed by vacuum distillation, and a silica gel column was used to secure purified and separated Compound 16-5 (2.3 g, yield 81.6%).

Synthesis of Compound 16-6

Compound 16-5 (2.3 g) was stirred well and dissolved in a dichloromethane solvent. After cooling the reaction solution to 0° C. using ice water, chlorosulfonyl isocyanate (2.0 equivalent) was introduced thereto, and the result was stirred at room temperature. When the reaction was completed, N,N-dimethylformamide (DMF) (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 16-6 (2.1 g, yield 88.3%) was secured.

Synthesis of Compound 16-7

Synthesis was progressed in the same manner as in Synthesis of Compound 15-7 except that Compound 16-6 (2.1 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 16-7 (1.8 g, yield 87.0%) was secured.

Synthesis of Compound 16

Synthesis was progressed in the same manner as in Synthesis of Compound 15 except that Compound 16-7 (1.8 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 16 (1.5 g, yield 84.2%) was secured.

HR LC/MS/MS m/z calculated for $C_{92}H_{100}CoN_6O_{10}$ (M+): 1507.6833; found: 1507.6835.

Preparation Example 17

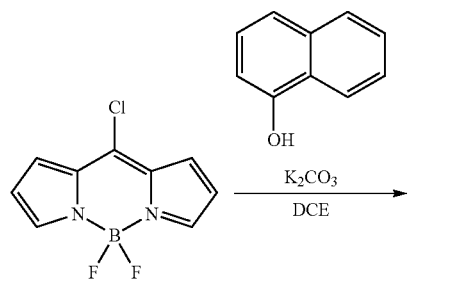
15-2

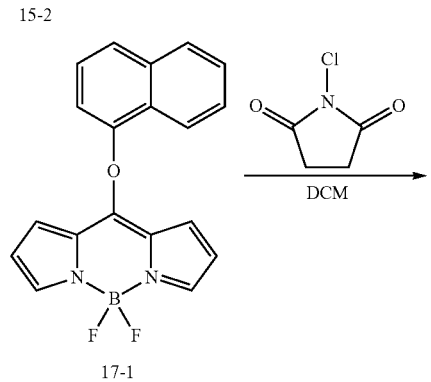
17-1

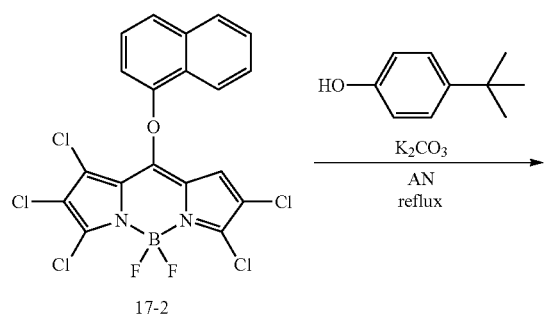
17-2

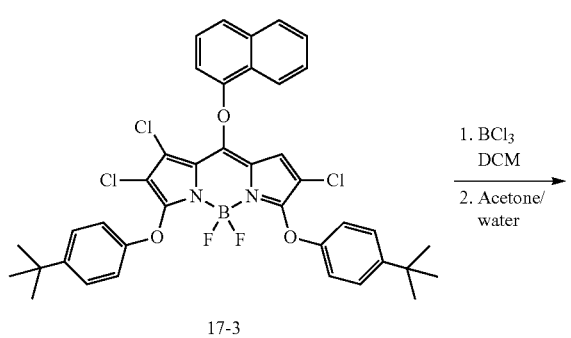
17-3

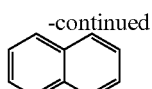

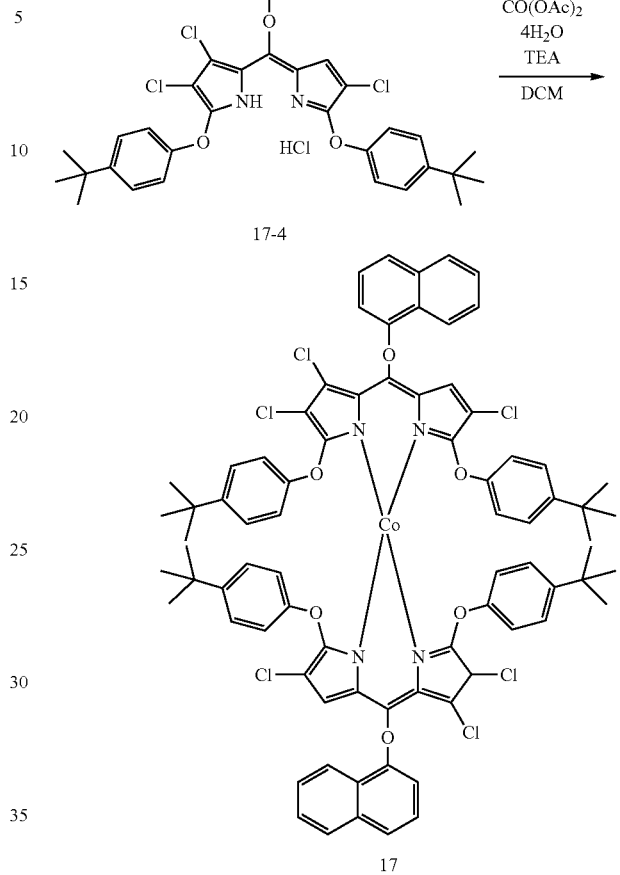
17-4

17

Synthesis of Compound 17-1

Synthesis was progressed in the same manner as in Synthesis of Compound 15-3 except that 1-naphthol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 17-1 (5.5 g, yield 93.2%).

Synthesis of Compound 17-2

Compound 17-1 (4.0 g) was stirred well and dissolved in a dichloromethane solvent. N-chlorosuccinimide (NCS) (10 equivalent) was slowly introduced thereto at room temperature. The result was stirred at room temperature to proceed a reaction, and after the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 17-2 (5.4 g, yield 89.1%) was secured.

Synthesis of Compound 17-3

Synthesis was progressed in the same manner as in Synthesis of Compound 15-5 except that Compound 17-2

(4.0 g) was used instead of Compound 15-4, and 4-t-butylphenol (2.1 equivalent) was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 17-3 (5.3 g, yield 91.4%) was secured.

Synthesis of Compound 17-4

Synthesis was progressed in the same manner as in Synthesis of Compound 15-7 except that Compound 17-3 (3.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 17-4 (2.3 g, yield 77.9%) was secured.

Synthesis of Compound 17

Synthesis was progressed in the same manner as in Synthesis of Compound 15 except that Compound 17-4 (2.3 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 17 (2.0 g, yield 87.9%) was secured.

HR LC/MS/MS m/z calculated for $C_{78}H_{68}Cl_6CoN_4O_6$ (M+): 1425.2602; found: 1425.2609.

Preparation Example 18

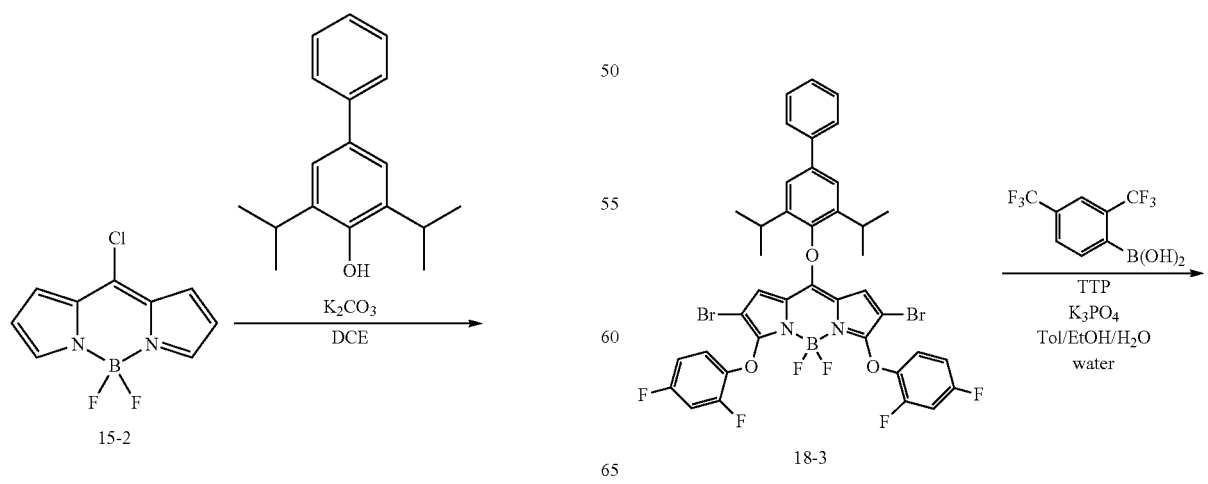

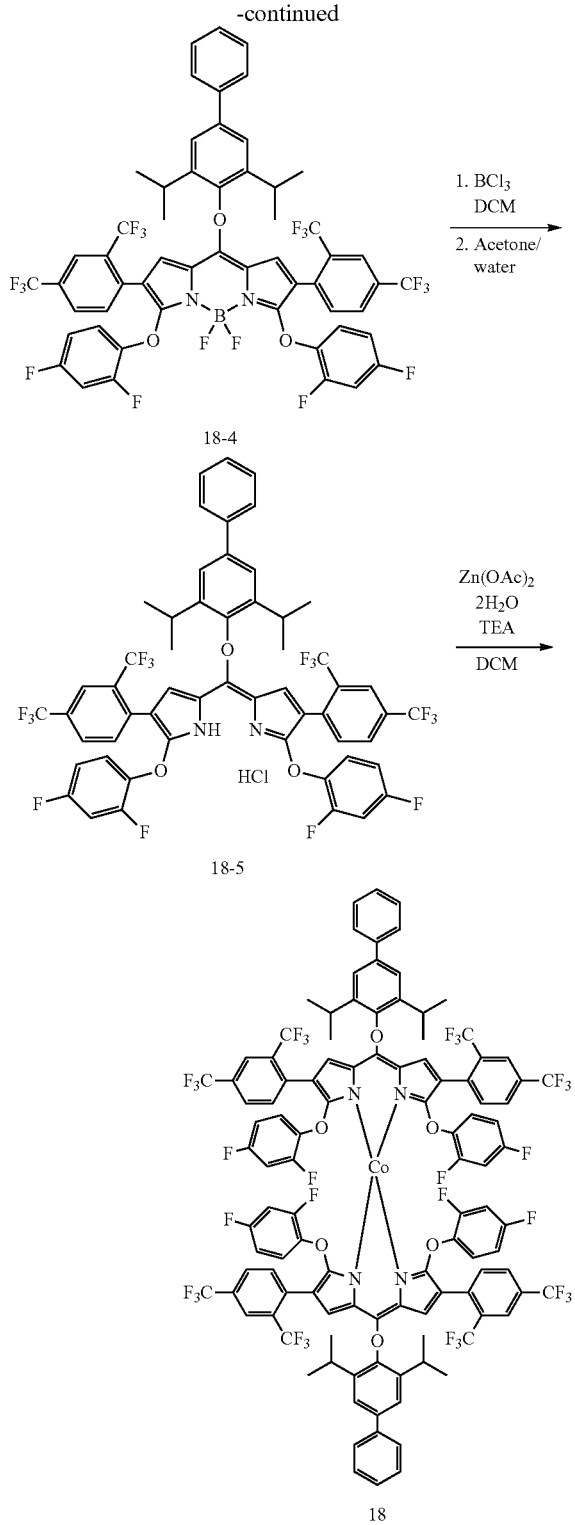

18-4

18-5

18

Synthesis of Compound 18-1

Synthesis was progressed in the same manner as in Synthesis of Compound 15-3 except that 3,5-diisopropyl-biphenyl-4-ol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 18-1 (7.1 g, yield 90.4%).

Synthesis of Compound 18-2

Synthesis was progressed in the same manner as in Synthesis of Compound 15-4 except that Compound 18-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 18-2 (6.2 g, yield 90.6%).

Synthesis of Compound 18-3

Synthesis was progressed in the same manner as in Synthesis of Compound 15-5 except that Compound 18-2 (4.0 g) was used instead of Compound 15-4, and 2,4-difluorophenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 18-3 (3.9 g, yield 86.3%) was secured.

Synthesis of Compound 18-4

Compound 18-3 (3.9 g) was introduced to a solvent with a toluene/ethanol/water ratio of 2/2/1 (volume ratio), stirred well and dissolved therein. 2,4-Bistrifluoromethylphenylboronic acid (4.2 equivalent) and tripotassium phosphate (10.0 equivalent) were introduced thereto, and the result was heated to 80° C. and stirred for 30 minutes. After 30 minutes, tetrakistriphenylphosphine palladium (0.20 equivalent) was introduced to the heated reaction solution, and the result was stirred under reflux. When the reaction was completed, the result was extracted using chloroform and water. The extracted organic layer was dried with sodium sulfate and, after removing the solvent by vacuum distillation, recrystallized using methanol. Through the recrystallization, purified and separated Compound 18-4 (4.3 g, yield 84.1%) was secured.

Synthesis of Compound 18-5

Synthesis was progressed in the same manner as in Synthesis of Compound 15-7 except that Compound 18-4 (3.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 18-5 (2.3 g, yield 77.4%) was secured.

Synthesis of Compound 18

Synthesis was progressed in the same manner as in Synthesis of Compound 15 except that Compound 18-5 (2.3 g) was used instead of Compound 15-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 18 (1.9 g, yield 83.0%) was secured.
HR LC/MS/MS m/z calculated for $C_{110}H_{70}F_{32}N_4O_6Zn$ (M+): 2214.4076; found: 2214.4085.
Preparation Example 19
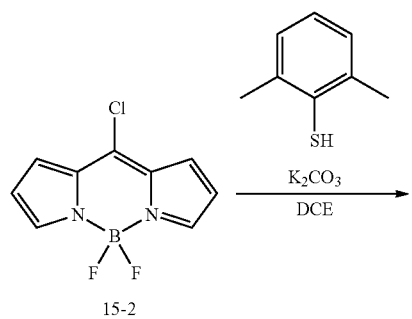
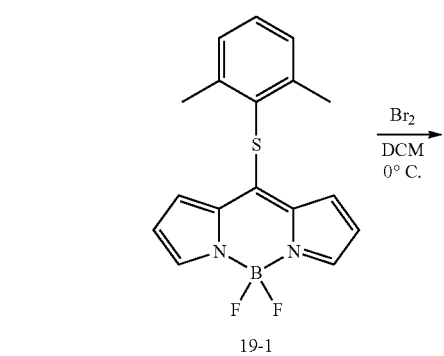
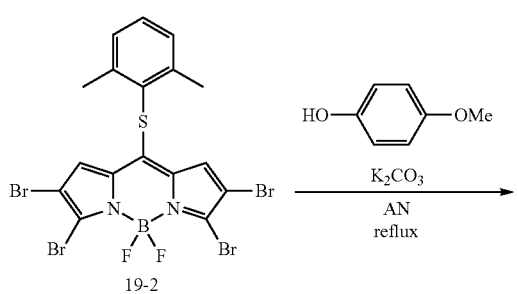
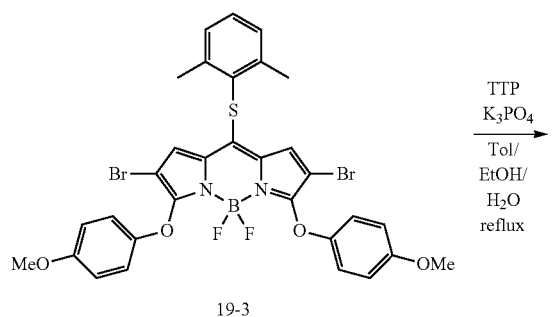
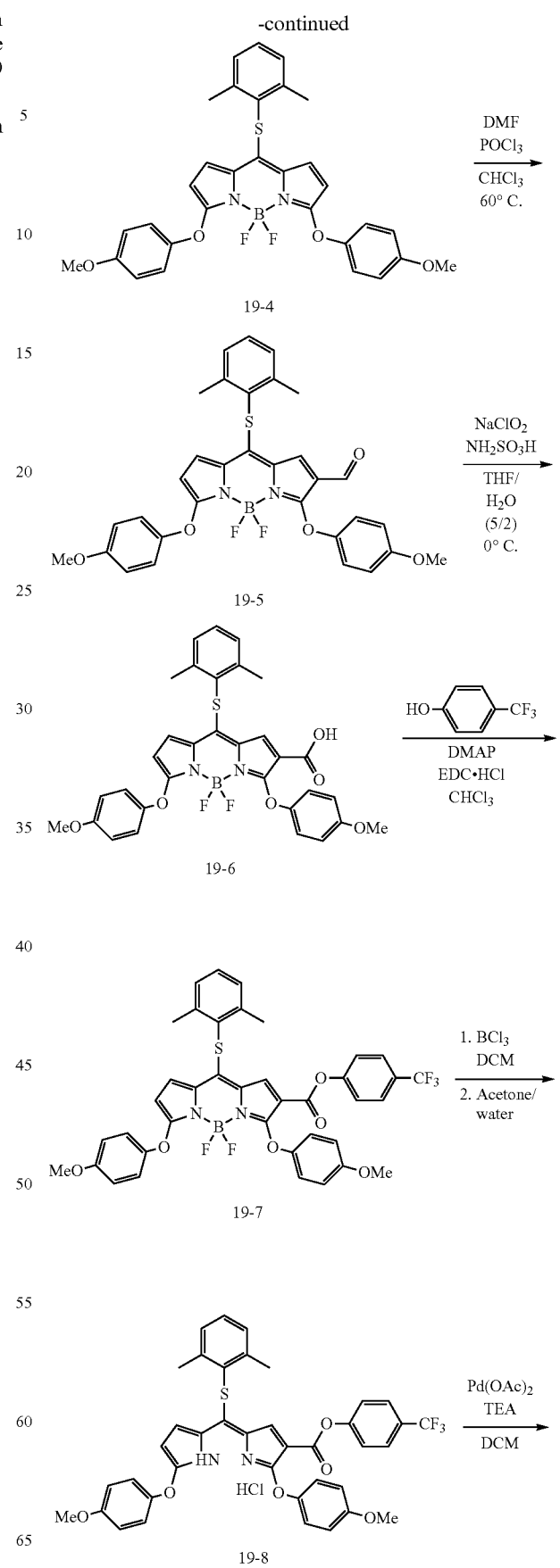

-continued

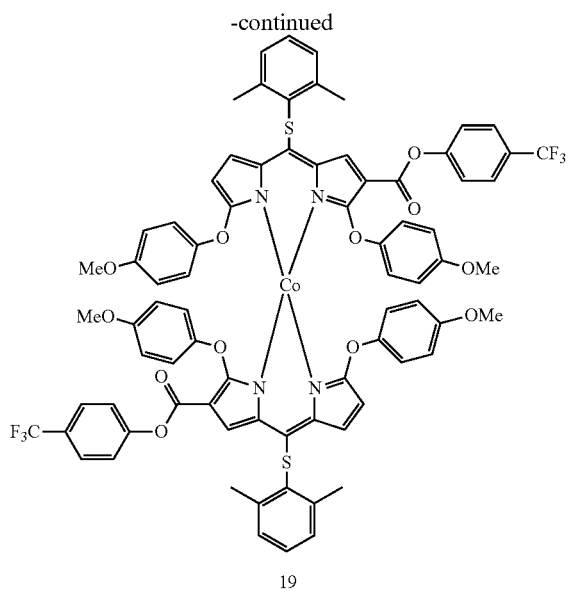

19

Synthesis of Compound 19-1

Synthesis was progressed in the same manner as in Synthesis of Compound 15-3 except that 2,6-dimethylbenzenethiol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 19-1 (5.1 g, yield 88.0%).

Synthesis of Compound 19-2

Synthesis was progressed in the same manner as in Synthesis of Compound 15-4 except that Compound 19-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 19-2 (7.3 g, yield 93.0%).

Synthesis of Compound 19-3

Synthesis was progressed in the same manner as in Synthesis of Compound 15-5 except that Compound 19-2 (4.0 g) was used instead of Compound 15-4, and 4-methoxyphenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 19-3 (4.2 g, yield 92.6%) was secured.

Synthesis of Compound 19-4

Synthesis was progressed in the same manner as in Synthesis of Compound 15-6 except that Compound 19-3 (4.2 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 19-4 (2.8 g, yield 85.1%) was secured.

Synthesis of Compound 19-5

Under the nitrogen atmosphere at 0° C., phosphorous oxychloride ($POCl_3$) (2.0 equivalent) and N,N-dimethylformamide (3.0 equivalent) were introduced to a chloroform solvent, and the mixture was stirred well for 1 hour. After 1 hour, Compound 19-4 (2.8 g) was introduced to the mixture solution, and the result was stirred under reflux at 60° C. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 19-5 (2.5 g, yield 85.1%) was secured.

Synthesis of Compound 19-6

Compound 19-5 (2.5 g) was stirred well and dissolved in a tetrahydrofuran solvent. Amidosulfonic acid (1.5 equivalent) dissolved in water was introduced thereto, and the result was stirred at room temperature. The reaction solution was cooled to 0° C., and the result was stirred well while slowly introducing sodium chlorite (1.0 equivalent) dissolved in water thereto. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 19-6 (2.1 g, yield 81.8%).

Synthesis of Compound 19-7

Compound 19-6 (2.1 g) was stirred well and dissolved in a chloroform solvent. 4-Hydroxybenzotrifluoride (2.1 equivalent), 4-dimethylaminopyridine (DMAP) (2.2 equivalent) and N-(3-dimethylaminopropyl)-N'-ethylcarbodiimide hydrochloride (EDC-HCl) (2.2 equivalent) were introduced thereto, and the result was heated and stirred. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 19-7 (2.2 g, yield 84.9%) was secured.

Synthesis of Compound 19-8

Synthesis was progressed in the same manner as in Synthesis of Compound 15-7 except that Compound 19-7 (2.2 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 19-8 (1.8 g, yield 83.1%) was secured.

Synthesis of Compound 19

Synthesis was progressed in the same manner as in Synthesis of Compound 15 except that Compound 19-8 (1.8 g) was used instead of Compound 15-7, and palladium acetate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 19 (1.5 g, yield 81.6%) was secured.

HR LC/MS/MS m/z calculated for $C_{78}H_{60}F_6N_4O_{12}PdS_2$ (M+): 1528.2588; found: 1528.2596.

Preparation Example 20

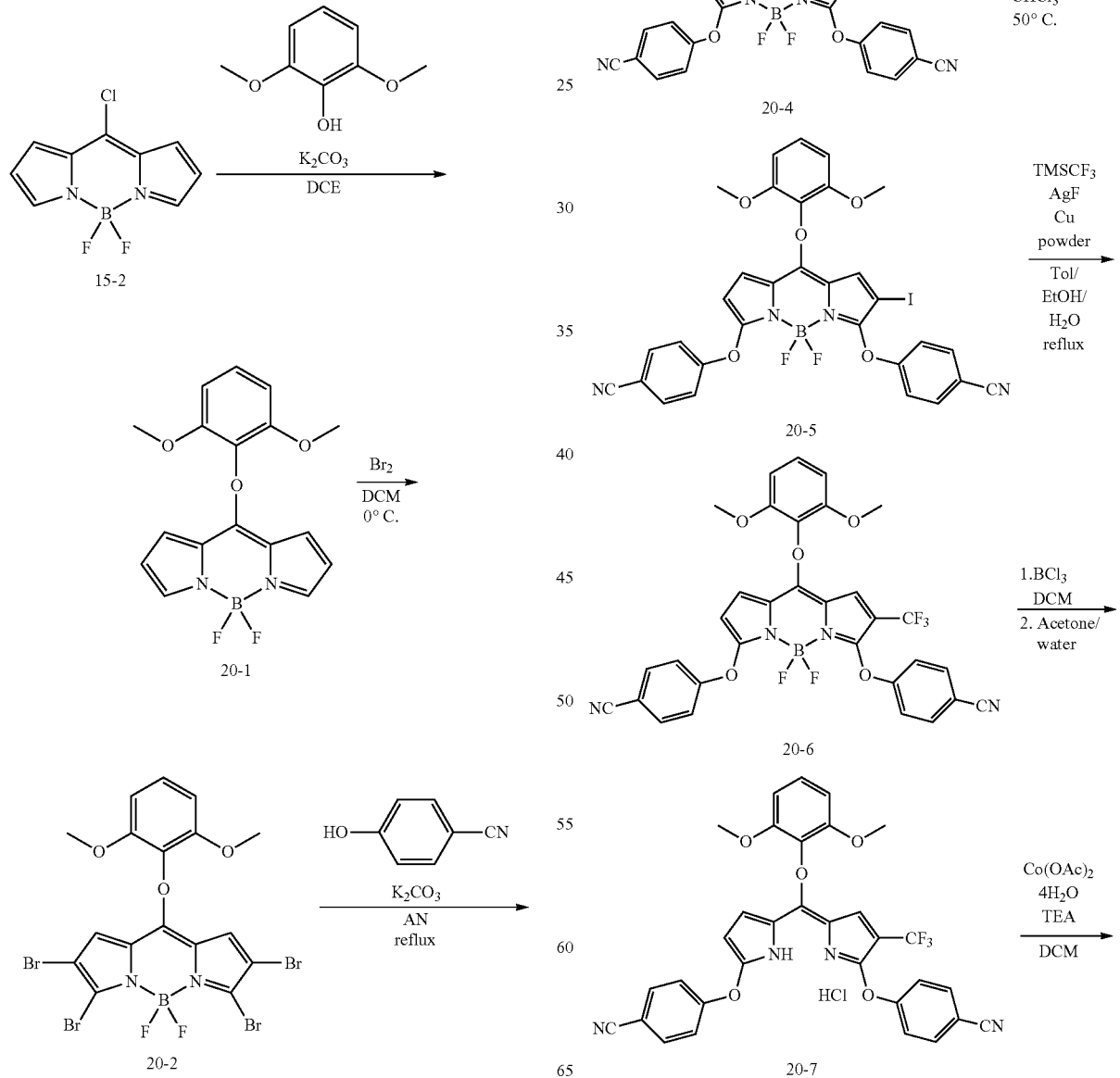

-continued

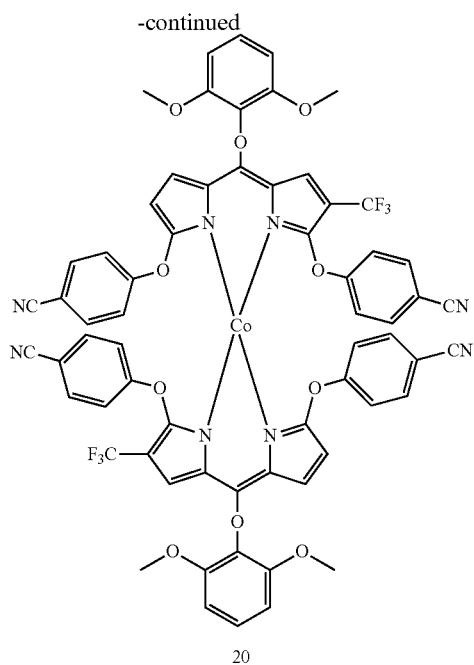

20

Synthesis of Compound 20-1

Synthesis was progressed in the same manner as in Synthesis of Compound 15-3 except that 2,6-dimethoxyphenol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 20-1 (5.6 g, yield 92.1%).

Synthesis of Compound 20-2

Synthesis was progressed in the same manner as in Synthesis of Compound 15-4 except that Compound 20-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 20-2 (7.1 g, yield 92.6%).

Synthesis of Compound 20-3

Synthesis was progressed in the same manner as in Synthesis of Compound 15-5 except that Compound 20-2 (4.0 g) was used instead of Compound 15-4, and 4-hydroxybenzonitrile was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 20-3 (3.9 g, yield 87.4%) was secured.

Synthesis of Compound 20-4

Synthesis was progressed in the same manner as in Synthesis of Compound 15-6 except that Compound 20-3 (3.9 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 20-4 (2.6 g, yield 84.9%) was secured.

Synthesis of Compound 20-5

Compound 20-4 (2.6 g) was stirred well and dissolved in a chloroform solvent. N-iodosuccinimide (NIS) (2.0 equivalent) was slowly introduced thereto at room temperature. The result was heated to 50° C. and stirred to proceed a reaction, and after the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 20-5 (3.0 g, yield 94.8%) was secured.

Synthesis of Compound 20-6

Under the nitrogen atmosphere at 0° C., silver fluoride (AgF) (2.0 equivalent) was introduced to an N,N-dimethylformamide solvent, and stirred well. Trimethyltrifluoromethylsilane ($TMSCF_3$) (2.0 equivalent) was slowly added dropwise to the reaction solution while maintaining the temperature. The result was stirred well for 30 minutes while slowly raising the temperature to room temperature. When the reaction solution became uniform, Cu powder (2.0 equivalent) was introduced thereto, and the result was stirred well for 2 hours. After 2 hours, Compound 20-5 (3.0 g) was introduced to the mixture solution, and the result was heated to 60° C. and stirred. After the reaction was completed, water was introduced to the reaction solution, and the result was stirred well and filtered to obtain a material in a solid state. This was extracted again using ethyl acetate and hexane. The extracted organic layer was dried with sodium sulfate, and after removing the solvent by vacuum distillation, Compound 20-6 (2.3 g, yield 83.5%) was secured without further purification.

Synthesis of Compound 20-7

Synthesis was progressed in the same manner as in Synthesis of Compound 15-7 except that Compound 20-6 (2.3 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 20-7 (2.0 g, yield 88.5%) was secured.

Synthesis of Compound 20

Synthesis was progressed in the same manner as in Synthesis of Compound 15 except that Compound 20-7 (2.0 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 20 (1.7 g, yield 86.1%) was secured.
HR LC/MS/MS m/z calculated for $C_{64}H_{40}CoF_6N_8O_{10}$ (M+): 1253.2104; found: 1253.2111.
Preparation Example 21
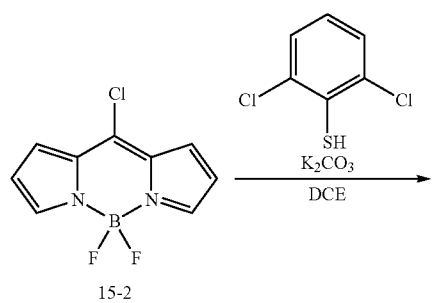
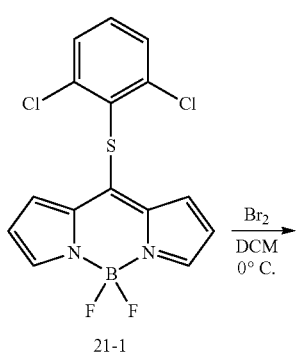
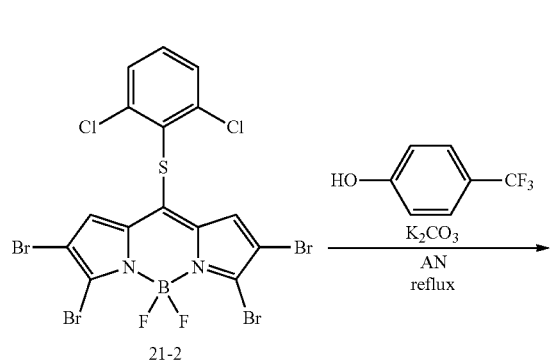
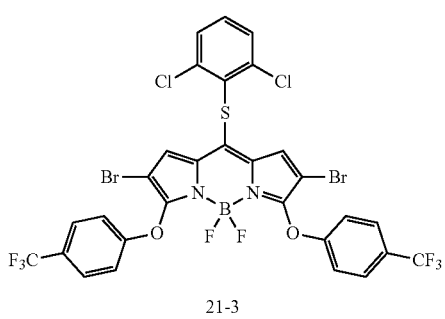
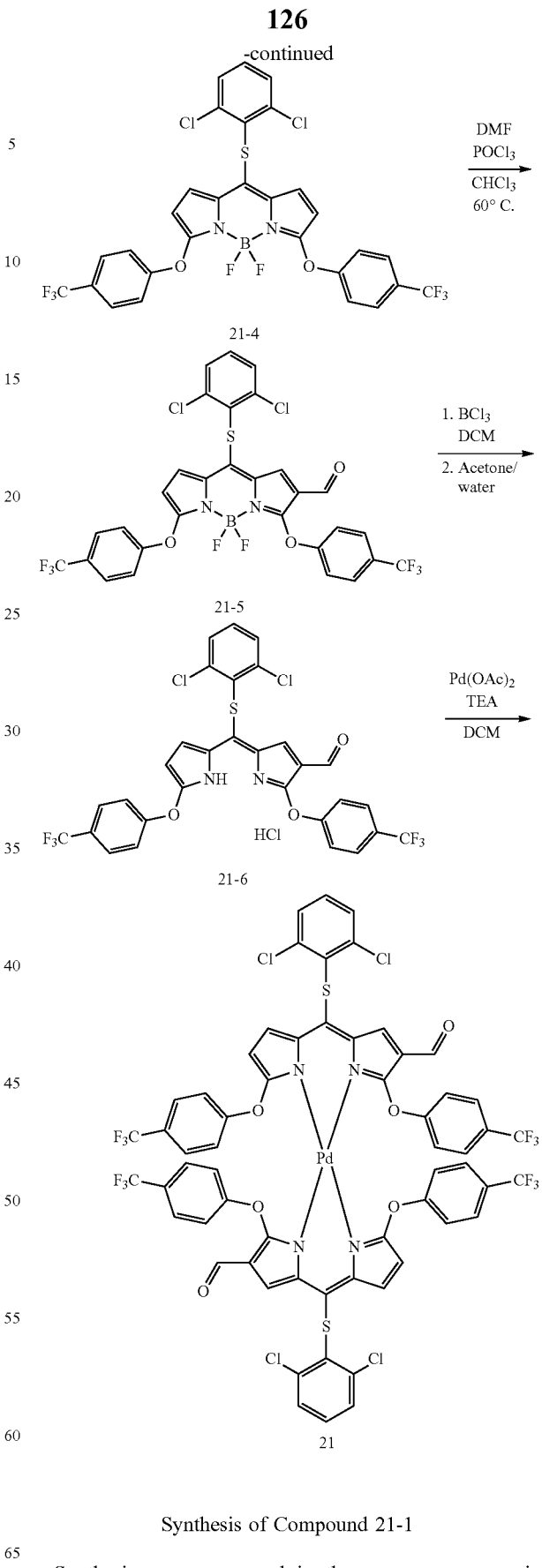
Synthesis of Compound 21-1
Synthesis was progressed in the same manner as in Synthesis of Compound 15-3 except that 2,6-dichlorobenzenethiol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 21-1 (6.1 g, yield 93.6%).

Synthesis of Compound 21-2

Synthesis was progressed in the same manner as in Synthesis of Compound 15-4 except that Compound 21-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 21-2 (6.9 g, yield 93.0%).

Synthesis of Compound 21-3

Synthesis was progressed in the same manner as in Synthesis of Compound 15-5 except that Compound 21-2 (4.0 g) was used instead of Compound 15-4, and 4-hydroxybenzotrifluoride was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 21-3 (4.2 g, yield 84.9%) was secured.

Synthesis of Compound 21-4

Synthesis was progressed in the same manner as in Synthesis of Compound 15-6 except that Compound 21-3 (4.2 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 21-4 (2.9 g, yield 84.8%) was secured.

Synthesis of Compound 21-5

Synthesis was progressed in the same manner as in Synthesis of Compound 19-5 except that Compound 21-4 (2.9 g) was used instead of Compound 19-4. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 21-5 (2.6 g, yield 86.1%) was secured.

Synthesis of Compound 21-6

Synthesis was progressed in the same manner as in Synthesis of Compound 15-7 except that Compound 21-5 (2.6 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 21-6 (2.1 g, yield 82.1%) was secured.

Synthesis of Compound 21

Synthesis was progressed in the same manner as in Synthesis of Compound 15 except that Compound 21-6 (2.1 g) was used instead of Compound 15-7, and palladium acetate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 21 (1.8 g, yield 83.8%) was secured.

HR LC/MS/MS m/z calculated for $C_{60}H_{30}Cl_4F_{12}N_4O_6PdS_2$ (M+): 1439.9204; found: 1439.9213.

Preparation Example 22

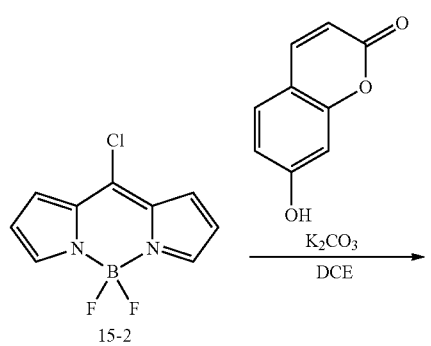

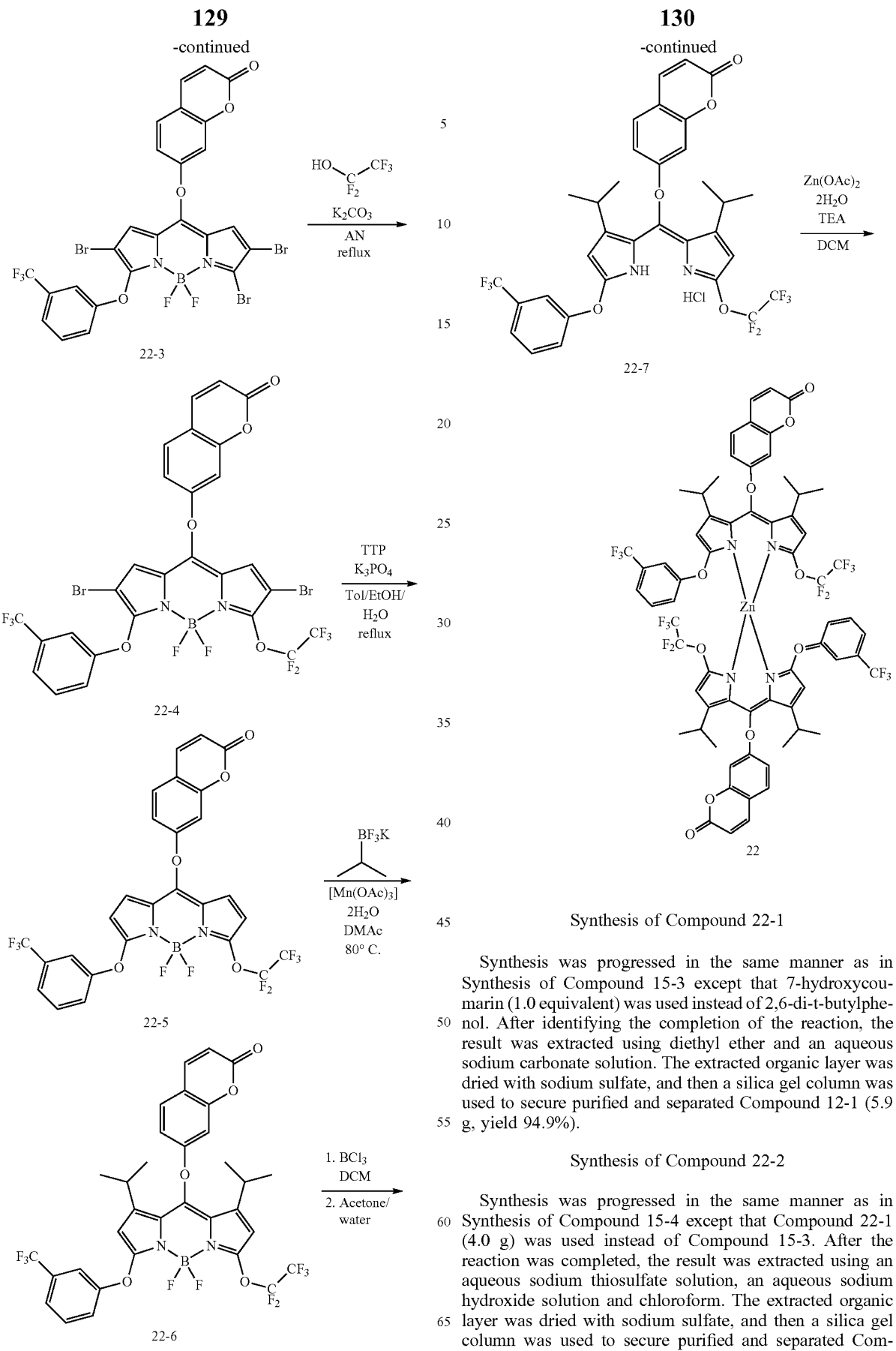

Synthesis of Compound 22-1

Synthesis was progressed in the same manner as in Synthesis of Compound 15-3 except that 7-hydroxycoumarin (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 12-1 (5.9 g, yield 94.9%).

Synthesis of Compound 22-2

Synthesis was progressed in the same manner as in Synthesis of Compound 15-4 except that Compound 22-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 22-2 (7.0 g, yield 92.3%).

Synthesis of Compound 22-3

Synthesis was progressed in the same manner as in Synthesis of Compound 15-5 except that Compound 22-2 (4.0 g) was used instead of Compound 15-4, and 3-hydroxybenzotrifluoride (1.1 equivalent) was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 22-3 (3.7 g, yield 82.5%) was secured.

Synthesis of Compound 22-4

Synthesis was progressed in the same manner as in Synthesis of Compound 15-5 except that Compound 22-3 (3.7 g) was used instead of Compound 15-4, and pentafluoroethanol (1.1 equivalent) was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 22-4 (3.3 g, yield 83.1%) was secured.

Synthesis of Compound 22-5

Synthesis was progressed in the same manner as in Synthesis of Compound 15-6 except that Compound 22-4 (3.3 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 22-5 (2.2 g, yield 83.0%) was secured.

Synthesis of Compound 22-6

Synthesis was progressed in the same manner as in Synthesis of Compound 16-5 except that Compound 22-5 (2.2 g) was used instead of Compound 16-4, and isopropyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 22-6 (2.1 g, yield 84.4%).

Synthesis of Compound 22-7

Synthesis was progressed in the same manner as in Synthesis of Compound 15-7 except that Compound 22-6 (2.1 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 22-7 (1.6 g, yield 77.4%) was secured.

Synthesis of Compound 22

Synthesis was progressed in the same manner as in Synthesis of Compound 15 except that Compound 22-7 (1.6 g) was used instead of Compound 15-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 22 (1.3 g, yield 81.8%) was secured.

HR LC/MS/MS m/z calculated for $C_{33}H_{26}F_8N_2O_5$(M+): 682.1714; found: 682.1719.

Preparation Example 23

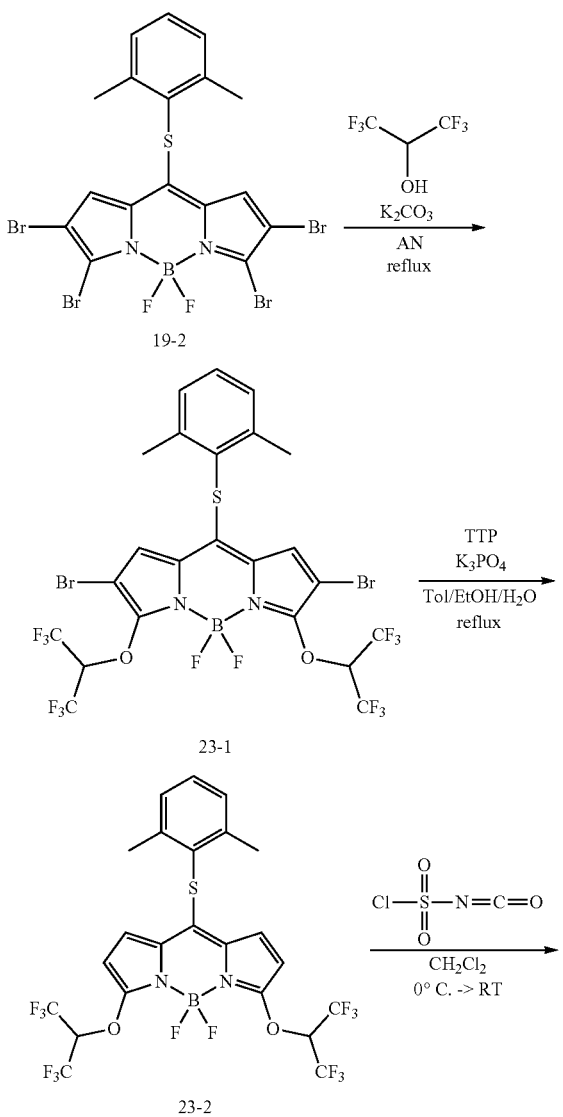

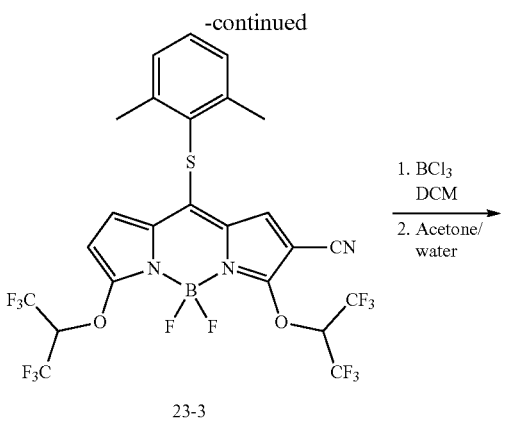

23-3

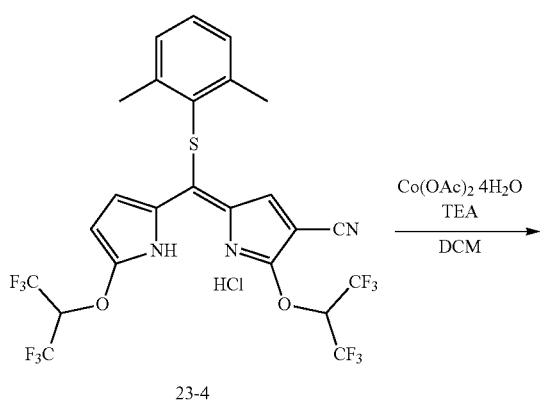

23-4

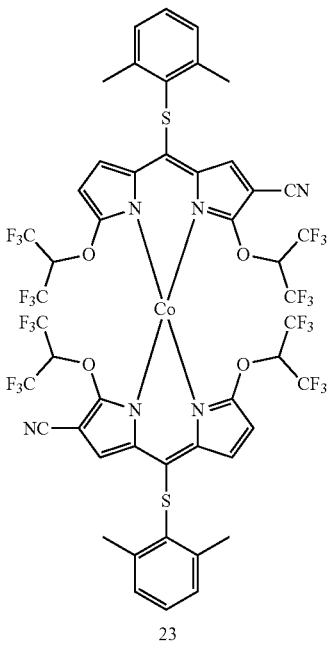

23

Synthesis of Compound 23-1

Synthesis was progressed in the same manner as in Synthesis of Compound 15-5 except that Compound 19-2 (3.0 g) was used instead of Compound 15-4, and hexafluoro-2-propanol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 23-1 (3.4 g, yield 89.2%) was secured.

Synthesis of Compound 23-2

Synthesis was progressed in the same manner as in Synthesis of Compound 15-6 except that Compound 23-1 (3.4 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 23-2 (2.3 g, yield 83.8%) was secured.

Synthesis of Compound 23-3

Synthesis was progressed in the same manner as in Synthesis of Compound 16-6 except that Compound 23-2 (2.3 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 23-3 (2.0 g, yield 83.8%) was secured.

Synthesis of Compound 23-4

Synthesis was progressed in the same manner as in Synthesis of Compound 15-7 except that Compound 23-3 (2.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 23-4 (1.6 g, yield 81.3%) was secured.

Synthesis of Compound 23

Synthesis was progressed in the same manner as in Synthesis of Compound 15 except that Compound 23-4 (1.6 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 23 (1.3 g, yield 82.2%) was secured.

HR LC/MS/MS m/z calculated for $C_{48}H_{28}CoF_{24}N_6O_4S_2$ (M+): 1331.0562; found: 1331.0566.

Preparation Example 24
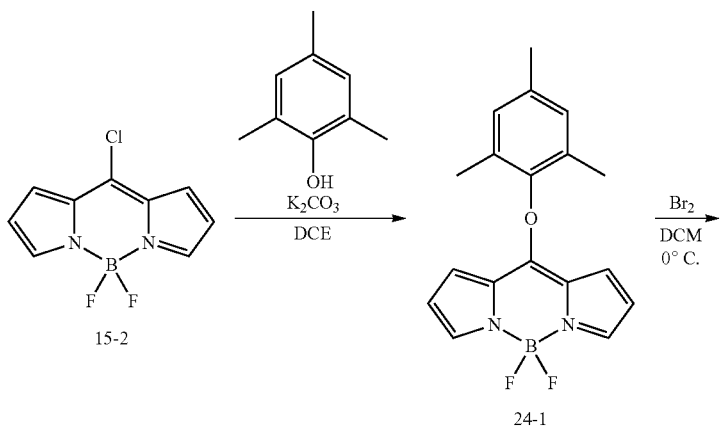
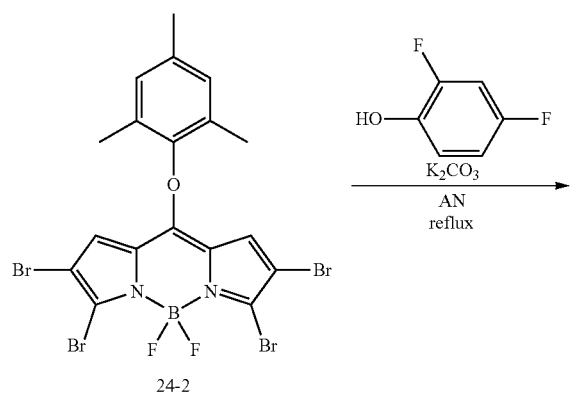
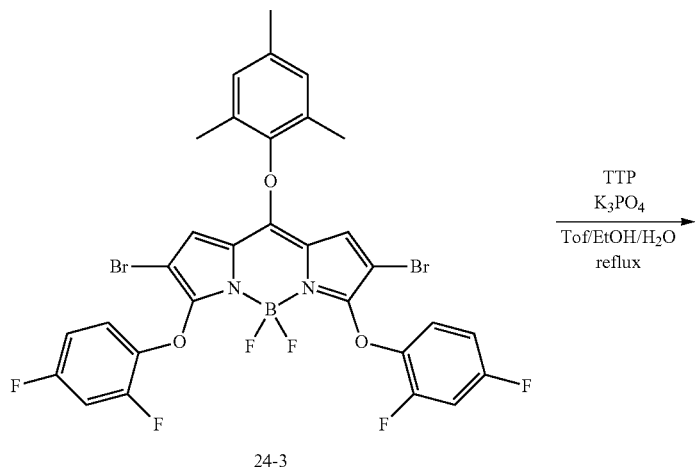

-continued
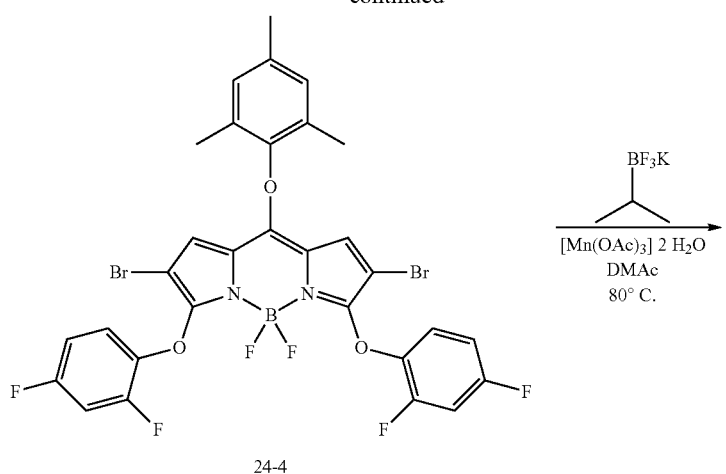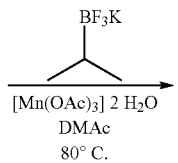
24-4
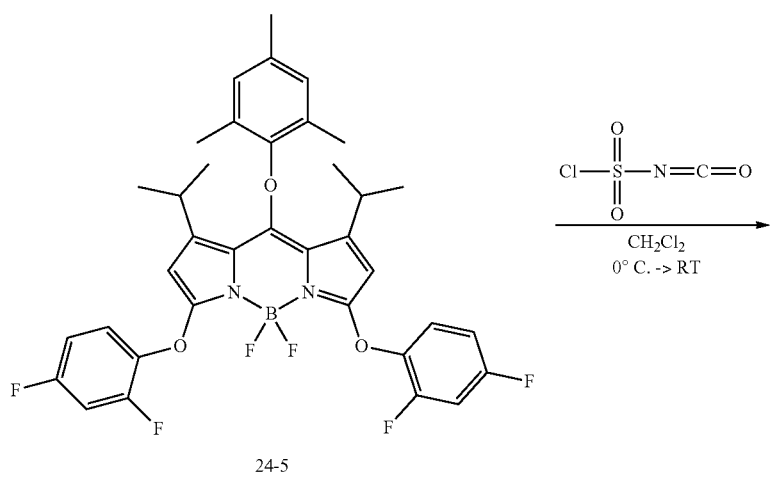
24-5
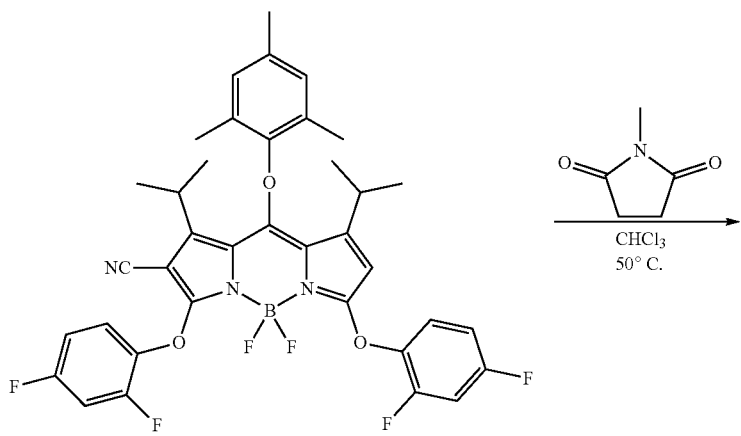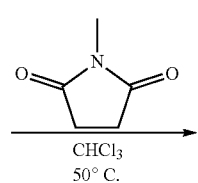
24-6

-continued
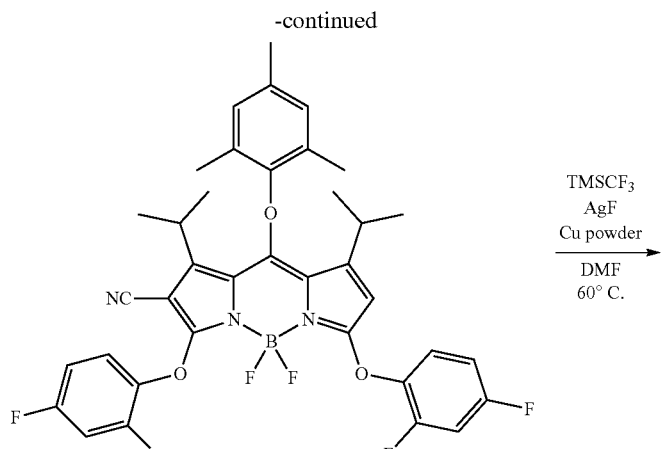
24-7
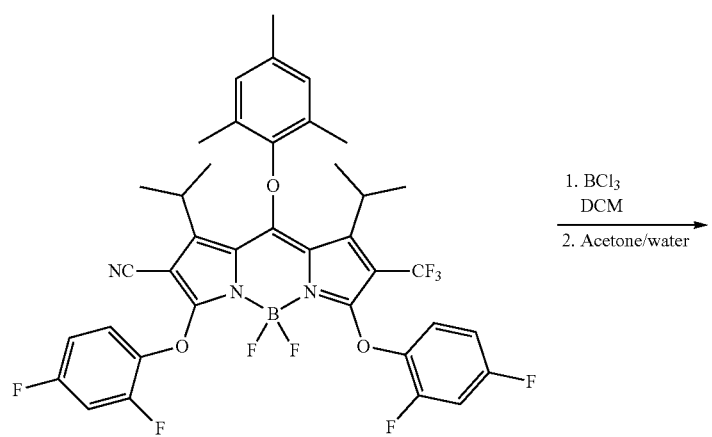
24-8
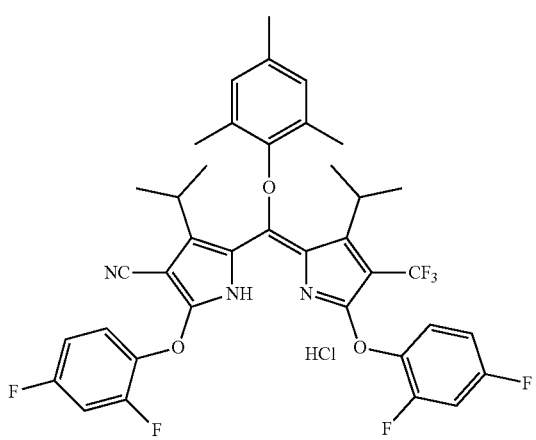
24-9

-continued
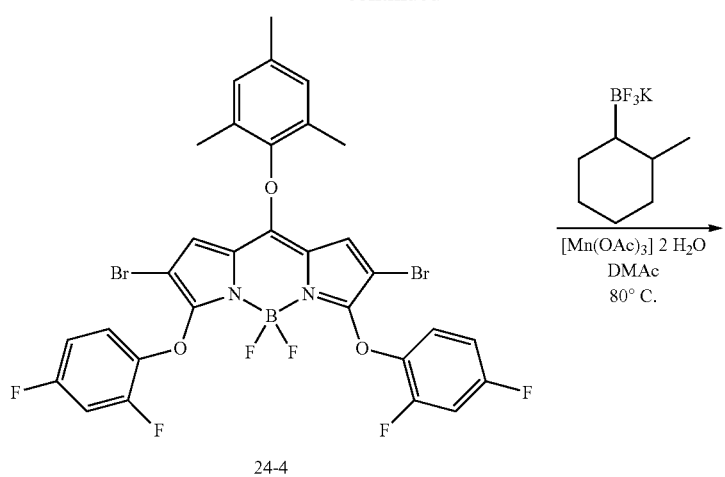
24-4
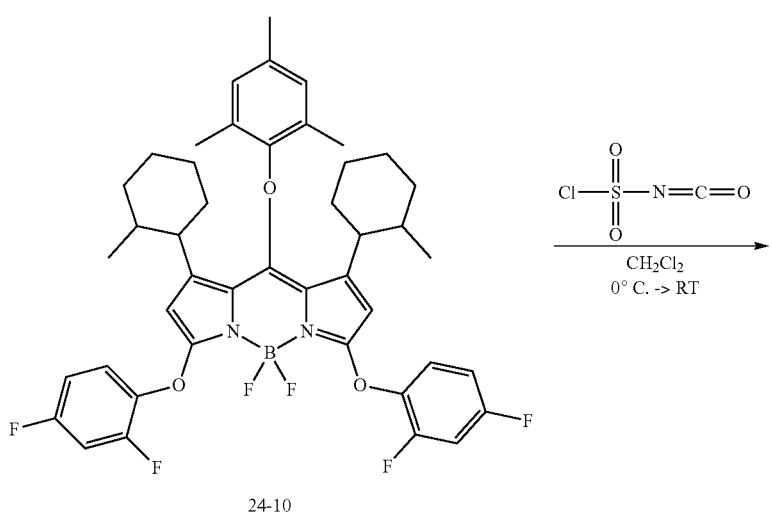
24-10
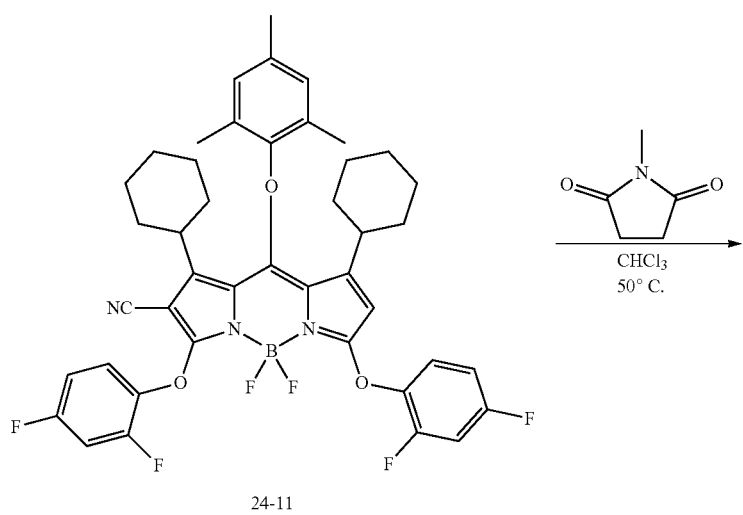
24-11

-continued
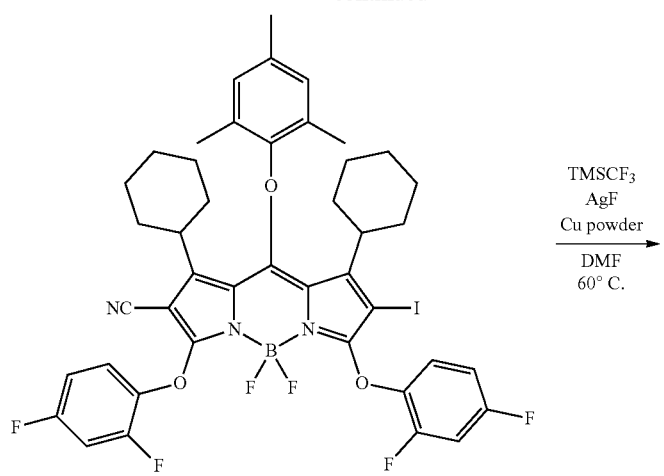
24-12
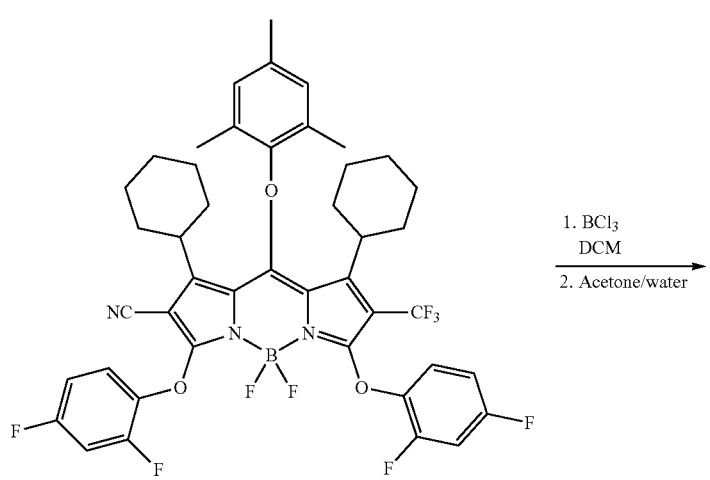
24-13
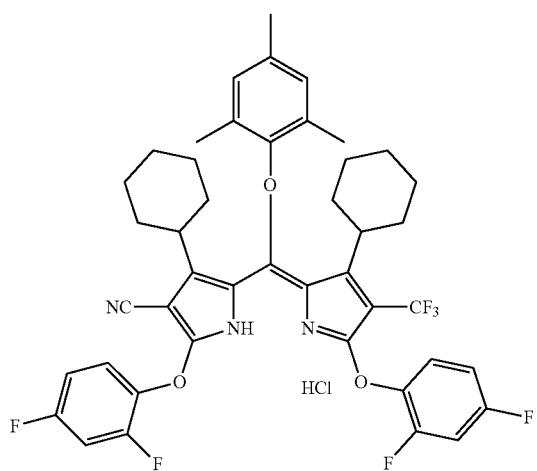
24-14

-continued
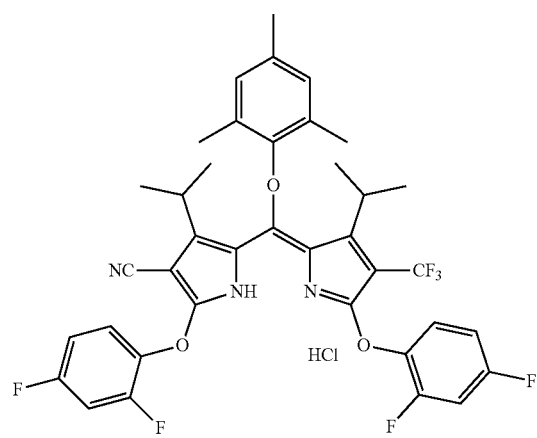
24-9
+
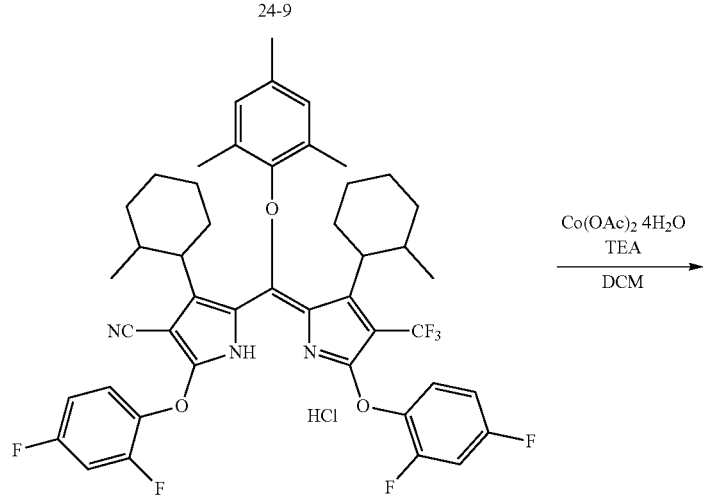
24-14
Co(OAc)₂ 4H₂O
TEA
———————→
DCM
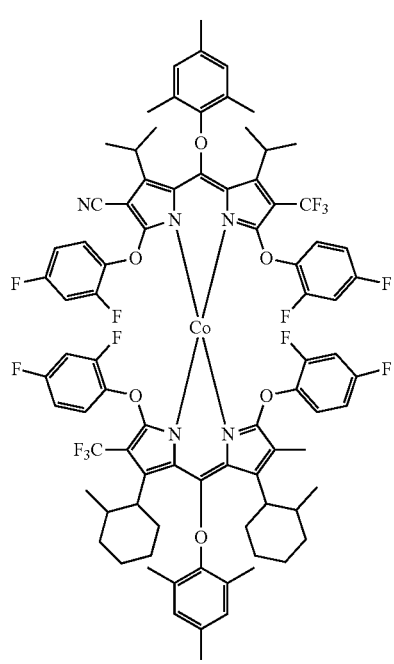

Synthesis of Compound 24-1

Synthesis was progressed in the same manner as in Synthesis of Compound 15-3 except that 2,4,6-trimethylphenol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 24-1 (5.5 g, yield 95.5%).

Synthesis of Compound 24-2

Synthesis was progressed in the same manner as in Synthesis of Compound 15-4 except that Compound 24-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 24-2 (7.4 g, yield 94.0%).

Synthesis of Compound 24-3

Synthesis was progressed in the same manner as in Synthesis of Compound 15-5 except that Compound 24-2 (6.0 g) was used instead of Compound 15-4, and 2,4-difluorophenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 24-3 (6.2 g, yield 89.6%) was secured.

Synthesis of Compound 24-4

Synthesis was progressed in the same manner as in Synthesis of Compound 15-6 except that Compound 24-3 (6.2 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 24-4 (4.2 g, yield 86.1%) was secured.

Synthesis of Compound 24-5

Synthesis was progressed in the same manner as in Synthesis of Compound 16-5 except that Compound 24-4 (2.1 g) was used instead of Compound 16-4, and isopropyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 24-5 (2.1 g, yield 87.4%).

Synthesis of Compound 24-6

Synthesis was progressed in the same manner as in Synthesis of Compound 16-6 except that Compound 24-5 (2.1 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 24-6 (2.0 g, yield 91.8%) was secured.

Synthesis of Compound 24-7

Synthesis was progressed in the same manner as in Synthesis of Compound 20-5 except that Compound 24-6 (2.0 g) was used instead of Compound 20-4, and N-iodosuccinimide (NIS) (3.0 equivalent) was used. After the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 24-7 (2.0 g, yield 84.6%) was secured.

Synthesis of Compound 24-8

Synthesis was progressed in the same manner as in Synthesis of Compound 20-6 except that Compound 24-7 (2.0 g) was used instead of Compound 20-5. After the reaction was completed, water was introduced to the reaction solution, and the result was stirred well and filtered to obtain a material in a solid state. This was extracted again using ethyl acetate and hexane. The extracted organic layer was dried with sodium sulfate, and after removing the solvent by vacuum distillation, Compound 24-8 (1.6 g, yield 86.1%) was secured without further purification.

Synthesis of Compound 24-9

Synthesis was progressed in the same manner as in Synthesis of Compound 15-7 except that Compound 24-8 (1.6 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 24-9 (1.4 g, yield 88.8%) was secured.

Synthesis of Compound 24-10

Synthesis was progressed in the same manner as in Synthesis of Compound 16-5 except that Compound 24-4 (2.1 g) was used instead of Compound 16-4, and 2-methylcyclohexyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 24-10 (2.3 g, yield 82.3%).

Synthesis of Compound 24-11

Synthesis was progressed in the same manner as in Synthesis of Compound 16-6 except that Compound 24-10

(2.3 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 24-11 (2.2 g, yield 92.7%) was secured.

Synthesis of Compound 24-12

Synthesis was progressed in the same manner as in Synthesis of Compound 20-5 except that Compound 24-11 (2.2 g) was used instead of Compound 20-4, and N-iodo-succinimide (NIS) (3.0 equivalent) was used. After the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 24-12 (2.2 g, yield 86.4%) was secured.

Synthesis of Compound 24-13

Synthesis was progressed in the same manner as in Synthesis of Compound 20-6 except that Compound 24-12 (2.2 g) was used instead of Compound 20-5. After the reaction was completed, water was introduced to the reaction solution, and the result was stirred well and filtered to obtain a material in a solid state. This was extracted again using ethyl acetate and hexane. The extracted organic layer was dried with sodium sulfate, and after removing the solvent by vacuum distillation, Compound 24-13 (1.9 g, yield 92.1%) was secured without further purification.

Synthesis of Compound 24-14

Synthesis was progressed in the same manner as in Synthesis of Compound 15-7 except that Compound 24-13 (1.9 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 24-14 (1.6 g, yield 85.3%) was secured.

Synthesis of Compound 24

Synthesis was progressed in the same manner as in Synthesis of Compound 15 except that Compound 24-9 (1.4 g) and Compound 24-14 (1.6 g) were used in a molar ratio of 1/1 instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. The mixture compound purified and separated through the recrystallization was purified and separated again using a silica gel column to secure Compound 24 (0.4 g, yield 23.6%).

HR LC/MS/MS m/z calculated for $C_{84}H_{74}CoF_{14}N_6O_6$ (M+): 1587.4778; found: 1587.4787.

Preparation Example 25

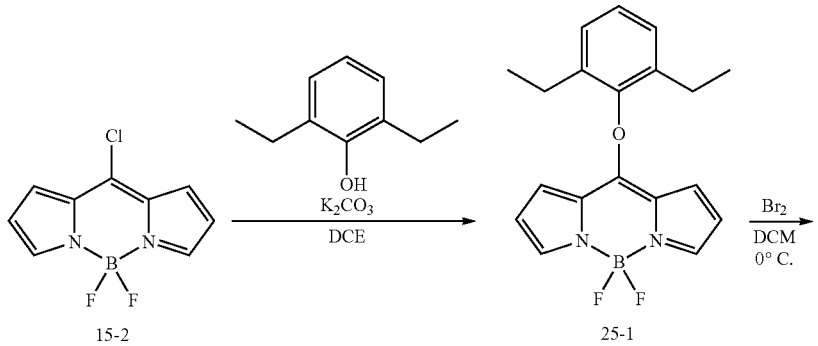

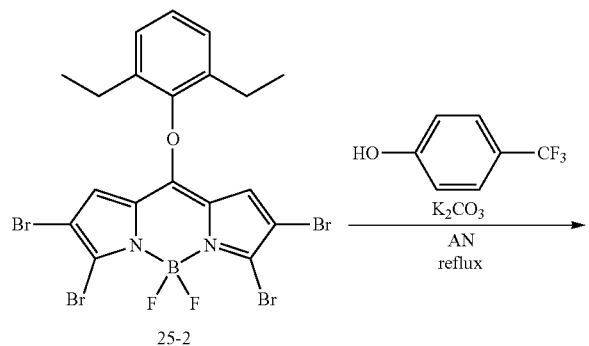

-continued
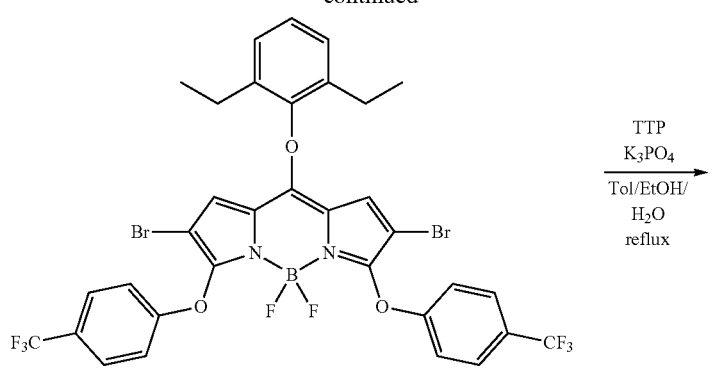
25-3
TTP
K₃PO₄
—————→
Tol/EtOH/
H₂O
reflux
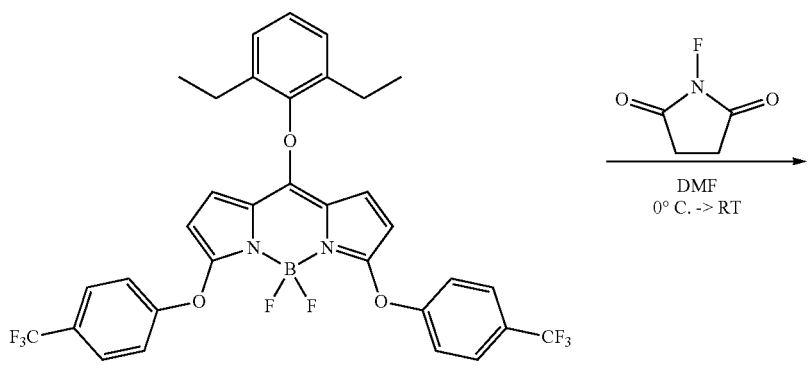
25-4
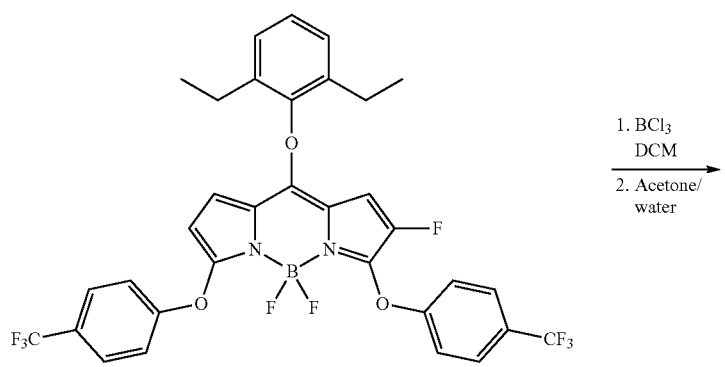
25-5
1. BCl₃
   DCM
—————→
2. Acetone/
   water
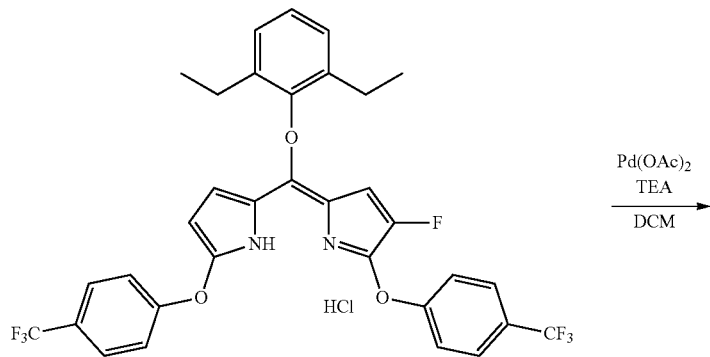
25-6
Pd(OAc)₂
TEA
—————→
DCM -continued

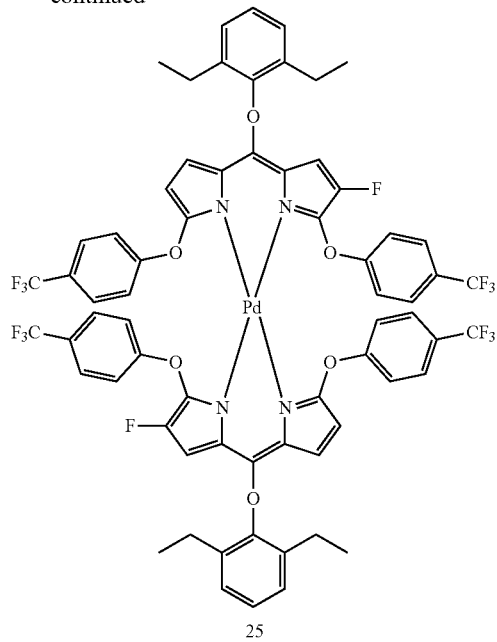

25

Synthesis of Compound 25-1

Synthesis was progressed in the same manner as in Synthesis of Compound 15-3 except that 2,6-diethylphenol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 25-1 (5.6 g, yield 93.2%).

Synthesis of Compound 25-2

Synthesis was progressed in the same manner as in Synthesis of Compound 15-4 except that Compound 25-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 25-2 (7.3 g, yield 94.7%).

Synthesis of Compound 25-3

Synthesis was progressed in the same manner as in Synthesis of Compound 15-5 except that Compound 25-2 (4.0 g) was used instead of Compound 15-4, and 4-hydroxybenzotrifluoride was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 25-3 (4.5 g, yield 90.2%) was secured.

Synthesis of Compound 25-4

Synthesis was progressed in the same manner as in Synthesis of Compound 15-6 except that Compound 25-3 (4.5 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 25-4 (3.2 g, yield 88.1%) was secured.

Synthesis of Compound 25-5

Compound 25-4 (3.2 g) was stirred well and dissolved in an N,N-dimethylformamide solvent. The reaction solution was cooled to 0° C. using ice water, and N-fluorosuccinimide (NFS) (2.0 equivalent) was slowly introduced thereto. The reaction solution was stirred well after raising the temperature to room temperature. After the reaction was completed, the result was extracted using an aqueous sodium thiosulfate solution and dichloromethane. The extracted organic layer was dried with sodium sulfate and, after removing the solvent by vacuum distillation, recrystallized using methanol. Through the recrystallization, purified and separated Compound 25-5 (2.9 g, yield 88.2%) was secured.

Synthesis of Compound 25-6

Synthesis was progressed in the same manner as in Synthesis of Compound 15-7 except that Compound 25-5 (2.9 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 25-6 (2.3 g, yield 80.6%) was secured.

Synthesis of Compound 25

Synthesis was progressed in the same manner as in Synthesis of Compound 15 except that Compound 25-6 (2.3 g) was used instead of Compound 15-7, and palladium acetate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 25 (2.0 g, yield 85.0%) was secured.

HR LC/MS/MS m/z calculated for $C_{66}H_{48}F_{14}N_4O_6Pd$ (M+): 1364.2385; found: 1364.2390.

Preparation Example 26

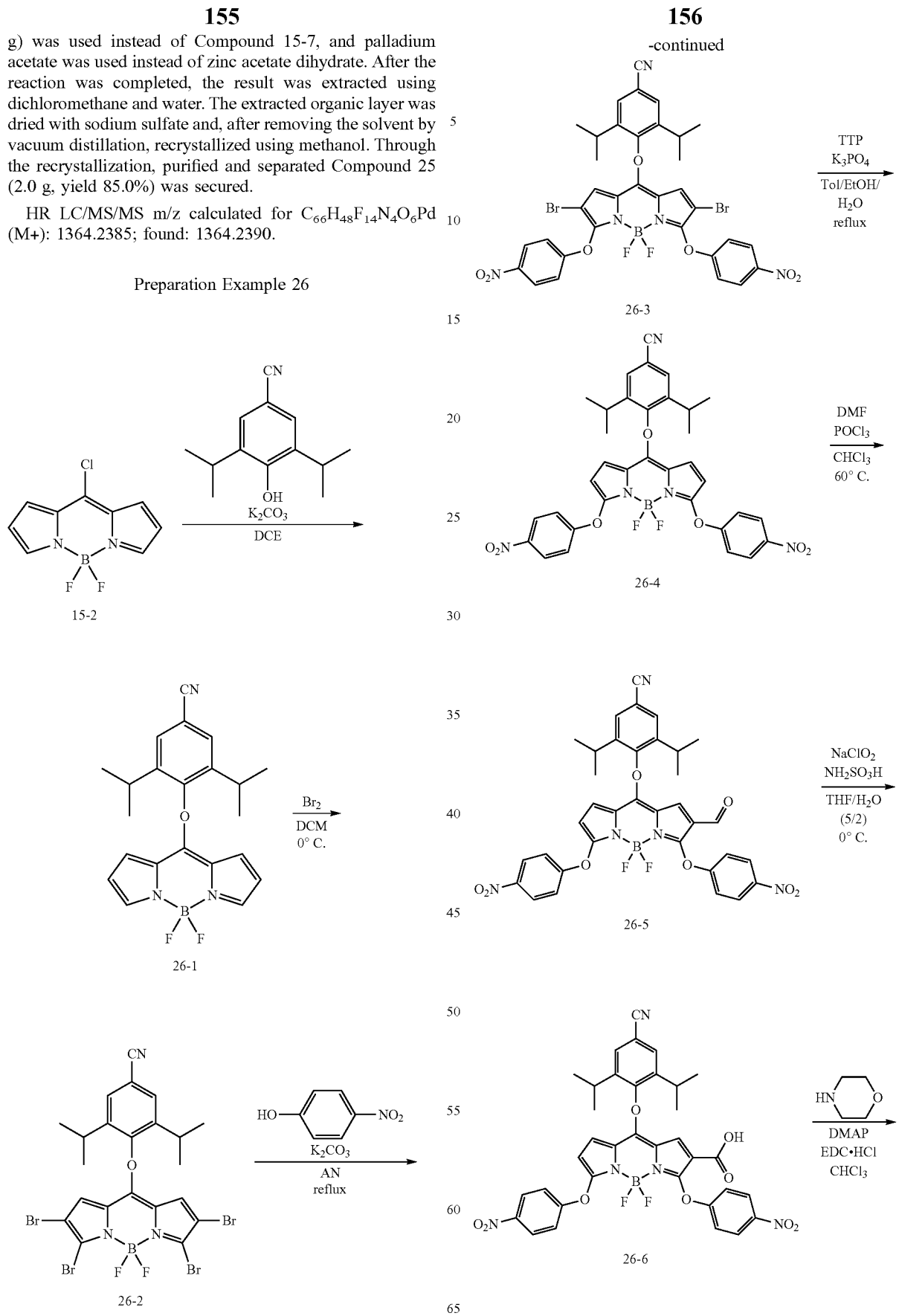

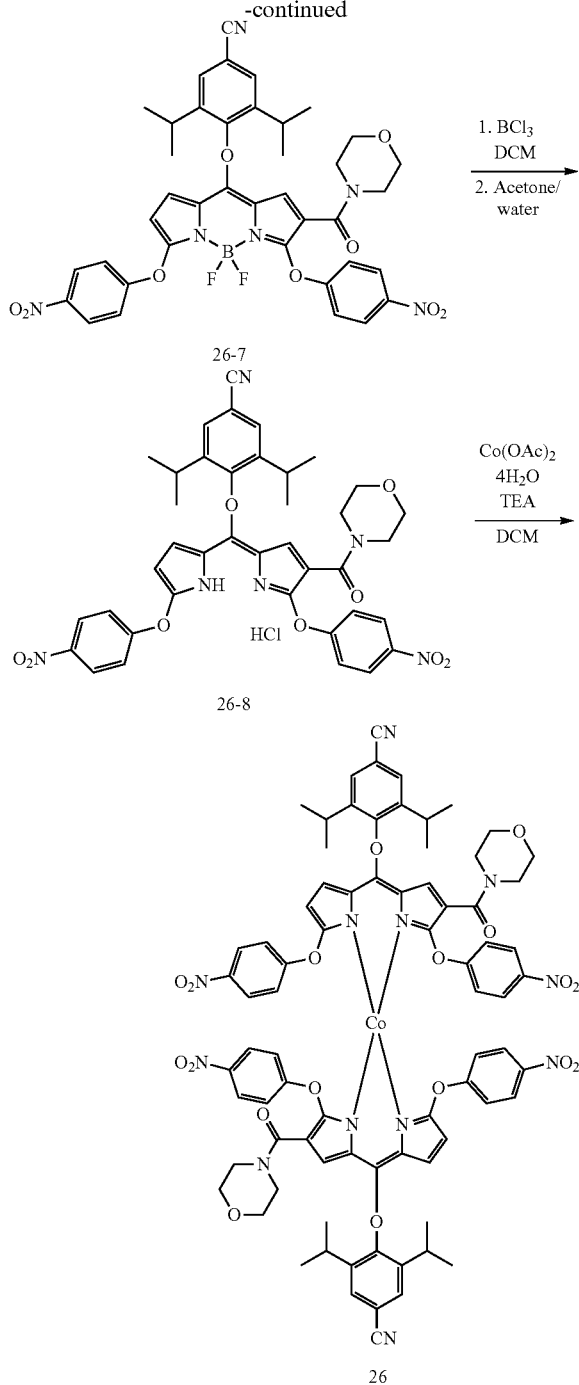

Synthesis of Compound 26-1

Synthesis was progressed in the same manner as in Synthesis of Compound 15-3 except that 4-hydroxy-3,5-diisopropylbenzonitrile (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 26-1 (6.6 g, yield 95.0%).

Synthesis of Compound 26-2

Synthesis was progressed in the same manner as in Synthesis of Compound 15-4 except that Compound 26-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 26-2 (6.8 g, yield 94.3%).

Synthesis of Compound 26-3

Synthesis was progressed in the same manner as in Synthesis of Compound 15-5 except that Compound 26-2 (4.0 g) was used instead of Compound 15-4, and 4-nitrophenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 26-3 (4.1 g, yield 88.0%) was secured.

Synthesis of Compound 26-4

Synthesis was progressed in the same manner as in Synthesis of Compound 15-6 except that Compound 26-3 (4.1 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 26-4 (2.8 g, yield 84.4%) was secured.

Synthesis of Compound 26-5

Synthesis was progressed in the same manner as in Synthesis of Compound 19-5 except that Compound 26-4 (2.8 g) was used instead of Compound 19-4. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 26-5 (2.4 g, yield 82.2%) was secured.

Synthesis of Compound 26-6

Synthesis was progressed in the same manner as in Synthesis of Compound 19-6 except that Compound 26-5 (2.4 g) was used instead of Compound 19-5. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 26-6 (2.1 g, yield 85.5%).

Synthesis of Compound 26-7

Synthesis was progressed in the same manner as in Synthesis of Compound 19-7 except that Compound 26-6

(2.1 g) was used instead of Compound 19-6, and morpholine (4.0 equivalent) was used instead of 4-hydroxybenzotrifluoride. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 26-7 (2.0 g, yield 86.8%) was secured.

Synthesis of Compound 26-8

Synthesis was progressed in the same manner as in Synthesis of Compound 15-7 except that Compound 26-7 (2.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 26-8 (1.6 g, yield 81.2%) was secured.

Synthesis of Compound 26

Synthesis was progressed in the same manner as in Synthesis of Compound 15 except that Compound 26-8 (1.6 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 26 (1.2 g, yield 75.8%) was secured.

HR LC/MS/MS m/z calculated for $C_{78}H_{70}CoN_{12}O_{18}$ (M+): 1521.4263; found: 1521.4271.

Preparation Example 27

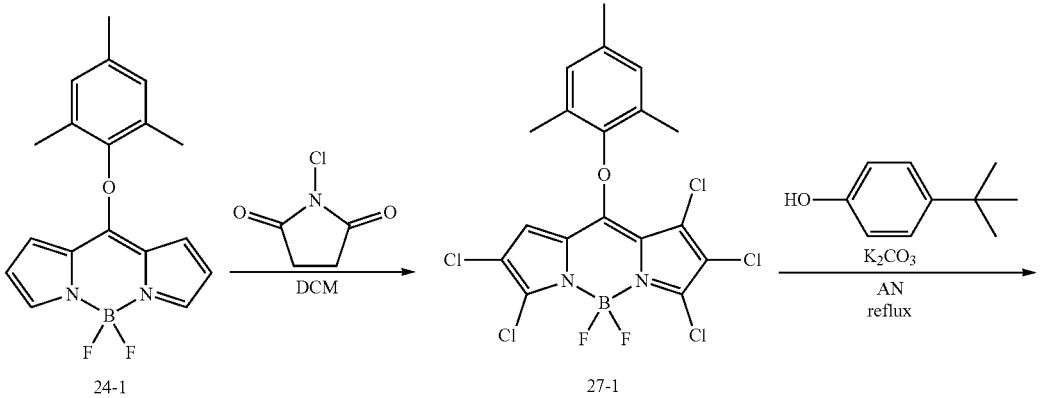

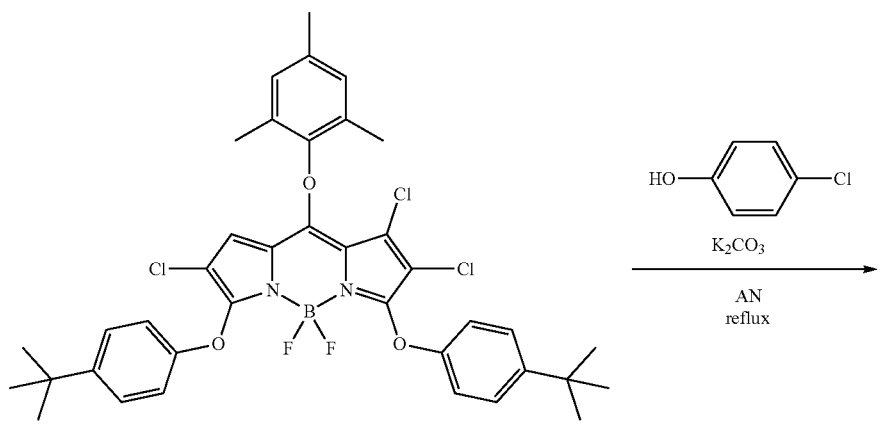

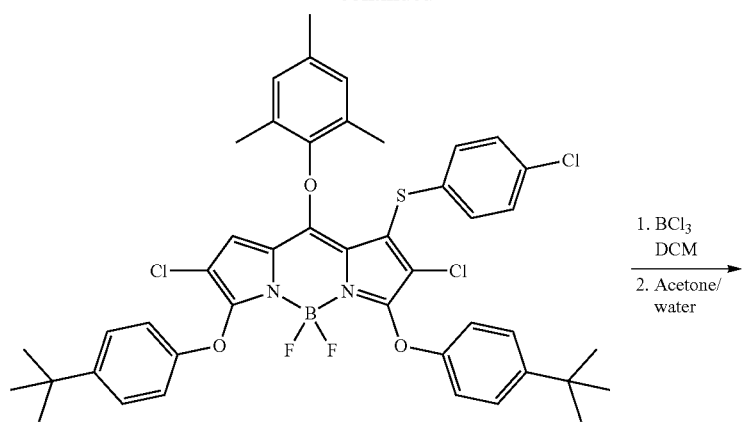
27-3
1. BCl₃ DCM
2. Acetone/ water
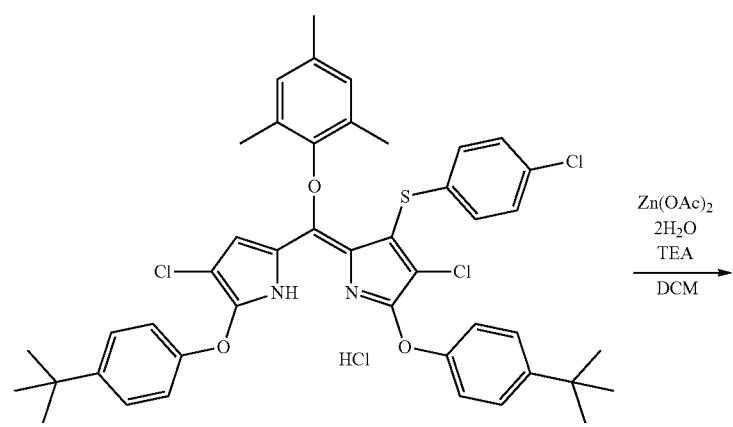
27-4
Zn(OAc)₂ 2H₂O TEA DCM
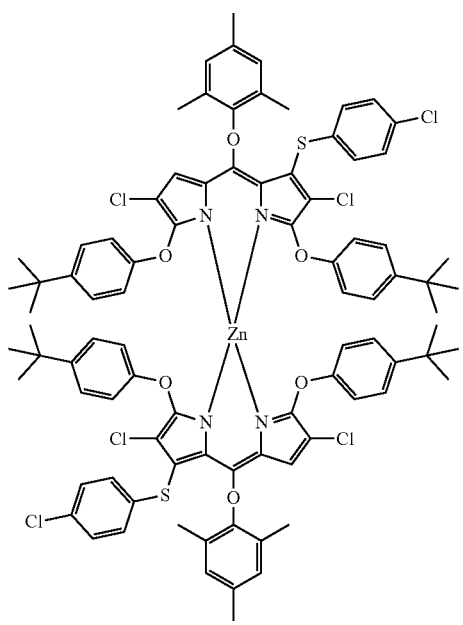
27

Synthesis of Compound 27-1

Synthesis was progressed in the same manner as in Synthesis of Compound 17-2 except that Compound 24-1 (3.0 g) was used instead of Compound 17-1. After the reaction was finished, the result was extracted using chloroform and an aqueous sodium thiosulfate solution. The extracted organic layer was dried with sodium sulfate and, after removing the solvent by vacuum distillation, recrystallized using methanol. Through the recrystallization, purified and separated Compound 27-1 (4.1 g, yield 89.4%) was secured.

Synthesis of Compound 27-2

Synthesis was progressed in the same manner as in Synthesis of Compound 15-5 except that Compound 27-1 (4.1 g) was used instead of Compound 15-4, and 4-t-butylphenol (2.1 equivalent) was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 27-2 (5.3 g, yield 88.7%) was secured.

Synthesis of Compound 27-3

Compound 27-2 (3.0 g) was stirred well and dissolved in an acetonitrile solvent. Sodium carbonate (4.0 equivalent) and 4-chlorobenzenethiol (2.0 equivalent) were introduced thereto, and the reaction solution was heated to 80° C. and stirred under reflux. After the reaction was completed, the result was extracted using chloroform and water. The extracted organic layer was dried with sodium sulfate and, after removing the solvent by vacuum distillation, recrystallized using methanol. Through the recrystallization, purified and separated Compound 27-3 (3.0 g, yield 87.0%) was secured.

Synthesis of Compound 27-4

Synthesis was progressed in the same manner as in Synthesis of Compound 15-7 except that Compound 27-3 (3.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 27-4 (2.5 g, yield 84.5%) was secured.

Synthesis of Compound 27

Synthesis was progressed in the same manner as in Synthesis of Compound 15 except that Compound 27-4 (2.5 g) was used instead of Compound 15-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 27 (2.1 g, yield 84.5%) was secured.

HR LC/MS/MS m/z calculated for $C_{88}H_{84}Cl_6N_4O_6S_2Zn$ (M+): 1630.3255; found: 1630.3264.

Preparation Example 28

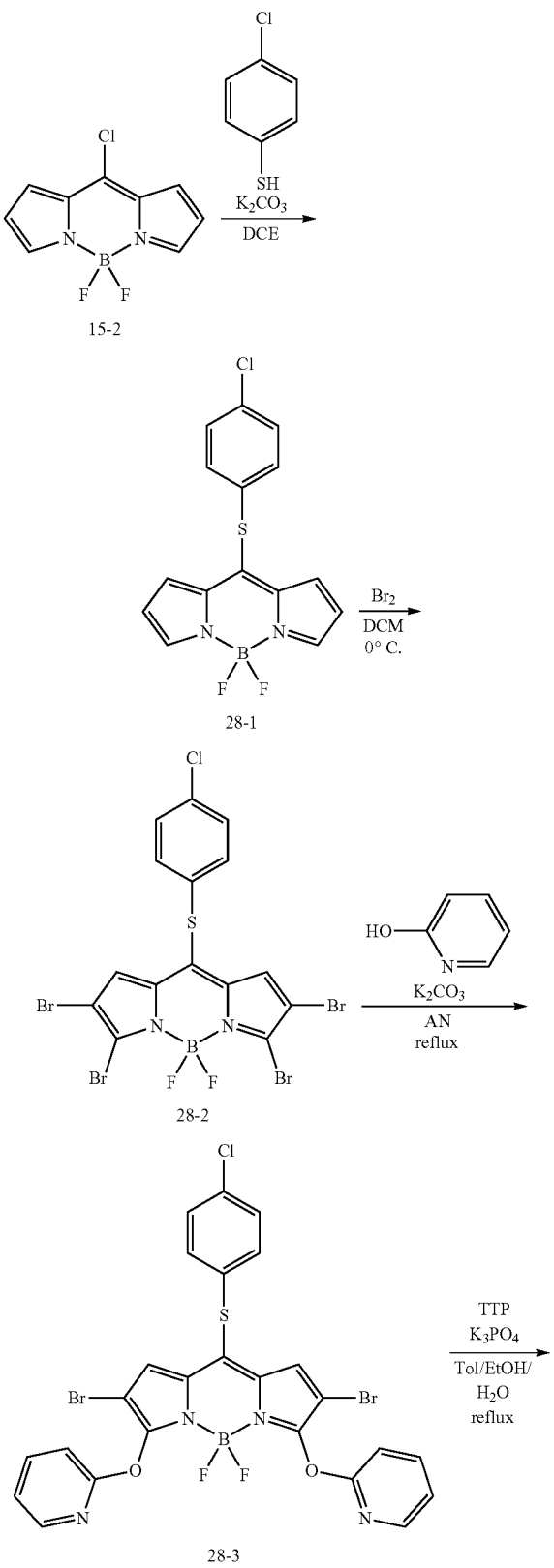

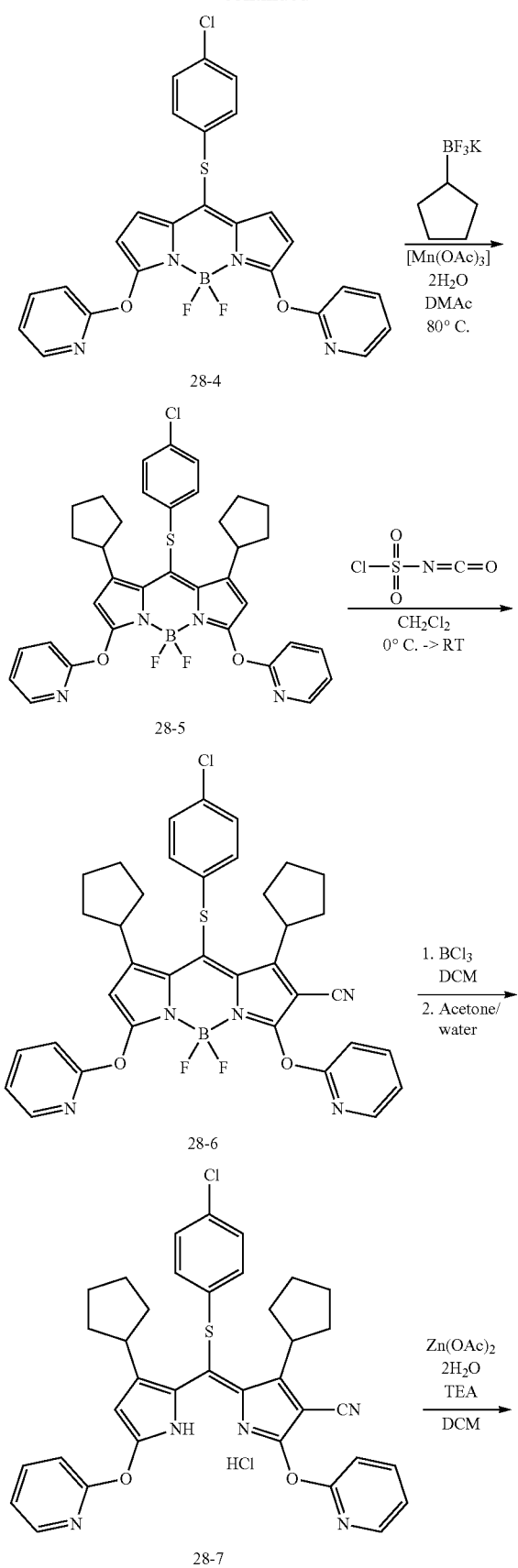

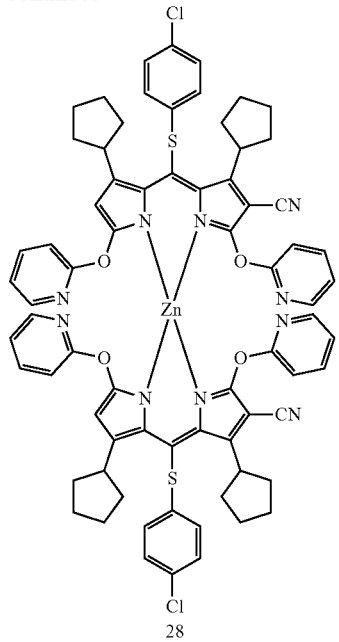

28

Synthesis of Compound 28-1

Synthesis was progressed in the same manner as in Synthesis of Compound 15-3 except that 4-chlorobenzenethiol (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 28-1 (5.5 g, yield 93.0%).

Synthesis of Compound 28-2

Synthesis was progressed in the same manner as in Synthesis of Compound 15-4 except that Compound 28-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 28-2 (7.2 g, yield 92.6%).

Synthesis of Compound 28-3

Synthesis was progressed in the same manner as in Synthesis of Compound 15-5 except that Compound 28-2 (4.0 g) was used instead of Compound 15-4, and 2-hydroxy-pyridine was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 28-3 (3.3 g, yield 79.0%) was secured.

Synthesis of Compound 28-4

Synthesis was progressed in the same manner as in Synthesis of Compound 15-6 except that Compound 28-3

(3.3 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 28-4 (2.2 g, yield 86.9%) was secured.

Synthesis of Compound 28-5

Synthesis was progressed in the same manner as in Synthesis of Compound 16-5 except that Compound 28-4 (2.2 g) was used instead of Compound 16-4, and cyclopentyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 28-5 (2.4 g, yield 86.5%).

Synthesis of Compound 28-6

Synthesis was progressed in the same manner as in Synthesis of Compound 16-6 except that Compound 28-5 (2.4 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 28-6 (2.2 g, yield 88.3%) was secured.

Synthesis of Compound 28-7

Synthesis was progressed in the same manner as in Synthesis of Compound 15-7 except that Compound 28-6 (2.2 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 28-7 (1.9 g, yield 87.8%) was secured.

Synthesis of Compound 28

Synthesis was progressed in the same manner as in Synthesis of Compound 15 except that Compound 28-7 (1.9 g) was used instead of Compound 15-7. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 28 (1.5 g, yield 79.5%) was secured.

HR LC/MS/MS m/z calculated for $C_{72}H_{62}Cl_2N_{10}O_4S_2Zn$ (M+): 1328.3065; found: 1328.3068.

Preparation Example 29

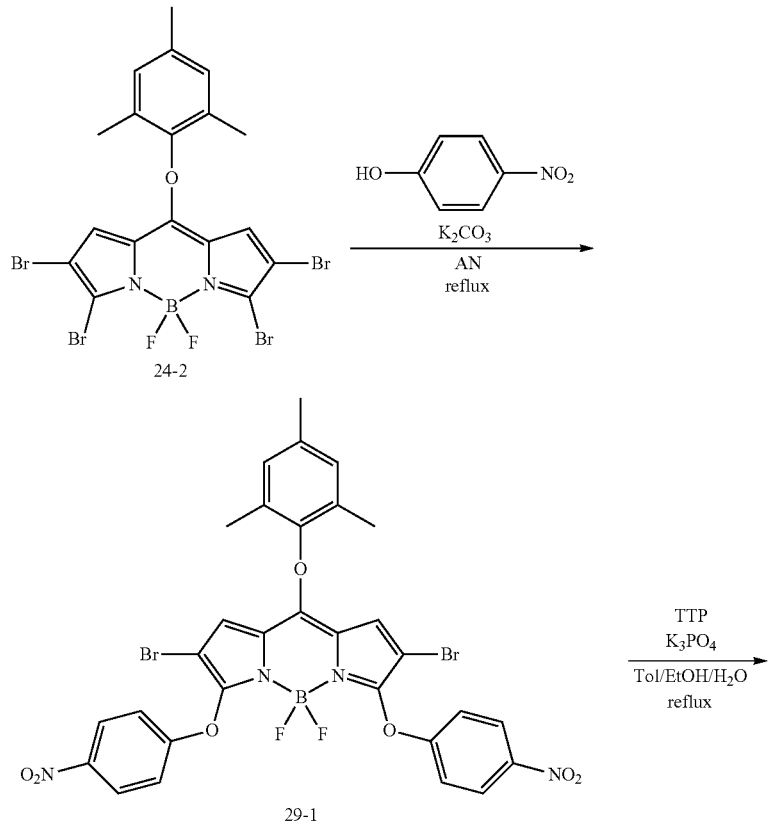

-continued
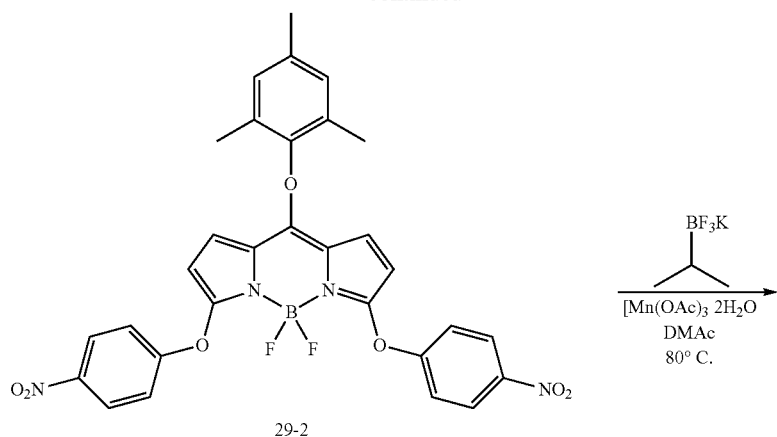
29-2
BF₃K
△
[Mn(OAc)₃ 2H₂O]
DMAc
80° C.
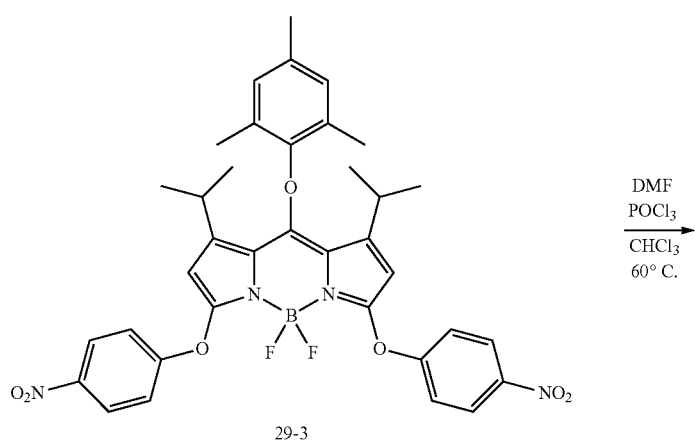
29-3
DMF
POCl₃
——→
CHCl₃
60° C.
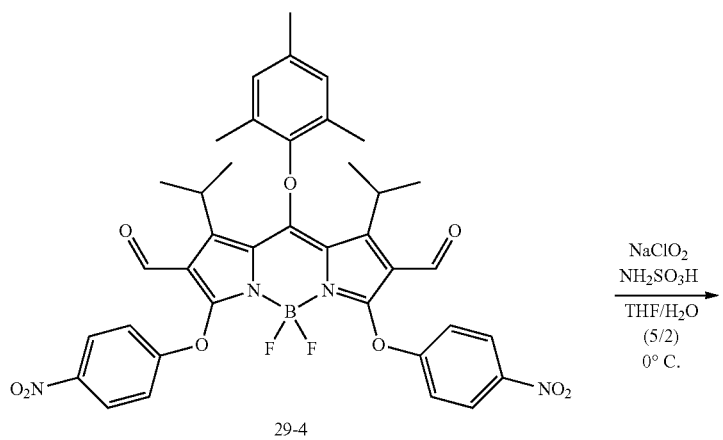
29-4
NaClO₂
NH₂SO₃H
————
THF/H₂O
(5/2)
0° C.

-continued
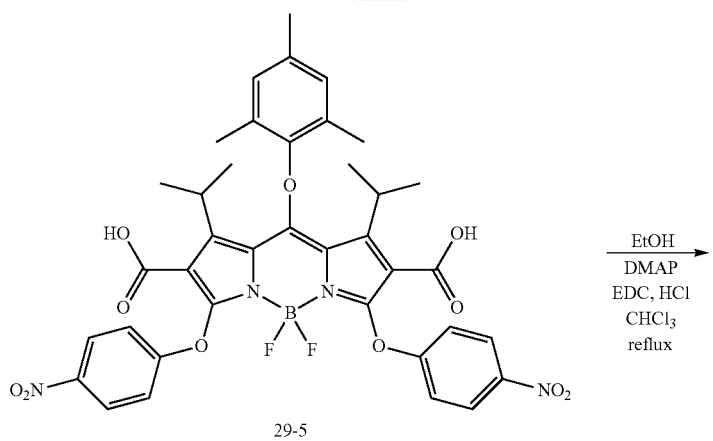
29-5
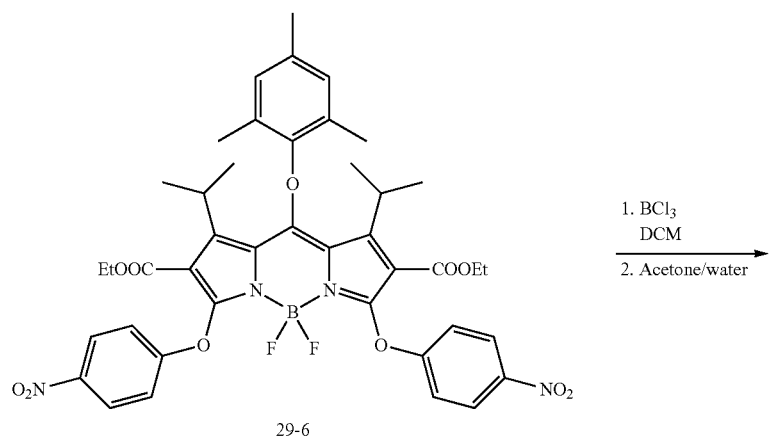
29-6
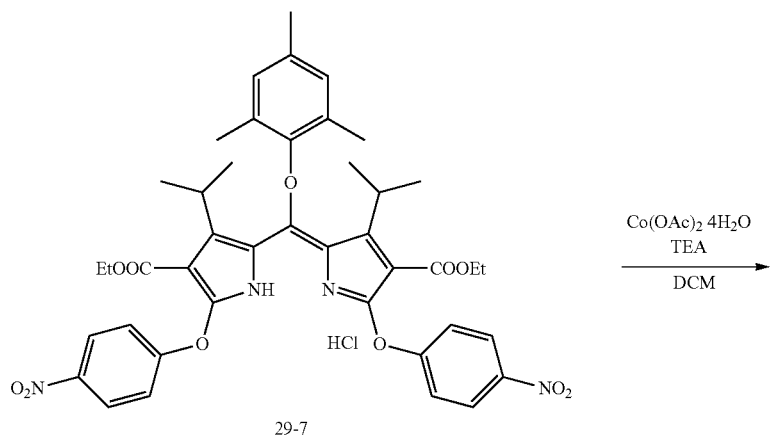
29-7

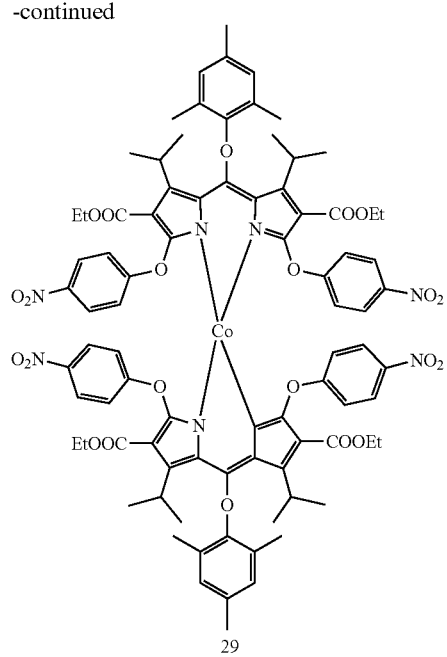

29

Synthesis of Compound 29-1

Synthesis was progressed in the same manner as in Synthesis of Compound 15-5 except that Compound 24-2 (3.0 g) was used instead of Compound 15-4, and 4-nitrophenol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 29-1 (3.3 g, yield 93.1%) was secured.

Synthesis of Compound 29-2

Synthesis was progressed in the same manner as in Synthesis of Compound 15-6 except that Compound 29-1 (3.3 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 29-2 (2.4 g, yield 91.8%) was secured.

Synthesis of Compound 29-3

Synthesis was progressed in the same manner as in Synthesis of Compound 16-5 except that Compound 29-2 (2.4 g) was used instead of Compound 16-4, and isopropyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 29-3 (2.5 g, yield 91.4%).

Synthesis of Compound 29-4

Under the nitrogen atmosphere at 0° C., phosphorous oxychloride ($POCl_3$) (2.0 equivalent) and N,N-dimethylformamide (DMF) (3.0 equivalent) were introduced to a chloroform solvent, and the mixture was stirred well for 1 hour. After 1 hour, Compound 29-3 (2.5 g) was introduced to the mixture solution, and the result was stirred under reflux at 60° C. After the reaction was completed, the reaction solution was cooled to 0° C. again, and the pH was adjusted to neutral using an aqueous sodium bicarbonate solution. The result was extracted using chloroform and water, and after drying the extracted organic layer with sodium sulfate, the solvent was removed by vacuum distillation. After that, the same reaction was proceeded once again with the reaction solution. After the reaction proceeded twice was all completed, the result was recrystallized using methanol. Through the recrystallization, purified and separated Compound 29-4 (2.1 g, yield 77.6%) was secured.

Synthesis of Compound 29-5

Compound 29-4 (2.1 g) was stirred well and dissolved in a tetrahydrofuran solvent. Amidosulfonic acid (3.0 equivalent) dissolved in water was introduced thereto, and the result was stirred at room temperature. The reaction solution was cooled to 0° C., and the result was stirred well while slowly introducing sodium chlorite (2.0 equivalent) dissolved in water thereto. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 29-5 (1.9 g, yield 86.7%).

Synthesis of Compound 29-6

Compound 29-5 (1.9 g) was stirred well and dissolved in a chloroform solvent. Ethanol (60.0 equivalent), 4-dimethylaminopyridine (DMAP) (4.4 equivalent) and N-(3-dimethylaminopropyl)-N'-ethylcarbodiimide hydrochloride (EDC-HCl) (4.4 equivalent) were introduced thereto, and the result was stirred at room temperature. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 29-6 (1.8 g, yield 88.3%) was secured.

Synthesis of Compound 29-7

Synthesis was progressed in the same manner as in Synthesis of Compound 15-7 except that Compound 29-6 (1.8 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 29-7 (1.5 g, yield 84.5%) was secured.

Synthesis of Compound 29

Synthesis was progressed in the same manner as in Synthesis of Compound 15 except that Compound 29-7 (1.5 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 29 (1.2 g, yield 80.8%) was secured.

HR LC/MS/MS m/z calculated for $C_{84}H_{86}CoN_8O_{22}$ (M+): 1617.5189; found: 1617.5194.

Preparation Example 30

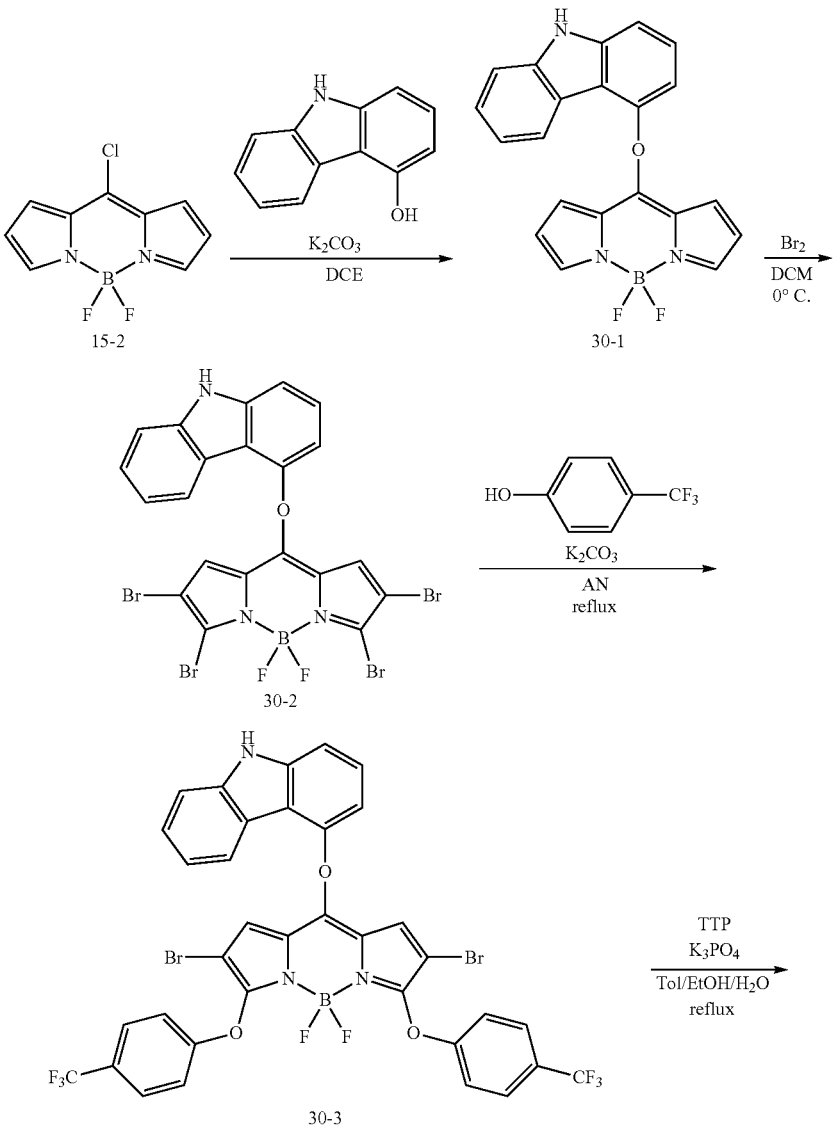

-continued
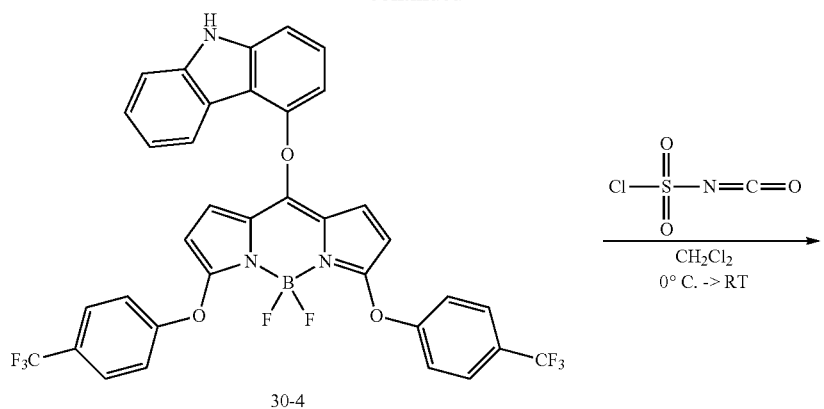
30-4
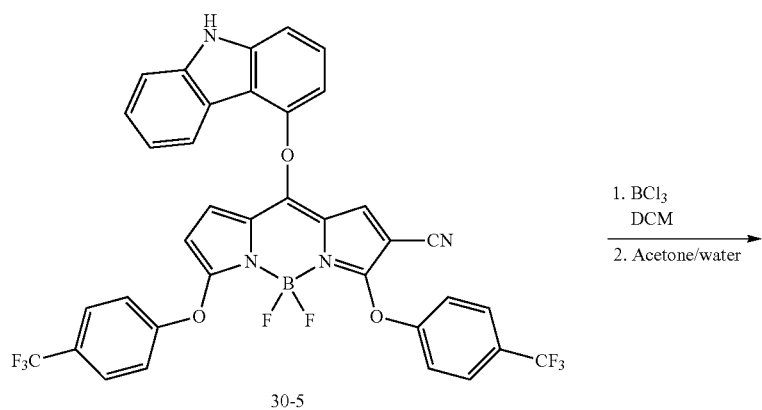
30-5
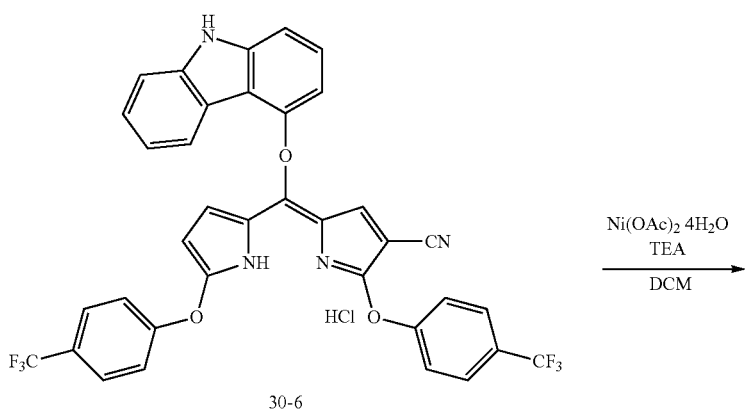
30-6

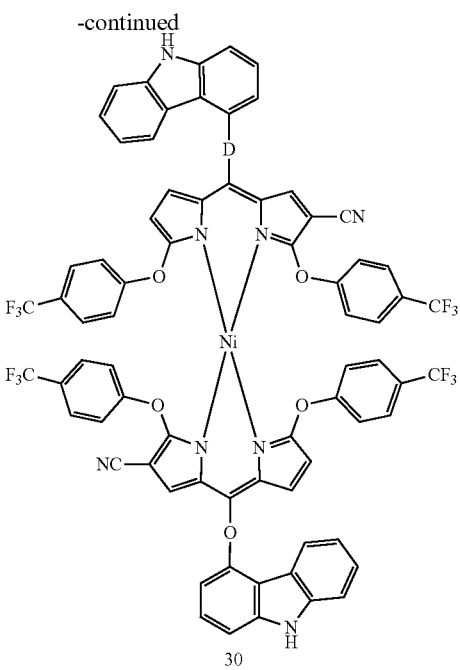

30

Synthesis of Compound 30-1

Synthesis was progressed in the same manner as in Synthesis of Compound 15-3 except that 4-hydroxycarbazole (1.0 equivalent) was used instead of 2,6-di-t-butylphenol. After identifying the completion of the reaction, the result was extracted using diethyl ether and an aqueous sodium carbonate solution. The extracted organic layer was dried with sodium sulfate, and then a silica gel column was used to secure purified and separated Compound 30-1 (5.9 g, yield 89.5%).

Synthesis of Compound 30-2

Synthesis was progressed in the same manner as in Synthesis of Compound 15-4 except that Compound 30-1 (4.0 g) was used instead of Compound 15-3. After the reaction was completed, the result was extracted using an aqueous sodium thiosulfate solution, an aqueous sodium hydroxide solution and chloroform. The extracted organic layer was dried with sodium sulfate, and then a silica gel column was used to secure purified and separated Compound 30-2 (6.8 g, yield 92.1%).

Synthesis of Compound 30-3

Synthesis was progressed in the same manner as in Synthesis of Compound 15-5 except that Compound 30-2 (4.0 g) was used instead of Compound 15-4, and 4-hydroxybenzotrifluoride was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 30-3 (4.4 g, yield 89.0%) was secured.

Synthesis of Compound 30-4

Synthesis was progressed in the same manner as in Synthesis of Compound 15-6 except that Compound 30-3 (4.4 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 30-4 (3.1 g, yield 86.5%) was secured.

Synthesis of Compound 30-5

Synthesis was progressed in the same manner as in Synthesis of Compound 16-6 except that Compound 30-4 (3.1 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 30-5 (2.8 g, yield 87.2%) was secured.

Synthesis of Compound 30-6

Synthesis was progressed in the same manner as in Synthesis of Compound 15-7 except that Compound 30-5 (2.8 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 30-6 (2.2 g, yield 79.8%) was secured.

Synthesis of Compound 30

Synthesis was progressed in the same manner as in Synthesis of Compound 15 except that Compound 30-6 (2.2 g) was used instead of Compound 15-7, and nickel acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 30 (1.8 g, yield 82.8%) was secured.

HR LC/MS/MS m/z calculated for $C_{72}H_{38}F_{12}N_8NiO_6$ (M+): 1396.2076; found: 1396.2078.

Preparation Example 31

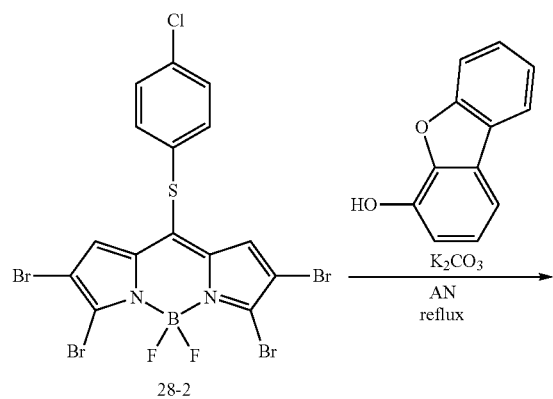

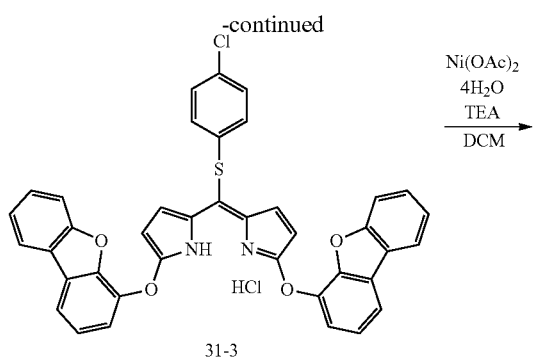

Synthesis of Compound 31-1

Synthesis was progressed in the same manner as in Synthesis of Compound 15-5 except that Compound 28-2 (3.0 g) was used instead of Compound 15-4, and 4-hydroxydibenzofuran was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 31-1 (3.5 g, yield 88.5%) was secured.

Synthesis of Compound 31-2

Synthesis was progressed in the same manner as in Synthesis of Compound 15-6 except that Compound 31-1 (3.5 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 31-2 (2.4 g, yield 84.1%) was secured.

Synthesis of Compound 31-3

Synthesis was progressed in the same manner as in Synthesis of Compound 15-7 except that Compound 31-2 (2.4 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 31-3 (2.0 g, yield 84.7%) was secured.

Synthesis of Compound 31

Synthesis was progressed in the same manner as in Synthesis of Compound 15 except that Compound 31-3 (2.0 g) was used instead of Compound 15-7, and nickel acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 31 (1.6 g, yield 81.0%) was secured.

HR LC/MS/MS m/z calculated for $C_{78}H_{44}C_{12}N_4NiO_8S_2$ (M+): 1356.1331; found: 1356.1337.

Preparation Example 32

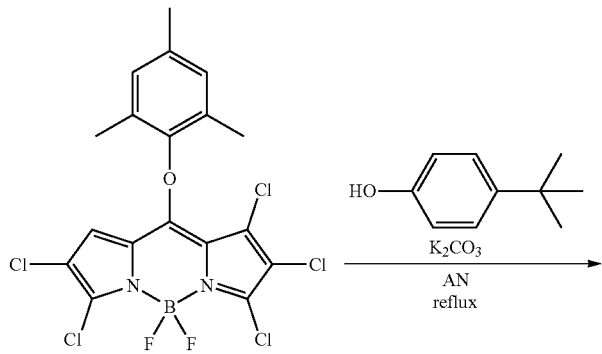

27-1

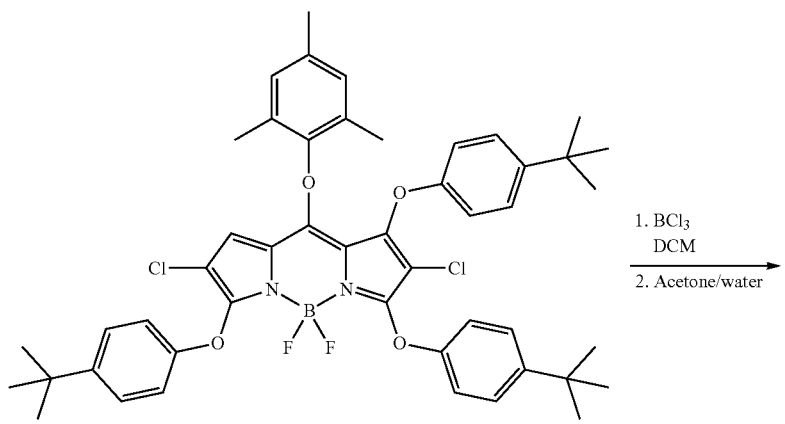

32-1

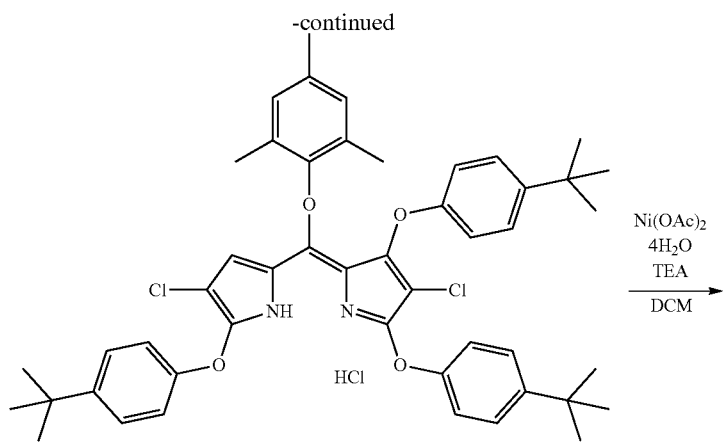

32-2

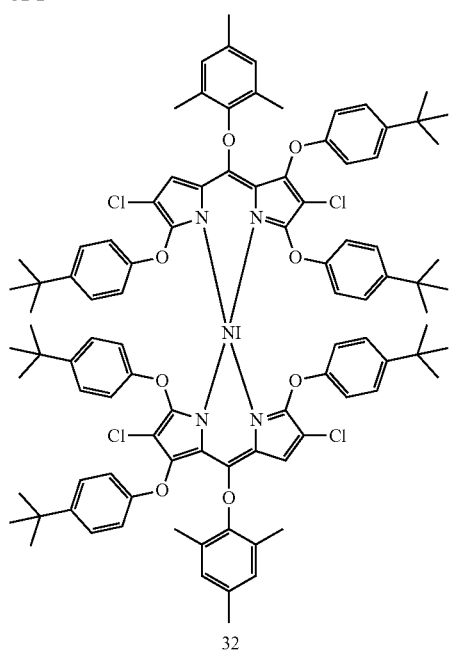

32

Synthesis of Compound 32-1

Compound 27-1 (3.0 g) was stirred well and dissolved in an acetonitrile solvent. Sodium carbonate (12.0 equivalent) and 4-t-butylphenol (6.0 equivalent) were introduced thereto, and the reaction solution was heated to 80° C. and stirred under reflux. After the reaction was completed, the result was extracted using chloroform and water. The extracted organic layer was dried with sodium sulfate and, after removing the solvent by vacuum distillation, recrystallized using methanol. Through the recrystallization, purified and separated Compound 32-1 (4.4 g, yield 87.1%) was secured.

Synthesis of Compound 32-2

Synthesis was progressed in the same manner as in Synthesis of Compound 15-7 except that Compound 32-1 (3.0 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 32-2 (2.4 g, yield 81.1%) was secured.

Synthesis of Compound 32

Synthesis was progressed in the same manner as in Synthesis of Compound 15 except that Compound 32-2 (2.4 g) was used instead of Compound 15-7, and nickel acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 32 (2.0 g, yield 84.2%) was secured.

HR LC/MS/MS m/z calculated for $C_{96}H_{102}Cl_4N_4NiO_8$ (M+): 1636.5805; found: 1636.5813.

Preparation Example 33
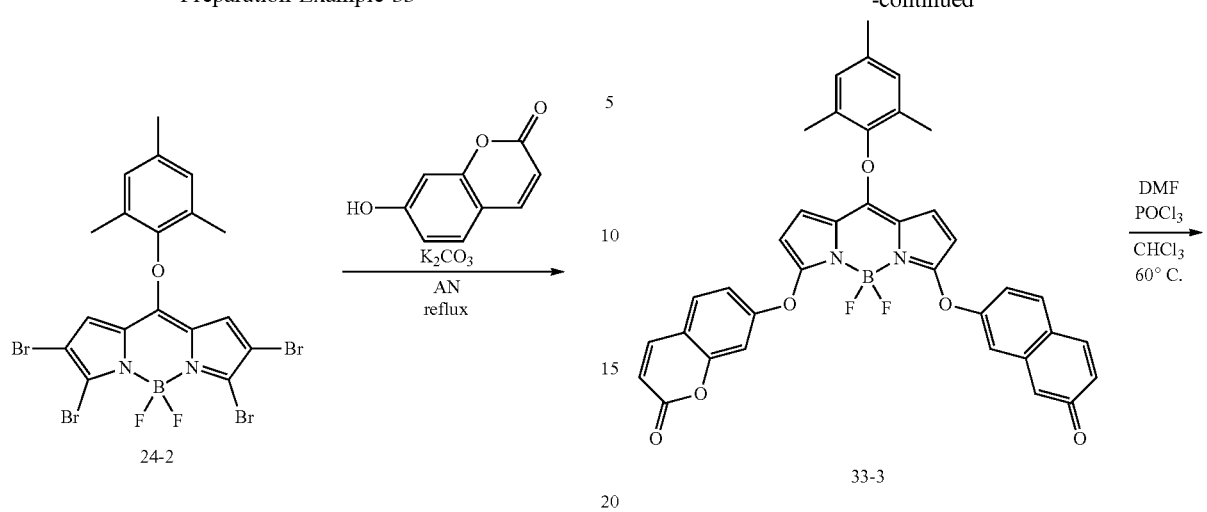
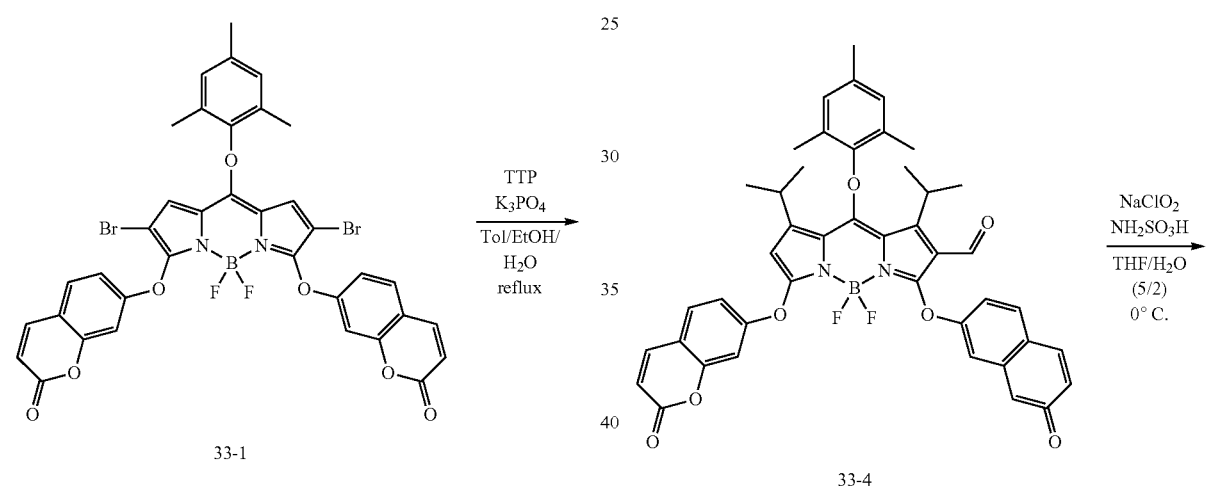
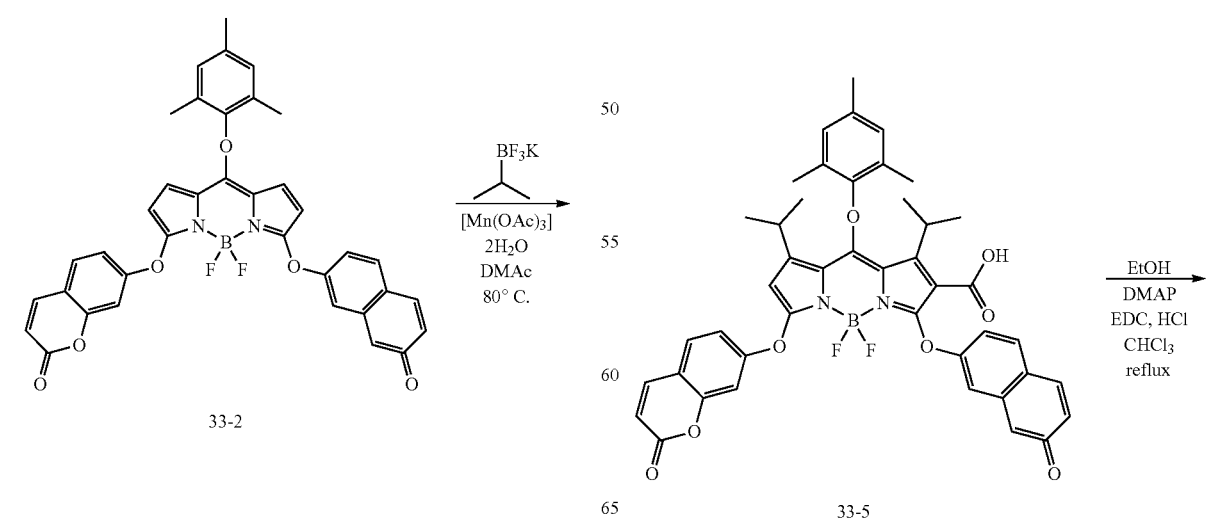

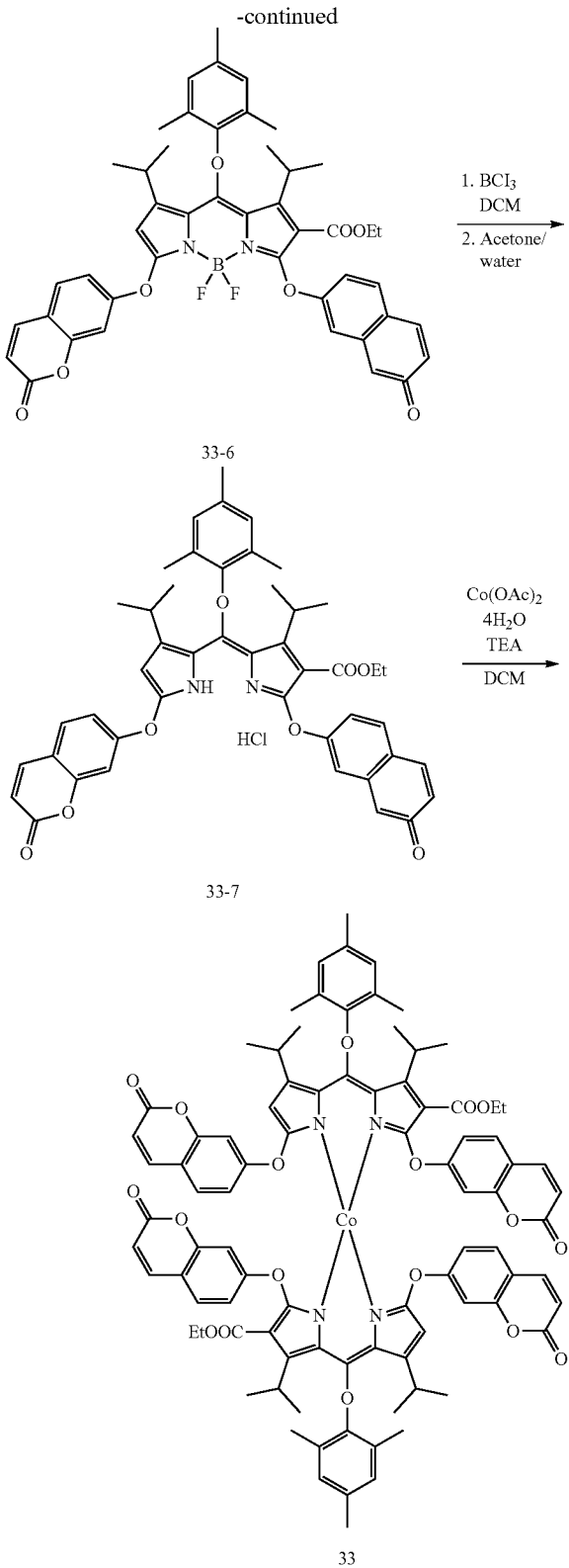

Synthesis of Compound 33-1

Synthesis was progressed in the same manner as in Synthesis of Compound 15-5 except that Compound 24-2 (3.0 g) was used instead of Compound 15-4, and 7-hydroxy-coumarin was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 33-1 (3.3 g, yield 87.8%) was secured.

Synthesis of Compound 33-2

Synthesis was progressed in the same manner as in Synthesis of Compound 15-6 except that Compound 33-1 (3.3 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 33-2 (2.3 g, yield 86.7%) was secured.

Synthesis of Compound 33-3

Synthesis was progressed in the same manner as in Synthesis of Compound 16-5 except that Compound 33-2 (2.3 g) was used instead of Compound 16-4, and isopropyltrifluoroborate potassium salt was used instead of cyclohexyltrifluoroborate potassium salt. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and a silica gel column was used to secure purified and separated Compound 33-3 (2.4 g, yield 92.3%).

Synthesis of Compound 33-4

Synthesis was progressed in the same manner as in Synthesis of Compound 19-5 except that Compound 33-3 (2.4 g) was used instead of Compound 19-4. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 33-4 (2.2 g, yield 88.3%) was secured.

Synthesis of Compound 33-5

Synthesis was progressed in the same manner as in Synthesis of Compound 19-6 except that Compound 33-4 (2.2 g) was used instead of Compound 19-5. After the reaction was completed, the result was extracted using chloroform, sodium thiosulfate and an aqueous sodium bicarbonate solution. The extracted organic layer was dried with sodium sulfate and, after removing the solvent by vacuum distillation, slurried with hexane to secure Compound 33-5 (2.0 g, yield 89.0%).

Synthesis of Compound 33-6

Compound 33-5 (2.0 g) was introduced to a chloroform solvent, stirred well and dissolved therein. Ethanol (30.0 equivalent), 4-dimethylaminopyridine (DMAP) (2.2 equivalent) and N-(3-dimethylaminopropyl)-N'-ethylcarbodiimide hydrochloride (EDC-HCl) (2.2 equivalent) were introduced thereto, and the result was stirred at room temperature. After the reaction was completed, the reaction solution was cooled to room temperature, and the result was extracted using chloroform and water. The extracted organic layer was dried with sodium sulfate and, after removing the solvent by vacuum distillation, recrystallized using ethanol. Through the recrystallization, purified and separated Compound 33-6 (1.8 g, yield 86.9%) was secured.

Synthesis of Compound 33-7

Synthesis was progressed in the same manner as in Synthesis of Compound 15-7 except that Compound 33-6 (1.8 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 33-7 (1.5 g, yield 84.5%) was secured.

Synthesis of Compound 33

Synthesis was progressed in the same manner as in Synthesis of Compound 15 except that Compound 33-7 (1.5 g) was used instead of Compound 15-7, and cobalt acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 33 (1.2 g, yield 80.8%) was secured.

HR LC/MS/MS m/z calculated for $C_{90}H_{82}CoN_4O_{18}$ (M+): 1565.4956; found: 1565.4994.

Preparation Example 34

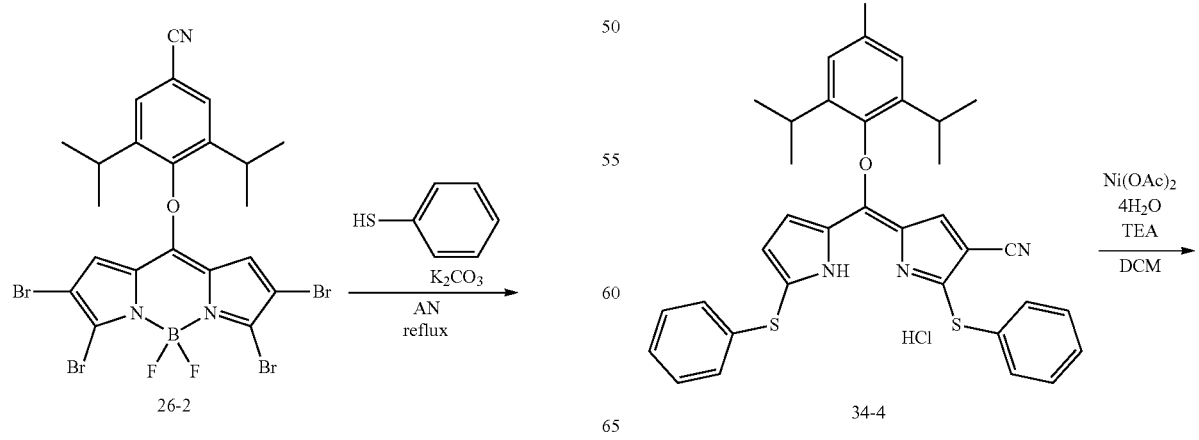

-continued

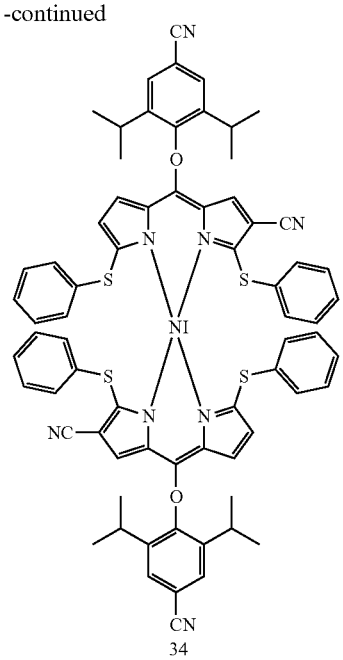

34

Synthesis of Compound 34-1

Synthesis was progressed in the same manner as in Synthesis of Compound 15-5 except that Compound 26-2 (3.0 g) was used instead of Compound 15-4, and benzenethiol was used instead of 4-hydroxy-3,5-dimethylbenzonitrile. After the reaction was completed, the result was extracted using chloroform and water. The extracted organic layer was dried with sodium sulfate and, after removing the solvent by vacuum distillation, recrystallized using methanol. Through the recrystallization, purified and separated Compound 34-1 (3.1 g, yield 95.4%) was secured.

Synthesis of Compound 34-2

Synthesis was progressed in the same manner as in Synthesis of Compound 15-6 except that Compound 34-1 (3.1 g) was used instead of Compound 15-5. When the reaction was completed, the result was extracted using chloroform and water. The extracted organic layer was dried with sodium sulfate and, after removing the solvent by vacuum distillation, recrystallized using methanol. Through the recrystallization, purified and separated Compound 34-2 (2.0 g, yield 81.2%) was secured.

Synthesis of Compound 34-3

Synthesis was progressed in the same manner as in Synthesis of Compound 16-6 except that Compound 34-2 (2.0 g) was used instead of Compound 16-5. When the reaction was completed, N,N-dimethylformamide (5.0 equivalent) was introduced thereto, and the result was stirred well again for a sufficient period of time. The result was extracted using chloroform and water, and the organic layer was dried using sodium sulfate. The solvent was removed by vacuum distillation, and the result was recrystallized using methanol. Through the recrystallization, purified and separated Compound 34-3 (1.8 g, yield 86.5%) was secured.

Synthesis of Compound 34-4

Synthesis was progressed in the same manner as in Synthesis of Compound 15-7 except that Compound 34-3 (1.8 g) was used instead of Compound 15-6. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 34-4 (1.4 g, yield 79.2%) was secured.

Synthesis of Compound 34

Synthesis was progressed in the same manner as in Synthesis of Compound 15 except that Compound 34-4 (1.4 g) was used instead of Compound 15-7, and nickel acetate tetrahydrate was used instead of zinc acetate dihydrate. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound 34 (1.1 g, yield 79.6%) was secured.

HR LC/MS/MS m/z calculated for $C_{70}H_{58}N_8NiO_2S_4$ (M+): 1228.2919; found: 1228.2923.

Comparative Preparation Example 1

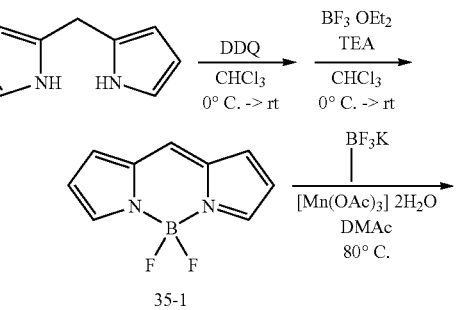

35-1

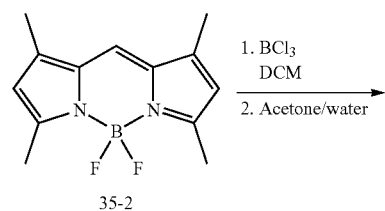

35-2

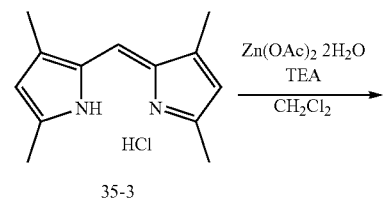

35-3

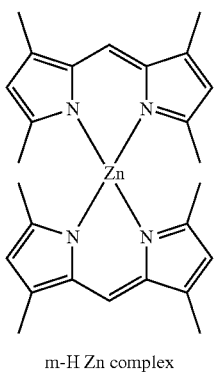

m-H Zn complex

Synthesis of Compound 35-1

2,2'-Dipyrrolylmethane (5.0 g) was stirred well and dissolved in a chloroform solvent. The reaction solution was cooled to 0° C. using ice water, and 2,3-dichloro-5,6-dicyano-1,4-benzoquinone (DDQ) (1.1 equivalent) was introduced thereto. The result was stirred well at room temperature, and when the reaction was completed, triethylamine (1.5 equivalent) was introduced thereto, and the result was extracted using diethyl ether and water. After drying the extracted organic layer with sodium sulfate, the reaction solution remaining in the container obtained by vacuum distilling the filtrate was stirred well again in a chloroform solvent. The reaction solution was cooled to 0° C. using ice water, and then triethylamine (20.0 equivalent) and a boron trifluoride ethyl ether complex ($BF_3 \cdot OEt_2$) (10.0 equivalent) were slowly introduced thereto. The reaction solution was stirred at room temperature, and when the reaction was finished, the result was extracted using chloroform and an aqueous sodium bicarbonate solution. The extracted organic layer was dried with sodium sulfate, and then a silica gel column was used to secure purified and separated Compound 35-1 (3.3 g, yield 50.3%).

Compound 35-2

Compound 35-1 (3.3 g) was stirred well and dissolved in an N,N-dimethylacetamide solvent. Methyltrifluoroborate potassium salt (5.0 equivalent) and manganese acetate hydrate (10.0 equivalent) were introduced thereto while stirring well, and the reaction solution was heated to between 80° C. to 100° C. When the reaction was finished, the reaction solution was cooled to room temperature, and then solids formed by introducing water thereto were filtered using a celite pad. The obtained solids and the celite pad were dissolved again in tetrahydrofuran, dried by introducing sodium sulfate thereto, and filtered. The solvent was removed by vacuum distillation, and the result was recrystallized using methanol. Through the recrystallization, purified and separated Compound 35-2 (2.9 g, yield 68.0%) was secured.

Synthesis of Compound 35-3

Compound 35-2 (2.9 g) was stirred well and dissolved in a dichloromethane solvent. A boron trichloride 1.0 M heptane solution (1.0 equivalent) was slowly added dropwise thereto. When the reaction was completed, the solvent was vacuum distilled at a low temperature of 30° C. or lower, then acetone and water in a ratio of 10/1 (volume ratio) were introduced to the reaction solution remaining in the container, and the result was stirred well again. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 35-3 (2.1 g, yield 75.9%) was secured.

Synthesis of Compound m-H Zn Complex

Compound 35-3 (2.1 g) was stirred well and dissolved in a dichloromethane solvent. Zinc acetate dihydrate (0.50 equivalent) was introduced to the reaction solution in a solid state, and triethylamine (2.5 equivalent) was further introduced thereto. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound m-H Zn complex (1.6 g, yield 77.7%) was secured.

HR LC/MS/MS m/z calculated for $C_{26}H_{30}N_4Zn$ (M+): 462.1762; found: 462.1765.

Comparative Preparation Example 2

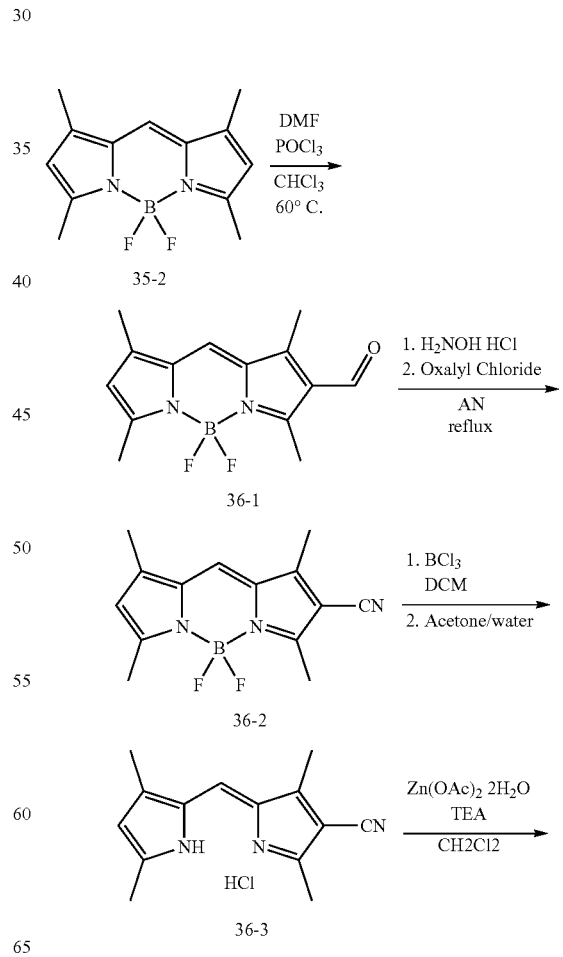

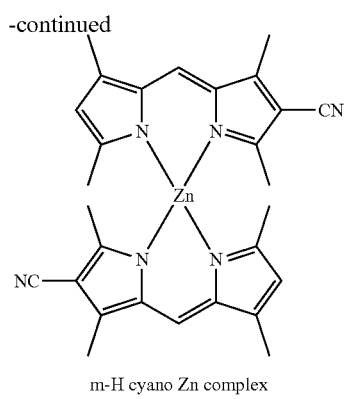

m-H cyano Zn complex

Synthesis of Compound 36-1

Under the nitrogen atmosphere at 0° C., phosphorous oxychloride (POCl$_3$) (2.0 equivalent) and N,N-dimethylformamide (DMF) (3.0 equivalent) were introduced to a chloroform solvent, and the mixture was stirred well for 1 hour. After 1 hour, Compound 35-2 (3.0 g) was introduced to the mixture solution, and the result was stirred under reflux at 60° C. After the reaction was completed, the reaction solution was cooled to 0° C. again, and the pH was adjusted to neutral using an aqueous sodium bicarbonate solution. The result was extracted using chloroform and water, and the extracted organic layer was dried with sodium sulfate and, after removing the solvent by vacuum distillation, recrystallized using methanol. Through the recrystallization, purified and separated Compound 36-1 (3.0 g, yield 89.8%) was secured.

Synthesis of Compound 36-2

Compound 36-1 (3.0 g) was stirred well and dissolved in an acetonitrile solvent. Hydroxylamine hydrochloride salt (1.5 equivalent) was introduced thereto, and the reaction solution was stirred under reflux. When the reaction was completed, the reaction solution was cooled to 0° C. using ice water, and oxalyl chloride (1.5 equivalent) was further introduced thereto. The reaction solution was stirred under reflux again. When the reaction was completed, the result was extracted using chloroform and water, and the organic layer was dried using sodium sulfate. The solvent was removed by vacuum distillation, and the result was recrystallized using methanol. Through the recrystallization, purified and separated Compound 36-2 (2.7 g, yield 91.0%) was secured.

Synthesis of Compound 36-3

Compound 36-2 (2.7 g) was stirred well and dissolved in a dichloromethane solvent. A boron trichloride 1.0 M heptane solution (1.0 equivalent) was slowly added dropwise thereto. When the reaction was completed, the solvent was vacuum distilled at a low temperature of 30° C. or lower, then acetone and water in a ratio of 10/1 (volume ratio) were introduced to the reaction solution remaining in the container, and the result was stirred well again. When the reaction was completed, the result was extracted using dichloromethane and water, and the extracted organic layer was dried with sodium sulfate. The solvent was removed by vacuum distillation, and the result was recrystallized using methanol. Through the recrystallization, purified and separated Compound 36-3 (2.1 g, yield 81.1%) was secured.

Synthesis of Compound m-H Cyano Zn Complex

Compound 36-3 (2.1 g) was stirred well and dissolved in a dichloromethane solvent. Zinc acetate dihydrate (0.50 equivalent) was introduced to the reaction solution in a solid state, and triethylamine (2.5 equivalent) was further introduced thereto. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound m-H cyano Zn complex (1.7 g, yield 82.4%) was secured.

HR LC/MS/MS m/z calculated for $C_{28}H_{28}N_6Zn$ (M+): 512.1667; found: 512.1673.

Comparative Preparation Example 3

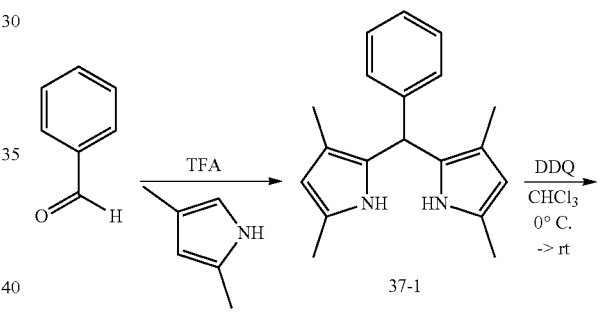

37-1

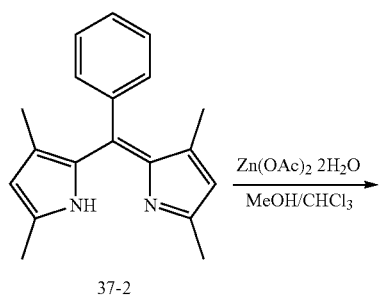

37-2

-continued

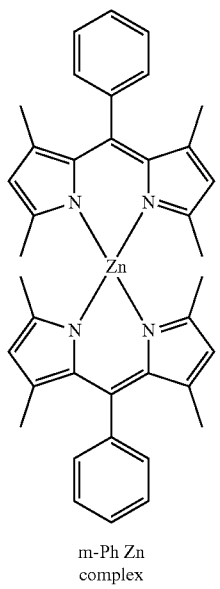

m-Ph Zn complex

Synthesis of Compound 37-1

Benzaldehyde (5.0 g) was introduced to a 2,4-dimethylpyrrole solvent and stirred well. Trifluoroacetic acid (0.10 equivalent) was slowly introduced thereto. After identifying the completion of the reaction, the result was extracted using dichloromethane and an aqueous sodium bicarbonate solution. The extracted organic layer was dried with sodium sulfate, and then a silica gel column was used to secure purified and separated Compound 37-1 (3.9 g, yield 29.7%).

Synthesis of Compound 37-2

Compound 37-1 (3.9 g) was stirred well and dissolved in a chloroform solvent. The reaction solution was cooled to 0° C. using ice water, and 2,3-dichloro-5,6-dicyano-1,4-benzoquinone (DDQ) (1.1 equivalent) was introduced thereto. The reaction solution was stirred well at room temperature, and when the reaction was completed, triethylamine (1.5 equivalent) was introduced thereto, and the result was extracted using diethyl ether and water. The extracted organic layer was dried with sodium sulfate, and then a silica gel column was used to secure purified and separated Compound 37-2 (3.3 g, yield 85.2%).

Synthesis of Compound m-Ph Zn Complex

Compound 37-2 (3.3 g) was stirred well and dissolved in a methanol/chloroform (1/1 volume ratio) solvent. Zinc acetate dihydrate (0.50 equivalent) was introduced to the reaction solution in a solid state. After the reaction was completed, the result was extracted using dichloromethane and water. The extracted organic layer was dried with sodium sulfate and, after removing the solvent by vacuum distillation, recrystallized using methanol. Through the recrystallization, purified and separated Compound m-Ph Zn complex (2.6 g, yield 70.7%) was secured.

HR LC/MS/MS m/z calculated for $C_{38}H_{38}N_4Zn$ (M+): 614.2388; found: 614.2391.

Comparative Preparation Example 4

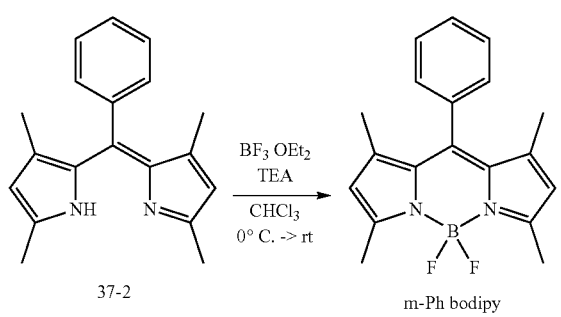

37-2             m-Ph bodipy

Synthesis of Compound m-Ph Bodipy

Compound 37-2 (3.0 g) was stirred well and dissolved in a chloroform solvent. The reaction solution was cooled to 0° C. using ice water, and then triethylamine (4.0 equivalent) and a boron trifluoride ethyl ether complex ($BF_3 \cdot OEt_2$) (2.0 equivalent) were slowly introduced thereto. The reaction solution was stirred at room temperature, and when the reaction was finished, the result was extracted using chloroform and an aqueous sodium bicarbonate solution. The extracted organic layer was dried with sodium sulfate, and then a silica gel column was used to secure purified and separated Compound m-Ph bodipy (2.8 g, yield 79.6%).

HR LC/MS/MS m/z calculated for $C_{19}H_{19}BF_2N_2$(M+): 324.1609; found: 324.1611.

Example: Manufacture of Color Conversion Film

Example 1

A first solution was prepared by dissolving Compound 1 of the preparation example (maximum absorption wavelength 494 nm, full width at half maximum 33 nm in toluene solution), a dye-type organic light absorber, in a xylene solvent.

A second solution was prepared by dissolving a thermoplastic resin SAN (styrene-acrylonitrile-based) in a xylene solvent. The first solution and the second solution were homogeneously mixed so that the amount of Compound 1 was 0.5 parts by weight based on 100 parts by weight of the SAN. The solid content in the mixed solution was 20% by weight and viscosity was 200 cps at 20° C. This solution was coated on a PET (polyethylene terephthalate) base, and dried to prepare a color conversion film.

A luminance spectrum of the prepared color conversion film was measured using a spectroradiometer (SR series of TOPCON Corporation). Specifically, the prepared color conversion film was laminated on one surface of a light guide plate of a backlight unit including an LED blue backlight (maximum emission wavelength 450 nm) and the light guide plate, and after laminating a prism sheet and a DBEF (double brightness enhancement film) on the color conversion film, a luminance spectrum of the film was measured. When measuring the luminance spectrum, an initial value was set so that the brightness of the blue LED light was 600 nit based on without the color conversion film.

Example 2

An experiment was performed in the same manner as in Example 1 except that Compound 2 (maximum absorption wavelength 502 nm, full width at half maximum 31 nm in toluene solution) was used instead of Compound 1.

Example 3

An experiment was performed in the same manner as in Example 1 except that Compound 3 (maximum absorption wavelength 503 nm, full width at half maximum 29 nm in toluene solution) was used instead of Compound 1.

Example 4

An experiment was performed in the same manner as in Example 1 except that Compound 4 (maximum absorption wavelength 490 nm, full width at half maximum 36 nm in toluene solution) was used instead of Compound 1.

Example 5

An experiment was performed in the same manner as in Example 1 except that Compound 5 (maximum absorption wavelength 516 nm, full width at half maximum 40 nm in toluene solution) was used instead of Compound 1.

Example 6

An experiment was performed in the same manner as in Example 1 except that Compound 6 (maximum absorption wavelength 514 nm, full width at half maximum 44 nm in toluene solution) was used instead of Compound 1.

Example 7

An experiment was performed in the same manner as in Example 1 except that Compound 7 (maximum absorption wavelength 487 nm, full width at half maximum 35 nm in toluene solution) was used instead of Compound 1.

Example 8

An experiment was performed in the same manner as in Example 1 except that Compound 8 (maximum absorption wavelength 506 nm, full width at half maximum 37 nm in toluene solution) was used instead of Compound 1.

Example 9

An experiment was performed in the same manner as in Example 1 except that Compound 9 (maximum absorption wavelength 523 nm, full width at half maximum 41 nm in toluene solution) was used instead of Compound 1.

Example 10

An experiment was performed in the same manner as in Example 1 except that Compound 10 (maximum absorption wavelength 519 nm, full width at half maximum 42 nm in toluene solution) was used instead of Compound 1.

Example 11

An experiment was performed in the same manner as in Example 1 except that Compound 11 (maximum absorption wavelength 512 nm, full width at half maximum 35 nm in toluene solution) was used instead of Compound 1.

Example 12

An experiment was performed in the same manner as in Example 1 except that Compound 12 (maximum absorption wavelength 518 nm, full width at half maximum 30 nm in toluene solution) was used instead of Compound 1.

Example 13

An experiment was performed in the same manner as in Example 1 except that Compound 13 (maximum absorption wavelength 520 nm, full width at half maximum 58 nm in toluene solution) was used instead of Compound 1.

Example 14

An experiment was performed in the same manner as in Example 1 except that Compound 14 (maximum absorption wavelength 518 nm, full width at half maximum 54 nm in toluene solution) was used instead of Compound 1.

Example 15

An experiment was performed in the same manner as in Example 1 except that Compound (maximum absorption wavelength 500 nm, full width at half maximum 35 nm in toluene solution) was used instead of Compound 1.

Example 16

An experiment was performed in the same manner as in Example 1 except that Compound 16 (maximum absorption wavelength 498 nm, full width at half maximum 42 nm in toluene solution) was used instead of Compound 1.

Example 17

An experiment was performed in the same manner as in Example 1 except that Compound 17 (maximum absorption wavelength 518 nm, full width at half maximum 38 nm in toluene solution) was used instead of Compound 1.

Example 18

An experiment was performed in the same manner as in Example 1 except that Compound 18 (maximum absorption wavelength 511 nm, full width at half maximum 36 nm in toluene solution) was used instead of Compound 1.

Example 19

An experiment was performed in the same manner as in Example 1 except that Compound 19 (maximum absorption wavelength 495 nm, full width at half maximum 38 nm in toluene solution) was used instead of Compound 1.

Example 20

An experiment was performed in the same manner as in Example 1 except that Compound 20 (maximum absorption wavelength 504 nm, full width at half maximum 41 nm in toluene solution) was used instead of Compound 1.

Example 21

An experiment was performed in the same manner as in Example 1 except that Compound 21 (maximum absorption wavelength 497 nm, full width at half maximum 40 nm in toluene solution) was used instead of Compound 1.

Example 22

An experiment was performed in the same manner as in Example 1 except that Compound 22 (maximum absorption wavelength 501 nm, full width at half maximum 37 nm in toluene solution) was used instead of Compound 1.

Example 23

An experiment was performed in the same manner as in Example 1 except that Compound 23 (maximum absorption wavelength 496 nm, full width at half maximum 42 nm in toluene solution) was used instead of Compound 1.

Example 24

An experiment was performed in the same manner as in Example 1 except that Compound 24 (maximum absorption wavelength 494 nm, full width at half maximum 46 nm in toluene solution) was used instead of Compound 1.

Example 25

An experiment was performed in the same manner as in Example 1 except that Compound 25 (maximum absorption wavelength 491 nm, full width at half maximum 39 nm in toluene solution) was used instead of Compound 1.

Example 26

An experiment was performed in the same manner as in Example 1 except that Compound 26 (maximum absorption wavelength 505 nm, full width at half maximum 37 nm in toluene solution) was used instead of Compound 1.

Example 27

An experiment was performed in the same manner as in Example 1 except that Compound 27 (maximum absorption wavelength 513 nm, full width at half maximum 42 nm in toluene solution) was used instead of Compound 1.

Example 28

An experiment was performed in the same manner as in Example 1 except that Compound 28 (maximum absorption wavelength 507 nm, full width at half maximum 48 nm in toluene solution) was used instead of Compound 1.

Example 29

An experiment was performed in the same manner as in Example 1 except that Compound 29 (maximum absorption wavelength 495 nm, full width at half maximum 33 nm in toluene solution) was used instead of Compound 1.

Example 30

An experiment was performed in the same manner as in Example 1 except that Compound 30 (maximum absorption wavelength 518 nm, full width at half maximum 108 nm in toluene solution) was used instead of Compound 1.

Example 31

An experiment was performed in the same manner as in Example 1 except that Compound 31 (maximum absorption wavelength 537 nm, full width at half maximum 95 nm in toluene solution) was used instead of Compound 1.

Example 32

An experiment was performed in the same manner as in Example 1 except that Compound 32 (maximum absorption wavelength 525 nm, full width at half maximum 96 nm in toluene solution) was used instead of Compound 1.

Example 33

An experiment was performed in the same manner as in Example 1 except that Compound 33 (maximum absorption wavelength 515 nm, full width at half maximum 41 nm in toluene solution) was used instead of Compound 1.

Example 34

An experiment was performed in the same manner as in Example 1 except that Compound 34 (maximum absorption wavelength 532 nm, full width at half maximum 115 nm in toluene solution) was used instead of Compound 1.

Comparative Example 1

An experiment was performed in the same manner as in Example 1 except that Compound m-H Zn complex (maximum absorption wavelength 497 nm, full width at half maximum 20 nm in toluene solution) was used instead of Compound 1.

Comparative Example 2

An experiment was performed in the same manner as in Example 1 except that Compound m-H cyano Zn complex (maximum absorption wavelength 493 nm, full width at half maximum 23 nm in toluene solution) was used instead of Compound 1.

Comparative Example 3

An experiment was performed in the same manner as in Example 1 except that Compound m-Ph Zn complex (maximum absorption wavelength 498 nm, full width at half maximum 21 nm in toluene solution) was used instead of Compound 1.

Comparative Example 4

An experiment was performed in the same manner as in Example 1 except that Compound m-Ph bodipy (maximum absorption wavelength 496 nm, full width at half maximum 23 nm in toluene solution) was used instead of Compound 1.

The maximum value of the film absorption wavelength, the full width at half maximum (FWHM) and the Abs intensity ratio (1000 hr, %) of each of the color conversion films according to Examples 1 to 34 and Comparative Examples 1 to 4 are as shown in the following Table 1.

TABLE 1

| | | Film Absorption Wavelength | | Abs Intensity |
|---|---|---|---|---|
| | Compound | $\lambda_{max}$ (nm) | FWHM (nm) | Ratio (1000 hr, %) |
| Example 1 | 1 | 505 | 36 | 85.4 |
| Example 2 | 2 | 512 | 34 | 86.7 |
| Example 3 | 3 | 512 | 32 | 92.1 |
| Example 4 | 4 | 499 | 39 | 91.5 |
| Example 5 | 5 | 523 | 44 | 89.9 |
| Example 6 | 6 | 522 | 48 | 89.4 |
| Example 7 | 7 | 496 | 38 | 84.5 |

TABLE 1-continued

| Compound | Film Absorption Wavelength | | Abs Intensity |
|---|---|---|---|
| | $\lambda_{max}$ (nm) | FWHM (nm) | Ratio (1000 hr, %) |
| Example 8 | 8 | 515 | 40 | 88.6 |
| Example 9 | 9 | 531 | 45 | 86.1 |
| Example 10 | 10 | 527 | 44 | 88.7 |
| Example 11 | 11 | 518 | 39 | 91.7 |
| Example 12 | 12 | 527 | 33 | 93.8 |
| Example 13 | 13 | 528 | 60 | 84.9 |
| Example 14 | 14 | 531 | 67 | 91.2 |
| Example 15 | 15 | 511 | 37 | 93.8 |
| Example 16 | 16 | 507 | 44 | 95.5 |
| Example 17 | 17 | 528 | 41 | 94.3 |
| Example 18 | 18 | 519 | 40 | 97.2 |
| Example 19 | 19 | 505 | 42 | 96.3 |
| Example 20 | 20 | 515 | 43 | 97.1 |
| Example 21 | 21 | 509 | 45 | 96.8 |
| Example 22 | 22 | 516 | 41 | 94.1 |
| Example 23 | 23 | 508 | 48 | 94.9 |
| Example 24 | 24 | 505 | 50 | 98.3 |
| Example 25 | 25 | 502 | 43 | 94.1 |
| Example 26 | 26 | 516 | 39 | 94.7 |
| Example 27 | 27 | 522 | 46 | 95.1 |
| Example 28 | 28 | 517 | 53 | 93.7 |
| Example 29 | 29 | 505 | 36 | 98.8 |
| Example 30 | 30 | 529 | 123 | 94.5 |
| Example 31 | 31 | 546 | 102 | 93.5 |
| Example 32 | 32 | 535 | 104 | 94.9 |
| Example 33 | 33 | 524 | 45 | 96.6 |
| Example 34 | 34 | 541 | 128 | 96.9 |
| Comparative Example 1 | m-H Zn Complex | 502 | 22 | 41.3 |
| Comparative Example 2 | m-H Cyano Zn Complex | 500 | 26 | 78.5 |
| Comparative Example 3 | m-PhZn Complex | 505 | 24 | 55.4 |
| Comparative Example 4 | m-Ph Bodipy | 501 | 25 | 90.8 |

In Table 1, $\lambda_{max}$ means a maximum value of the film absorption wavelength, and FWHM means, as a full width at half maximum in the absorption peak, a width of the absorption peak at half the maximum height in the maximum absorption peak. In addition, the Abs intensity ratio of Table 1 means, with respect to absorption intensity at $\lambda_{max}$, absorption intensity after 1,000 hours compared to initial absorption intensity of 100% under the backlight.

According to Table 1, it was seen that Examples 1 to 14 had a lower absorption intensity decrease rate compared to Comparative Examples 1 to 3. This is due to the fact that, by using the compound of Chemical Formula 1 having an aromatic ring in which a withdrawing group is introduced to the substituents R5, R6, R7 and/or R8 and an O or S linker such as the substituents -L1-R13 and -L2-R14 is present at the meso position, Examples 1 to 14 had significantly increased enhancement in the light resistance compared to Comparative Examples 1 to 3.

In addition, it was seen that Examples 15 to 34 had a lower absorption intensity decrease rate compared to Comparative Examples 1, 3 and 4. This is due to the fact that, by using the compound of Chemical Formula 1 in which a substituent including O or S is present in R9, R10, R11 and R12 and an electron withdrawing group is introduced to R5, R6, R7 and/or R8, Examples 15 to 34 had significantly increased enhancement in the light resistance compared to Comparative Examples 1, 3 and 4.

The invention claimed is:
1. A compound represented by the following Chemical Formula 1:

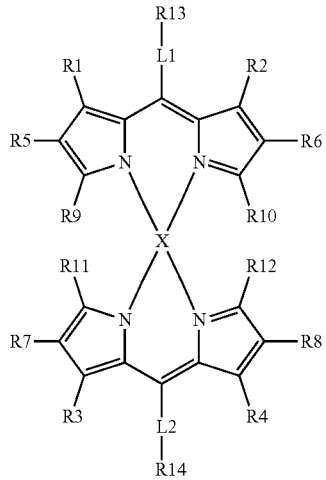

[Chemical Formula 1]

wherein, in the Chemical Formula 1,
R1 to R8 are the same as or different from each other, and each independently hydrogen; a halogen group; an aldehyde group; a nitrile group; a nitro group; a substituted or unsubstituted ester group; a substituted or unsubstituted amide group; a substituted or unsubstituted alkyl group; a substituted or unsubstituted cycloalkyl group; a substituted or unsubstituted aryl group; a substituted or unsubstituted aryloxy group; a substituted or unsubstituted arylthio group; or a substituted or unsubstituted heteroaryl group;
R9 to R12 are the same as or different from each other, and each independently hydrogen; a substituted or unsubstituted alkyl group; a substituted or unsubstituted cycloalkyl group; or -L-R;
L1, L2 and L are the same as or different from each other, and each independently O or S;
R is a substituted or unsubstituted alkyl group; a substituted or unsubstituted aryl group; or a substituted or unsubstituted heteroaryl group;
R13 and R14 are the same as or different from each other, and each independently a substituted or unsubstituted aryl group; or a substituted or unsubstituted heteroaryl group; and
X is Zn, Co, Ni or Pd.
2. The compound of claim 1, wherein R1 to R8 are the same as or different from each other, and each independently hydrogen; a halogen group; a nitrile group; a nitro group; —CHO; —COOR; —(C=O)NR'R"; a linear or branched alkyl group; a fluoroalkyl group; a cycloalkyl group unsubstituted or substituted with an alkyl group; an aryl group unsubstituted or substituted with one or more substituents selected from among a nitrile group, a halogen group, an alkyl group and a fluoroalkyl group; a polycyclic heteroaryl group; an aryloxy group unsubstituted or substituted with one or more substituents selected from among a halogen group and an alkyl group; or an arylthio group unsubstituted or substituted with one or more substituents selected from among a halogen group and an alkyl group; and
R, R' and R" are the same as or different from each other, and each independently a substituted or unsubstituted alkyl group; a substituted or unsubstituted aryl group; or a substituted or unsubstituted heteroaryl group, and R' and R" bond to each other to form a ring.

3. A composition for forming an optical film, the composition comprising:
a binder resin; and
the compound of claim 2.

4. The compound of claim 1, wherein Chemical Formula 1 is any one of the following Chemical Formulae 1-1 to 1-16:

[Chemical Formula 1-1]

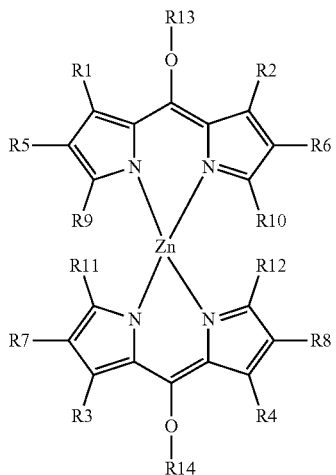

[Chemical Formula 1-2]

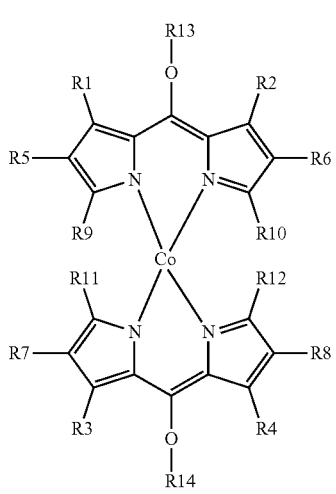

[Chemical Formula 1-3]

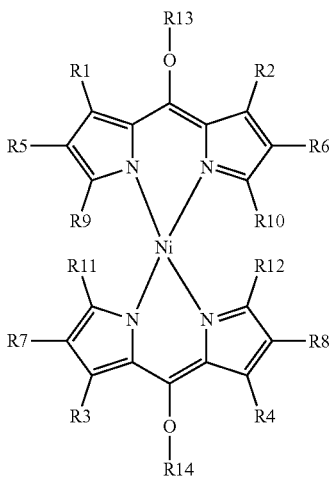

[Chemical Formula 1-4]

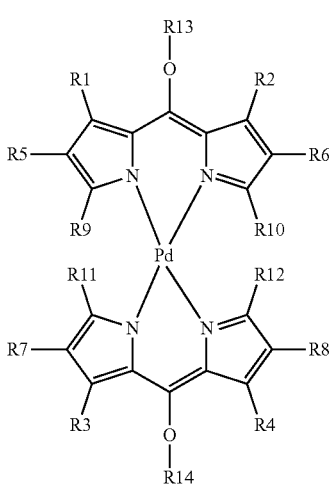

[Chemical Formula 1-5]

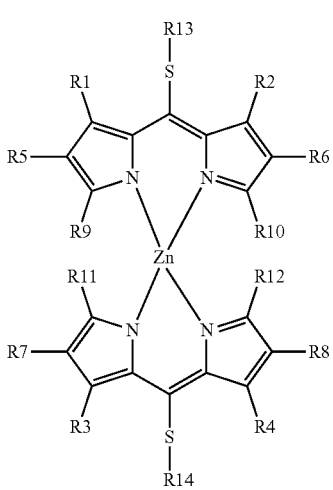

[Chemical Formula 1-6]
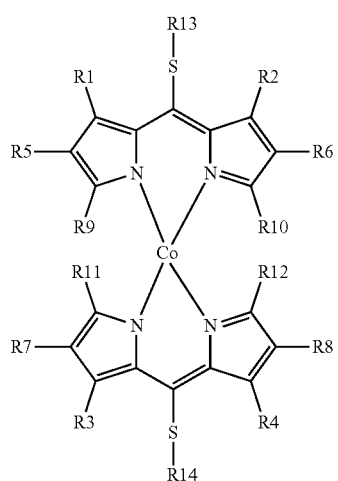
[Chemical Formula 1-9]
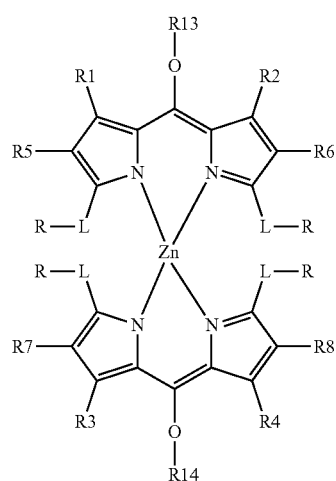
[Chemical Formula 1-7]
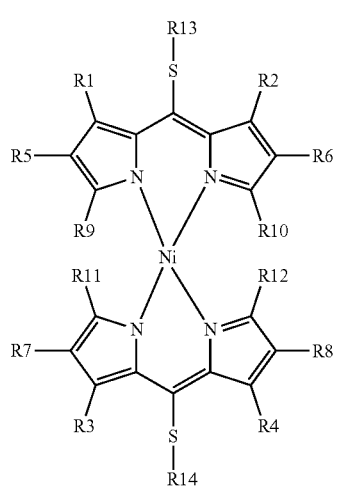
[Chemical Formula 1-10]
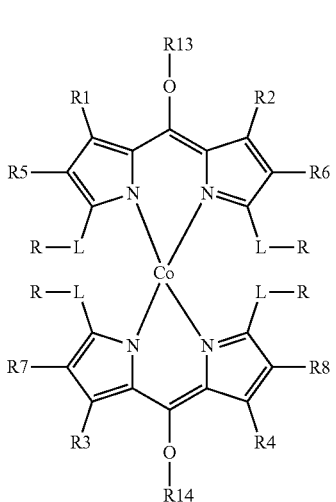
[Chemical Formula 1-8]
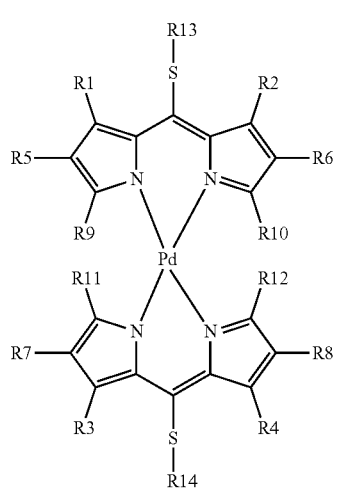
[Chemical Formula 1-11]
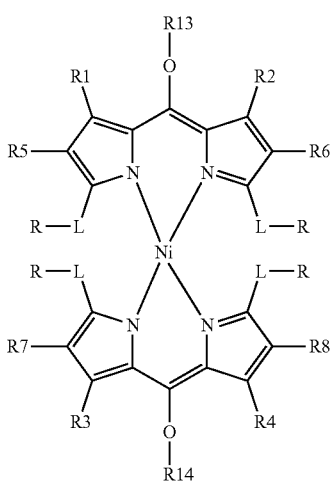

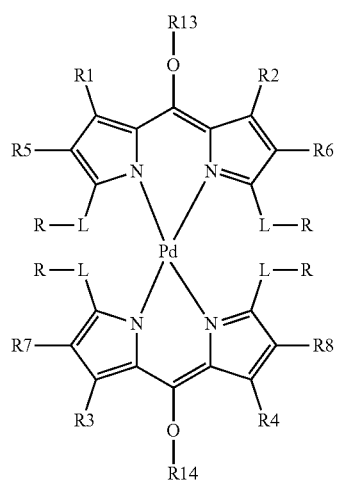

[Chemical Formula 1-12]

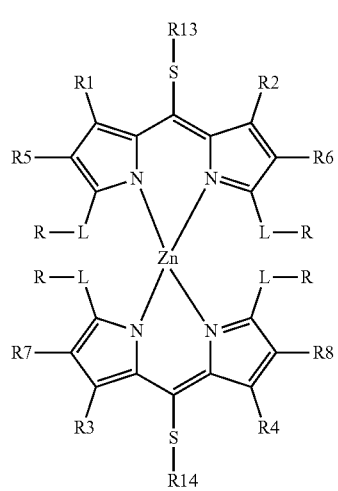

[Chemical Formula 1-13]

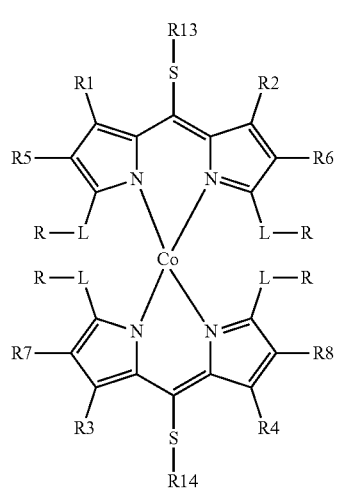

[Chemical Formula 1-14]

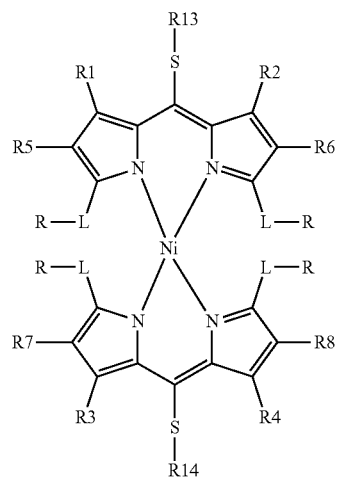

[Chemical Formula 1-15]

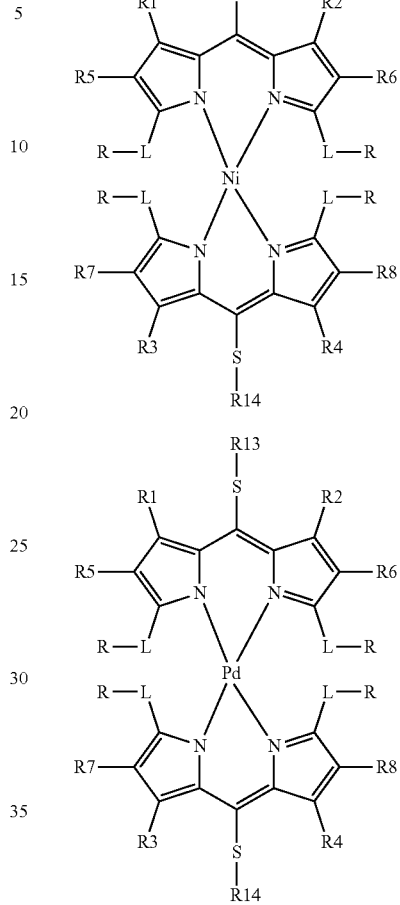

[Chemical Formula 1-16]

in the Chemical Formulae 1-1 to 1-16,

R1 to R14, L and R are as defined in claim 1.

5. A composition for forming an optical film, the composition comprising:
a binder resin; and
the compound of claim 4.

6. The compound of claim 1, wherein R9 to R12 are the same as or different from each other, and each independently hydrogen; a linear or branched alkyl group; or a cycloalkyl group unsubstituted or substituted with an alkyl group.

7. A composition for forming an optical film, the composition comprising:
a binder resin; and
the compound of claim 6.

8. The compound of claim 1, wherein R is an alkyl group unsubstituted or substituted with a halogen group; an aryl group unsubstituted or substituted with one or more substituents selected from the group of a nitrile group, a nitro group, a halogen group, an alkyl group and an alkoxy group; or a substituted or unsubstituted heteroaryl group including one or more of N and O.

9. A composition for forming an optical film, the composition comprising:
a binder resin; and
the compound of claim 8.

10. The compound of claim 1, wherein R13 and R14 are the same as or different from each other, and each independently an aryl group unsubstituted or substituted with one or more substituents selected from the group of an alkyl group, a fluoroalkyl group, a halogen group, a nitrile group, an alkoxy group, an alkoxyaryl group and an aryl group; a heteroaryl group unsubstituted or substituted with an alkyl group or =O; or a substituted or unsubstituted heteroaryl group including one or more of N and O.

11. A composition for forming an optical film, the composition comprising:
    a binder resin; and
    the compound of claim 10.

12. The compound of claim 1, wherein the compound has any one of the following structures:

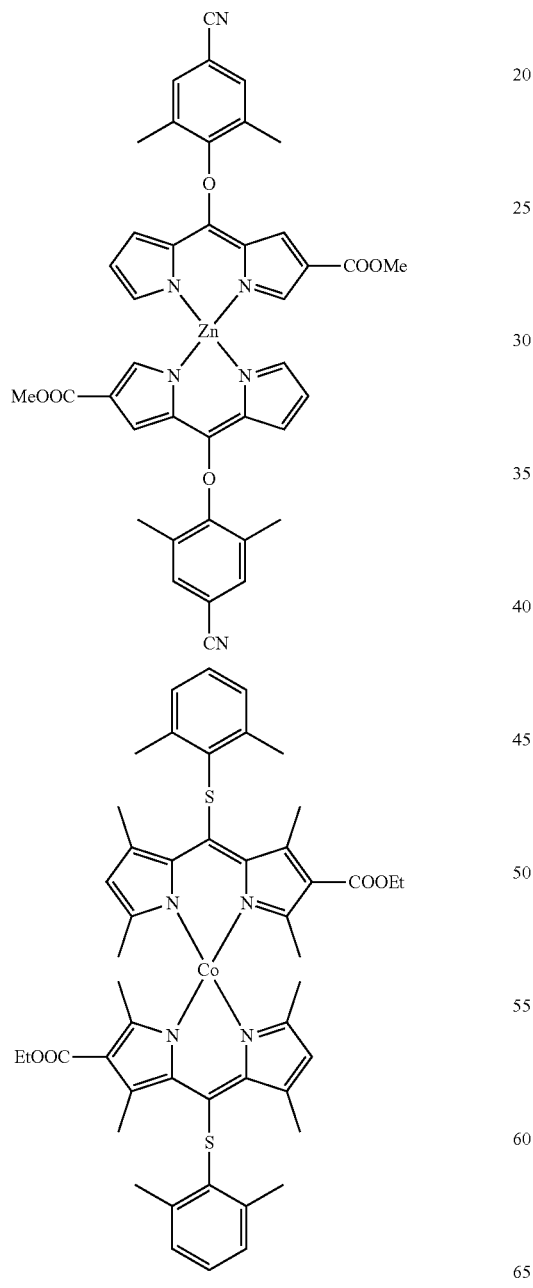

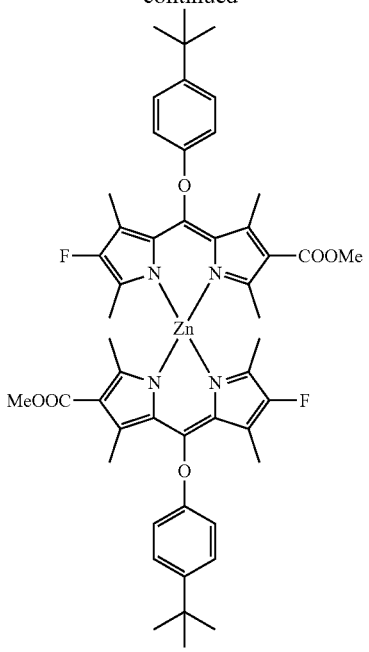

-continued

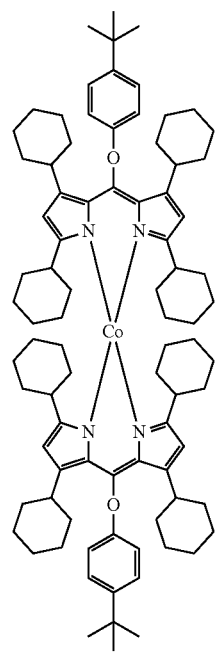

215
-continued
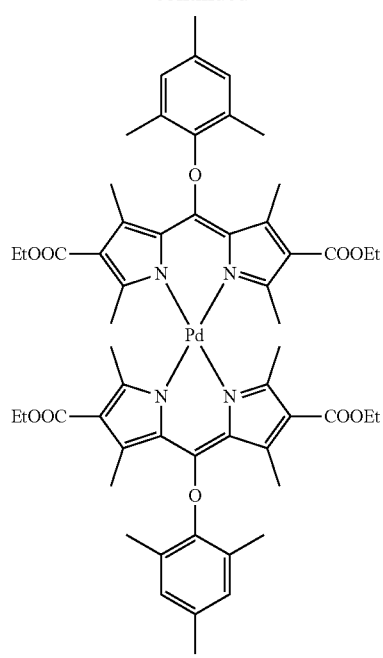
216
-continued
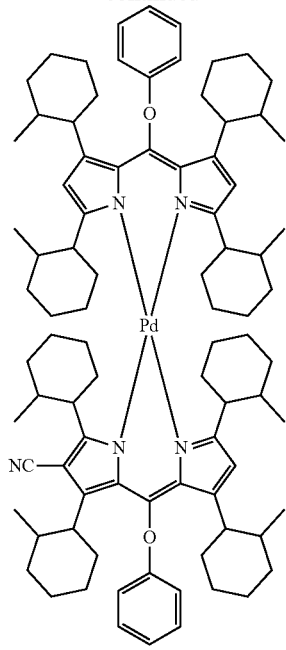
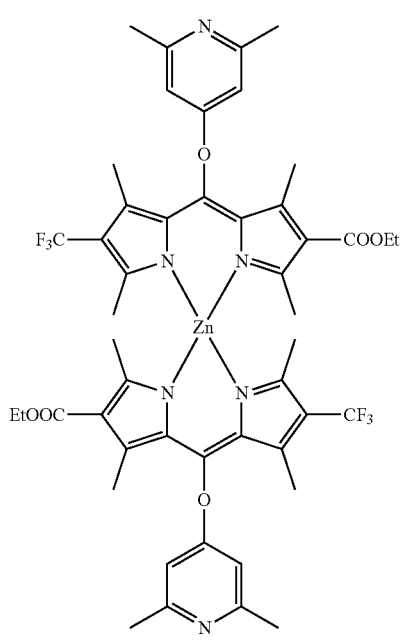
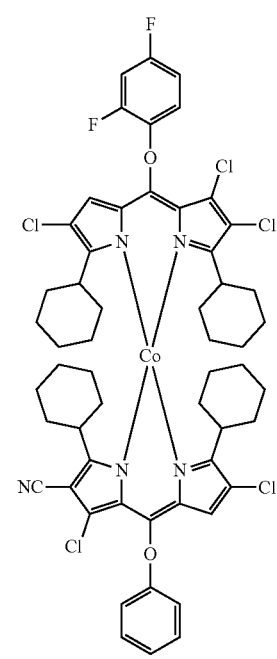

217
-continued
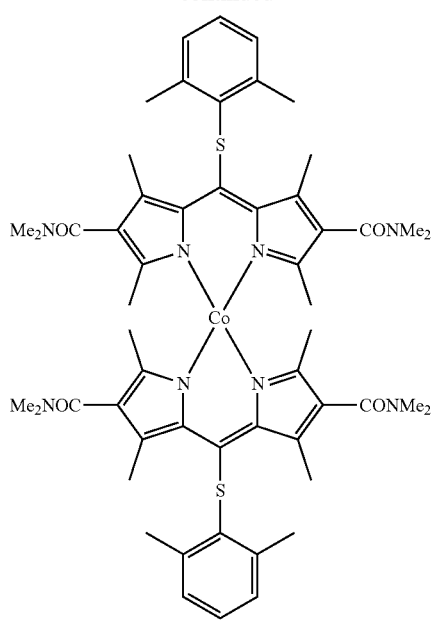
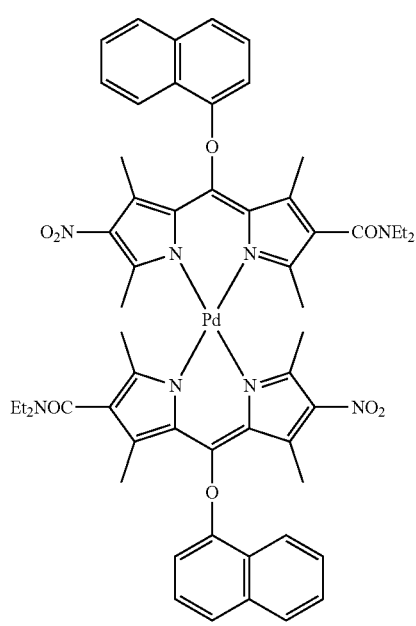
218
-continued
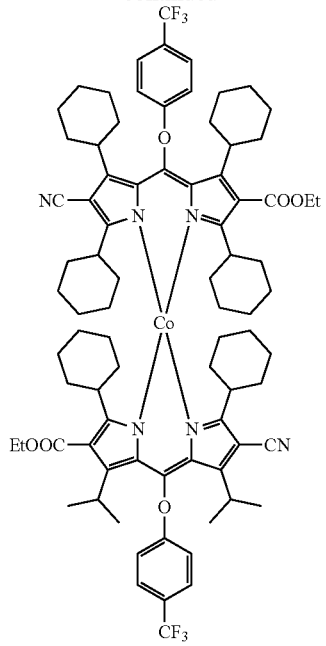
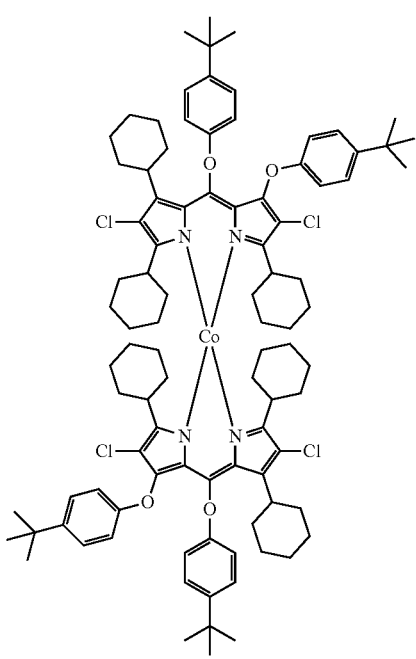

219
-continued
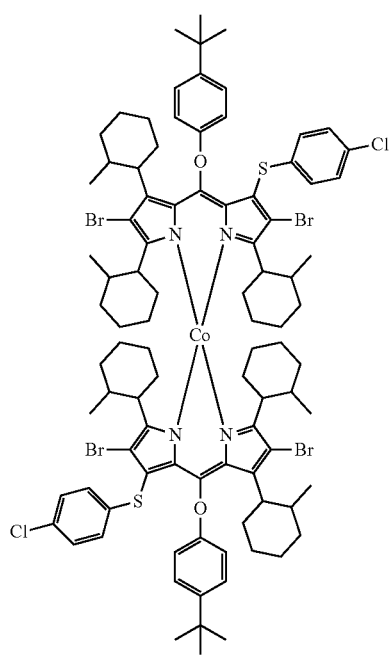
220
-continued
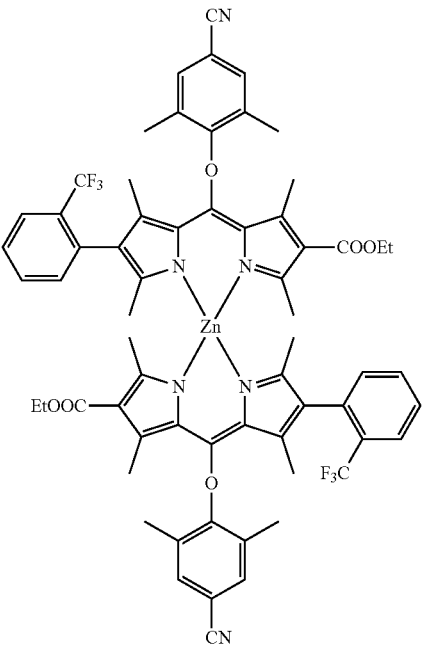
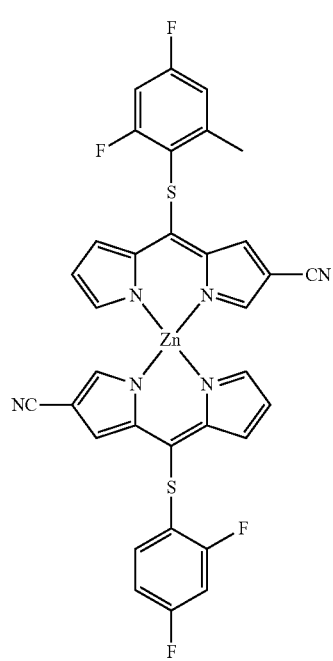
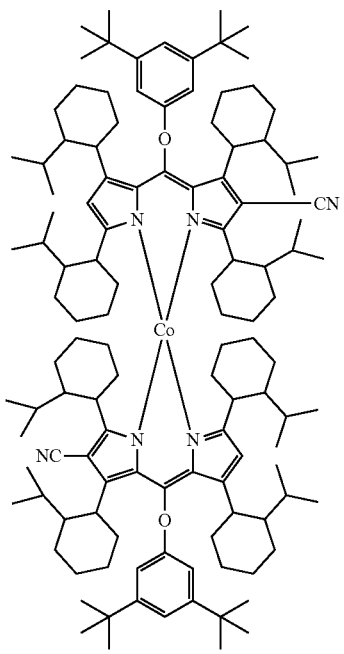

221
-continued
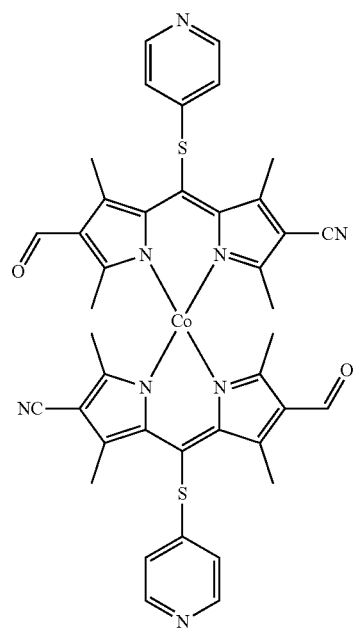
222
-continued
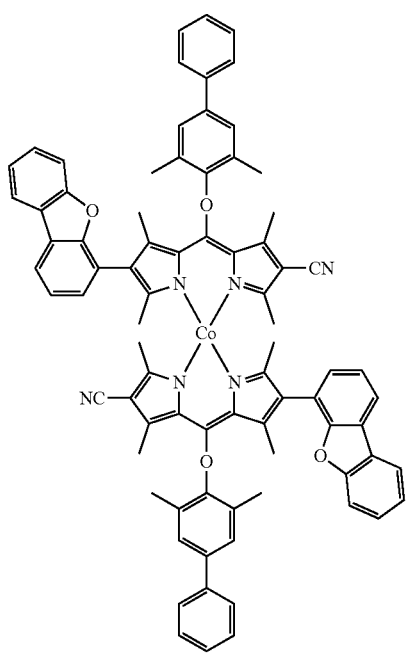
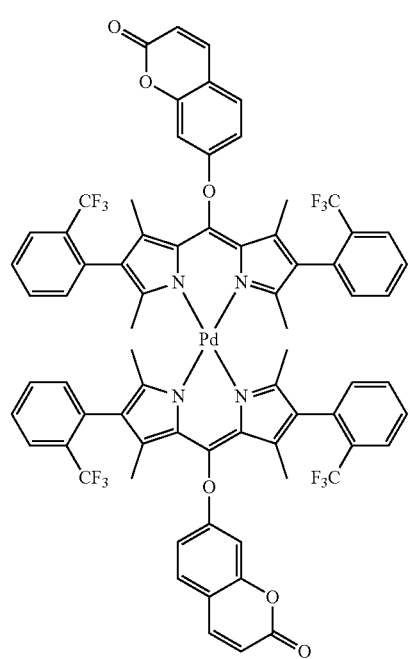
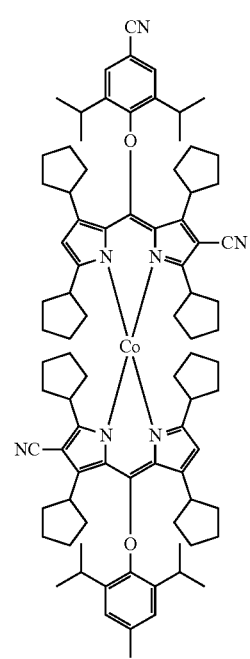

223
-continued
224
-continued
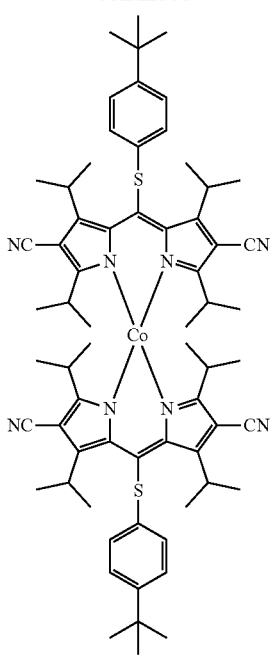
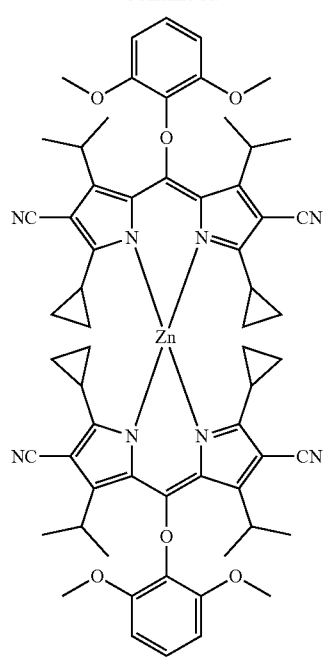
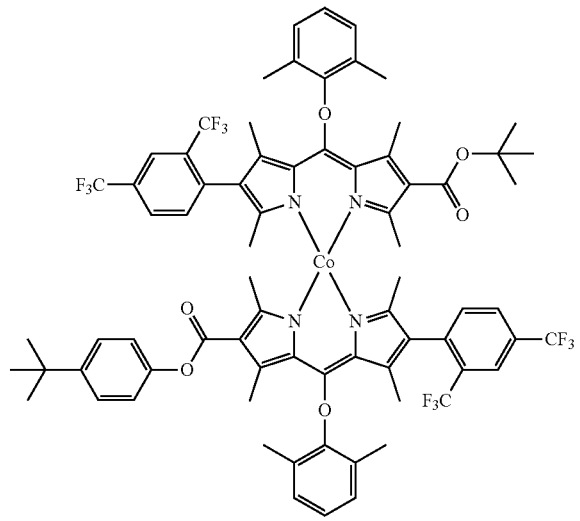

225
-continued
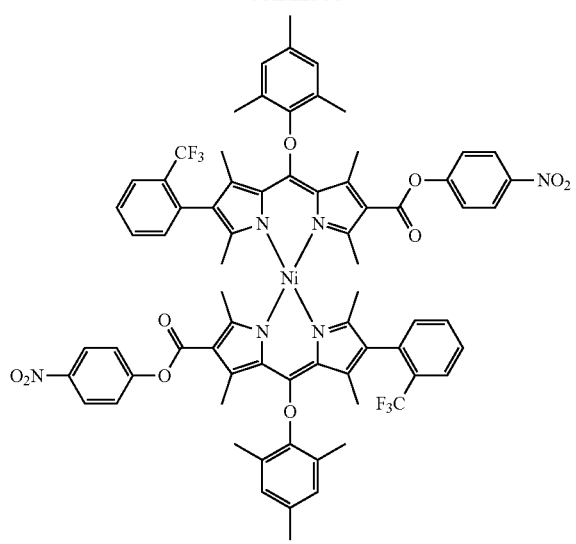
226
-continued
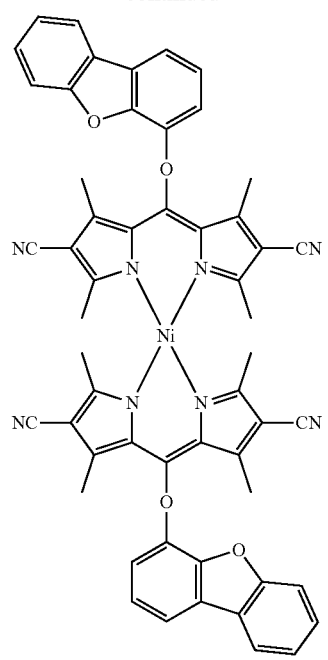
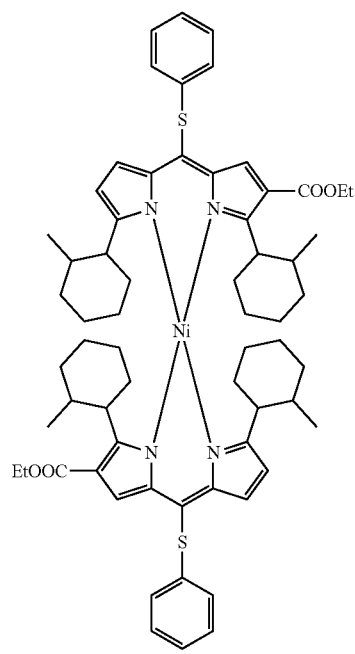
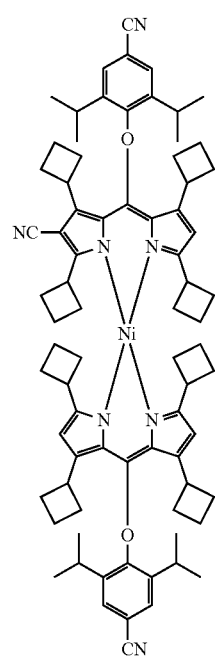

227
-continued
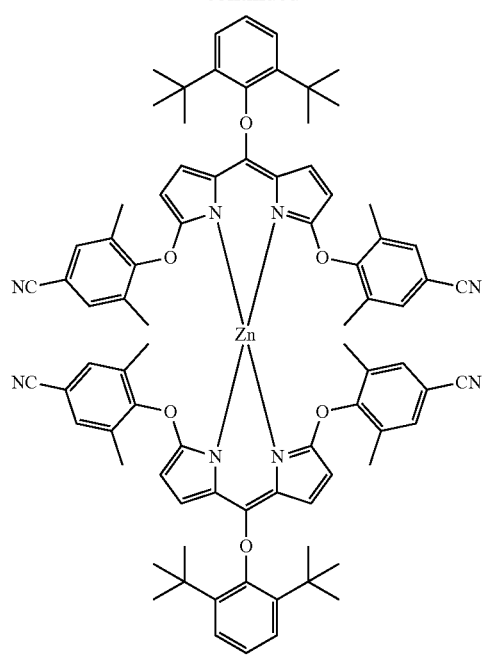
228
-continued
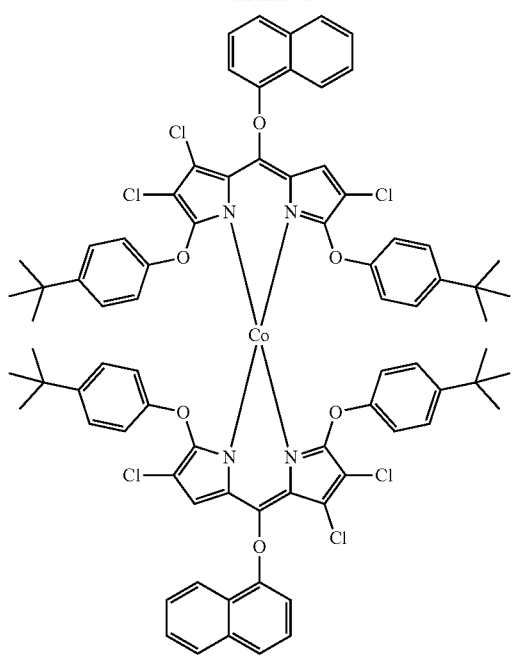
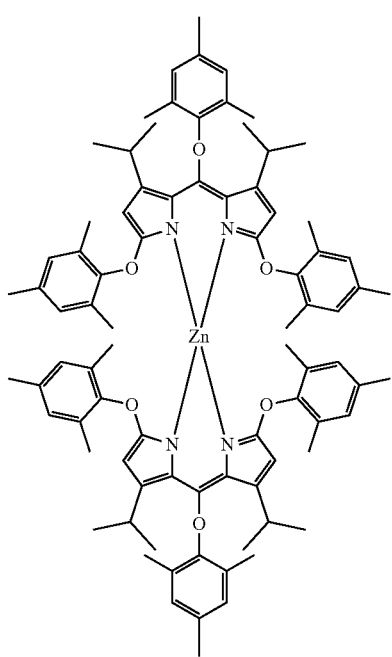
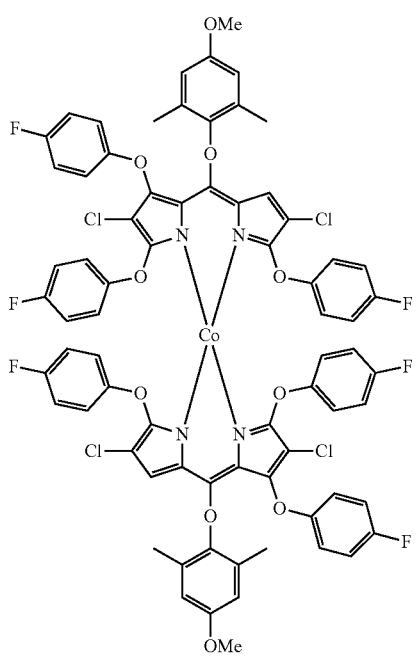

-continued
229
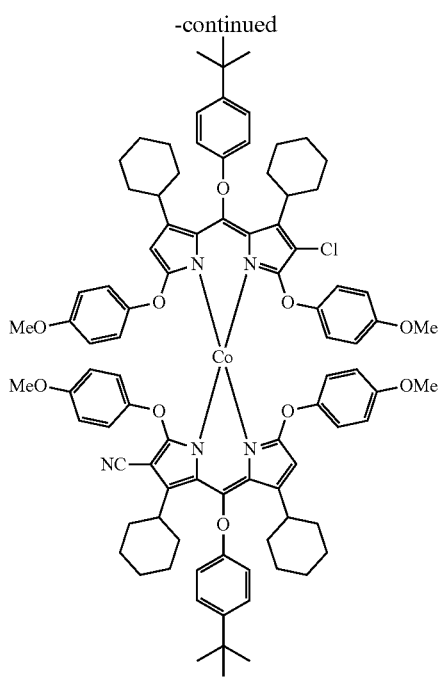
230
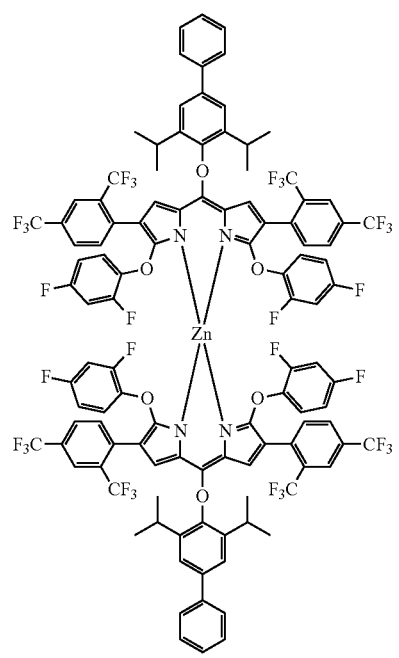
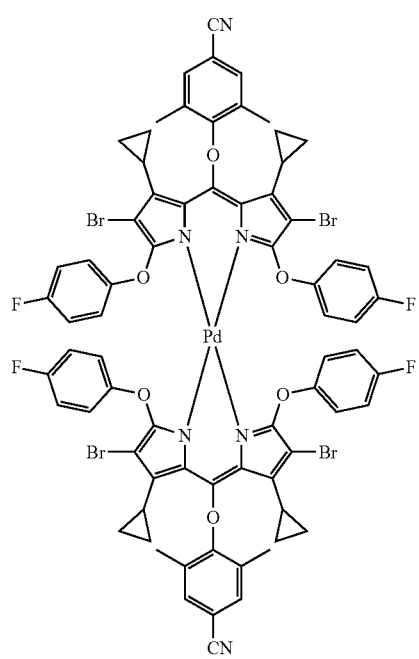
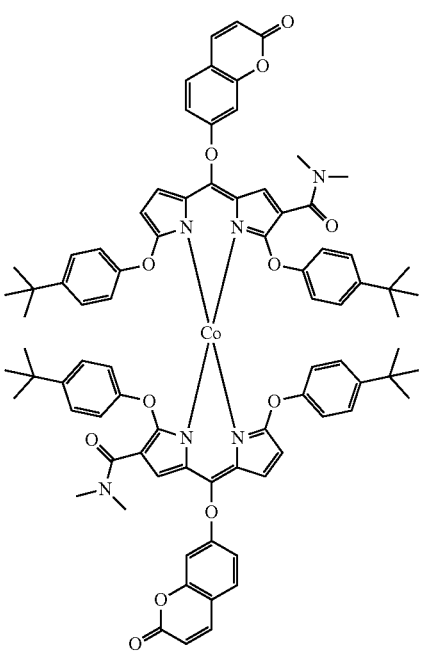

231
-continued
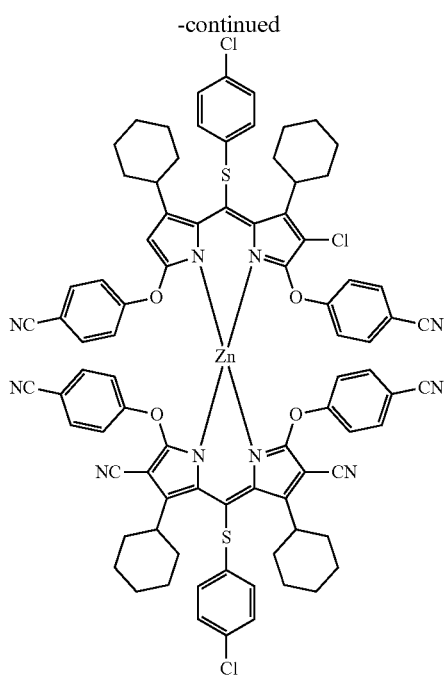
232
-continued
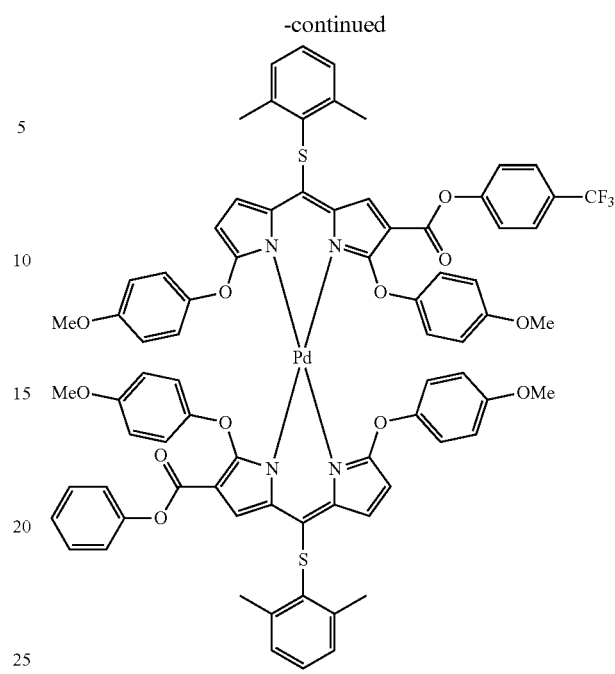
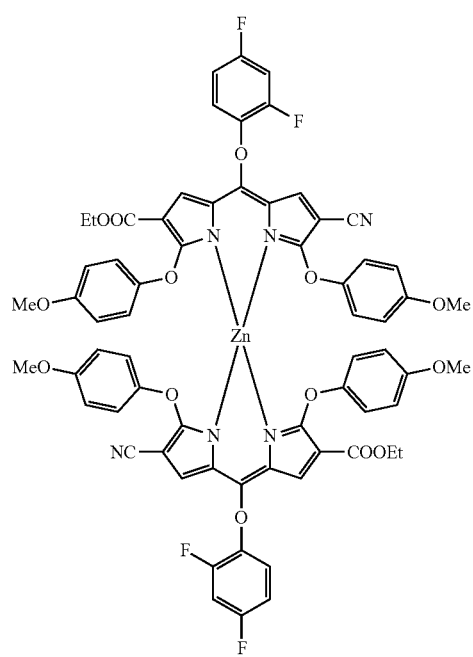
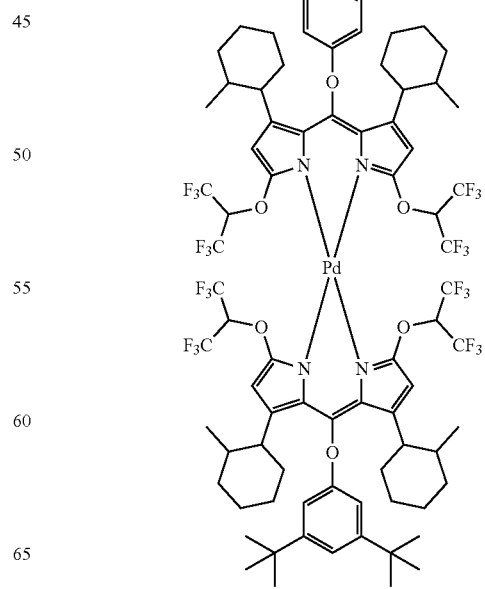

233
-continued
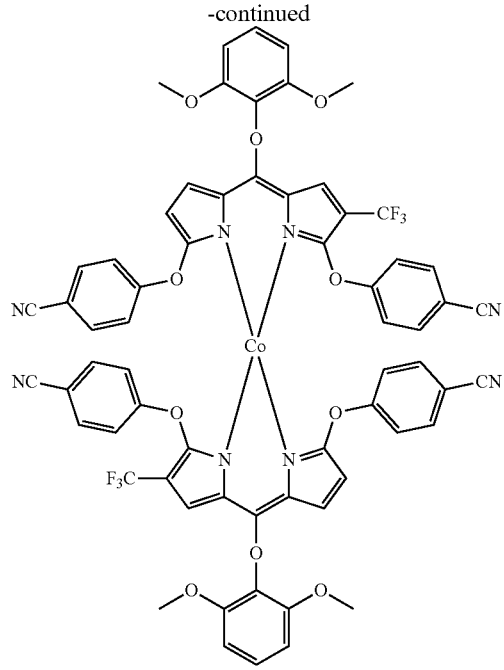
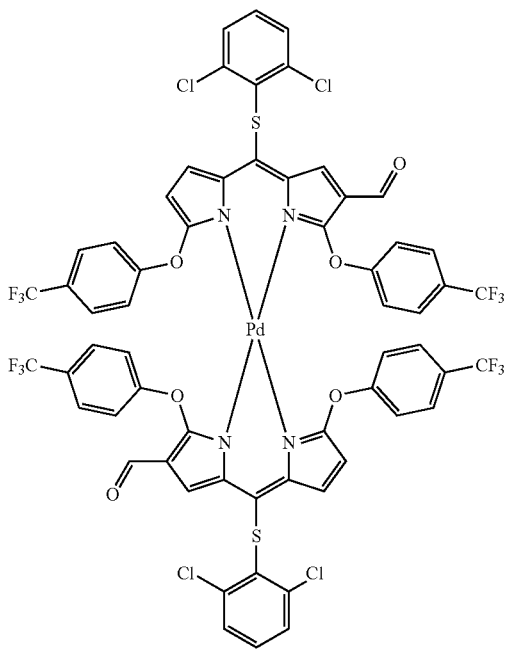
234
-continued
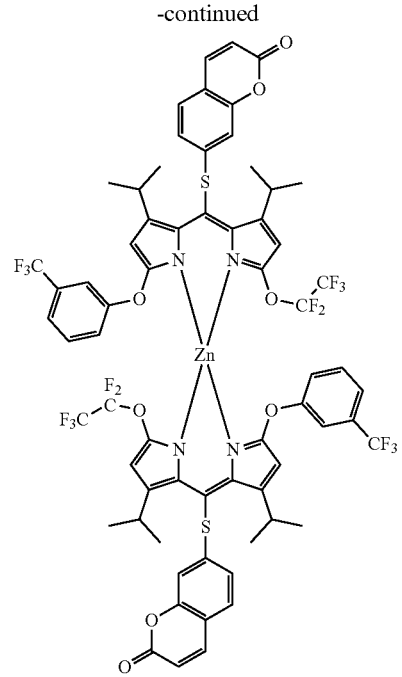
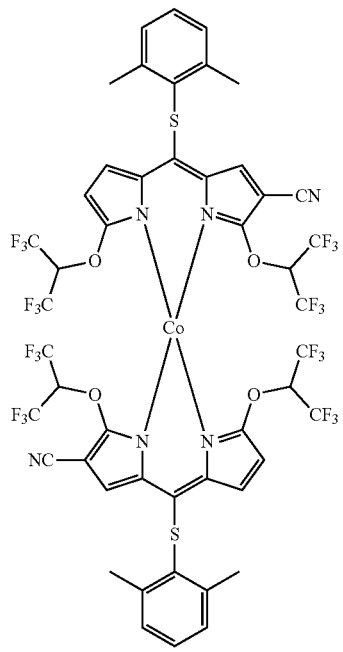

235
-continued
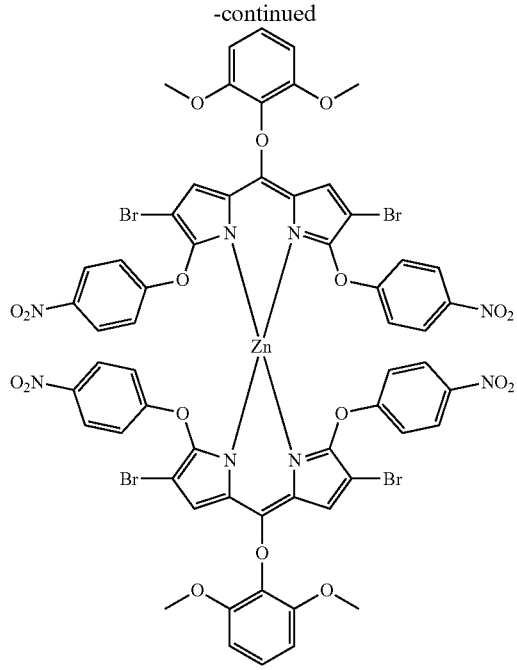
236
-continued
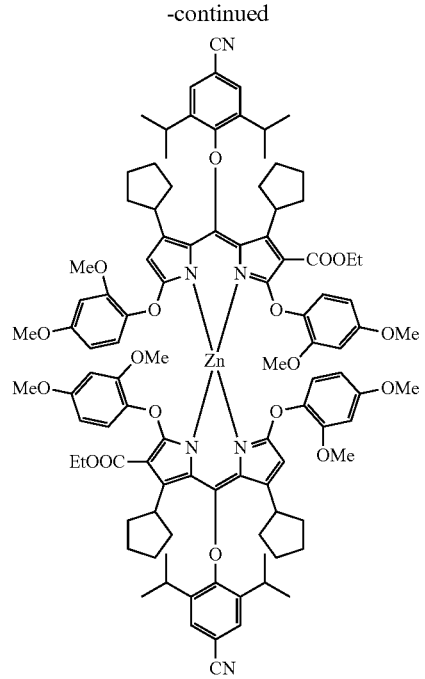
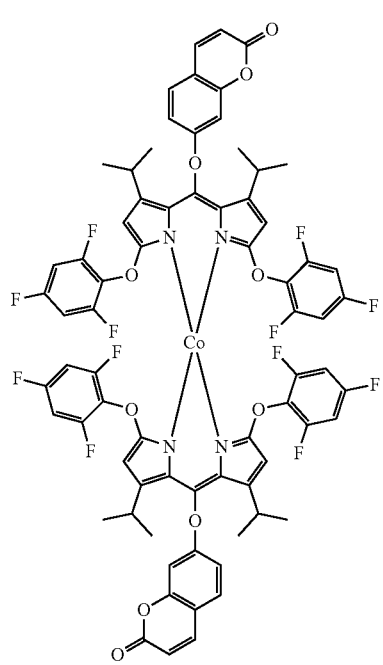
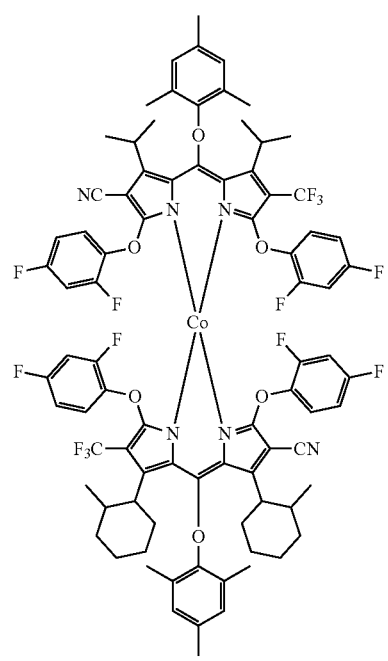

237
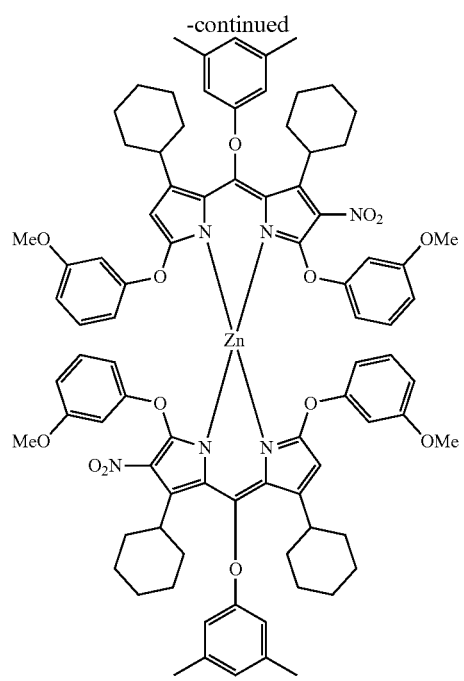
238
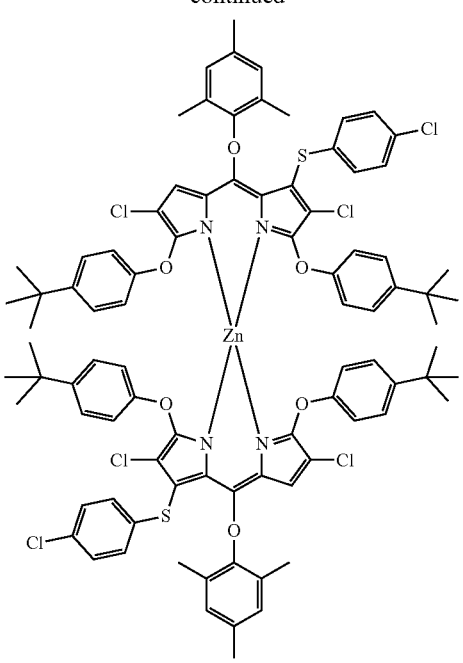
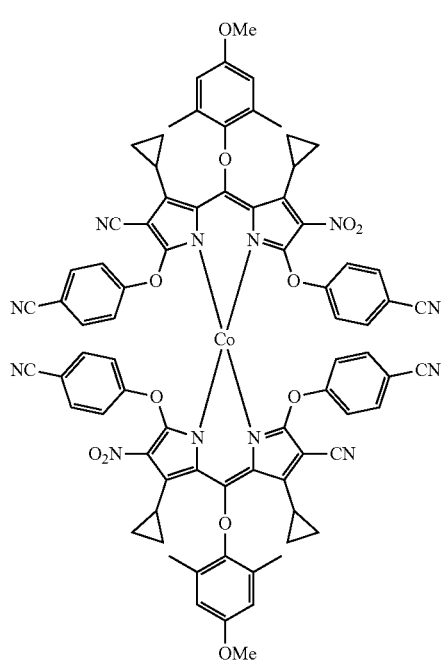

239
-continued
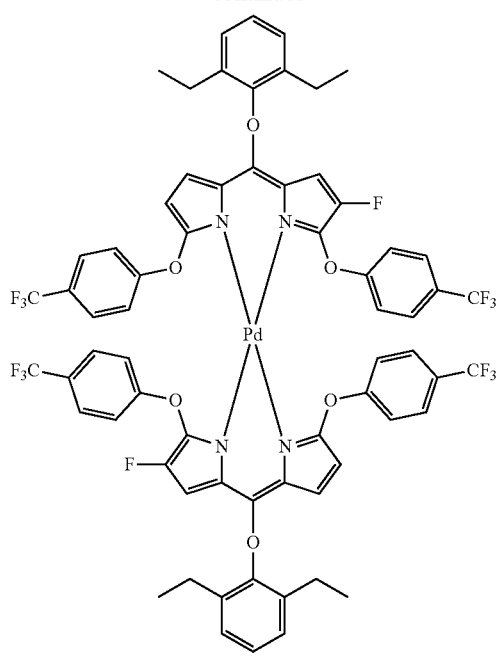
240
-continued
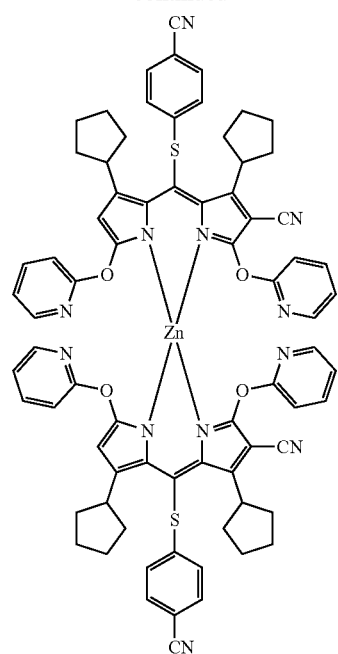
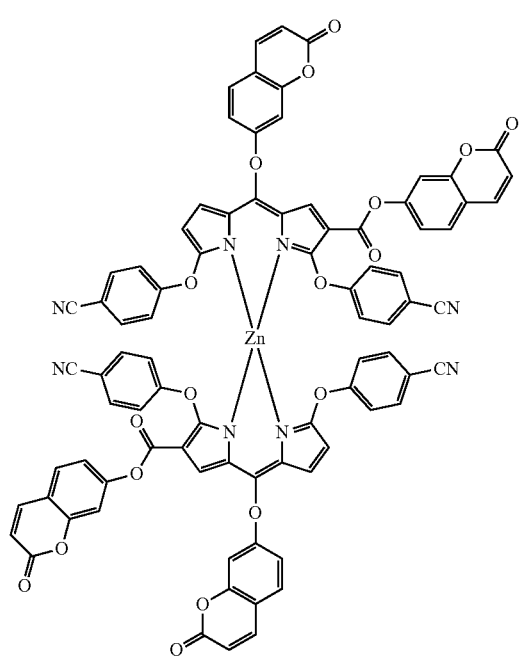
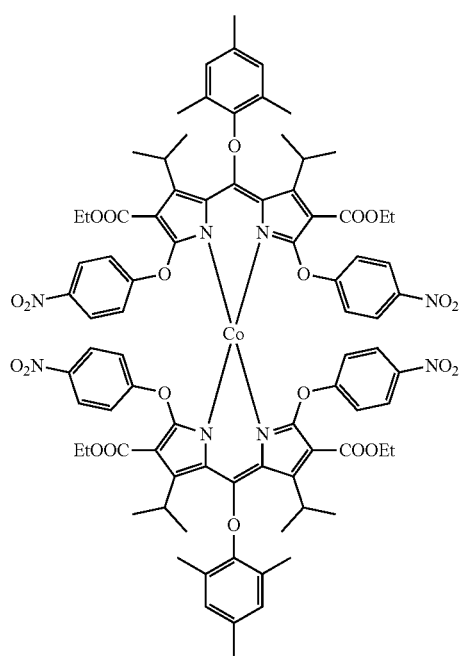

241
-continued
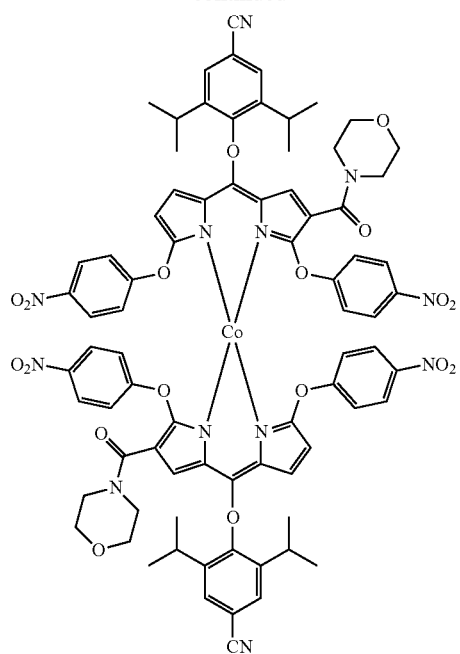
242
-continued
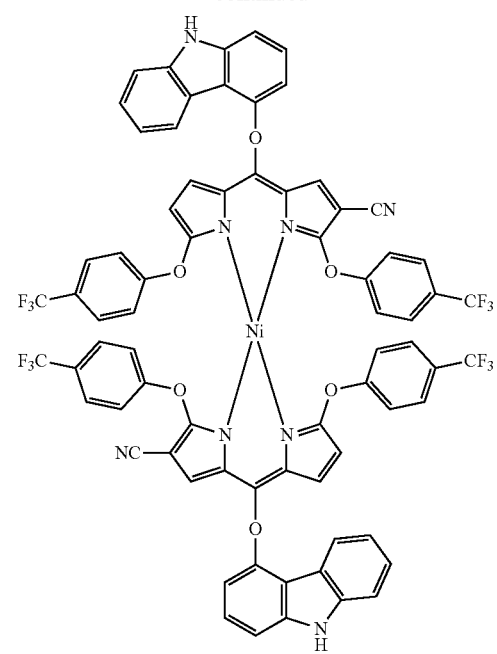
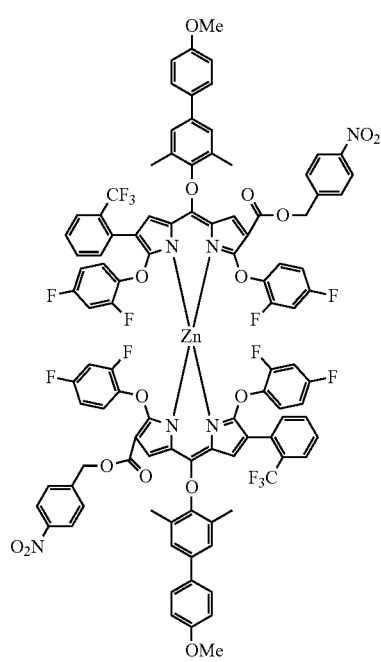
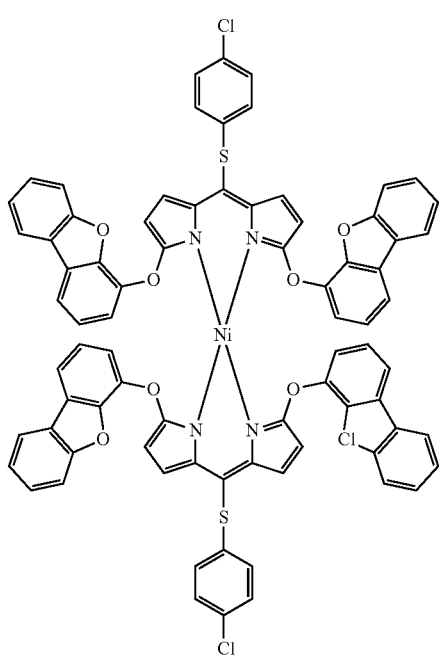

243
-continued
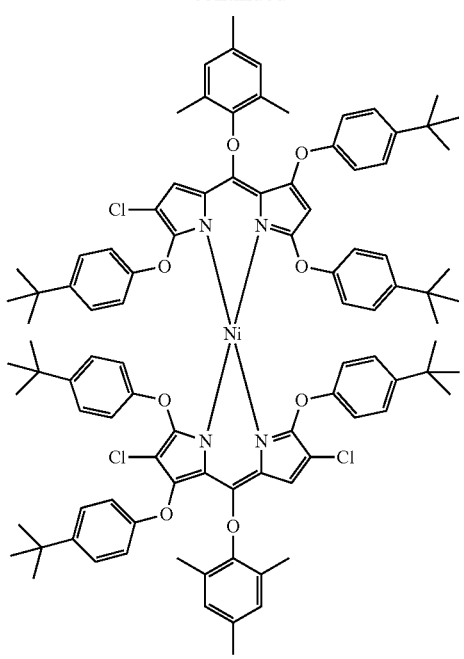
244
-continued
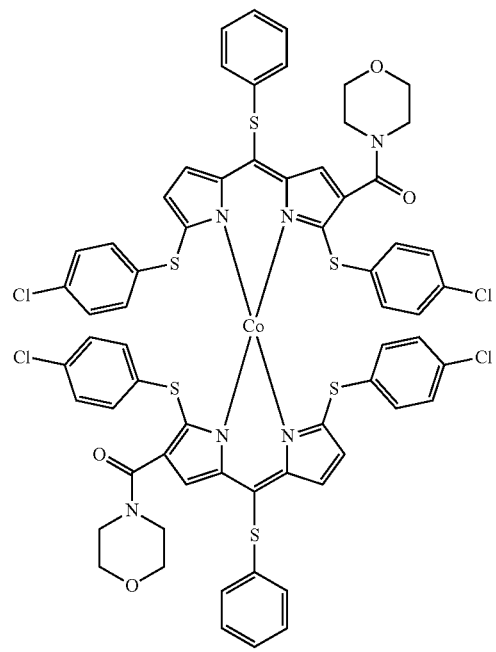
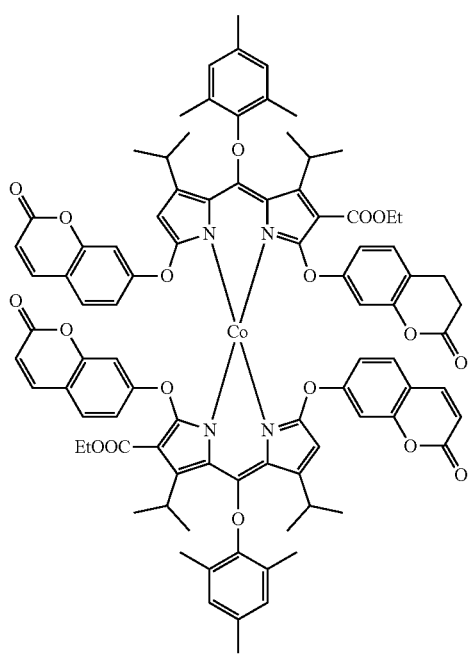
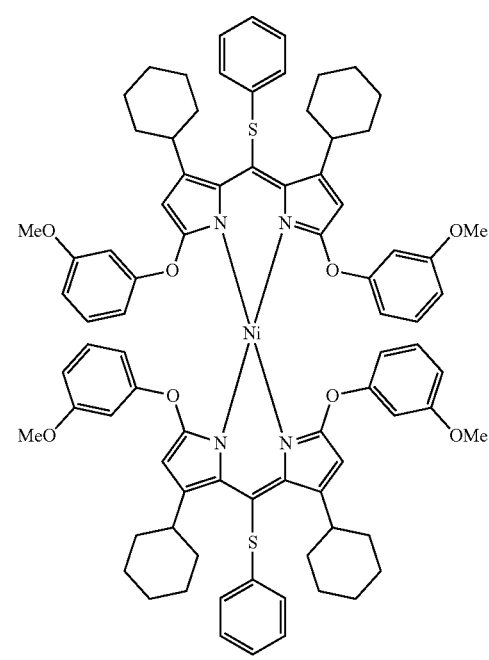

-continued

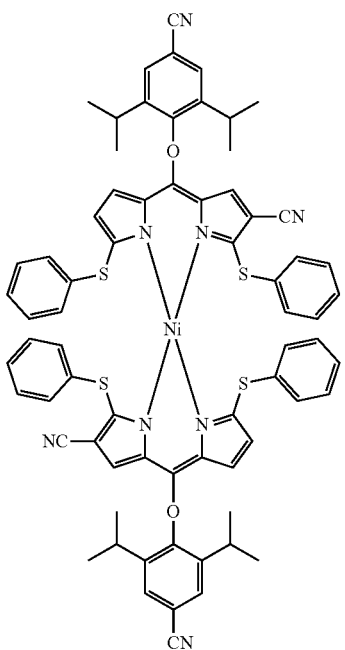

-continued

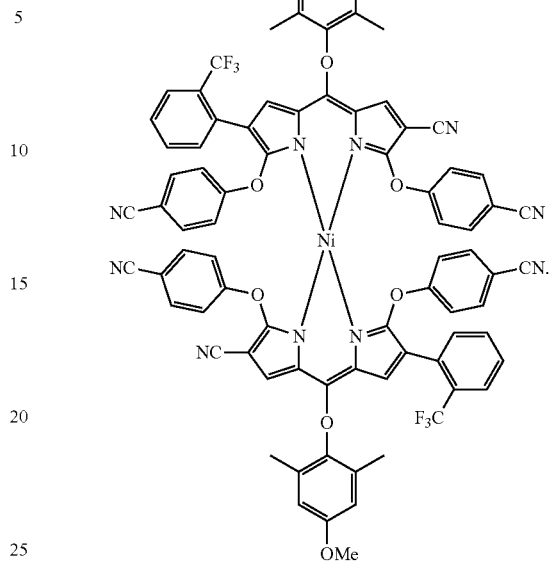

13. A composition for forming an optical film, the composition comprising:
   a binder resin; and
   the compound of claim 12.

14. A composition for forming an optical film, the composition comprising:
   a binder resin; and
   the compound of claim 1.

15. The composition for forming an optical film of claim 14, wherein a content of the compound is from 0.001 wt % to 10 wt % with respect to 100 wt % of the binder resin.

16. An optical film comprising a resin matrix into which the compound of claim 1 is dispersed.

17. The optical film of claim 16, wherein a content of the compound is from 0.001 wt % to 10 wt % with respect to 100 wt % of the optical film.

18. A display device comprising the optical film of claim 16.

* * * * *